US008598192B2

(12) United States Patent
Kshirsagar et al.

(10) Patent No.: US 8,598,192 B2
(45) Date of Patent: *Dec. 3, 2013

(54) HYDROXYLAMINE SUBSTITUTED IMIDAZOQUINOLINES

(75) Inventors: Tushar A. Kshirsagar, Woodbury, MN (US); Gregory D. Lundquist, Jr., Eagan, MN (US); David T. Amos, St. Paul, MN (US); Joseph F. Dellaria, Jr., Woodbury, MN (US); Bernhard M. Zimmermann, Eagan, MN (US); Philip D. Heppner, Forest Lake, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1163 days.

This patent is subject to a terminal disclaimer.

(21) Appl. No.: 10/595,790

(22) PCT Filed: Nov. 12, 2004

(86) PCT No.: PCT/US2004/038033
§ 371 (c)(1),
(2), (4) Date: May 11, 2006

(87) PCT Pub. No.: WO2005/048945
PCT Pub. Date: Jun. 2, 2005

(65) Prior Publication Data
US 2009/0105295 A1  Apr. 23, 2009

Related U.S. Application Data

(60) Provisional application No. 60/520,215, filed on Nov. 14, 2003.

(51) Int. Cl.
*A61K 31/437* (2006.01)
*C07D 471/04* (2006.01)

(52) U.S. Cl.
USPC .......................................... 514/292; 546/82

(58) Field of Classification Search
USPC .......................................... 546/82; 514/292
See application file for complete search history.

(56) References Cited

U.S. PATENT DOCUMENTS

| | | |
|---|---|---|
| 3,314,941 A | 4/1967 | Littell et al. |
| 3,450,693 A | 6/1969 | Suzuki et al. |
| 3,670,086 A | 6/1972 | Pryor et al. |
| 3,692,907 A | 9/1972 | Fleming et al. |
| 3,891,660 A | 6/1975 | Denzel et al. |
| 3,899,508 A | 8/1975 | Wikel |
| 3,917,624 A | 11/1975 | Abu El-Haj et al. |
| 4,006,237 A | 2/1977 | Buckle et al. |
| 4,053,588 A | 10/1977 | Konig et al. |
| 4,381,344 A | 4/1983 | Rideout et al. |
| 4,552,874 A | 11/1985 | Mardin et al. |
| 4,563,525 A | 1/1986 | Campbell, Jr. |
| 4,593,821 A | 6/1986 | Brule |
| 4,668,686 A | 5/1987 | Meanwell et al. |
| 4,689,338 A | 8/1987 | Gerster |
| 4,690,930 A | 9/1987 | Takada et al. |
| 4,698,346 A | 10/1987 | Musser et al. |
| 4,698,348 A | 10/1987 | Gerster |
| 4,753,951 A | 6/1988 | Takada et al. |
| 4,758,574 A | 7/1988 | Robertson et al. |
| 4,774,339 A | 9/1988 | Haugland et al. |
| 4,775,674 A | 10/1988 | Meanwell et al. |
| 4,800,206 A | 1/1989 | Alig et al. |
| 4,826,830 A | 5/1989 | Han et al. |
| 4,837,378 A | 6/1989 | Borgman |
| 4,880,779 A | 11/1989 | Gallaher |
| 4,904,669 A | 2/1990 | Knoll et al. |
| 4,929,624 A | 5/1990 | Gerster et al. |
| 4,988,714 A | 1/1991 | Alig et al. |
| 4,988,815 A | 1/1991 | Andre et al. |
| 5,037,986 A | 8/1991 | Gerster |
| 5,175,296 A | 12/1992 | Gerster |
| 5,187,288 A | 2/1993 | Kang et al. |
| 5,225,183 A | 7/1993 | Purewal et al. |
| 5,238,944 A | 8/1993 | Wick et al. |
| 5,248,782 A | 9/1993 | Haugland et al. |
| 5,266,575 A | 11/1993 | Gerster |
| 5,268,376 A | 12/1993 | Gester |
| 5,274,113 A | 12/1993 | Kang et al. |
| 5,342,784 A | 8/1994 | Yamada et al. |
| 5,346,905 A | 9/1994 | Gerster |
| 5,352,680 A | 10/1994 | Portoghese et al. |
| 5,352,784 A | 10/1994 | Nikolaides et al. |
| 5,367,076 A | 11/1994 | Gerster |
| 5,376,501 A | 12/1994 | Marien et al. |

(Continued)

FOREIGN PATENT DOCUMENTS

| AU | 2004220534 A1 | 9/2004 |
|---|---|---|
| AU | 2004229478 A1 | 10/2004 |

(Continued)

OTHER PUBLICATIONS

Dorwald F. A. Side Reactions in Organic Synthesis, 2005, Wiley: VCH, Weinheim p. IX of Preface.*
Wozniak, et al., "The Amination of 3-nitro-1, 5-naphthyridines by Liquid Ammonia/Potassium Permanganate[1,2]. A New and Convenient Amination Method.", *Journal of the Royal Netherlands Chemical Society*, 102, pp. 511-513, Dec. 12, 1983.
Brennan, et al., "Automated Bioassay of Interferons in Micro-test Plates", *Biotechniques*, June/July, 78, 1983.
Testerman, et al., "Cytokine Induction by the Immunomodulators Imiquimod and S-27609", *Journal of Leukocyte Biology*, vol. 58, pp. 365-372, Sep. 1995.
Bachman, et al., "Synthesis of Substituted Quinolylamines. Derivatives of 4-Amino-7-Chloroquinoline", *J. Org. Chem*, 15, pp. 1278-1284 (1950).
Jain, et al., "Chemical and Pharmacological Investigations of Some ω-Substituted Alkylamino-3-aminopyridines", *J. Med. Chem.*, 11, pp. 87-92 (1968).

(Continued)

Primary Examiner — Rita Desai

(57) ABSTRACT

Imidazo ring compounds (e.g., imidazoquinolines, 6,7,8,9-tetrahydroimidazoquinolines, imidazonaphthyridines, and imidazopyridines) with a hydroxylamine substituent at the 2-position, pharmaceutical compositions containing the compounds, intermediates, and methods of use of these compounds as immunomodulators, for inducing cytokine biosynthesis in animals and in the treatment of diseases including viral and neoplastic diseases are disclosed.

40 Claims, No Drawings

(56) References Cited

U.S. PATENT DOCUMENTS

| | | | |
|---|---|---|---|
| 5,378,848 | A | 1/1995 | Takada et al. |
| 5,389,640 | A | 2/1995 | Gerster et al. |
| 5,395,937 | A | 3/1995 | Nikolaides et al. |
| 5,444,065 | A | 8/1995 | Nikolaides et al. |
| 5,446,153 | A | 8/1995 | Lindstrom et al. |
| 5,446,160 | A | 8/1995 | Stucky et al. |
| 5,482,936 | A | 1/1996 | Lindstrom |
| 5,494,916 | A | 2/1996 | Lindstrom et al. |
| 5,500,228 | A | 3/1996 | Lawter et al. |
| 5,525,612 | A | 6/1996 | Gerster |
| 5,530,114 | A | 6/1996 | Bennett et al. |
| 5,569,450 | A | 10/1996 | Duan et al. |
| 5,571,819 | A | 11/1996 | Sabb et al. |
| 5,578,727 | A | 11/1996 | Andre et al. |
| 5,585,612 | A | 12/1996 | Harp, Jr. |
| 5,602,256 | A | 2/1997 | Andre et al. |
| 5,605,899 | A | 2/1997 | Gerster et al. |
| 5,612,377 | A | 3/1997 | Crooks et al. |
| 5,627,281 | A | 5/1997 | Nikolaides et al. |
| 5,644,063 | A | 7/1997 | Lindstrom et al. |
| 5,648,516 | A | 7/1997 | Nikolaides et al. |
| 5,693,811 | A | 12/1997 | Lindstrom |
| 5,714,608 | A | 2/1998 | Gerster |
| 5,731,193 | A | 3/1998 | Mori et al. |
| 5,736,553 | A | 4/1998 | Wick et al. |
| 5,741,908 | A | 4/1998 | Gerster et al. |
| 5,741,909 | A | 4/1998 | Gerster et al. |
| 5,750,134 | A | 5/1998 | Scholz et al. |
| 5,756,747 | A | 5/1998 | Gerster et al. |
| 5,776,432 | A | 7/1998 | Schultz et al. |
| 5,780,045 | A | 7/1998 | McQuinn et al. |
| 5,837,809 | A | 11/1998 | Grandy et al. |
| 5,840,744 | A | 11/1998 | Borgman |
| 5,854,257 | A | 12/1998 | Armitage et al. |
| 5,861,268 | A | 1/1999 | Tang et al. |
| 5,886,006 | A | 3/1999 | Nikolaides et al. |
| 5,939,047 | A | 8/1999 | Jernberg |
| 5,939,090 | A | 8/1999 | Beaurline et al. |
| 5,962,479 | A | 10/1999 | Chen |
| 5,962,636 | A | 10/1999 | Bachmaier et al. |
| 5,977,366 | A | 11/1999 | Gerster et al. |
| 6,028,076 | A | 2/2000 | Hirota et al. |
| 6,039,969 | A | 3/2000 | Tomai et al. |
| 6,057,371 | A | 5/2000 | Glennon |
| 6,069,140 | A | 5/2000 | Sessler et al. |
| 6,069,149 | A | 5/2000 | Nanba et al. |
| 6,071,949 | A | 6/2000 | Mulshine et al. |
| 6,077,349 | A | 6/2000 | Kikuchi |
| 6,083,505 | A | 7/2000 | Miller et al. |
| 6,110,929 | A | 8/2000 | Gerster et al. |
| 6,113,918 | A | 9/2000 | Johnson et al. |
| 6,121,323 | A | 9/2000 | Merrill |
| 6,123,957 | A | 9/2000 | Jernberg |
| 6,126,938 | A | 10/2000 | Guy et al. |
| 6,194,388 | B1 | 2/2001 | Krieg et al. |
| 6,194,425 | B1 | 2/2001 | Gerster et al. |
| 6,200,592 | B1 | 3/2001 | Tomai et al. |
| 6,207,646 | B1 | 3/2001 | Krieg et al. |
| 6,239,116 | B1 | 5/2001 | Krieg et al. |
| 6,245,776 | B1 | 6/2001 | Skwierczynski et al. |
| 6,294,271 | B1 | 9/2001 | Sumita et al. |
| 6,303,347 | B1 | 10/2001 | Johnson et al. |
| 6,309,623 | B1 | 10/2001 | Weers et al. |
| 6,315,985 | B1 | 11/2001 | Wu et al. |
| 6,323,200 | B1 | 11/2001 | Gerster et al. |
| 6,329,381 | B1 | 12/2001 | Kurimoto et al. |
| 6,331,539 | B1 | 12/2001 | Crooks et al. |
| 6,339,068 | B1 | 1/2002 | Krieg et al. |
| 6,348,462 | B1 | 2/2002 | Gerster et al. |
| 6,365,166 | B2 | 4/2002 | Beaurline et al. |
| 6,376,501 | B1 | 4/2002 | Isobe et al. |
| 6,376,669 | B1 | 4/2002 | Rice et al. |
| 6,387,383 | B1 | 5/2002 | Dow et al. |
| 6,387,938 | B1 | 5/2002 | Mizuguchi et al. |
| 6,406,705 | B1 | 6/2002 | Davis et al. |
| 6,426,334 | B1 | 7/2002 | Agrawal et al. |
| 6,440,992 | B1 | 8/2002 | Gerster et al. |
| 6,451,485 | B1 | 9/2002 | James et al. |
| 6,451,810 | B1 | 9/2002 | Coleman et al. |
| 6,465,654 | B2 | 10/2002 | Gerster et al. |
| 6,476,000 | B1 | 11/2002 | Agrawal |
| 6,486,168 | B1 | 11/2002 | Skwierczynski et al. |
| 6,486,186 | B2 | 11/2002 | Fowler et al. |
| 6,511,485 | B2 | 1/2003 | Hirt et al. |
| 6,514,985 | B1 | 2/2003 | Gerster et al. |
| 6,518,239 | B1 | 2/2003 | Kuo et al. |
| 6,518,265 | B1 | 2/2003 | Kato et al. |
| 6,518,280 | B2 | 2/2003 | Gerster et al. |
| 6,525,028 | B1 | 2/2003 | Johnson et al. |
| 6,525,064 | B1 | 2/2003 | Dellaria et al. |
| 6,541,485 | B1 | 4/2003 | Crooks et al. |
| 6,545,016 | B1 | 4/2003 | Dellaria et al. |
| 6,545,017 | B1 | 4/2003 | Dellaria et al. |
| 6,558,951 | B1 | 5/2003 | Tomai et al. |
| 6,573,273 | B1 | 6/2003 | Crooks et al. |
| 6,582,957 | B1 | 6/2003 | Turner, Jr. et al. |
| 6,610,319 | B2 | 8/2003 | Tomai et al. |
| 6,627,638 | B2 | 9/2003 | Gerster et al. |
| 6,627,639 | B2 | 9/2003 | Stack et al. |
| 6,627,640 | B2 | 9/2003 | Gerster et al. |
| 6,630,588 | B2 | 10/2003 | Rice et al. |
| 6,638,944 | B2 | 10/2003 | Mickelson |
| 6,649,172 | B2 | 11/2003 | Johnson |
| 6,656,938 | B2 | 12/2003 | Crooks et al. |
| 6,660,735 | B2 | 12/2003 | Crooks et al. |
| 6,660,747 | B2 | 12/2003 | Crooks et al. |
| 6,664,260 | B2 | 12/2003 | Charles et al. |
| 6,664,264 | B2 | 12/2003 | Dellaria et al. |
| 6,664,265 | B2 | 12/2003 | Crooks et al. |
| 6,667,312 | B2 | 12/2003 | Bonk et al. |
| 6,670,372 | B2 | 12/2003 | Charles et al. |
| 6,677,334 | B2 | 1/2004 | Gerster et al. |
| 6,677,347 | B2 | 1/2004 | Crooks et al. |
| 6,677,348 | B2 | 1/2004 | Heppner et al. |
| 6,677,349 | B1 | 1/2004 | Griesgraber |
| 6,683,088 | B2 | 1/2004 | Crooks et al. |
| 6,696,076 | B2 | 2/2004 | Tomai et al. |
| 6,696,465 | B2 | 2/2004 | Dellaria et al. |
| 6,703,402 | B2 | 3/2004 | Gerster et al. |
| 6,706,728 | B2 | 3/2004 | Hedenstrom et al. |
| 6,716,988 | B2 | 4/2004 | Dellaria et al. |
| 6,720,333 | B2 | 4/2004 | Dellaria et al. |
| 6,720,334 | B2 | 4/2004 | Dellaria et al. |
| 6,720,422 | B2 | 4/2004 | Dellaria et al. |
| 6,743,920 | B2 | 6/2004 | Lindstrom et al. |
| 6,756,382 | B2 | 6/2004 | Coleman et al. |
| 6,780,873 | B2 | 8/2004 | Crooks et al. |
| 6,784,188 | B2 | 8/2004 | Crooks et al. |
| 6,790,961 | B2 | 9/2004 | Gerster et al. |
| 6,797,718 | B2 | 9/2004 | Dellaria et al. |
| 6,800,624 | B2 | 10/2004 | Crooks et al. |
| 6,818,650 | B2 | 11/2004 | Griesgraber |
| 6,825,350 | B2 | 11/2004 | Crooks et al. |
| 6,841,678 | B2 | 1/2005 | Merli et al. |
| 6,852,861 | B2 | 2/2005 | Merli et al. |
| 6,855,217 | B2 | 2/2005 | Suzuki |
| 6,855,350 | B2 | 2/2005 | Lu |
| 6,878,719 | B2 | 4/2005 | Lindstrom et al. |
| 6,888,000 | B2 | 5/2005 | Crooks et al. |
| 6,894,060 | B2 | 5/2005 | Slade |
| 6,894,165 | B2 | 5/2005 | Gerster et al. |
| 6,897,221 | B2 | 5/2005 | Crooks et al. |
| 6,900,016 | B1 | 5/2005 | Venter et al. |
| 6,903,113 | B2 | 6/2005 | Heppner et al. |
| 6,916,925 | B1 | 7/2005 | Rice et al. |
| 6,921,826 | B2 | 7/2005 | Dellaria et al. |
| 6,924,293 | B2 | 8/2005 | Lindstrom |
| 6,943,240 | B2 | 9/2005 | Bauer et al. |
| 6,943,255 | B2 | 9/2005 | Lindstrom et al. |
| 6,949,649 | B2 | 9/2005 | Bonk et al. |
| 6,953,804 | B2 | 10/2005 | Dellaria et al. |
| 6,969,722 | B2 | 11/2005 | Heppner et al. |
| 6,989,389 | B2 | 1/2006 | Heppner et al. |
| 7,030,129 | B2 | 4/2006 | Miller et al. |

(56) References Cited

U.S. PATENT DOCUMENTS

| | | |
|---|---|---|
| 7,030,131 B2 | 4/2006 | Crooks et al. |
| 7,038,053 B2 | 5/2006 | Lindstrom et al. |
| 7,049,439 B2 | 5/2006 | Crooks et al. |
| 7,078,253 B2 | 7/2006 | Brunner et al. |
| 7,078,523 B2 | 7/2006 | Crooks et al. |
| 7,091,214 B2 | 8/2006 | Hays et al. |
| 7,098,221 B2 | 8/2006 | Heppner et al. |
| 7,112,677 B2 | 9/2006 | Griesgraber |
| 7,115,622 B2 | 10/2006 | Crooks et al. |
| 7,125,890 B2 | 10/2006 | Dellaria et al. |
| 7,132,429 B2 | 11/2006 | Griesgraber et al. |
| 7,163,947 B2 | 1/2007 | Griesgraber et al. |
| 7,179,253 B2 | 2/2007 | Graham et al. |
| 7,199,131 B2 | 4/2007 | Lindstrom |
| 7,214,675 B2 | 5/2007 | Griesgraber |
| 7,220,758 B2 | 5/2007 | Dellaria et al. |
| 7,226,928 B2 | 6/2007 | Mitra et al. |
| 7,276,515 B2 | 10/2007 | Dellaria et al. |
| 7,288,550 B2 | 10/2007 | Dellaria et al. |
| 7,375,180 B2 | 5/2008 | Gorden et al. |
| 7,387,271 B2 | 6/2008 | Noelle et al. |
| 7,393,859 B2 | 7/2008 | Coleman et al. |
| 7,427,629 B2 | 9/2008 | Kedl et al. |
| 7,544,697 B2 | 6/2009 | Hays et al. |
| 7,598,382 B2 | 10/2009 | Hays et al. |
| 7,612,083 B2 | 11/2009 | Griesgraber |
| 7,648,997 B2 | 1/2010 | Kshirsagar et al. |
| 2001/0046968 A1 | 11/2001 | Zagon et al. |
| 2002/0016332 A1 | 2/2002 | Slade |
| 2002/0055517 A1 | 5/2002 | Smith |
| 2002/0058674 A1 | 5/2002 | Hedenstrom et al. |
| 2002/0107262 A1 | 8/2002 | Lindstrom |
| 2002/0110840 A1 | 8/2002 | Tomai et al. |
| 2002/0137101 A1 | 9/2002 | Meyers |
| 2002/0173655 A1 | 11/2002 | Dellaria et al. |
| 2002/0193729 A1 | 12/2002 | Cormier et al. |
| 2003/0022302 A1 | 1/2003 | Lewis et al. |
| 2003/0044429 A1 | 3/2003 | Aderem et al. |
| 2003/0082108 A1 | 5/2003 | Mulshine et al. |
| 2003/0088102 A1 | 5/2003 | Matsubara et al. |
| 2003/0096835 A1 | 5/2003 | Crooks et al. |
| 2003/0096998 A1 | 5/2003 | Gerster et al. |
| 2003/0130299 A1 | 7/2003 | Crooks et al. |
| 2003/0133733 A1 | 7/2003 | Korhonen |
| 2003/0133913 A1 | 7/2003 | Tomai et al. |
| 2003/0139364 A1 | 7/2003 | Krieg et al. |
| 2003/0144283 A1 | 7/2003 | Coleman et al. |
| 2003/0144286 A1 | 7/2003 | Frenkel et al. |
| 2003/0158192 A1 | 8/2003 | Crooks et al. |
| 2003/0161797 A1 | 8/2003 | Miller et al. |
| 2003/0172391 A1 | 9/2003 | Turner et al. |
| 2003/0185835 A1 | 10/2003 | Braun |
| 2003/0187016 A1 | 10/2003 | Crooks et al. |
| 2003/0199461 A1 | 10/2003 | Averett et al. |
| 2003/0199538 A1 | 10/2003 | Skwierczynski et al. |
| 2003/0212092 A1 | 11/2003 | Heppner et al. |
| 2003/0216481 A1 | 11/2003 | Jia |
| 2003/0232074 A1 | 12/2003 | Lipford et al. |
| 2003/0232763 A1 | 12/2003 | Jia |
| 2003/0232852 A1 | 12/2003 | Lindstrom et al. |
| 2004/0010007 A1 | 1/2004 | Dellaria et al. |
| 2004/0014779 A1 | 1/2004 | Gorden et al. |
| 2004/0023870 A1 | 2/2004 | Dedera et al. |
| 2004/0067975 A1 | 4/2004 | Crooks et al. |
| 2004/0072858 A1 | 4/2004 | Charles et al. |
| 2004/0076633 A1 | 4/2004 | Thomsen et al. |
| 2004/0091491 A1 | 5/2004 | Kedl et al. |
| 2004/0092545 A1 | 5/2004 | Crooks et al. |
| 2004/0097542 A1 | 5/2004 | Crooks et al. |
| 2004/0106638 A1 | 6/2004 | Lindstrom |
| 2004/0132079 A1 | 7/2004 | Gupta et al. |
| 2004/0132748 A1 | 7/2004 | Isobe et al. |
| 2004/0132766 A1 | 7/2004 | Griesgraber |
| 2004/0141950 A1 | 7/2004 | Noelle et al. |
| 2004/0147543 A1 | 7/2004 | Hays et al. |
| 2004/0157874 A1 | 8/2004 | Crooks et al. |
| 2004/0162309 A1 | 8/2004 | Gorden et al. |
| 2004/0167157 A1 | 8/2004 | Masui et al. |
| 2004/0171086 A1 | 9/2004 | Fink et al. |
| 2004/0175336 A1 | 9/2004 | Egging et al. |
| 2004/0176367 A1 | 9/2004 | Griesgraber et al. |
| 2004/0180919 A1 | 9/2004 | Miller et al. |
| 2004/0181130 A1 | 9/2004 | Lee et al. |
| 2004/0181211 A1 | 9/2004 | Elliott et al. |
| 2004/0191833 A1 | 9/2004 | Fink et al. |
| 2004/0192585 A1 | 9/2004 | Fox et al. |
| 2004/0197865 A1 | 10/2004 | Gupta et al. |
| 2004/0202720 A1 | 10/2004 | Wightman et al. |
| 2004/0204436 A1 | 10/2004 | Gerster et al. |
| 2004/0214851 A1 | 10/2004 | Birmachu et al. |
| 2004/0258698 A1 | 12/2004 | Wightman et al. |
| 2004/0265351 A1 | 12/2004 | Miller et al. |
| 2005/0009858 A1 | 1/2005 | Martinez-Colon et al. |
| 2005/0032829 A1 | 2/2005 | Lindstrom et al. |
| 2005/0048072 A1 | 3/2005 | Kedl et al. |
| 2005/0054590 A1 | 3/2005 | Averett |
| 2005/0054640 A1 | 3/2005 | Griesgraber et al. |
| 2005/0054665 A1 | 3/2005 | Miller et al. |
| 2005/0059072 A1 | 3/2005 | Birmachu et al. |
| 2005/0070460 A1 | 3/2005 | Hammerbeck et al. |
| 2005/0085500 A1 | 4/2005 | Gutman et al. |
| 2005/0096259 A1 | 5/2005 | Tomai et al. |
| 2005/0119273 A1 | 6/2005 | Lipford et al. |
| 2005/0136065 A1 | 6/2005 | Valiante |
| 2005/0148620 A1 | 7/2005 | Crooks et al. |
| 2005/0158325 A1 | 7/2005 | Hammerbeck et al. |
| 2005/0165236 A1 | 7/2005 | Colombo et al. |
| 2005/0171072 A1 | 8/2005 | Tomai et al. |
| 2005/0226878 A1 | 10/2005 | Tomai et al. |
| 2005/0234088 A1 | 10/2005 | Griesgraber |
| 2005/0239733 A1 | 10/2005 | Jurk et al. |
| 2005/0239735 A1 | 10/2005 | Miller et al. |
| 2005/0245562 A1 | 11/2005 | Garcia-Echeverria et al. |
| 2005/0267145 A1 | 12/2005 | Merrill et al. |
| 2005/0281813 A1 | 12/2005 | Dedera et al. |
| 2006/0009482 A1 | 1/2006 | Tomai et al. |
| 2006/0100229 A1 | 5/2006 | Hays et al. |
| 2006/0106052 A1 | 5/2006 | Crooks et al. |
| 2007/0060754 A1 | 3/2007 | Lindstrom et al. |
| 2007/0066639 A1 | 3/2007 | Kshirsagar et al. |
| 2007/0072893 A1 | 3/2007 | Krepski et al. |
| 2007/0099901 A1 | 5/2007 | Krepski et al. |
| 2007/0155767 A1 | 7/2007 | Radmer et al. |
| 2007/0167476 A1 | 7/2007 | Kshirsagar et al. |
| 2007/0208052 A1 | 9/2007 | Prince et al. |
| 2007/0213356 A1 | 9/2007 | Merrill et al. |
| 2007/0219196 A1 | 9/2007 | Krepski et al. |
| 2007/0219228 A1 | 9/2007 | Niwas et al. |
| 2007/0259881 A1 | 11/2007 | Dellaria et al. |
| 2007/0259907 A1 | 11/2007 | Prince |
| 2007/0287725 A1 | 12/2007 | Miser et al. |
| 2007/0292456 A1 | 12/2007 | Hammerbeck et al. |
| 2008/0015184 A1 | 1/2008 | Kshirsagar et al. |
| 2008/0070907 A1 | 3/2008 | Griesgraber et al. |
| 2008/0085895 A1 | 4/2008 | Griesgraber et al. |
| 2008/0114019 A1 | 5/2008 | Kshirsagar et al. |
| 2008/0119508 A1 | 5/2008 | Slade et al. |
| 2008/0207674 A1 | 8/2008 | Stoesz et al. |
| 2008/0269192 A1 | 10/2008 | Griesgraber et al. |
| 2008/0306252 A1 | 12/2008 | Crooks et al. |
| 2008/0312434 A1 | 12/2008 | Lindstrom et al. |
| 2008/0318998 A1 | 12/2008 | Prince et al. |
| 2009/0005371 A1 | 1/2009 | Rice et al. |
| 2009/0017076 A1 | 1/2009 | Miller et al. |
| 2009/0018122 A1 | 1/2009 | Lindstrom et al. |
| 2009/0023722 A1 | 1/2009 | Coleman et al. |
| 2009/0029988 A1 | 1/2009 | Kshirsagar et al. |
| 2009/0030030 A1 | 1/2009 | Bonk et al. |
| 2009/0030031 A1 | 1/2009 | Kshirsagar et al. |
| 2009/0042925 A1 | 2/2009 | Kshirsagar et al. |
| 2009/0062272 A1 | 3/2009 | Bonk et al. |
| 2009/0062328 A1 | 3/2009 | Kshirsagar et al. |
| 2009/0069299 A1 | 3/2009 | Merrill et al. |
| 2009/0069314 A1 | 3/2009 | Kshirsagar et al. |

(56) References Cited

U.S. PATENT DOCUMENTS

| | | |
|---|---|---|
| 2009/0075980 A1 | 3/2009 | Hays et al. |
| 2009/0099161 A1 | 4/2009 | Rice et al. |
| 2009/0124611 A1 | 5/2009 | Hays et al. |
| 2009/0163532 A1 | 6/2009 | Perman et al. |
| 2009/0163533 A1 | 6/2009 | Hays et al. |
| 2009/0176821 A1 | 7/2009 | Kshirsagar et al. |
| 2009/0240055 A1 | 9/2009 | Krepski et al. |
| 2009/0253695 A1 | 10/2009 | Kshirsagar et al. |
| 2009/0270443 A1 | 10/2009 | Stoermer et al. |
| 2009/0318435 A1 | 12/2009 | Hays et al. |
| 2010/0113565 A1 | 5/2010 | Gorden et al. |

FOREIGN PATENT DOCUMENTS

| | | |
|---|---|---|
| AU | 2004264336 A1 | 2/2005 |
| AU | 2004268625 A1 | 3/2005 |
| AU | 2002239547 B2 | 11/2006 |
| CA | 2044087 A1 | 12/1991 |
| CA | 2158996 A1 | 10/1994 |
| CN | 1354663 A | 6/2002 |
| EP | 0 145 340 A2 | 6/1985 |
| EP | 0 223 420 A1 | 5/1987 |
| EP | 0 310 950 A1 | 4/1989 |
| EP | 0 385 630 A2 | 9/1990 |
| EP | 0 389 302 A1 | 9/1990 |
| EP | 0 394 026 | 10/1990 |
| EP | 0 425 306 A2 | 5/1991 |
| EP | 0 510 260 A2 | 10/1992 |
| EP | 0 645 389 A1 | 3/1995 |
| EP | 0 778 277 A1 | 6/1997 |
| EP | 0 894 797 A1 | 2/1999 |
| EP | 1 082 960 A2 | 3/2001 |
| EP | 1 097 709 A2 | 5/2001 |
| EP | 1 104 764 | 6/2001 |
| EP | 1 145 340 A2 | 10/2001 |
| EP | 1 256 582 A1 | 11/2002 |
| EP | 1 341 791 A2 | 9/2003 |
| EP | 1 495 758 A2 | 1/2005 |
| HU | 34479 A2 | 3/1985 |
| HU | 210051 A2 | 6/1991 |
| HU | 218950 A2 | 9/1995 |
| IL | 73534 A | 12/1990 |
| JP | 53050197 A | 5/1978 |
| JP | 63010787 A | 1/1988 |
| JP | 4066571 A | 3/1992 |
| JP | 4327587 A | 11/1992 |
| JP | 5286973 A | 11/1993 |
| JP | 9-208584 | 8/1997 |
| JP | 11-080156 A | 3/1999 |
| JP | 11-222432 | 8/1999 |
| JP | 2000-247884 | 9/2000 |
| NZ | 545412 A | 12/2008 |
| RU | 2076105 C1 | 3/1997 |
| RU | 2127273 C1 | 3/1999 |
| RU | 2221798 C2 | 1/2004 |
| WO | WO-91/06682 A1 | 5/1991 |
| WO | WO-92/06093 A1 | 4/1992 |
| WO | WO-92/15581 A1 | 9/1992 |
| WO | WO-92/15582 A1 | 9/1992 |
| WO | WO-93/05042 A1 | 3/1993 |
| WO | WO-93/09119 A1 | 5/1993 |
| WO | WO-93/20847 A1 | 10/1993 |
| WO | WO-94/10171 A1 | 5/1994 |
| WO | WO-95/02597 A1 | 1/1995 |
| WO | WO-95/02598 A1 | 1/1995 |
| WO | WO-96/11199 A1 | 4/1996 |
| WO | WO-96/21663 A1 | 7/1996 |
| WO | WO-97/48703 A1 | 12/1997 |
| WO | WO-97/48704 A1 | 12/1997 |
| WO | WO-98/17279 A1 | 4/1998 |
| WO | WO-98/30562 A1 | 7/1998 |
| WO | WO-98/48805 A1 | 11/1998 |
| WO | WO-98/50547 A2 | 11/1998 |
| WO | WO-98/54226 A1 | 12/1998 |
| WO | WO-99/18105 A1 | 4/1999 |
| WO | WO-99/29693 A1 | 6/1999 |
| WO | WO-00/06577 A1 | 2/2000 |
| WO | WO-00/09506 A1 | 2/2000 |
| WO | WO-00/19987 A1 | 4/2000 |
| WO | WO-00/40228 A2 | 7/2000 |
| WO | WO-00/47719 A2 | 8/2000 |
| WO | WO-00/75304 A1 | 12/2000 |
| WO | WO-00/76505 A1 | 12/2000 |
| WO | WO-00/76518 A1 | 12/2000 |
| WO | WO-00/76519 A1 | 12/2000 |
| WO | WO-01/34709 A1 | 5/2001 |
| WO | WO-01/51486 A2 | 7/2001 |
| WO | WO-01/55439 A1 | 8/2001 |
| WO | WO-01/58900 A1 | 8/2001 |
| WO | WO-01/74343 A2 | 10/2001 |
| WO | WO-01/74821 A1 | 10/2001 |
| WO | WO-02/07725 A1 | 1/2002 |
| WO | WO-02/22809 A2 | 3/2002 |
| WO | WO-02/24225 A1 | 3/2002 |
| WO | WO 02/36592 | 5/2002 |
| WO | WO 02/46188 A2 | 6/2002 |
| WO | WO-02/46189 A2 | 6/2002 |
| WO | WO 02/46190 A2 | 6/2002 |
| WO | WO-02/46191 A2 | 6/2002 |
| WO | WO-02/46192 A2 | 6/2002 |
| WO | WO-02/46193 A2 | 6/2002 |
| WO | WO-02/46194 A2 | 6/2002 |
| WO | WO-02/46749 A2 | 6/2002 |
| WO | WO-02/085905 A1 | 10/2002 |
| WO | WO-02/102377 A1 | 12/2002 |
| WO | WO-03/008421 A1 | 1/2003 |
| WO | WO-03/009852 A1 | 2/2003 |
| WO | WO-03/020889 A2 | 3/2003 |
| WO | WO-03/043572 A2 | 5/2003 |
| WO | WO-03/045391 A1 | 6/2003 |
| WO | WO-03/045494 A2 | 6/2003 |
| WO | WO-03/045929 A1 | 6/2003 |
| WO | WO-03/050117 A1 | 6/2003 |
| WO | WO-03/050118 A1 | 6/2003 |
| WO | WO-03/050119 A2 | 6/2003 |
| WO | WO-03/050121 A1 | 6/2003 |
| WO | WO-03/077944 A1 | 9/2003 |
| WO | WO-03/080114 A2 | 10/2003 |
| WO | WO-03/086280 A2 | 10/2003 |
| WO | WO-03/086350 A1 | 10/2003 |
| WO | WO-03/089602 A2 | 10/2003 |
| WO | WO-03/097641 A2 | 11/2003 |
| WO | WO-03/101949 A2 | 12/2003 |
| WO | WO-03/103584 A2 | 12/2003 |
| WO | WO-2004/028539 A2 | 4/2004 |
| WO | WO-2004/041285 A1 | 5/2004 |
| WO | WO-2004/043913 A2 | 5/2004 |
| WO | WO-2004/053057 A2 | 6/2004 |
| WO | WO-2004/053452 A2 | 6/2004 |
| WO | WO-2004/058759 A1 | 7/2004 |
| WO | WO-2004/071459 A2 | 8/2004 |
| WO | WO-2004/075865 A2 | 9/2004 |
| WO | WO-2004/080398 A2 | 9/2004 |
| WO | WO-2004/091500 A2 | 10/2004 |
| WO | WO-2004/096144 A2 | 11/2004 |
| WO | WO-2004/110991 A2 | 12/2004 |
| WO | WO-2004/110992 A2 | 12/2004 |
| WO | WO-2005/003064 A2 | 1/2005 |
| WO | WO-2005/003065 A2 | 1/2005 |
| WO | WO-2005/016273 A2 | 2/2005 |
| WO | WO-2005/016275 A2 | 2/2005 |
| WO | WO 2005/018551 | 3/2005 |
| WO | WO 2005/018555 | 3/2005 |
| WO | WO 2005/018556 | 3/2005 |
| WO | WO 2005/020999 | 3/2005 |
| WO | WO-2005/023190 A2 | 3/2005 |
| WO | WO-2005/025614 A2 | 3/2005 |
| WO | WO-2005/029037 A2 | 3/2005 |
| WO | WO 2005/032484 | 4/2005 |
| WO | WO-2005/041891 A2 | 5/2005 |
| WO | WO 2005/048933 | 6/2005 |
| WO | WO 2005/048945 | 6/2005 |
| WO | WO-2005/049076 A1 | 6/2005 |

(56) References Cited

FOREIGN PATENT DOCUMENTS

| WO | WO 2005/051317 | 6/2005 |
| WO | WO 2005/051324 | 6/2005 |
| WO | WO 2005/054237 | 6/2005 |
| WO | WO 2005/054238 | 6/2005 |
| WO | WO-2005/065678 A1 | 7/2005 |
| WO | WO 2005/066169 | 7/2005 |
| WO | WO 2005/066170 | 7/2005 |
| WO | WO 2005/066172 | 7/2005 |
| WO | WO-2005/067500 A2 | 7/2005 |
| WO | WO 2005/076783 | 8/2005 |
| WO | WO 2005/079195 | 9/2005 |
| WO | WO 2005/094531 | 10/2005 |
| WO | WO-2005/110013 A2 | 11/2005 |
| WO | WO 2005/123079 | 12/2005 |
| WO | WO 2005/123080 | 12/2005 |
| WO | WO-2006/004737 A2 | 1/2006 |
| WO | WO 2006/009826 | 1/2006 |
| WO | WO 2006/009832 | 1/2006 |
| WO | WO 2006/026760 | 3/2006 |
| WO | WO 2006/028451 | 3/2006 |
| WO | WO 2006/028545 | 3/2006 |
| WO | WO 2006/028962 | 3/2006 |
| WO | WO 2006/029115 | 3/2006 |
| WO | WO 2006/031878 | 3/2006 |
| WO | WO 2006/038923 | 4/2006 |
| WO | WO-2006/063072 A2 | 6/2006 |
| WO | WO-2006/063152 A2 | 6/2006 |
| WO | WO-2006/065280 A2 | 6/2006 |
| WO | WO-2006/073940 A2 | 7/2006 |
| WO | WO-2006/074003 A2 | 7/2006 |
| WO | WO-2006/074045 A2 | 7/2006 |
| WO | WO-2006/083440 A2 | 8/2006 |
| WO | WO-2006/084251 A2 | 8/2006 |
| WO | WO-2006/086449 A2 | 8/2006 |
| WO | WO-2006/086633 A2 | 8/2006 |
| WO | WO-2006/086634 A2 | 8/2006 |
| WO | WO-2006/091394 A2 | 8/2006 |
| WO | WO-2006/091567 A2 | 8/2006 |
| WO | WO-2006/091568 A2 | 8/2006 |
| WO | WO-2006/091647 A2 | 8/2006 |
| WO | WO-2006/093514 A2 | 9/2006 |
| WO | WO-2006/098852 A2 | 9/2006 |
| WO | WO-2006/107753 A2 | 10/2006 |
| WO | WO-2006/107771 A2 | 10/2006 |
| WO | WO-2006/107851 A1 | 10/2006 |
| WO | WO-2006/107853 A2 | 10/2006 |
| WO | WO-2006/121528 A2 | 11/2006 |
| WO | WO-2006/122806 A2 | 11/2006 |
| WO | WO-2007/028129 A1 | 3/2007 |
| WO | WO-2007/030775 A2 | 3/2007 |
| WO | WO-2007/030777 A2 | 3/2007 |
| WO | WO-2007/035935 A1 | 3/2007 |
| WO | WO-2007/056112 A2 | 5/2007 |
| WO | WO-2007/062043 A1 | 5/2007 |
| WO | WO-2007/075468 A1 | 7/2007 |
| WO | WO-2007/079086 A1 | 7/2007 |
| WO | WO-2007/079146 A1 | 7/2007 |
| WO | WO-2007/079169 A2 | 7/2007 |
| WO | WO-2007/079171 A2 | 7/2007 |
| WO | WO-2007/079202 A2 | 7/2007 |
| WO | WO-2007/079203 A2 | 7/2007 |
| WO | WO-2007/092641 A2 | 8/2007 |
| WO | WO-2007/106852 A2 | 9/2007 |
| WO | WO-2007/106854 A2 | 9/2007 |
| WO | WO-2007/120121 A2 | 10/2007 |
| WO | WO-2007/143526 A2 | 12/2007 |
| WO | WO-2008/008432 A2 | 1/2008 |
| WO | WO-2008/030511 A2 | 3/2008 |
| WO | WO-2008/036312 A1 | 3/2008 |
| WO | WO-2008/045543 A1 | 4/2008 |

OTHER PUBLICATIONS

Baranov, et al., *Chem. Abs.* 85, 94362, (1976).
Berényi, et al., "Ring Transformation of Condensed Dihydro-as-triazines", *J. Heterocyclic Chem.*, 18, pp. 1537-1540 (1981).
Chollet, et al., "Development of a Topically Active Imiquimod Formulation", *Pharmaceutical Development and Technology*, 4(1), pp. 35-43 (1999).
Izumi, et al., "1H-Imidazo[4,5-c]quinoline Derivatives as Novel Potent TNF-α Suppressors: Synthesis and Structure-Activity Relationship of 1-, 2- and 4-Substituted 1H-Imidazo[4,5-c]pyridines", *Bioorganic & Medicinal Chemistry*, 11, pp. 2541-2550 (2003).
Supplemental Europen Search Report for EP 04810969.8 mailed Apr. 7, 2009.
International Search Report and Written Opinion for PCT/US2004/038033 mailed Jan. 25, 2006.
International Preliminary Report on Patentability for PCT/US2004/038033 mailed May 26, 2006.
[No Author Listed] "Comparative Tests." Filed Apr. 8, 2005 during prosecution for EP 00938205.2, EP 00950215.4 and EP 00938211.0 in the name of 3M Innovative Properties Co.
[No Author Listed] Chemical Abstracts. 1964;61(1):6060g.
[No Author Listed] Encyclopedia of Pharmaceutical Technology. 2nd Ed. Marcel Dekker, Inc. 2002:856-60.
Agrawal et al., Synthetic agonists of Toll-like receptors 7, 8 and 9. Biochem Soc Trans. Dec. 2007;35(Pt 6):1461-7.
Ahmed et al., A new rapid and simple non-radioactive assay to monitor and determine the proliferation of lymphocytes: an alternative to [3H]thymidine incorporation assay. J Immunol Methods. Apr. 15, 1994;170(2):211-24.
Akira et al., Recognition of pathogen-associated molecular patterns by TLR family. Immunol Lett. 2003;85:85-95.
Akira et al., Toll-like receptors: critical proteins linking innate and acquired immunity. Nature Immunol. 2001;2(8):675-80.
Alexopoulou et al., Recognition of double-stranded RNA and activation of NF-kappaB by Toll-like receptor 3. Nature. Oct. 18, 2001;413(6857):732-8.
Assuma et al., IL-1 and TNF Antagonists Inhibit the Inflammatory Response and Bone Loss in Experimental Periodontitis. J Immunol. 2000;160:403-09.
Au et al., Virus-mediated induction of interferon A gene requires cooperation between multiple binding factors in the interferon alpha promoter region. J Biol Chem. Nov. 15, 1993;268(32):24032-40.
Auerbach et al., *Erythema nodosum* following a jellyfish sting. J Emerg Med. Nov.-Dec. 1987;5(6):487-91.
Auwers, [Uber die Isomerie-Verhaltnisse in der Pyrazol-Reihe. Berichte. VI.] 1926;601-607. German.
Baffis et al., Use of interferon for prevention of hepatocellular carcinoma in cirrhotic patients with hepatitis B or hepatitis C virus infection. Ann Intern Med. Nov. 2, 1999;131(9):696-701.
Baker et al., Oral infection with *Porphyromonas gingivalis* and induced alveolar bone loss in immunocompetent and severe combined immunodeficient mice. Arch Oral Biol. Dec. 1994;39(12):1035-40.
Baldwin et al., Amino Acid Synthesis via Ring Opening of N-Sulphonyl Aziridine-2-Carboxylate Esters with Organometallic Reagents. Tetrahedron. 1993;49:6309-30.
Bártová et al., Th1 and Th2 cytokine profile in patients with early onset periodontitis and their healthy siblings. Mediators Inflamm. 2000;9(2):115-20.
Beck et al., Dental Infections and Atherosclerosis. Am Heart J. 1999;13:528-33.
Beckett et al., Configurational Studies in Synthetic Analgesics: the Synthesis of (x)-Methadone from D-(x)-Alanine. J Chem Soc. 1957;1:858-61.
Beilman et al., Experimental brown spider bite in the guinea pig: Results of treatment with dapsone or hyperbaric oxygen. J Wilderness Medicine. 1994;5:287-94.
Belikov, Abbreviated Guide to Synthetic and Natural Medications. Pharmaceutical Chemistry. Higher School. 1993;1:43-47. Russian.
Beltrami et al., Some Methylhydrazonium Salts; An Improved Synthesis of Tetramethylhydrazine. J Am Chem Soc. 1956;78:2467-68.
Bernstein et al., Daily or weekly therapy with resiquimod (R-848) reduces genital recurrences in herpes simplex virus-infected guinea pigs during and after treatment. J Infect Dis. Mar. 15, 2001;183(6):844-9. Epub Feb. 13, 2001.

(56) References Cited

OTHER PUBLICATIONS

Bertino et al., Principles of Cancer Therapy. Cecil Textbook of Medicine. Goldman et al., eds. 21th Ed. W.B. Saunders Company. 2000:1:1060-74.

Beutler et al., Tumor necrosis factor in the pathogenesis of infectious diseases. Crit Care Med. Oct. 1993;21(10 Suppl):S423-35.

Beutner et al., Therapeutic response of basal cell carcinoma to the immune response modifier imiquimod 5% cream. J Am Acad Dermatol. Dec. 1999;41(6):1002-7.

BEUTNER et al., Treatment of genital warts with an immune-response modifier (imiquimod). J Am Acad Dermatol. Feb. 1998;38(2 Pt 1):230-9.

Binder, Acute arthropod envenomation. Incidence, clinical features and management. Med Toxicol Adverse Drug Exp. May-Jun. 1989;4(3):163-73.

Bishop et al., Molecular mechanisms of B lymphocyte activation by the immune response modifier R-848. J Immunol. Nov. 15, 2000;165(10):5552-7.

Bitterman-Deutsch et al., [Brown spider bite]. Harefuah. Sep. 1990;119(5-6):137-9. Hebrew.

Booth et al., Dapsone suppresses integrin-mediated neutrophil adherence function. J Invest Dermatol. Feb. 1992;98(2):135-40.

Borkan et al., An outbreak of venomous spider bites in a citrus grove. Am J Trop Med Hyg. Mar. 1995;52(3):228-30.

Bourke et al., The toll-like receptor repertoire of human B lymphocytes: inducible and selective expression of TLR9 and TLR10 in normal and transformed cells. Blood. Aug. 1, 2003;102(3):956-63. Epub Apr. 10, 2003.

Brants, The Distribution of Tobacco Mosaic Virus (TMV) in Excised Tomato Roots Cultivated in Vitro. Tijdschr Plantenziekten, 1962;68:198-207.

Brassard et al., Interferon-α as an immunotherapeutic protein. J Leukoc Biol. Apr. 2002;71(4):565-81.

Breathnach, Azelaic acid: potential as a general antitumoural agent. Med Hypotheses. Mar. 1999;52(3):221-6.

Broughton, Management of the brown recluse spider bite to the glans penis. Mil Med. Oct. 1996;161(10):627-9.

Buckle et al., 4-hydroxy-3-nitro-2-quinolones and related compounds as inhibitors of allergic reactions. J Med Chem. Jul. 1975;18(7):726-32.

Buisson et al., Preparation and use of (S)-O-acetyllactyl chloride (Mosandl's reagent) as a chiral derivatizing agent. Tetrahedron Assym. 1999;10:2997-3002.

Bulut et al., Cooperation of Toll-like receptor 2 and 6 for cellular activation by soluble tuberculosis factor and Borrelia burgdorferi outer surface protein A lipoprotein: role of Toll-interacting protein and IL-1 receptor signaling molecules in Toll-like receptor 2 signaling. J Immunol. Jul. 15, 2001;167(2):987-94.

Burleson, Chapter 14. Influenza Virus Host Resistance Model for Assessment of Immunostimulation, and Antiviral Compounds. Methods in Immunology. 1995;2:181-202.

Buschle et al., Interferon γ inhibits apoptotic cell death in B cell chronic lymphocytic leukemia. J Exp Med. Jan. 1, 1993;177(1):213-8.

Cai et al., Evaluation of trifluoroacetic acid as an ion-pair reagent in the separation of small ionizable molecules by reversed-phase liquid chromatography. Analytica Chmica Acta. 1999;399:249-258.

Cantell et al., IFN-γ Enhances Production of IFN-α in Human Macrophages but Not in Monocytes. J Interferon and Cytokine Res. 1996;16:461-63.

Carceller et al., Design, synthesis, and structure-activity relationship studies of novel 1-[(1-acyl-4-piperidyl)methyl]-1H-2-methylimidazo[4,5-c]pyridine derivatives as potent, orally active platelet-activating factor antagonists. J Med Chem. Jan. 19, 1996;39(2):487-93.

Carrigan et al., Synthesis and in vitro pharmacology of substituted quinoline-2,4-dicarboxylic acids as inhibitors of vesicular glutamate transport. J Med Chem. May 23, 2002;45(11):2260-76.

Catarzi et al., Tricyclic heteroaromatic systems. Pyrazolo[3,4-c]quinolin-4-ones and pyrazolo[3,4-c]quinoline-1,4-diones: synthesis and benzodiazepine receptor activity. Arch Pharm (Weinheim). Dec. 1997;330(12):383-6.

Cheson et al., National Cancer Institute-sponsored Working Group guidelines for chronic lymphocytic leukemia: revised guidelines for diagnosis and treatment. Blood. Jun. 15, 1996;87(12):4990-7.

Chuang et al., Toll-like receptor 9 mediates CpG-DNA signaling. J Leukoc Biol. Mar. 2002;71(3):538-44.

Claisen, [Uber α-Methyl-isoxazol.] Berichte. 1909;42:59-69. German.

Cohen et al., Cytokine function: a study in biologic diversity. Am J Clin Pathol. May 1996;105(5):589-98.

Cole et al., Brown recluse spider envenomation of the eyelid: an animal model. Ophthal Plast Reconstr Surg. Sep. 1995;11(3):153-64.

Colotta et al., Synthesis and structure-activity relationships of a new set of 2-arylpyrazolo[3,4-c]quinoline derivatives as adenosine receptor antagonists. J Med Chem. Aug. 10, 2000;43(16):3118-24.

Cristalli et al., Adenosine deaminase inhibitors: synthesis and structure-activity relationships of imidazole analogues of erythro-9-(2-hydroxy-3-nonyl)adenine. J Med Chem. Mar. 1991;34(3):1187-92.

Dai et al., Synthesis of a novel C2-symmetric thiourea and its application in the Pd-catalyzed cross-coupling reactions with arenediazonium salts under aerobic conditions. Org Lett. Jan. 22, 2004;6(2):221-4.

Davis, Current therapy for chronic hepatitis C. Gastroenterology. Feb. 2000;118(2 Suppl 1):S104-14.

Davis et al., Heterocyclic Syntheses with Malonyl Chloride. Part VI. 3-Substituted Pyridine Derivatives from α-Methylene-nitriles. J Chem Soc. 1962:3638-44.

Davis et al., Self-administered topical imiquimod treatment of vulvar intraepithelial neoplasia. A report of four cases. J Reprod Med. Aug. 2000;45(8):619-23.

De Clerq, Synthetic interferon inducers. Top Curr Chem. 1974;52:173-208.

De et al., Structure-activity relationships for antiplasmodial activity among 7-substituted 4-aminoquinolines. J Med Chem. Dec. 3, 1998;41(25):4918-26.

Debol et al., Anti-inflammatory action of dapsone: inhibition of neutrophil adherence is associated with inhibition of chemoattractant-induced signal transduction. J Leukoc Biol. Dec. 1997;62(6):827-36.

Decker et al., Immunostimulatory CpG-oligonucleotides cause proliferation, cytokine production, and an immunogenic phenotype in chronic lymphocytic leukemia B cells. Blood. Feb. 1, 2000;95(3):999-1006.

Decker et al., Immunostimulatory CpG-oligonucleotides induce functional high affinity IL-2 receptors on B-CLL cells: costimulation with IL-2 results in a highly immunogenic phenotype. Exp Hematol. May 2000;28(5):558-68.

Delgado, Textbook of Organic Medicinal and Pharmaceutical Chemistry, Ninth Edition, Remers, ed., 1991:30-1.

Denzel et al. Imidazo [4,5-c]- and [4,5-b]pyridines. J. Heterocyclic Chem. 1977;14:813-821.

Diaz-Arrastia et al., Clinical and molecular responses in high-grade intraepithelial neoplasia treated with topical imiquimod 5%. Clin Cancer Res. Oct. 2001;7(10):3031-3.

Di Carlo et al., Neutrophils in anti-cancer immunological strategies: old players in new games. J Hematother Stem Cell Res. Dec. 2001;10(6):739-48.

Dicken et al., Reactions at High Pressures. [3 + 2] Dipolar Cycloaddition of Nitrones with Vinyl Ethers. J Org Chem. 1982;47:2047-51.

Dockrell et al., Imiquimod and resiquimod as novel immunomodulators. J Antimicrob Chemother. Dec. 2001;48(6):751-5.

Douglas, Introduction to Viral Diseases. In: Cecil Textbook of Medicine. Bennet et al., eds. 20th Ed. W.B. Saunders Company. 1996:2:1739-47.

Doyle et al., Toll-like receptor 3 mediates a more potent antiviral response than Toll-like receptor 4. J Immunol. Apr. 1, 2003;170(7):3565-71.

Drexler et al., Bryostatin 1 induces differentiation of B-chronic lymphocytic leukemia cells. Blood. Oct. 1989;74(5):1747-57.

(56) References Cited

OTHER PUBLICATIONS

Dzionek et al. BDCA-2, BDCA-3, and BDCA-4: three markers for distinct subsets of dendritic cells in human peripheral blood. J Immunol. Dec. 1, 2000;165(11):6037-46.

Edwards et al., Toll-like receptor expression in murine DC subsets: lack of TLR7 expression by CD8 alpha+ DC correlates with unresponsiveness to imidazoquinolines. Eur J Immunol. Apr. 2003;33(4):827-33.

Eriks et al., Histamine H2-receptor agonists. Synthesis, in vitro pharmacology, and qualitative structure-activity relationships of substituted 4- and 5-(2-aminoethyl)thiazoles. J Med Chem. Aug. 21, 1992;35(17):3239-46.

Fecci et al., The history, evolution, and clinical use of dendritic cell-based immunization strategies in the therapy of brain tumors. J Neurooncol. Aug.-Sep. 2003;64(1-2):161-76.

Fitzgerald-Bocarsly et al., Virally-Responsive IFN-α Producing Cells in Human Blood and Tonsil Are CD11C/CD123+ Cells Identical to Precursors of Type Two Dendritic Cells (pDC2). J Interferon Cytokine Res. 1999;19(1):S117. Abstract P81.

Flo et al., Involvement of toll-like receptor (TLR) 2 and TLR4 in cell activation by mannuronic acid polymers. J Biol Chem. Sep. 20, 2002;277(38):35489-95. Epub Jun. 27, 2002.

Fonteneau et al., Human Immunodeficiency Virus Type 1 Activates Plasmacytoid Dendritic Cells and Concomitantly Induces the Bystander Maturation of Myeloid Dendritic Cells. J Virol. 2003;78(10):5223-32.

Frankel et al., The Preparation of N-Disubstituted Formamides. Tetrahedron Lett. 1959;7:5-7.

Frantz et al., Toll4 (TLR4) expression in cardiac myocytes in normal and failing myocardium. J Clin Invest. Aug. 1999;104(3):271-80.

Fu et al., Regioselective Catalytic Hydrogenation of Polycyclic Aromatic Hydocarbons under Mild conditions. J Org Chem. 1980;45:2979-803.

Fuchsberger et al., Priming Interferon-a 1 or Interferon-a 2 Enhances the Production of Both Subtypes Simultaneously. J Interferon and Cytokine Res. 1995;15:637-39.

Galose, Dapsone (diaminodiphenylsulphone DDS). Clinical Toxicology Review. 1999:21(9). 3 pages.

Gendron, *Loxosceles ignali* Envenomation. Am J Emerg Med. Jan. 1990;8(1):51-4.

Genevois-Borella et al., Synthesis of 1-(3-R-Amino-4-Hydroxy Butyl)thymine Acyclonucleoside. Analogs as Potential Anti-AIDS Drugs. Tetrahedron Lett. 1990;31:4879-82.

Giannini et al., Influence of the Mucosal Epithelium Microenvironment on Langerhans Cells: Implications for the Development of Squamous Intraepithelial Lesions of the Cervix. Int J Cancer. 2002;97:654-59.

Gibson et al., Cellular requirements for cytokine production in response to the immunomodulators imiquimod and S-27609. J Interferon Cytokine Res. Jun. 1995;15(6):537-45.

Gibson et al., Plasmacytoid dendritic cells produce cytokines and mature in response to the TLR7 agonists, imiquimod and resiquimod. Cell Immunol. Jul.-Aug. 2002;218(1-2):74-86.

Gitelson et al., Chronic lymphocytic leukemia-reactive T cells during disease progression and after autologous tumor cell vaccines. Clin Cancer Res. May 2003;9(5):1656-65.

Gomez et al., Intradermal anti-loxosceles Fab fragments attenuate dermonecrotic arachnidism. Acad Emerg Med. 1999;6:1195-202.

Gorden et al., Synthetic TLR agonists reveal functional differences between human TLR7 and TLR8. J Immunol. Feb. 1, 2005;174(3):1259-68.

Gordon, Pattern recognition receptors: doubling up for the innate immune response. Cell. Dec. 2002 27;111(7):927-30.

Gunning et al., Chemoprevention by lipoxygenase and leukotriene pathway inhibitors of vinyl carbamate-induced lung tumors in mice. Cancer Res. Aug. 1, 2002;62(15):4199-201.

Gürsel et al., Differential and competitive activation of human immune cells by distinct classes of CpG oligodeoxynucleotide. J Leukoc Biol. May 2002;71(5):813-20.

Hart, Napthyridines Hydroxynaphthyridies, Journal of Chemical Society, 1956;Part III:212-4.

Hartmann et al., Rational design of new CpG oligonucleotides that combine B cell activation with high IFN-alpha induction in plasmacytoid dendritic cells. Eur J Immunol. Jun. 2003;33(6):1633-41.

Hayashi Toll-like receptors stimulate human neutrophil function. Blood. Oct. 1, 2003;102(7):2660-9. Epub Jun. 26, 2003.

Hayes et al., Regulation of Interferon Production by Human Monocytes: Requirements for Priming for Lipopolysaccharide-Induced Production. J Leukocyte Biol. 1991;50:176-81.

Heil et al., Species-specific recognition of single-stranded RNA via toll-like receptor 7 and 8. Science. Mar. 5, 2004 5;303(5663):1526-9. Epub Feb. 19, 2004.

Heil et al., Synthetic immunostimulatory compounds activate immune cells via TLR7 and TLR8. 33th Annual Meeting of the Deutsche Gessellschaft Mr Immunologie, Marburg 2002. Abstract C.6.

Hemmi et al., Small anti-viral compounds activate immune cells via the TLR7 MyD88-dependent signaling pathway. Nat Immunol. Feb. 2002;3(2):196-200. Epub Jan. 22, 2002.

Hobbs et al., Comparison of hyperbaric oxygen and dapsone therapy for loxosceles envenomation. Acad Emerg Med. Aug. 1996;3(8):758-61.

Hoffman et al., Conformational requirements for histamine H2-receptor inhibitors: a structure-activity study of phenylene analogues related to cimetidine and tiotidine. J Med Chem. Feb. 1983;26(2):140-4.

Hofmanová et al., Lipoxygenase inhibitors induce arrest of tumor cells in S-phase of the cell cycle. Neoplasma. 2002;49(6):362-7.

Holladay et al., Structure-activity studies related to ABT-594, a potent nonopioid analgesic agent: effect of pyridine and azetidine ring substitutions on nicotinic acetylcholine receptor binding affinity and analgesic activity in mice. Bioorg Med Chem Lett. Oct. 6, 1998;8(19):2797-802.

Horng et al., The adaptor molecule TIRAP provides signaling specificity for Toll-like receptors. Nature. Nov. 21, 2002;420(6913):329-33.

Hornung et al., Quantitative Expression of Toll-Like Receptor 1-10 mRNA in Cellular Subsets of Human Peripheral Blood Mononuclear Cells and Sensitivity to CpG Oligodeoxynucleotides. Journal of Immunol. 2002;168:4531-37.

Houben-Weyl, Quinoline and Isoquinoline. Methoden der Organischen Chemie. 1980:271-79. German.

Houston et al., Potential inhibitors of S-adenosylmethionine-dependent methyltransferases. 8. Molecular dissections of carbocyclic 3-deazaadenosine as inhibitors of S-adenosylhomocysteine hydrolase. J Med Chem. Apr. 1985;28(4):467-71.

Huppatz, Systemic fungicides. The synthesis of certain pyrazole analogues of carboxin. Aust J Chem. 1983;36:135-47.

Iino et al., Treatment of Chronic Hepatitis C With High-Dose Interferon α-2b. Multicenter Study. Dig Dis Sci. 1993;38(4):612-18.

Ito et al., Interferon-alpha and interleukin-12 are induced differentially by Toll-like receptor 7 ligands in human blood dendritic cell subsets. J Exp Med. Jun. 3, 2002;195(11):1507-12.

Iwashita et al., Syntheses of Isoretronecanol and Lupinine. J Org Chem. 1982;47:230-33.

Jacobs, The Synthesis of Acetylenes. In: Organic Reactions. New York: Wiley & Sons, Inc., 1949. vol. 5. 1-78.

Jahnsen et al., Extensive recruitment of IL-3Rαhigh dendritic-cell precursors to allergic nasal mucosa during allergen challenge. Immunology Lett. 1999;69(1):123. Abstract #32.2.

Jurk et al. Human TLR7 and TLR8 independently confer responsiveness to the antiviral compound R-848. Nat Immunol. Jun. 2002;3(6):499.

Juweid, Radioimmunotherapy of B-Cell Non-Hodgkin's Lymphoma: From Clinical Trials to Clinical Practice. J Nuclear Med. 2002;43(11):1507-29.

Katritsky et al., Comprehensive Heterocyclic Chemistry: The Structure, Reactions, Synthesis and Uses of Heterocyclic Compounds. 1984;2:586-587.

(56) References Cited

OTHER PUBLICATIONS

Keating et al., Long-term follow-up of patients with chronic lymphocytic leukemia treated with fludarabine as a single agent. Blood. Jun. 1, 1993;81(11):2878-84.
Klausen et al., Two complementary methods of assessing periodontal bone level in rats. Scand J Dent Res. Dec. 1989;97(6):494-9.
Klinman, Immunotherapeutic uses of CpG oligodeoxynucleotides. Nat Rev Immunol. Apr. 2004;4(4):249-58.
Kloek et al., An improved method for the synthesis of stabilized primary enamines and imines. J Org Chem. 1978;43:1460-62.
Kloetzel, Reactions of nitroparaffins. I. Synthesis and reduction of some ò-nitrokenes. J Am Chem Soc. 1947;69:2271-2275.
Kornman, Host modulation as a therapeutic strategy in the treatment of periodontal disease. Clin Infect Dis. Mar. 1999,28(3):520-6.
Kourafalos et al., Synthesis of 7-aminopyrazolo[3,4-c]pyridine as a probe for the preparation of compounds of pharmacological interest. Heterocycles. 2002;57(12):2335-2343.
Krause et al., Autoimmune aspects of cytokine and anticytokine therapies. Am J Med. Oct. 1, 2003;115(5):390-7.
Krenitsky et al., Imidazo[4,5-c]pyridines (3-deazapurines) and their nucleosides as immunosuppressive and anti-inflammatory agents. J Med Chem. Jan. 1986;29(1):138-43.
Kurt-Jones et al., Role of toll-like receptor 2 (TLR2) in neutrophil activation: GM-CSF enhances TLR2 expression and TLR2-mediated interleukin 8 responses in neutrophils. Blood. Sep. 1, 2002;100(5):1860-8.
Lall et al., Serine and threonine beta-lactones: a new class of hepatitis A virus 3C cysteine proteinase inhibitors. J Org Chem. Mar. 8, 2002;67(5):1536-47.
Lee et al., p38 mitogen-activated protein kinase inhibitors—mechanisms and therapeutic potentials. Pharmacol Ther. 1999;82:389-97.
Lee et al., Saturated fatty acid activates but polyunsaturated fatty acid inhibits Toll-like receptor 2 dimerized with Toll-like receptor 6 or 1. J Biol Chem. Apr. 23, 2004;279(17):16971-9. Epub Feb. 13, 2004.
Lehner et al., The role of γσ cells and β-chemokines in mucosal protection against SIV infection. Immunology Lett. 1999;69:25-192. Abstract 2.1.
Levy et al., Unique efficacy of Toll-like receptor 8 agonists in activating human neonatal antigen-presenting cells. Blood. Aug. 15, 2006;108(4):1284-90. Epub Apr. 25, 2006.
Leynadier et al., Allergic reactions to North African scorpion venom evaluated by skin test and specific IgE. J Allergy Clin Immunol. Jun. 1997;99(6 Pt 1):851-3. 4 pages.
Li et al., An improved protocol for the preparation of 3-pyridyl- and some arylboronic acids. J Org Chem. Jul. 26, 2002;67(15):5394-7.
Li et al., Solubility behavior of imiquimod in alkanoic acids. Pharmaceutical Research. 1997 American Association of Pharmaceutical Scientists Annual Meeting. Poster Presentation, Boston, MA, Nov. 2-6, 1997;S475:Abstract 3029.
Li et al., Synthesis, CoMFA analysis, and receptor docking of 3,5-diacyl-2, 4-dialkylpyridine derivatives as selective A3 adenosine receptor antagonists. J Med Chem. Feb. 25, 1999;42(4):706-21.
Litt et al., Mucosal delivery of vaccine antigens displayed on the surface of *Lactococcus lactis*. Immunology Lett. 1999:69(1):61. Abstract #11.26.
Liu et al., Synthesis of halogen-substituted 3-deazaadenosine and 3-deazaguanosine analogues as potential antitumor/antiviral agents. Nucleosides Nucleotides Nucleic Acids. Dec. 2001;20(12):1975-2000.
Loesche et al., Treatment paradigms in periodontal disease. Compend Contin Educ Dent. Mar. 1997;18(3):221-6, 228-30, 232 passim; quiz 234. Review.
Luger et al., Evidence for an epidermal cytokine network. J Invest Dermatol. Dec. 1990;95(6 Suppl):100S-104S.
Luskin et al., Olefinic Derivatives of 2,4-Diamino-s-triazines. J Org Chem. 1958;23:1032-37.
Macchia et al., Synthesis and antiviral properties of 9-[(2-methyleneaminoxyethoxy)methyl]guanine derivatives as novel Acyclovir analogues. Farmaco. Feb. 2000;55(2):104-8.

Majeski et al., Action of venom from the brown recluse spider (*Loxosceles reclusa*) on human neutrophils. Toxicon. 1977;15(5):423-7.
Makarenkova et al., Identification of delta- and mu-type opioid receptors on human and murine dendritic cells. J Neuroimmunol. 2001;117:68-77.
Male et al., Introduction to the Immune System. In: Immunology. Elsevier. 2006:6-7.
Masihi, Progress on novel immunomodulatory agents for HIV-1 infection and other infectious diseases. Expert Opin Ther Patents. 2003;13(6):867-82.
Masiukiewicz et al., Scalable Syntheses of $N^\circ$-Benzyloxycarbonyl-$_L$-Ornithine and of $N^\alpha$-(9-Fluorenylmethoxy)Carbonyl-$_L$-Ornithine. Org Prep Proced Int. 2002;34:531-37.
Mataka et al., Condensation reaction of 3,4-Dibenzoyl-1-methyl-2,5-diphenylpyrrole and -1-phenylpyrazole with methylamine derivatives affording pyrrolo [3,4-c] pyridine and 2H-pyrazolo[3,4-c]- and [4,3-c]pyridines. Journal of Heterocyclic Chemistry. 1981;18(6):1073-5.
Mathur et al., Cell-mediated immune system regulation in periodontal diseases. Crit Rev Oral Biol Med. 1997;8(1):76-89.
Maynor et al., Brown recluse spider envenomation: a prospective trial of hyperbaric oxygen therapy. Acad Emerg Med. Mar. 1997;4(3):184-92.
Mbow et al., Small molecule and biologic modulators of the immune response to hepatitis C virus. Mini Rev Med Chem. May 2006;6(5):527-31.
McCarthy et al., Opioids, opioid receptors, and the immune response. Drug & Alcohol Dependence. 2001;62:111-23.
McKennon et al., A Convenient Reduction of Amino Acids and Their Derivatives. J Org Chem. 1993;58:3568-71.
McLaughlin et al., Opioid growth factor (OGF) inhibits the progression of human squamous cell carcinoma of the head and neck transplanted into nude mice. Cancer Lett. 2003;199:209-17.
Medzhitov, Toll-Like Receptors and Innate Immunity. Nature Rev Immunol. 2001;1:135-45.
Mee et al., Stille coupling made easier—the synergic effect of copper(I) salts and the fluoride ion. Angew Chem. 2004;116:1152-56.
Merigian et al., Envenomation From the Brown Recluse Spider: Review of Mechanism and Treatment Options. Am J Ther. Oct. 1996;3(10):724-734.
Miller et al., Imiquimod applied topically: a novel immune response modifier and new class of drug. Int J Immunopharmacol. Jan. 1999;21(1):1-14.
Minakawa et al., Nucleosides and Nucleotides. 184. Synthesis and Conformational Investigation of Anti-Fixed 3-Deaza-3-halopurine Ribonucleosides. J Org Chem. 1999;64:7158-72.
Moebius et al., The mysteries of sigma receptors: new family members reveal a role in cholesterol synthesis. Trends Pharmacol Sci. Mar. 1997;18(3):67-70.
Moldoveanu et al., Poly-L-lysine as a potential mucosal adjuvant. Immunology Lett. 1999;69(1):62. Abstract #11.28.
Mollick et al., MUC1-like tandem repeat proteins are broadly immunogenic in cancer patients. Cancer Immun. Mar. 17, 2003;3:3. 17 pages.
Moody et al., Lipoxygenase inhibitors prevent lung carcinogenesis and inhibit non-small cell lung cancer growth. Exp Lung Res. Jul.-Aug. 1998;24(4):617-28.
Moraczewski et al., Using Hydrogen Bonding to Control Carbamate C—N Rotamer Equilibria. Org Chem. Oct. 16, 1998;63(21):7258-7262.
Mosbech et al., [Allergy to insect stings] Ugeskr Laeger. Oct. 28, 1991;153(44):3067-71. Danish.
Muche et al., Imiquimod treatment of cutaneous T cell lymphoma. Journal of Investigative Dermatology. Jul. 2003;121(1):0975. Joint Meeting of the European Society for Dermatologi; Miami Beach, Florida, USA. Apr. 30-May 4, 2003. Abstract 0975.
Muller et al., An improved one-pot procedure for the synthesis of alkynes from aldehydes. Synlett. 1996;6:521-522.
Mutschler et al., 9.2 Anti-infectives. In: Drug Actions: Basic Principles and Therapeutic Aspects. 1995:515-80.

(56) References Cited

OTHER PUBLICATIONS

Muzio et al., Differential expression and regulation of toll-like receptors (TLR) in human leukocytes: selective expression of TLR3 in dendritic cells. J Immunol. Jun. 1, 2000;164(11):5998-6004.
Nagarajan et al., Condensed heterotricycles: synthesis of pyrazolo[3,4-c]quinoline derivatives. Indian Journal of Chemistry. 1992;31B:316-321.
Nagase et al., Expression and function of Toll-like receptors in eosinophils: activation by Toll-like receptor 7 ligand. J Immunol. Oct. 15, 2003;171(8):3977-82.
Nanjappan et al., An efficient synthesis of some 6-substituted 4,8-diaza-3,3,9,9-tetramethylundeca-2,10-dione dioximes (propylene amine oximes, PnAOs): Ligands for 99mTc complexes used in structure distribution relationship (SDR) studies. Tetrahedron. 1994;50(29):8617-32.
Ohana et al., Differential effect of adenosine on tumor and normal cell growth: focus on the A3 adenosine receptor. Journal of Cellular Physiology. Jan. 2001;186(1):19-23. Review.
O'Mahony et al., New patient-applied therapy for anogenital warts is rated favourably by patients. Intl J STD & AIDS. 2001;12:565-70.
Osol et al., Chapter 27: Structure-Activtiy Relationship and Drug Design. In: Remington's Pharmaceutical Sciences. 16th Ed. Mach Publishing. 1980:420-35.
Ottonello et al., Sulphonamides as anti-inflammatory agents: old drugs for new therapeutic strategies in neutrophilic inflammation? Clin Sci (Lond). Mar. 1995;88(3):331-6.
Ozinsky et al., The repertoire for pattern recognition of pathogens by the innate immune system is defined by cooperation between Toll-like receptors. Proc. Nat. Acad. Sci. 2000; 97(25):13766-71.
Page et al., Advances in the pathogenesis of periodontitis: summary of developments, clinical implications and future directions. Periodontol 2000. Jun. 1997;14:216-48.
Park et al., Immunotherapy Cancer Treatment. Reprinted from Supportive Cancer Care, Rosenbaum et al. 2001. Available at http://www.cancersupportivecare.com/immunotherapy.html. Last accessed Jul. 13, 2010. 3 pages.
Park et al., Sodium Dithionite Reduction of Nitroarenes Using Viologen as an Electron Phase-Transfer Catalyst. Tetrahedron Lett. 1993;34(46):7445-46.
Patel et al., The necrotic venom of the brown recluse spider induces dysregulated endothelial cell-dependent neutrophil activation. Differential induction of GM-CSF, IL-8, and E-selectin expression. J Clin Invest. Aug. 1994;94(2):631-42.
Patrick et al., Paragraph 10.3: Drug optimization: strategies in drug design. In: An Introduction to Medicinal Chemistry. Oxford: Oxford University Press. Jan. 2005. 200-218.
Pavletic et al., Outcome of allogeneic stem cell transplantation for B cell chronic lymphocytic leukemia. Bone Marrow Transplant. Apr. 2000;25(7):717-22.
Pawlas et al., Novel anionic annelation tactics for construction of fused heteroaromatic frameworks. 1. Synthesis of 4-substituted pyrazolo[3,4-c]quinolines, 9-substituted pyrazolo[3,4-c]quinolines, and 1,4-dihydrochromeno[4,3-c]pyrazoles. Org Chem. Jun. 15, 2001;66(12):4214-9.
Payvandi et al., Exogenous and Endogenous IL-10 Regulate IFN-α Production by Peripheral Blood Mononuclear Cells in Response to Viral Stimulation. J Immunol. 1998;160:5861-68.
Peschke et al., Synthesis and in vitro characterization of new growth hormone secretagogues derived from ipamorelin with dipeptidomimetic N-terminals. Eur J Med Chem. 1999;34:363-380.
Peterson et al., The opioid-cytokine connection. J Neuroimmunol. 1998;83:63-69.
Phillips et al., Therapy of brown spider envenomation: a controlled trial of hyperbaric oxygen, dapsone, and cyproheptadine. Ann Emerg Med. Mar. 1995;25(3):363-8.
Pickersgill et al., Preparation of functionalized, conformationally constrained DTPA analogues from L- or D-serine and trans-4-hydroxy-L-proline. Hydroxymethyl substituents on the central acetic acid and on the backbone. J Org Chem. Jun. 30, 2000;65(13):4048-57.
Poljakovic et al., iNOS and COX-2 immunoreactivity in the mice bladder and kidney after bacterial instillation. Immunology Lett. 1999;69(1):122. Abstract #31.5.
Powell et al., Compendium of excipients for parenteral formulations. PDA J Pharm Sci Technol. Sep.-Oct. 1998;52(5):238-311.
Prelog et al., Cycloalkeno-pyridine. Hely Chem Acta. 1945;28:1684-93. German.
Rees et al., Brown recluse spider bites. A comparison of early surgical excision versus dapsone and delayed surgical excision. Ann Surg. Nov. 1985;202(5):659-63.
Regan et al., Activation of p38 MAPK by feline infectious peritonitis virus regulates pro-inflammatory cytokine production in primary blood-derived feline mononuclear cells. Virology. Feb. 5, 2009;384(1):135-43. Epub Dec. 5, 2008.
Rhodes, Discovery of immunopotentiatory drugs: current and future strategies. Clin Exp Immunol. Dec. 2002;130(3):363-9.
Ribera et al., "Spontaneous" complete remissions in chronic lymphocytic leukemia: report of three cases and review of the literature. Blood Cells. 1987;12(2):471-79.
Ritter et al., A new reaction of nitriles; amides from alkenes and mononitriles. J Am Chem Soc. Dec. 1948;70(12):4045-8.
Rocca et al., Carbolines. Part VII. Ansidines, Convenient tools to synthesize fficien-β-carbolines. J Heterocyclic Chem. 1995;32:1171-1175.
Rocca et al., Connection between metalation and cross-coupling strategies. Anew convergent route to azacarbazoles. Tetrahedron. 1993;49(1):49-64.
Rollins, Chemokines. Blood. Aug. 1, 1997;90(3):909-28. Review.
Rosenberg et al., Treatment of 283 consecutive patients with metastatic melanoma or renal cell cancer using high-dose bolus interleukin 2. JAMA. Mar. 23-30, 1994;271(12):907-13.
Rothel et al., The use of recombinant ovine IL-1 beta and TNF-alpha as natural adjuvants and their physiological effects in vivo. Immunol Cell Biol. Apr. 1998;76(2):167-72.
Roy et al., QSAR of adenosine receptor antagonists II: exploring physicochemical requirements for selective binding of 2-arlypyrazolo[3,4-c] quinoline derivatives with adenosine A1 and A3 receptor subtypes. QSAR & Comb Sci. 2003;22:614-621.
Royals et al., Studies in mixed ester condensations. IV. Acylations with methyl dimethoxyacetate. J Am Chem Soc. 1956;78:4161-4164.
Rozman et al., Chronic lymphocyte leukemia. N Engl J Med. Oct. 19, 1995;333(16):1052-7.
Sakthivel et al. Direct SnAr amination of fluorinated imizazo[4,5-c]pyridine nucleosides: efficient synthesis of 3-fluoro-3-3-deazaadenosine analogs. Tetrahedron Letters. May 2005;46(22):3883-3887.
Salaun et al., TLR3 Can Directly Trigger Apoptosis in Human Cancer Cells. J of Immunology. 2006;176:4894-901.
Salemink, Uber 2-Propyl-1- Und 2-Propyl-Desaza-Adenin. Recueil. 1961;80:545-55. German.
Sambhi et al., Local production of tumor necrosis factor encoded by recombinant vaccinia virus is effective in controlling viral replication in vivo. Proc Natl Acad Sci U S A. May 1, 1991;88(9):4025-9.
Sams et al., Necrotic arachnidism. J Am Acad Dermatol. Apr. 2001;44(4):561-73; quiz 573-6.
Sauder et al., Randomized, Single-Blind, Placebo-Controlled Study of Topical Application of the Immune Response Modulator Resiquimod in Healthy Adults. Antimicrobial Agents Chemo. 2003;47(12):3846-52.
Scheerlinck, Genetic adjuvants for DNA vaccines. Vaccine. Mar. 21, 2001;19(17-19):2647-56.
Scheuer et al., Application of the Ritter reaction to mesityl oxide and chalcone. J Am Chem Soc. 1957;22:674-676.
Schofield et al., Reply. Low-Dose Interferon-alpha in Chronic Myeloid Leukemia. Ann Internal Med. 1995;122(9):728-29. 1 page.
Schwandner et al., Peptidoglycan- and lipoteichoic acid-induced cell activation is mediated by toll-like receptor 2. J Biol Chem. Jun. 18, 1999;274(25):17406-9.
Seeman et al., Steric and Conformational Effects in Nicotine Chemistry. J Org Chem. 1981;46:3040-48.

(56) References Cited

OTHER PUBLICATIONS

Serrat et al., A highly efficient and straightforward stereoselective synthesis of novel chiral α-acetylenic ketones. Tetrahedron: Assymmetry. 1999;10:3417-30.
Severa et al., Sensitization to TLR7 agonist in IFN-beta-preactivated dendritic cells. J Immunol. May 15, 2007;178(10):6208-16.
Seymour et al., Cellular immunity and hypersensitivity as components of periodontal destruction. Oral Dis. Mar. 1996;2(1):96-101. Review.
Shelburne et al., Quantitation of Bacteroids forsythus in subgingival plaque comparison on immunoassay and quantitative polymerase chain reaction. J Microbiol Methods. 2000;39:97-107.
Sidky et al., Inhibition of murine tumor growth by an interferon-inducing imidazoquinolinamine. Cancer Res. Jul. 1, 1992;52(13):3528-33.
Siegal et al., The nature of the principal type 1 interferon-producing cells in human blood. Science. Jun. 11, 1999;284(5421):1835-7.
Sletzinger et al., the Synthesis of Isomethadone. J Am Chem Soc. 1952;74:5619-20.
Smith et al., The role of polymorphonuclear leukocytes in the lesion caused by the venom of the brown spider, Loxosceles reclusa. Lab Invest. Jan. 1970;22(1):90-3.
Sofina et al., C: Possibility of Predicting the Spectrum of Antitumor Effect of Drugs on the Basis of Experimental Data. Experimental evaluation of antitumor drugs in the USA and USSR and clinical correlations. NCI Monograph 55. NIH Publication No. 80/1933. 1980:76-8.
Sommer et al., Recent Findings on How Proinflammatory Cytokines Cause Pain: Peripheral Mechanisms in Inflammatory and Neuropathic Hyperalgesia. Neurosci Letts. 2004;361:184-87.
Sonogashira et al., A convenient synthesis of acetylenes: catalytic substitutions of acetylenic hydrogen with bromoalkenes, Iodoarenes, and bromopyridines. Tetrahedron Letts. 1975;50:4467-4470.
Soria et al., Effect of food on the pharmacokinetics and bioavailability of oral imiquimod relative to a subcutaneous dose. Int J Clin Pharmacol Ther. Oct. 2000;38(10):476-81.
Spaner et al., A phase I/II trial of TLR-7 agonist immunotherapy in chronic lymphocytic leukemia. Leukemia. 2010; 24:222-26.
Spaner et al., Immunomodulatory effects of Toll-like receptor-7 activation on chronic lymphocytic leukemia cells. Leukemia. Feb. 2006;20(2):286-95.
Spaner et al., Toll-like receptor agonists in the treatment of chronic lymphocytic leukemia. Leukemia. Jan. 2007;21(1):53-60. Epub Oct. 26, 2006.
Spivey et al., Configurationally stable biaryl analogues of 4-(dimethylamino)pyridine: A novel class of chiral nucleophilic catalysts. J Org Chem. 1999;64:9430-9443.
Spruance et al., Application of a topical immune response modifier, resiquimod gel, to modify the recurrence rate of recurrent genital herpes: a pilot study. J Infect Dis. Jul. 15, 2001;184(2):196-200. Epub Jun. 8, 2001.
Stack, Images in clinical medicine. Latrodectus mactans. N Engl J Med. Jun. 5, 1997;336(23):1649.
Stanley, Imiquimod and the imidazoquinolones: mechanism of action and therapeutic potential. Clin Exp Dermatol. Oct. 2002;27(7):571-7. Review.
Stashenko et al., Periapical inflammatory responses and their modulation. Crit Rev Oral Biol Med. 1998;9(4):498-521.
Steele et al., Lipoxygenase inhibitors as potential cancer chemopreventives. Cancer Epidemiol Biomarkers Prev. May 1999;8(5):467-83.
Steele et al., Potential use of lipoxygenase inhibitors for cancer chemoprevention. Expert Opin Investig Drugs. Sep. 2000;9(9):2121-38.
Steinmann et al., Topical imiquimod treatment of a cutaneous melanoma metastasis. J Am Acad Dermatol. Sep. 2000;43(3):555-6.
Stewart et al., Synthesis of a Carba-analog of S-Acetyl Coenzyme A, Acetonyl-dethio Coenzyme A; an Effective Inhibitor of Citrate Synthase. Liebigs Ann Chem. 1978:57-65.
Stillings et al., Substituted 1,3,4-thiadiazoles with anticonvulsant activity. 2. Aminoalkyl derivatives. J Med Chem. Nov. 1986;29(11):2280-4.
Strandtmann et al., Reaction of cyclic β-diketones with 3,4-dihydroisoquinolines and related compounds. Preparation and anti-cancer activity of 2-substituted 1,3-cyclohexanediones. J Med Chem. Nov. 1967;10(6):1063-5.
Stringfellow, Induction of interferon with low molecular weight compounds: fluorenone esters, ethers (tilorone), and pyrimidinones. Methods Enzymol. 1981;78(Pt A):262-84.
Ströher et al., Progress towards the treatment of Ebola haemorrhagic fever. Expert Opin Investig Drugs. Dec. 2006;15(12):1523-35.
Sugisaka et al., The Physicochemical properties of imiquimod, the first imidazoquinoline immune response modifier. Pharmaceutical Research. 1997 American Association of Pharmaceutical Scientists Annual Meeting. Poster Presentation, Boston, MA, Nov. 2-6, 1997;S475:Abstract 3030.
Surrey et al., The Synthesis of Some 3-Nitro- and 3-Amino-4-dialkylaminoalkylaminoquinoline Derivatives. J Am Chem Soc. 1951;73:2413-16.
Takeichi et al., Cytokine profiles of T-lymphocytes from gingival tissues with pathological pocketing. J Dent Res. Aug. 2000;79(8):1548-55.
Takeshita et al., Signal transduction pathways mediated by the interaction of CpG DNA with Toll-like receptor 9. Semin Immunol. Feb. 2004;16(1):17-22.
Takeuchi et al., Discrimination of bacterial lipoproteins by Toll-like receptor 6. Int Immunol. Jul. 2001;13(7):933-40.
Temple et al., Potential anticancer agents: 5-(N-substituted-aminocarbonyl)-and 5-(N-substituted-aminothiocarbonyl)-5,6,7,8-tetrahydrofolic acids. J Med Chem. Mar. 1988;31(3):697-700.
Thesing et al., [Darstellung and Eigenschaften des $\Delta^1$-Pyrrolin-$N$-oxyds]. Chem Ber. 1959;92:1748-55. German.
Thiruvikraman et al., Synthesis and reactions of pyrazolo-[3,4-c]quinoline derivatives. Indian Journal of Chemistry. 1987;26B:695-696.
Tomai et al., Imiquimod: in vivo and in vitro characteristics and toxicology. In: Cutaneous Infection and Therapy. Aly et al., eds. Marcel Dekkar, Inc., New York. 1997:405-15.
Tomic et al., Sensitization of IL-2 Signaling through TLR-7 Enhances B Lymphoma Cell Immunogenicity. J Immunol. 2006;176:3830-39.
Tomioka et al., Asymmetric Alkylation of α-Alkyl β-Keto Esters. J Am Chem Soc. 1984;106:2718-19.
Totterman et al., Phorbol ester-induced differentiation of chronic lymphocytic leukaemia cells. Nature. Nov. 13, 1980;288(5787):176-8.
Tracy et al., Studies in the Pyridine Series. II. Synthesis of 2-Methyl-3-(β-Hydroxyethyl)pyridine and of the Pyridine Analog of Thiamine (Vitamin B2). J Org Chem. 1941;6:54-62.
Uno et al., TNF-related apoptosis-inducing ligand (TRAIL) frequently induces apoptosis in Philadelphia chromosome-positive leukemia cells. Blood. May 1, 2003;101(9):3658-67. Epub Dec. 27, 2002.
Urosevic et al., Imiquimod treatment induces expression of opioid growth factor receptor: a novel tumor antigen induced by interferon-alpha? Clin Cancer Res. Aug. 1, 2004;10(15):4959-70.
Van De Kerhof, New Immunomodulatory Drugs. In: Skin and Environment: Perception and Protection. Ring et al., eds., 10th EADV Congress, Oct. 10-14, Munich, Germany. 2001:1:343-48.
Vasilakos et al., Adjuvant Activities of Immune Response Modifier R-848: Comparison with CoG ODN. Cell Immunol. 2000;204:64-74.
Vieweg et al., Tumor vaccines: from gene therapy to dendritic cells—the emerging frontier. Urol Clin North Am. Aug. 2003;30(3):633-43.
Vilcek, The cytokines: An overview. In: The Cytokine Handbook, Fourth Ed. M. Lotze and a.W. Thompson (eds.), 2003;1:3-14.
Volhardt, 18-5. Amides: The Least-Reactive Carboxylic Acid Derivatives. Organic Chemistry. 1987:813.
Vollmer et al., Highly immunostimulatory CpG-free oligodeoxynucleotides for activation of human leukocytes. Antisense Nudeic Acid Drug Dev. Jun. 2002;12(3):165-75.

(56) References Cited

OTHER PUBLICATIONS

Wagner et al., Induction of cytokines in cynomolgus monkeys by the immune response modifiers, imiquimod, S-27609 and S-28463. Cytokine. Nov. 1997;9(11):837-45.
Wagner of al., Modulation of TH1 and TH2 Cytokine Production with the Immune Response Modifiers, R-848 and Imiguimod. Cellular Immunology. 1999;191:10-19.
Wang, Structure and Chemistry of 4-Hydroxy-6-methyl-2-pyridone. J Heterocyclic Chem. 1970;7:389-92.
Warren et al., Macrophage Growth Factor CSF-1 Stimulates Human Monocyte Production of Interferon, Tumor Necrosis Factor, and Colony Stimulating Activity. J Immunol. 1986;137(7):2281-85.
Wasserman et al., Loxoscelism and necrotic arachnidism. J Toxicol Clin Toxicol. 1983-1984;21(4-5):451-72.
Wedlock et al., Physiological effects and adjuvanticity of recombinant brushtail possum TNF-alpha. Immunol Cell Biol. Feb. 1999;77(1):28-33.
Wells, Additivity of Mutational Effects in Proteins. Biochemistry. 1990;29(37):8509-17.
Wermuth, Molecular Variations Based on Isosteric Replacements. Practice of Medicinal Chemistry.1996:203-37.
Wexler et al., Accurate identification of experimental pulmonary metastases. J Natl Cancer Inst. Apr. 1966;36(4):641-5.
Wibaut et al., Syntheses of 3,4-Dimethylpyridine, 2,3-Dimethylpridine and 2-Methyl-3-Ethylpyridine. Rec Tray Chim. 1944;63:231-38.
Wierda et al., CD40-ligand (CD154) gene therapy for chronic lymphocytic leukemia. Blood. Nov. 1, 2000;96(9):2917-24.
Wieseler-Frank et al., Central proinflammatory cytokines and pain enhancement. Neurosignals. 2005;14(4):166-74.
Williams et al., Grignard Reactions to Chiral Oxazolidine Aldehydes. Tetrahedron. 1996;52:11673-94.
Wilson et al., Spiders and spider bites. Dermatol Clin. Apr. 1990;8(2):277-86.
Wright et al., Clinical presentation and outcome of brown recluse spider bite. Ann Emerg Med. Jul. 1997;30(1):28-32.
Wu et al., Murine B16 melanoma vaccination-induced tumor immunity: identification of specific immune cells and functions involved. J Interferon Cytokine Res. Dec. 2001;21(12):1117-27.

Yamamoto et al., Essential role for TIRAP in activation of the signalling cascade shared by TLR2 and TLR4. Nature. Nov. 21, 2002;420(6913):324-9.
Yeung-Yue et al., The management of herpes simplex virus infections. Curr Opin Infect Dis. Apr. 2002;15(2):115-22.
Yutilov et al., Synthesis and some reactions of 4-nitroimidazo[4-5-c]pyridin-2-ones. CAPLUS English Abstract DN 91:175261. VINITI.1978:1193-78. Abstract Only.
Zagon et al., Immunoelectron microscopic localization of the opioid growth factor receptor (OGFr) and OGF in the cornea. Brain Res. 2003;967:37-47.
Zagon et al., Opioids and the apoptotic pathway in human cancer cells. Neuropeptides. 2003;37:79-88.
Zagon et al., The biology of the opioid growth factor receptor (OGFr). Brain Res Brain Res Rev. Feb. 2002;38(3):351-76. Review.
Zagon et al., The expression and function of the OGF-OGFr axis—a tonically active negative regulator of growth—in COS cells. Neuropeptides. Oct. 2003;37(5):290-7.
Zambon, Periodontal diseases: microbial factors. Ann Periodontol. Nov. 1996;1(1):879-925.
Zarubin et al., Theoretical Study of Antagonists and Inhibitors of Mammalian Adenosine Deaminase: I. Adenosine and Its Aza- and Deazaanalogues. Russ J Bioorg Chem. 2002;28(4):284-92.
Zhang et al., Structural features of azidopyridinyl neonicotinoid probes conferring high affinity and selectivity for mammalian alpha4beta2 and Drosophila nicotinic receptors. J Med Chem. Jun. 20, 2002;45(13):2832-40.
Zhu et al., Inhibition of murine dendritic cell activation by synthetic phosphorothioate oligodeoxynucleotides. J Leukoc Biol. Dec. 2002;72(6):1154-63.
Zhu et al., Inhibition of murine macrophage nitric oxide production by synthetic oligonucleotides. J Leukoc Biol. Apr. 2002;71(4):686-94.
Ziegler-Heitbrock et al., Favorable response of early stage B CLL patients to treatment with IFN-alpha 2. Blood. May 1, 1989;73(6):1426-30.
Zyryanov et al., Heterocydization of 1-(2'-Carbethoxyphenyl)-5-Methyltetrazole. Chemistry of Heterocylic Compounds. English Edition. 1981;16(12):1286-88.

\* cited by examiner

HYDROXYLAMINE SUBSTITUTED IMIDAZOQUINOLINES

CROSS-REFERENCE TO RELATED APPLICATIONS

This application is the National Stage of International Application No. PCT/US2004/038033, filed Nov. 12, 2004, which claims priority to U.S. Provisional Application Ser. No. 60/520,215, filed on Nov. 14, 2003, which is incorporated herein by reference in its entirety.

BACKGROUND

In the 1950's the 1H-imidazo[4,5-c]quinoline ring system was developed, and 1-(6-methoxy-8-quinolinyl)-2-methyl-1H-imidazo[4,5-c]quinoline was synthesized for possible use as an antimalarial agent. Subsequently, syntheses of various substituted 1H-imidazo[4,5-c]quinolines were reported. For example, 1-[2-(4-piperidyl)ethyl]-1H-imidazo[4,5-c]quinoline was synthesized as a possible anticonvulsant and cardiovascular agent. Also, several 2-oxoimidazo[4,5-c]quinolines have been reported.

Certain 1H-imidazo[4,5-c]quinolin-4-amines and 1- and 2-substituted derivatives thereof were later found to be useful as antiviral agents, bronchodilators and immunomodulators. Subsequently, certain substituted 1H-imidazo[4,5-c]pyridin-4-amine, quinolin-4-amine, tetrahydroquinolin-4-amine, naphthyridin-4-amine, and tetrahydronaphthyridin-4-amine compounds as well as certain analogous thiazolo and oxazolo compounds were synthesized and found to be useful as immune response modifiers (IRMs), rendering them useful in the treatment of a variety of disorders.

There continues to be interest in and a need for compounds that have the ability to modulate the immune response, by induction of cytokine biosynthesis or other mechanisms.

SUMMARY

The present invention provides a new class of compounds that are useful in inducing cytokine biosynthesis in animals. Such compounds are of the following Formula I:

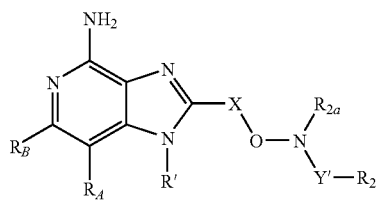

I and, more particularly, compounds of the following Formula II:

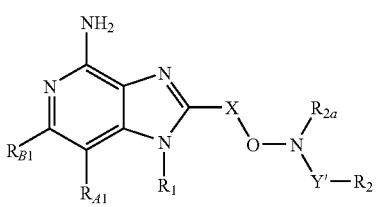

II wherein: R', $R_A$, $R_B$, $R_{A1}$, $R_{B1}$, $R_1$, $R_2$, $R_{2a}$, X, and Y' are as defined below.

The compounds of Formulas I and II are useful as immune response modifiers (IRMs) due to their ability to induce cytokine biosynthesis (e.g., induce the biosynthesis or production of one or more cytokines) and otherwise modulate the immune response when administered to animals. This makes the compounds useful in the treatment of a variety of conditions, such as viral diseases and neoplastic diseases, that are responsive to such changes in the immune response.

In another aspect, the present invention provides pharmaceutical compositions containing the immune response modifier compounds, and methods of inducing cytokine biosynthesis in an animal, treating a viral disease in an animal, and treating a neoplastic disease in an animal, by administering an effective amount of one or more compounds of Formula I and/or Formula II and/or pharmaceutically acceptable salts thereof to the animal.

In another aspect, the invention provides methods of synthesizing compounds of Formulas I and II and intermediates useful in the synthesis of these compounds.

As used herein, "a," "an," "the," "at least one," and "one or more" are used interchangeably.

The terms "comprising" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. Guidance is also provided herein through lists of examples, which can be used in various combinations. In each instance, the recited list serves only as a representative group and should not be interpreted as an exclusive list.

DETAILED DESCRIPTION OF ILLUSTRATIVE EMBODIMENTS OF THE INVENTION

The present invention provides compounds of the following Formulas I through VI:

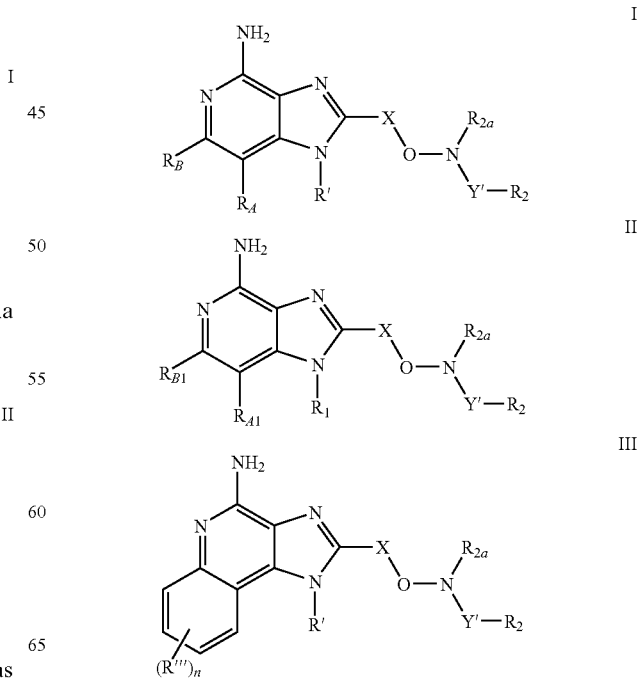

-continued

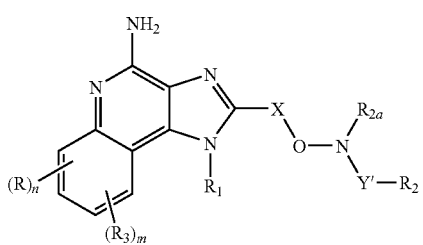
IIIa

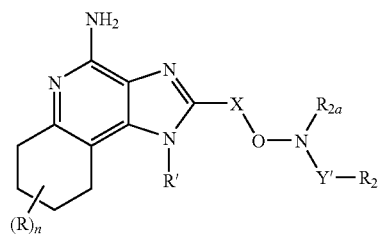
IV

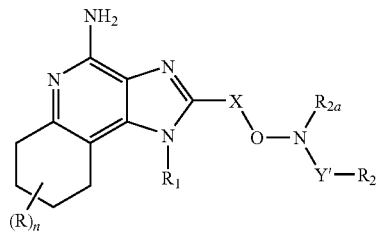
IVa

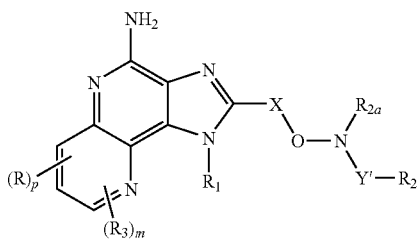
V

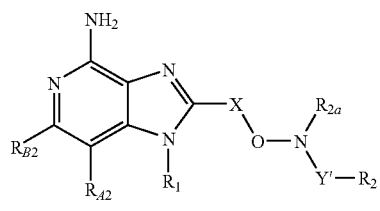
VI wherein: R, R', R''', $R_A$, $R_B$, $R_{A1}$, $R_{B1}$, $R_{A2}$, $R_{B2}$, $R_1$, $R_2$, $R_{2a}$, $R_3$, n, m, p, X, and Y' are as defined below.

In one aspect of the invention, compounds are provided that are of the following Formula I:

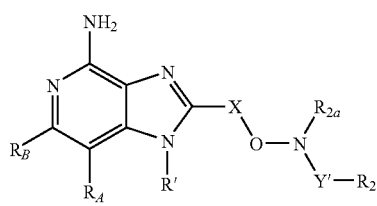
I wherein:
X is $C_{1-10}$ alkylene or $C_{2-10}$ alkenylene;

$R_A$ and $R_B$ are each independently selected from the group consisting of:
  hydrogen,
  halogen,
  alkyl,
  alkenyl,
  alkoxy,
  alkylthio, and
  —N($R_9$)$_2$;
or when taken together, $R_A$ and $R_B$ form a fused aryl ring or heteroaryl ring containing one heteroatom selected from the group consisting of N and S, wherein the aryl or heteroaryl ring is unsubstituted or substituted by one or more R''' groups;
or when taken together, $R_A$ and $R_B$ form a fused 5 to 7 membered saturated ring, optionally containing one heteroatom selected from the group consisting of N and S, and unsubstituted or substituted by one or more R groups;

R is selected from the group consisting of:
  halogen,
  hydroxy,
  alkyl,
  alkenyl,
  haloalkyl,
  alkoxy,
  alkylthio, and
  —N($R_9$)$_2$;

Y' is selected from the group consisting of:
  a bond,
  —C(O)—,
  —C(S)—,
  —S(O)$_2$—,
  —S(O)$_2$—N($R_8$)—,

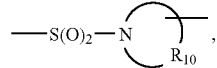

—C(O)—O—,
  —C(O)—N($R_8$)—,
  —C(S)—N($R_8$)—,
  —C(O)—N($R_8$)—S(O)$_2$—,
  —C(O)—N($R_8$)—C(O)—,
  —C(S)—N($R_8$)—C(O)—,

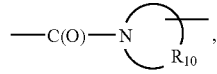

—C(O)—C(O)—,
  —C(O)—C(O)—O—, and
  —C(=NH)—N($R_8$)—;

$R_2$ and $R_{2a}$ are independently selected from the group consisting of:
  hydrogen,
  alkyl,
  alkenyl,
  aryl,
  arylalkylenyl,
  heteroaryl,
  heteroarylalkylenyl,
  heterocyclyl,
  heterocyclylalkylenyl, and alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
dialkylamino,
—S(O)$_{0-2}$-alkyl,
—S(O)$_{0-2}$-aryl,
—NH—S(O)$_2$-alkyl,
—NH—S(O)$_2$-aryl,
haloalkoxy,
halogen,
cyano,
nitro,
aryl,
heteroaryl,
heterocyclyl,
aryloxy,
arylalkyleneoxy,
—C(O)—O-alkyl,
—C(O)—N(R$_8$)$_2$,
—N(R$_8$)—C(O)-alkyl,
—O—(CO)-alkyl, and
—C(O)-alkyl;
or R$_2$ and R$_{2a}$ together with the nitrogen atom and Y' to which they are bonded can join to form a ring selected from the group consisting of:

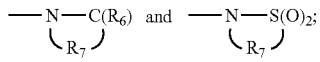

R' is hydrogen or a non-interfering substituent;
R''' is a non-interfering substituent;
R$_6$ is selected from the group consisting of =O and =S;
R$_7$ is C$_{2-7}$ alkylene;
R$_8$ is selected from the group consisting of hydrogen, C$_{1-10}$ alkyl, C$_{2-10}$ alkenyl, C$_{1-10}$ alkoxy-C$_{1-10}$ alkylenyl, and aryl-C$_{1-10}$ alkylenyl;
R$_9$ is selected from the group consisting of hydrogen and alkyl; and
R$_{10}$ is C$_{3-8}$ alkylene;
or a pharmaceutically acceptable salt thereof.

In one aspect of the invention, compounds are provided that are of the following Formula II:

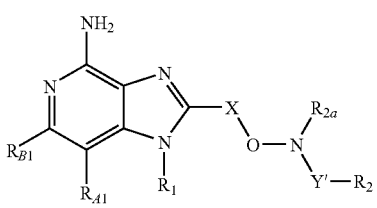

wherein:
X is C$_{1-10}$ alkylene or C$_{2-10}$ alkenylene;

R$_{A1}$ and R$_{B1}$ are each independently selected from the group consisting of:
hydrogen,
halogen,
allyl,
alkenyl,
alkoxy,
alkylthio, and
—N(R$_9$)$_2$;
or when taken together, R$_{A1}$ and R$_{B1}$ form a fused aryl ring or heteroaryl ring containing one heteroatom selected from the group consisting of N and S, wherein the aryl or heteroaryl ring is unsubstituted or substituted by one or more R groups, or substituted by one R$_3$ group, or substituted by one R$_3$ group and one R group;
or when taken together, R$_{A1}$ and R$_{B1}$ form a fused 5 to 7 membered saturated ring, optionally containing one heteroatom selected from the group consisting of N and S, and unsubstituted or substituted by one or more R groups;
R is selected from the group consisting of:
halogen,
hydroxy,
alkyl,
alkenyl,
haloalkyl,
alkoxy,
alkylthio, and
—N(R$_9$)$_2$;
R$_3$ is selected from the group consisting of:
—Z—R$_4$,
—Z—X—R$_4$,
—Z—X'—Y—R$_4$,
—Z—X'—Y—X'—Y—R$_4$, and
—Z—X'—R$_5$;
Y' is selected from the group consisting of:
a bond,
—C(O)—,
—C(S)—,
—S(O)$_2$—,
—S(O)$_2$—N(R$_8$)—,

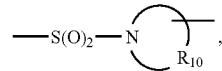

—C(O)—O—,
—C(O)—N(R$_8$)—,
—C(S)—N(R$_8$)—,
—C(O)—N(R$_9$)—S(O)$_2$—,
—C(O)—N(R$_8$)—C(O)—,
—C(S)—N(R$_8$)—C(O)—,

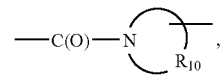

—C(O)—C(O)—,
—C(O)—C(O)—O—, and
—C(=NH)—N(R$_8$)—;
R$_1$ is selected from the group consisting of:
—R$_4$,
—X'—R$_4$,
—X'—Y—R$_4$,
—X'—Y—X'—Y—R$_4$,
—X'—R$_5$,
—X''—O—NR$_{1a}$—Y'—R$_{1b}$, and
—X''—O—N=C(R$_1$')(R$_1$'');

$R_{1a}$, $R_{1b}$, $R_1'$, $R_1''$, $R_2$, and $R_{2a}$ are independently selected from the group consisting of:
  hydrogen,
  alkyl,
  alkenyl,
  aryl,
  arylalkylenyl,
  heteroaryl,
  heteroarylalkylenyl,
  heterocyclyl,
  heterocyclylallylenyl, and
  alkyl, alkenyl, aryl, arylalkylenyl, heteroaryl, heteroarylalkylenyl, heterocyclyl, or heterocyclylalkylenyl, substituted by one or more substituents selected from the group consisting of:
    hydroxy,
    alkyl,
    haloalkyl,
    hydroxyalkyl,
    alkoxy,
    dialkylamino,
    —S(O)$_{0-2}$-alkyl,
    —S(O)$_{0-2}$-aryl,
    —NH—S(O)$_2$-alkyl,
    —NH—S(O)$_2$-aryl,
    haloalkoxy,
    halogen,
    cyano,
    nitro,
    aryl,
    heteroaryl,
    heterocyclyl,
    aryloxy,
    arylalkyleneoxy,
    —C(O)—O-alkyl,
    —C(O)—N(R$_8$)$_2$,
    —N(R$_8$)—C(O)-alkyl,
    —O—(CO)-alkyl, and
    —C(O)-alkyl;
  or $R_{1a}$ and $R_{1b}$ and/or $R_2$ and $R_{2a}$ together with the nitrogen atom and Y' to which they are bonded can join to form a ring selected from the group consisting of:

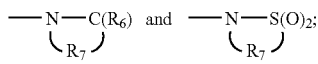

or $R_1'$ and $R_1''$ can join together to form a ring system selected from the group consisting of:

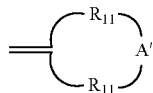

wherein the total number of atoms in the ring is 4 to 9, and

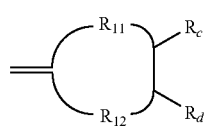

wherein the total number of atoms in the ring is 4 to 9;

$R_c$ and $R_d$ are independently selected from the group consisting of hydrogen, halogen, hydroxy, alkyl, alkenyl, aryl, haloalkyl, alkoxy, alkylthio, and —N(R$_9$)$_2$; or $R_c$ and $R_d$ can join to form a fused aryl ring or fused 5-10 membered heteroaryl ring containing one to four heteroatoms;

X' is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocylylene and optionally interrupted by one or more —O— groups;

X'' is —CH(R$_{13}$)-alkylene- or —CH(R$_{13}$)-alkenylene-, wherein the alkylene and alkenylene are optionally interrupted by one or more —O— groups;

Y is selected from the group consisting of:
  —S(O)$_{0-2}$—,
  —S(O)$_2$—N(R$_8$)—,
  —C(R$_6$)—,
  —C(R$_6$)—O—,
  —O—C(R$_6$)—,
  —O—C(O)—O—,
  —N(R$_8$)-Q-,
  —C(R$_6$)—N(R$_8$)—,
  —O—C(R$_6$)—N(R$_9$)—,
  —C(R$_6$)—N(OR$_9$)—,

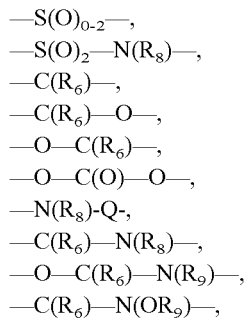

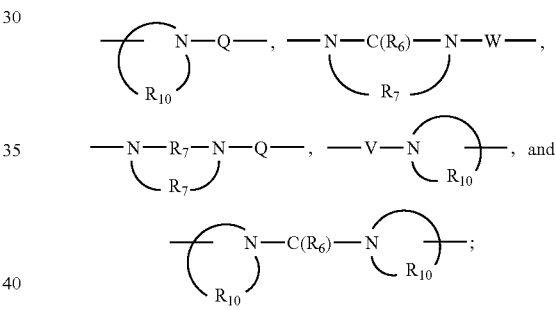

Z is a bond or —O—;

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$ is selected from the group consisting of:

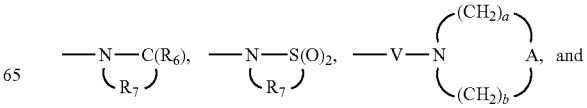

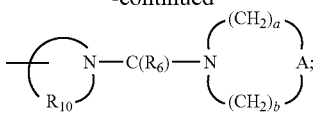

$R_6$ is selected from the group consisting of =O and =S;

$R_7$ is $C_{2-7}$ alkylene;

$R_8$ is selected from the group consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl;

$R_9$ is selected from the group consisting of hydrogen and alkyl;

$R_{10}$ is $C_{3-8}$ alkylene;

$R_{11}$ is $C_{1-6}$ alkylene or $C_{2-6}$ alkenylene, wherein the alkylene or alkenylene is optionally interrupted by one heteroatom;

$R_{12}$ is selected from the group consisting of a bond, $C_{1-5}$ alkylene, and $C_{2-5}$ alkenylene, wherein the alkylene or alkenylene is optionally interrupted by one heteroatom;

$R_{13}$ is selected from the group consisting of hydrogen and alkyl which may be optionally interrupted by one or more —O— groups;

A is selected from the group consisting of —CH$_2$—, —O—, —C(O)—, —S(O)$_{0-2}$—, and —N(R$_4$)—;

A' is selected from the group consisting of —O—, —S(O)$_{0-2}$—, —N(-Q-R$_4$)—, and —CH$_2$—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≥7;

or a pharmaceutically acceptable salt thereof.

In one aspect of the invention, compounds are provided that are of the following Formula III:

III

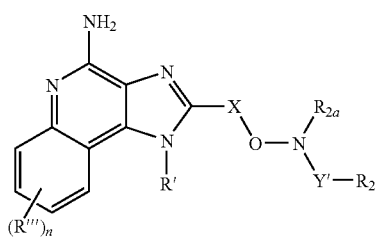

wherein:

X is $C_{1-10}$ alkylene or $C_{2-10}$ alkenylene;

Y' is selected from the group consisting of:
a bond,
—C(O)—,
—C(S)—,
—S(O)$_2$—,
—S(O)$_2$—N(R$_8$)—,

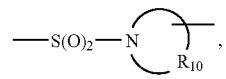

—C(O)—O—,
—C(O)—N(R$_8$)—,
—C(S)—N(R$_8$)—,
—C(O)—N(R$_8$)—S(O)$_2$—,
—C(O)—N(R$_8$)—C(O)—,
C(S)—N(R$_8$)—C(O)—,

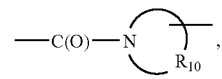

—C(O)—C(O)—,
—C(O)—C(O)—O—, and
—C(=N—H)—N(R$_8$)—;

$R_2$ and $R_{2a}$ are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
dialkylamino,
—S(O)$_{0-2}$-alkyl,
—S(O)$_{1-2}$-aryl,
—NH—S(O)$_2$-alkyl,
—NH—S(O)$_2$-aryl,
haloalkoxy,
halogen,
cyano,
nitro,
aryl,
heteroaryl,
heterocyclyl,
aryloxy,
arylalkyleneoxy,
—C(O)—O-alkyl,
—C(O)—N(R$_8$)$_2$,
—N(R$_8$)—C(O)-alkyl,
—O—(CO)-alkyl, and
—C(O)-alkyl;

$R_8$ is selected from the group consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl;

$R_{10}$ is $C_{3-8}$ alkylene;

n is an integer from 0 to 4;

R''' is a non-interfering substituent; and

R' is hydrogen or a non-interfering substituent;

or a pharmaceutically acceptable salt thereof.

In one aspect of the invention, compounds are provided that are of the following Formula IIIa:

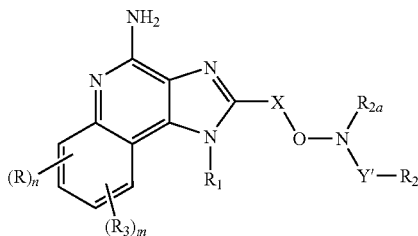

wherein:
X is $C_{1-10}$ alkylene or $C_{2-10}$ alkenylene;
Y' is selected from the group consisting of:
a bond,
—C(O)—,
—C(S)—,
—S(O)$_2$—,
—S(O)$_2$—N(R$_8$)—,

—C(O)—O—,
—C(O)—N(R$_8$)—,
—C(S)—N(R$_8$)—,
—C(O)—N(R$_8$)—S(O)$_2$—,
—C(O)—N(R$_8$)—C(O)—,
—C(S)—N(R$_8$)—C(O)—,

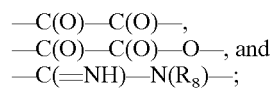

—C(O)—C(O)—,
—C(O)—C(O)—O—, and
—C(=NH)—N(R$_8$)—;
R is selected from the group consisting of:
halogen,
hydroxy,
alkyl,
alkenyl,
haloalkyl,
alkoxy,
alkylthio, and
—N(R$_9$)$_2$;
R$_1$ is selected from the group consisting of:
—R$_4$,
—X'—R$_4$,
—X'—Y—X'—Y—R$_4$,
—X'—Y—X'—Y—R$_4$,
—X'—R$_5$,
—X"—O—NR$_{1a}$—Y'—R$_{1b}$, and
—X"—O—N=C(R$_1$')(R$_1$");
R$_{1a}$, R$_{1b}$, R$_1$', R$_1$", R$_2$, and R$_{2a}$ are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylelnyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
dialkylamino,
—S(O)$_{0-2}$-alkyl,
—S(O)$_{0-2}$-aryl,
—NH—S(O)$_2$-alkyl,
—NH—S(O)$_2$-aryl,
haloalkoxy,
halogen,
cyano,
nitro,
aryl,
heteroaryl,
heterocyclyl,
aryloxy,
arylalkyleneoxy,
—C(O)—O-alkyl,
—C(O)—N(R$_8$)$_2$,
—N(R$_8$)—C(O)-alkyl,
—O—(CO)-alkyl, and
—C(O)-alkyl;
or R$_{1a}$ and R$_{1b}$ and/or R$_2$ and R$_{2a}$ together with the nitrogen atom and Y' to which they are bonded can join to form a ring selected from the group consisting of:

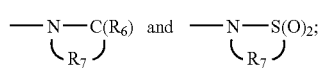

or R$_1$' and R$_1$" can join together to form a ring system selected from the group consisting of:

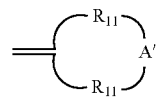

wherein the total number of atoms in the ring is 4 to 9, and

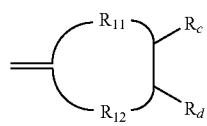

wherein the total number of atoms in the ring is 4 to 9;
R$_c$ and R$_d$ are independently selected from the group consisting of hydrogen, halogen, hydroxy, alkyl, alkenyl, aryl, haloalkyl, alkoxy, alkylthio, and —N(R$_9$)$_2$; or R$_c$, and R$_d$ can join to form a fused aryl ring or fused 5-10 membered heteroaryl ring containing one to four heteroatoms;

$R_3$ is selected from the group consisting of:
—Z—$R_4$,
—Z—X'—$R_4$,
—Z—X'—Y—$R_4$,
—Z—X'—Y—X'—Y—$R_4$, and
—Z—X'—$R_5$;

n is an integer from 0 to 4;

m is 0 or 1; with the proviso that when m is 1, then n is 0 or 1;

X' is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

X" is —CH($R_{13}$)-alkylene- or —CH($R_{13}$)-alkenylene-, wherein the alkylene and alkenylene are optionally interrupted by one or more —O— groups;

Y is selected from the group consisting of:
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,

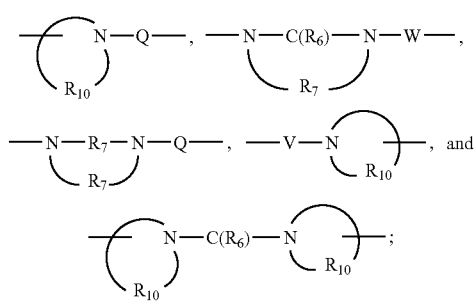

Z is a bond or —O—;

$R_4$ is selected from the group consisting of hydrogen, alkyl, alkenyl, alkynyl, aryl, arylalkylelnyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino) alkyleneoxy, and in the case of alkyl, alkenyl, alkynyl, and heterocyclyl, oxo;

$R_5$ is selected from the group consisting of:

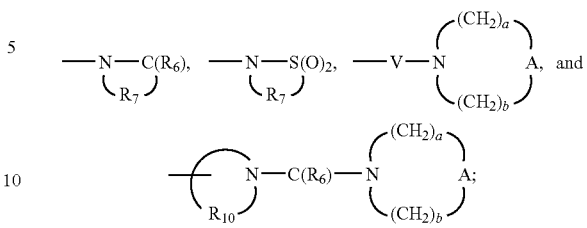

$R_6$ is selected from the group consisting of =O and =S;
$R_7$ is $C_{2-7}$ alkylene;
$R_8$ is selected from the group consisting of hydrogen, $C_{1-10}$ alkyl, $C_{2-10}$ alkenyl,
$C_{1-10}$ alkoxy-$C_{1-10}$ alkylenyl, and aryl-$C_{1-10}$ alkylenyl;
$R_9$ is selected from the group consisting of hydrogen and alkyl;
$R_{10}$ is $C_{3-8}$ alkylene;
$R_{11}$ is $C_{1-6}$ alkylene or $C_{2-6}$ alkenylene, wherein the alkylene or alkenylene is optionally interrupted by one heteroatom;
$R_{12}$ is selected from the group consisting of a bond, $C_{1-5}$ alkylene, and $C_{2-5}$ alkenylene, wherein the alkylene or alkenylene is optionally interrupted by one heteroatom;
$R_{13}$ is selected from the group consisting of hydrogen and alkyl which may be optionally interrupted by one or more —O— groups;

A is selected from the group consisting of —CH$_2$—, —O—, —C(O)—, —S(O)$_{0-2}$—, and —N($R_4$)—;

A' is selected from the group consisting of —O—, —S(O)$_{0-2}$—, —N(-Q-$R_4$)—, and —CH$_2$—;

Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, and —C($R_6$)—N(O$R_9$)—;

V is selected from the group consisting of —C($R_6$)—, —O—C($R_6$)—, —N($R_8$)—C($R_6$)—, and —S(O)$_2$—;

W is selected from the group consisting of a bond, —C(O)—, and —S(O)$_2$—; and a and b are independently integers from 1 to 6 with the proviso that a+b is ≤7;

or a pharmaceutically acceptable salt thereof.

In one aspect of the invention, compounds are provided that are of the following Formula IIIa:

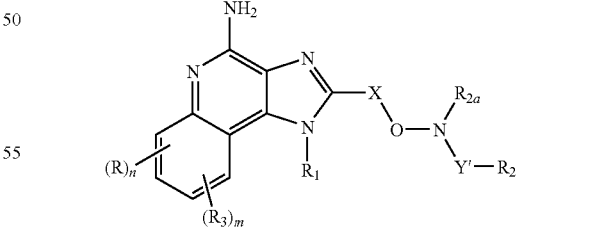

IIIa wherein:
X is $C_{1-10}$ alkylene or $C_{2-10}$ alkenylene;
Y' is selected from the group consisting of:
a bond,
—C(O)—,
—C(S)—,
—S(O)$_2$—,
—S(O)$_2$—N($R_8$)—,

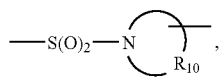

—C(O)—O—,
—C(O)—N($R_8$)—,
—C(S)—N($R_9$)—,
—C(O)—N($R_8$)—S(O)$_2$—,
—C(O)—N($R_8$)—C(O)—,
—C(S)—N($R_8$)—C(O)—,

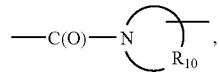

—C(O)—C(O)—,
—C(O)—C(O)—O—, and
—C(=NH)—N($R_8$)—;

$R_2$ and $R_{2a}$ are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
dialkylamino,
—S(O)$_{0-2}$-alkyl,
—S(O)$_{0-2}$-aryl,
—NH—S(O)$_2$-alkyl,
—NH—S(O)$_2$-aryl,
haloalkoxy,
halogen,
cyano,
nitro,
aryl,
heteroaryl,
heterocyclyl,
aryloxy,
arylalkyleneoxy,
—C(O)—O-alkyl,
—C(O)—N($R_8$)$_2$,
—N($R_9$)—C(O)-alkyl,
—O—(CO)-alkyl, and
—C(O)-alkyl;

R is selected from the group consisting of:
halogen,
hydroxy,
alkyl,
alkenyl,
haloalkyl,
alkoxy,
alkylthio, and —N($R_9$)$_2$;

$R_1$ is selected from the group consisting of:
—$R_4$,
—X'—$R_4$,
—X'—Y—$R_4$,
—X'—Y—X'—Y—$R_4$,
—X'—$R_5$,
—X"—O—NH—Y'—$R_1$', and
—X"—O—N=C($R_1$')($R_1$");

$R_3$ is selected from the group consisting of:
—Z—$R_4$,
—Z—X'—$R_4$,
—Z—X—Y—$R_4$,
—Z—X'—Y—X'—Y—$R_4$, and
—Z—X'—$R_5$;

n is an integer from 0 to 4;
m is 0 or 1; with the proviso that when m is 1, then n is 0 or 1;

X' is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

X" is —CH($R_{13}$)-alkylene- or —CH($R_{13}$)-alkenylene-;
Y is selected from the group consisting of:
—S(O)$_{0-2}$—,
—S(O)$_2$—N($R_9$)—,
—C($R_6$)—,
—O—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,

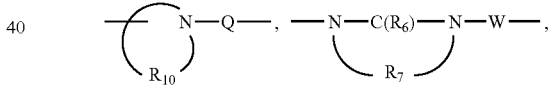

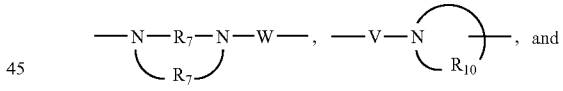

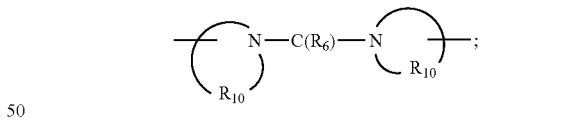

Z is a bond or —O—;
$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino) alkyleneoxy, and in the case of alkyl, alkenyl, alkynyl, and heterocyclyl, oxo;

$R_5$ is selected from the group consisting of:

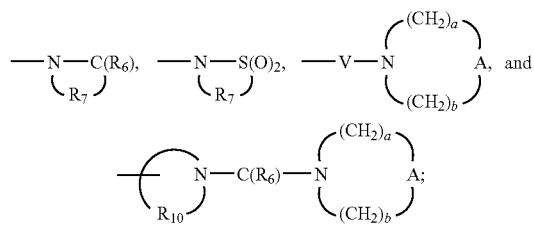

$R_1'$ and $R_1''$ are independently the same as $R_2$, or $R_1'$ and $R_1''$ can join together to form a ring system selected from the group consisting of:

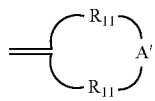

wherein the total number of atoms in the ring is 4 to 9, and

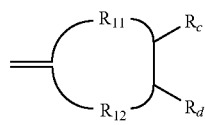

wherein the total number of atoms in the ring is 4 to 9;

$R_c$ and $R_d$ are independently selected from the group consisting of hydrogen, halogen, hydroxy, alkyl, alkenyl, aryl, haloalkyl, alkoxy, alkylthio, and —N($R_9$)$_2$; or $R_c$ and $R_d$ can join to form a fused aryl ring or fused 5-10 membered heteroaryl ring containing one to four heteroatoms;

$R_6$ is selected from the group consisting of =O and =S;

$R_7$ is $C_{2-7}$ alkylene;

$R_8$ is selected from the group consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl;

$R_9$ is selected from the group consisting of hydrogen and alkyl;

$R_{10}$ is $C_{3-8}$ alkylene;

$R_{11}$ is $C_{1-6}$ alkylene or $C_{2-6}$ alkenylene, wherein the alkylene or alkenylene is optionally interrupted by one heteroatom;

$R_{12}$ is selected from the group consisting of a bond, $C_{1-5}$ alkylene, and $C_{2-5}$ alkenylene, wherein the alkylene or alkenylene is optionally interrupted by one heteroatom;

$R_{13}$ is selected from the group consisting of hydrogen and alkyl which may be optionally interrupted by one or more —O— groups;

A is selected from the group consisting of —CH$_2$—, —O—, —C(O)—, —S(O)$_{0-2}$—, and —N(R$_4$)—;

A' is selected from the group consisting of —O—, —S(O)$_{0-2}$—, —N(-Q-R$_4$)—, and —CH$_2$—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≤7;

or a pharmaceutically acceptable salt thereof.

In one aspect of the invention, compounds are provided that are of the following Formula IV:

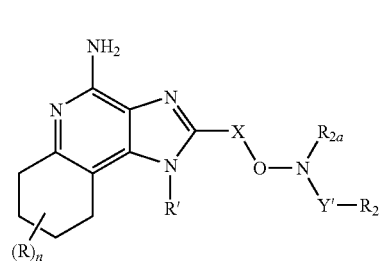

wherein:

X is $C_{1-10}$ alkylene or $C_{2-10}$ alkenylene;

Y' is selected from the group consisting of:

a bond,

—C(O)—,

—C(S)—,

—S(O)$_2$—,

—S(O)$_2$—N(R$_8$)—,

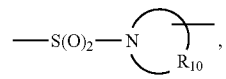

—C(O)—O—,

—C(O)—N(R$_8$)—,

—C(S)—N(R$_8$)—,

—C(O)—N(R$_9$)—S(O)$_2$—,

—C(O)—N(R$_8$)—C(O)—,

—C(S)—N(R)—X(O)—,

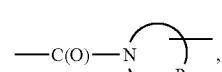

—C(O)—C(O)—,

—C(O)—C(O)—O—, and

—C(=NH)—N(R$_8$)—;

R is selected from the group consisting of:

halogen, hydroxy, alkyl, alkenyl, haloalkyl, alkoxy, alkylthio, and

—N(R$_9$)$_2$;

n is an integer from 0 to 4;

$R_2$ and $R_{2a}$ are independently selected from the group consisting of:

hydrogen, alkyl, alkenyl, aryl, arylalkylenyl, heteroaryl, heteroarylalkylenyl, heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
dialkylamino,
—S(O)$_{0-2}$-alkyl,
—S(O)$_{0-2}$-aryl,
—NH—S(O)$_2$-alkyl,
—NH—S(O)$_2$-aryl,
haloalkoxy,
halogen,
cyano,
nitro,
aryl,
heteroaryl,
heterocyclyl,
aryloxy,
arylalkyleneoxy;
—C(O)—O-alkyl,
—C(O)—N(R$_8$)$_2$,
—N(R$_8$)—C(O)-alkyl,
—O—(CO)-alkyl, and
—C(O)-alkyl;

R$_8$ is selected from the group consisting of hydrogen, C$_{1-10}$ alkyl, C$_{2-10}$ alkenyl, C$_{1-10}$ alkoxy-C$_{1-10}$ alkylenyl, and aryl-C$_{1-10}$ alkylenyl;

R$_9$ is selected from the group consisting of hydrogen and alkyl;

R$_{10}$ is C$_{3-8}$ alkylene; and

R' is hydrogen or a non-interfering substituent;

or a pharmaceutically acceptable salt thereof.

In one aspect of the invention, compounds are provided that are of the following Formula (IVa):

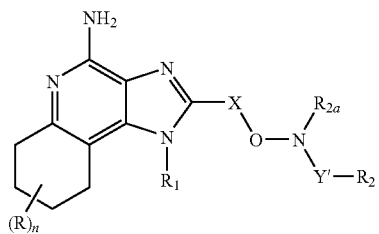

wherein:
X is C$_{1-10}$ alkylene or C$_{2-10}$ alkenylene;
Y' is selected from the group consisting of:
a bond,
—C(O)—,
—C(S)—,
—S(O)$_2$—,
—S(O)$_2$—N(R$_9$)—,

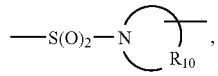

—C(O)—O—,
—C(O)—N(R$_8$)—,
—C(S)—N(R$_8$)—,
—C(O)—N(R$_8$)—S(O)$_2$—,
—C(O)—N(R$_8$)—C(O)—,
—C(S)—N(R$_{85}$)—C(O)—,

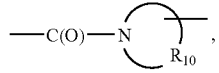

—C(O)—C(O)—,
—C(O)—C(O)—O—, and
—C(=NH)—N(R$_8$)—;

R is selected from the group consisting of:
halogen,
hydroxy,
alkyl,
alkenyl,
haloalkyl,
alkoxy,
alkylthio, and
—N(R$_9$)$_2$;

R$_1$ is selected from the group consisting of:
—R$_4$,
—X'—R$_4$,
—X'—Y—R$_4$,
—X'—Y—X'—Y—R$_4$,
—X'—R$_5$,
—X"—O—NR$_{1a}$—Y'—R$_{1b}$, and
—X"—O—N=C(R$_1$')(R$_1$");

R$_{1a}$, R$_{1b}$, R$_1$', R$_1$", R$_2$, and R$_{2a}$ are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
dialkylamino,
—S(O)$_{0-2}$-alkyl,
—S(O)$_{0-2}$-aryl,
—NH—S(O)$_2$-alkyl,
—NH—S(O)$_2$-aryl,
haloalkoxy,
halogen,
cyano,
nitro, aryl,
heteroaryl,
heterocyclyl,
aryloxy,
arylalkyleneoxy,
—C(O)—O-alkyl,
—C(O)—N(R$_8$)$_2$,
—N(R$_8$)—C(O)-alkyl,
—O—(CO)-alkyl, and
—C(O)-alkyl;

or R$_{1a}$ and R$_{1b}$ and/or R$_2$ and R$_{2a}$ together with the nitrogen atom and Y' to which they are bonded can join to form a ring selected from the group consisting of:

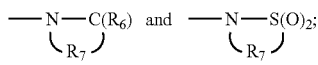

or R$_1$' and R$_1$" can join together to form a ring system selected from the group consisting of:

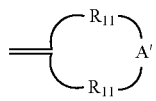

wherein the total number of atoms in the ring is 4 to 9, and

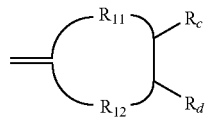

wherein the total number of atoms in the ring is 4 to 9;

R$_c$ and R$_d$ are independently selected from the group consisting of hydrogen, halogen, hydroxy, alkyl, alkenyl, aryl, haloalkyl, alkoxy, alkylthio, and —N(R$_9$)$_2$; or R$_c$ and R$_d$ can join to form a fused aryl ring or fused 5-10 membered heteroaryl ring containing one to four heteroatoms;

n is an integer from 0 to 4;

X' is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups; X" is —CH(R$_{13}$)-alkylene- or —CH(R$_{13}$)-alkenylene-, wherein the alkylene and alkenylene are optionally interrupted by one or more —O— groups;

Y is selected from the group consisting of:
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_9$)—,
—O—C(R$_6$)—N(R$_8$)—,
—C(R$_6$)—N(OR$_9$)—,

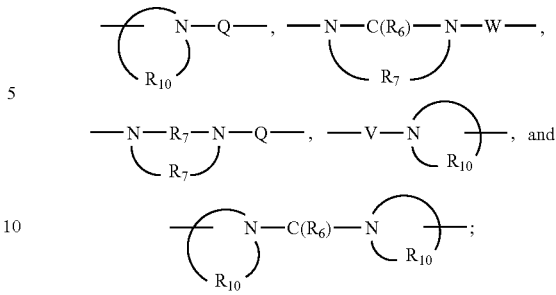

R is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of allyl, alkenyl, alkynyl, and heterocyclyl, oxo;

R$_5$ is selected from the group consisting of:

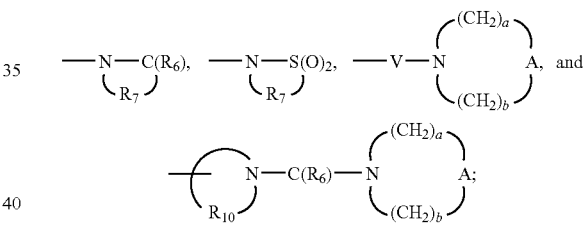

R$_6$ is selected from the group consisting of =O and =S;
R$_7$ is C$_{2-7}$ alkylene;
R$_8$ is selected from the group consisting of hydrogen, C$_{1-10}$ alkyl, C$_{2-10}$ alkenyl, C$_{1-10}$ alkoxy-C$_{1-10}$ alkylenyl, and aryl-C$_{1-10}$ alkylenyl;
R$_9$ is selected from the group consisting of hydrogen and alkyl;
R$_{10}$ is C$_{3-8}$ alkylene;
R$_{11}$ is C$_{1-6}$ alkylene or C$_{2-6}$ alkenylene, wherein the alkylene or alkenylene is optionally interrupted by one heteroatom;
R$_{12}$ is selected from the group consisting of a bond, C$_{1-5}$ alkylene, and C$_{2-5}$ alkenylene, wherein the alkylene or alkenylene is optionally interrupted by one heteroatom;
R$_{13}$ is selected from the group consisting of hydrogen and alkyl which may be optionally interrupted by one or more —O— groups;
A is selected from the group consisting of —CH$_2$—, —O—, —C(O)—, —S(O)$_{0-2}$—, and —N(R$_4$)—;
A' is selected from the group consisting of —O—, —S(O)$_{0-2}$—, —N(-Q-R$_4$)—, and —CH$_2$—;
Q is selected from the group consisting of a bond, —C(R$_6$)—, —C(R$_6$)—C(R$_6$)—, —S(O)$_2$—, —C(R$_6$)—N(R$_9$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≤7;

or a pharmaceutically acceptable salt thereof.

In one aspect of the invention, compounds are provided that are of the following Formula IVa:

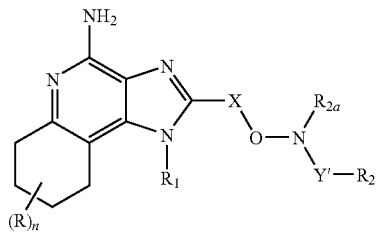

IVa wherein:
X is C$_{1-10}$ alkylene or C$_{2-10}$ alkenylene;
Y' is selected from the group consisting of:
a bond,
—C(O)—,
—C(S)—,
—S(O)$_2$—,
—S(O)$_2$—N(R$_8$)—,

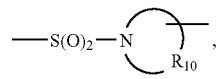

—C(O)—O—,
—C(O)—N(R$_8$)—,
—C(S)—N(R$_8$)—,
—C(O)—N(R$_8$)—S(O)$_2$—,
—C(O)—N(R$_8$)—C(O)—,
—C(S)—N(R$_8$)—C(O)—,

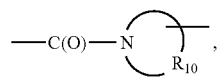

—C(O)—C(O)—,
—C(O)—C(O)—O—, and
—C(=NH)—N(R$_8$)—;

R$_2$ and R$_{2a}$ are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
dialkylamino,
—S(O)$_{0-2}$-alkyl,
—S(O)$_{0-2}$-aryl,
—NH—S(O)$_2$-alkyl,
—NH—S(O)$_2$-aryl,
haloalkoxy,
halogen,
cyano,
nitro,
aryl,
heteroaryl,
heterocyclyl,
aryloxy,
arylalkyleneoxy;
—C(O)—O-alkyl,
—C(O)—N(R$_8$)$_2$,
—N(R$_8$)—C(O)-alkyl,
—O—(CO)-alkyl, and
—C(O)-alkyl;

R is selected from the group consisting of:
halogen,
hydroxy,
alkyl,
alkenyl,
haloalkyl,
alkoxy,
alkylthio, and
—N(R$_9$)$_2$;

n is an integer from 0 to 4;

R$_1$ is selected from the group consisting of:
—R$_4$,
—X'—R$_4$,
—X'—Y—R$_4$,
—X'—Y—X'—Y—R$_4$,
—X'—R$_5$,
—X"—O—NH—Y'—R$_1$', and
—X"—O—N=C(R$_1$')(R$_1$");

X' is selected from the group consisting of alkylene, alkenylene, alkynylene, arylene, heteroarylene, and heterocyclylene wherein the alkene, alkenylene, and alkynylene groups can be optionally interrupted or terminated by arylene, heteroarylene or heterocyclylene and optionally interrupted by one or more —O— groups;

X" is —CH(R$_{13}$)-alkylene- or —CH(R$_{13}$)-alkenylene-;

Y is selected from the group consisting of:
—S(O)$_{0-2}$—,
—S(O)$_2$—N(R$_9$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,

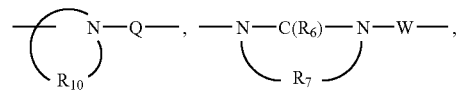

-continued

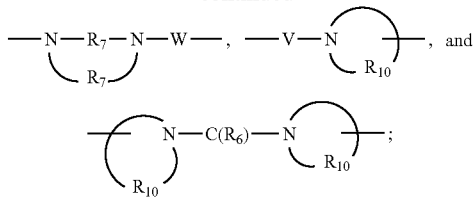

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino) alkyleneoxy, and in the case of alkyl, alkenyl, alkynyl, and heterocyclyl, oxo;

$R_5$ is selected from the group consisting of:

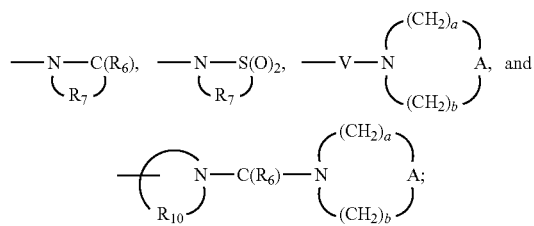

$R_1'$ and $R_1''$ are independently $R_2$, or $R_1'$ and $R_1''$ can join together to form a ring system selected from the group consisting of:

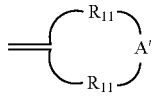

wherein the total number of atoms in the ring is 4 to 9, and

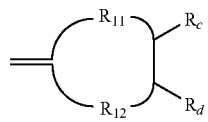

wherein the total number of atoms in the ring is 4 to 9;

$R_c$ and $R_d$ are independently selected from the group consisting of hydrogen, halogen, hydroxy, alkyl, alkenyl, aryl, haloalkyl, alkoxy, alkylthio, and —N($R_9$)$_2$; or $R_c$ and $R_d$ can join to form a fused aryl ring or fused 5-10 membered heteroaryl ring containing one to four heteroatoms;

$R_6$ is selected from the group consisting of =O and =S;

$R_7$ is $C_{2-7}$ alkylene;

$R_8$ is selected from the group consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl;

$R_9$ is selected from the group consisting of hydrogen and alkyl;

$R_{10}$ is $C_{3-8}$ alkylene;

$R_{11}$ is $C_{1-6}$ alkylene or $C_{2-6}$ alkenylene, wherein the alkylene or alkenylene is optionally interrupted by one heteroatom;

$R_{12}$ is selected from the group consisting of a bond, $C_{1-5}$ alkylene, and $C_{2-5}$ alkenylene, wherein the alkylene or alkenylene is optionally interrupted by one heteroatom;

$R_{13}$ is selected from the group consisting of hydrogen and alkyl which may be optionally interrupted by one or more —O— groups;

A is selected from the group consisting of —CH$_2$—, —O—, —C(O)—, —S(O)$_{0-2}$—, and —N(R$_4$)—;

A' is selected from the group consisting of —O—, —S(O)$_{0-2}$—, —N(-Q-R$_4$)—, and —CH$_2$—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_9$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≤7;

or a pharmaceutically acceptable salt thereof.

In one aspect of the invention, compounds are provided that are of the following Formula V:

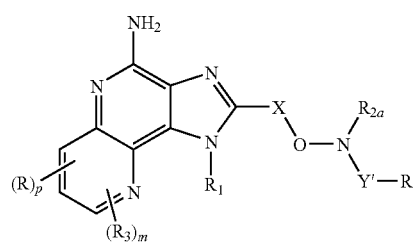

wherein:

X is $C_{1-10}$ alkylene or $C_{2-10}$ alkenylene;

Y' is selected from the group consisting of:

a bond,

—C(O)—,

—C(S)—,

—S(O)$_2$—,

—S(O)$_2$—N(R$_8$)—,

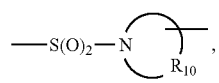

—C(O)—O—,

—C(O)—N(R$_8$)—,

—C(S)—N(R$_8$)—,

—C(O)—N(R$_8$)—S(O)$_2$—,

C(O)—N(R$_8$)—C(O)—,

C(S)—N(R$_8$)—C(O)—,

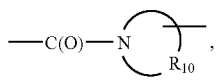

—C(O)—C(O)—,
—C(O)—C(O)—O—, and
—C(=NH)—N($R_5$)—;

R is selected from the group consisting of:
halogen,
hydroxy,
alkyl,
alkenyl,
haloalkyl,
alkoxy,
alkylthio, and
—N($R_9$)$_2$;

$R_1$ is selected from the group consisting of:
—$R_4$,
—X'—$R_4$,
—X'—Y—$R_4$,
—X'—Y—X'—Y—$R_4$,
—X'—$R_5$,
—X'—O—N$R_{1a}$—Y'—$R_{1b}$, and
—X"—O—N=C($R_1$')($R_1$");

$R_{1a}$, $R_{1b}$, $R_1$', $R_1$", $R_2$, and $R_{2a}$ are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
dialkylamino,
—S(O)$_{0-2}$-alkyl,
—S(O)$_{0-2}$-aryl,
—NH—S(O)$_2$-alkyl,
—NH—S(O)$_2$-aryl,
haloalkoxy,
halogen,
cyano,
nitro,
aryl,
heteroaryl,
heterocyclyl,
aryloxy,
arylalkyleneoxy,
—C(O)—O-alkyl,
—C(O)—N($R_8$)$_2$,
—N($R_8$)—C(O)-alkyl,
—O—(CO)-alkyl, and
—C(O)-alkyl;

or $R_{1a}$ and $R_{1b}$ and/or $R_2$ and $R_{2a}$ together with the nitrogen atom and Y' to which they are bonded can join to form a ring selected from the group consisting of:

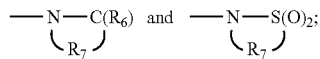

or $R_1$' and $R_1$" can join together to form a ring system selected from the group consisting of:

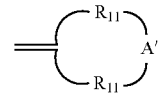

wherein the total number of atoms in the ring is 4 to 9, and

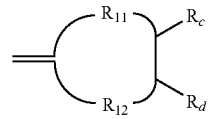

wherein the total number of atoms in the ring is 4 to 9;

$R_c$ and $R_d$ are independently selected from the group consisting of hydrogen, halogen, hydroxy, alkyl, alkenyl, aryl, haloalkyl, alkoxy, alkylthio, and —N($R_9$)$_2$; or $R_c$ and $R_d$ can join to form a fused aryl ring or fused 5-10 membered heteroaryl ring containing one to four heteroatoms;

$R_3$ is selected from the group consisting of:
—Z—$R_4$,
—Z—X'—$R_4$,
—Z—X'—Y—$R_4$,
—Z—X'—Y—X'—Y—$R_4$, and
—Z—X'—$R_5$;

p is an integer from 0 to 3;
m is 0 or 1, with the proviso that when m is 1, p is 0 or 1;

X' is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

X" is —CH($R_{13}$)-alkylene- or —CH($R_{13}$)-alkenylene-, wherein the alkylene and alkenylene are optionally interrupted by one or more —O— groups;

Y is selected from the group consisting of:
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,

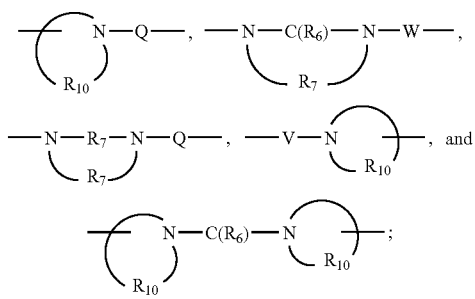

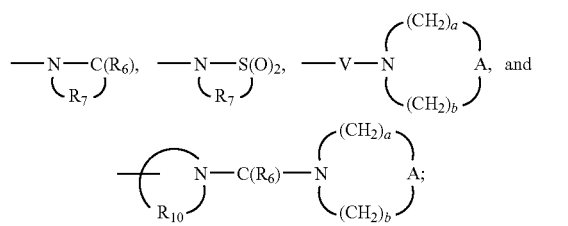

Z is a bond or —O—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

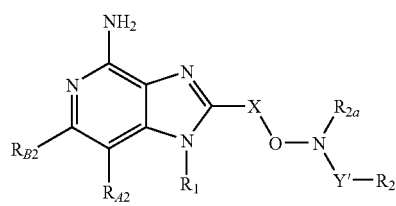

$R_6$ is selected from the group consisting of =O and =S;
$R_7$ is $C_{2-7}$ alkylene;
$R_8$ is selected from the group consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl;
$R_9$ is selected from the group consisting of hydrogen and alkyl;
$R_{10}$ is $C_{3-8}$ alkylene;
$R_{11}$ is $C_{1-6}$ alkylene or $C_{2-6}$ alkenylene, wherein the alkylene or alkenylene is optionally interrupted by one heteroatom;
$R_{12}$ is selected from the group consisting of a bond, $C_{1-5}$ alkylene, and $C_{2-5}$ alkenylene, wherein the alkylene or alkenylene is optionally interrupted by one heteroatom;
$R_{13}$ is selected from the group consisting of hydrogen and alkyl which may be optionally interrupted by one or more —O— groups;
A is selected from the group consisting of —CH$_2$—, —O—, —C(O)—, —S(O)$_{0-2}$—, and —N(R$_4$)—;
A' is selected from the group consisting of —O—, —S(O)$_{0-2}$—, —N(-Q-R$_4$)—, and —CH$_2$—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_9$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≤7;
or a pharmaceutically acceptable salt thereof.

In one aspect of the invention, compounds are provided that are of the following Formula VI:

VI

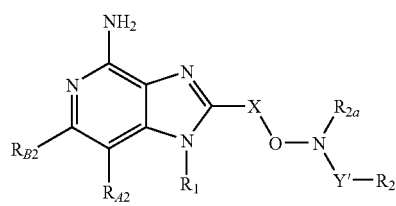

wherein:
X is $C_{1-10}$ alkylene or $C_{2-10}$ alkenylene;
$R_{A2}$ and $R_{B2}$ are each independently selected from the group consisting of:
hydrogen,
halogen,
alkyl,
alkenyl,
alkoxy,
alkylthio, and
—N(R$_9$)$_2$;
Y' is selected from the group consisting of:
a bond,
—C(O)—,
—C(S)—,
—S(O)$_2$—,
—S(O)$_2$—N(R$_8$)—,

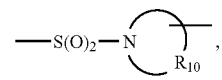

—C(O)—O—,
—C(O)—N(R$_8$)—,
—C(S)—N(R$_8$)—,
—C(O)—N(R$_8$)—S(O)$_2$—,
—C(O)—N(R$_8$)—C(O)—,
—C(S)—N(R$_8$)—C(O)—,

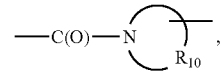

—C(O)—C(O)—,
—C(O)—C(O)—O—, and
—C(=NH)—N(R$_8$)—;
$R_1$ is selected from the group consisting of:
—R$_4$,
—X'—R$_4$,
—X'—Y—R$_4$,
—X'—Y—X'—Y—R$_4$,
—X'—R$_5$,
—X'—O—NR$_{1a}$—Y'—R$_{1b}$, and
—X''—O—N=C(R$_1$')(R$_1$'');

$R_{1a}$, $R_{1b}$, $R_1'$, $R_1''$, $R_2$, and $R_{2a}$ are independently selected from the group consisting of:
  hydrogen,
  alkyl,
  alkenyl,
  aryl,
  arylalkylenyl,
  heteroaryl,
  heteroarylalkylenyl,
  heterocyclyl,
  heterocyclylalkylenyl, and
  alkyl, alkenyl, aryl, arylalkylenyl, heteroaryl, heteroarylalkylenyl, heterocyclyl, or heterocyclylalkylenyl, substituted by one or more substituents selected from the group consisting of:
    hydroxy,
    alkyl,
    haloalkyl,
    hydroxyalkyl,
    alkoxy,
    dialkylamino,
    —S(O)$_{0-2}$-alkyl,
    —S(O)$_{0-2}$-aryl,
    —NH—S(O)$_2$-alkyl,
    —NH—S(O)$_2$-aryl,
    haloalkoxy,
    halogen,
    cyano,
    nitro,
    aryl,
    heteroaryl,
    heterocyclyl,
    aryloxy,
    arylalkyleneoxy,
    —C(O)—O-alkyl,
    —C(O)—N(R$_8$)$_2$,
    —N(R$_8$)—C(O)-alkyl,
    —O—(CO)-alkyl, and
    —C(O)-alkyl;
  or $R_{1a}$ and $R_{1b}$ and/or $R_2$ and $R_{2a}$ together with the nitrogen atom and Y' to which they are bonded can join to form a ring selected from the group consisting of:

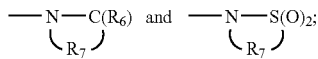

or $R_1'$ and $R_1''$ can join together to form a ring system selected from the group consisting of:

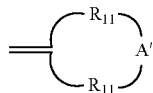

wherein the total number of atoms in the ring is 4 to 9, and

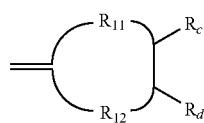

wherein the total number of atoms in the ring is 4 to 9;

$R_c$ and $R_d$ are independently selected from the group consisting of hydrogen, halogen, hydroxy, alkyl, alkenyl, aryl, haloalkyl, alkoxy, alkylthio, and —N(R$_9$)$_2$; or $R_c$, and $R_d$ can join to form a fused aryl ring or fused 5-10 membered heteroaryl ring containing one to four heteroatoms;

X' is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

X" is —CH(R$_{13}$)-alkylene- or —CH(R$_{13}$)-alkenylene-, wherein the alkylene and alkenylene are optionally interrupted by one or more —O— groups;

Y is selected from the group consisting of:
  —S(O)$_{0-2}$—,
  —S(O)$_2$—N(R$_8$)—,
  —C(R$_6$)—,
  —C(R$_6$)—O—,
  —C(R$_6$)—,
  —O—C(O)—O—,
  —N(R$_8$)-Q-,
  —C(R$_6$)—N(R$_8$)—,
  —O—C(R$_6$)—N(R$_8$)—,
  —C(R$_6$)—N(OR$_9$)—,

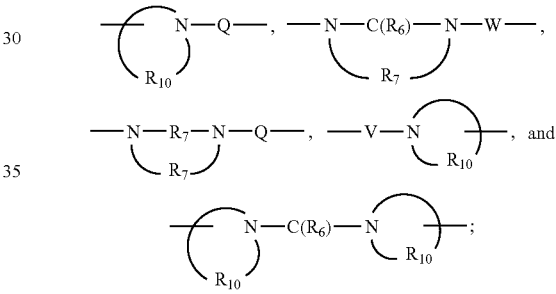

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

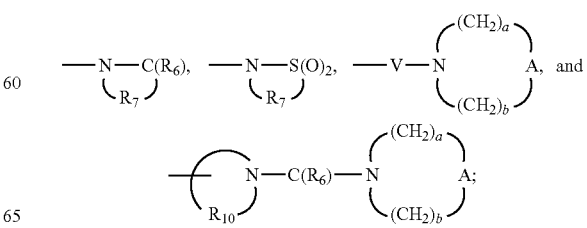

$R_6$ is selected from the group consisting of =O and =S;

$R_7$ is $C_{2-7}$ alkylene;

$R_8$ is selected from the group consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl;

$R_9$ is selected from the group consisting of hydrogen and alkyl;

$R_{10}$ is $C_{3-8}$ alkylene;

$R_{11}$ is $C_{1-6}$ alkylene or $C_{2-6}$ alkenylene, wherein the alkylene or alkenylene is optionally interrupted by one heteroatom;

$R_{12}$ is selected from the group consisting of a bond, $C_{1-5}$ alkylene, and $C_{2-5}$ alkenylene, wherein the alkylene or alkenylene is optionally interrupted by one heteroatom;

$R_{13}$ is selected from the group consisting of hydrogen and alkyl which may be optionally interrupted by one or more —O— groups;

A is selected from the group consisting of —CH$_2$—, —O—, —C(O)—, —S(O)$_{0-2}$—, and —N(R$_4$)—;

A' is selected from the group consisting of —O—, —S(O)$_{0-2}$—, —N(-Q-R$_4$)—, and —CH$_2$—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≤7;

or a pharmaceutically acceptable salt thereof.

Certain embodiments of the present invention include non-interfering substituents. For example, in certain embodiments, R' is hydrogen or a non-interfering substitutent, and in certain embodiments, R''' is a non-interfering substituent.

Herein, "non-interfering" means that the ability of the compound or salt, which includes a non-interfering substituent, to modulate (e.g., induce or inhibit) the biosynthesis of one or more cytokines is not destroyed by the non-interfering substitutent. Illustrative non-interfering R' groups include those described herein for $R_1$. Illustrative non-interfering R''' groups include those described herein for R and $R_3$.

As used herein, the terms "alkyl", "alkenyl", "alkynyl" and the prefix "alk-" are inclusive of both straight chain and branched chain groups and of cyclic groups, i.e. cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene", "alkenylene", and "alkynylene" are the divalent forms of the "alkyl", "alkenyl", and "alkynyl" groups defined above. The terms, "alkylenyl", "alkenylenyl", and "alkynylenyl" are use when "alkylene", "alkenylene", and "alkynylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

Unless otherwise indicated, the term "heteroatom" refers to the atoms O, S, or N.

The term "heteroaryl" includes aromatic rings or ring systems that contain at least one ring heteroatom (e.g., O, S, N). Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. Exemplary heterocyclic groups include pyrrolidinyl, tetrahydrofuranyl, morpholinyl, thiomorpholinyl, piperidinyl, piperazinyl, thiazolidinyl, imidazolidinyl, isothiazolidinyl, tetrahydropyranyl, quinuclidinyl, homopiperidinyl (azepanyl), homopiperazinyl (diazepanyl), 1,3-dioxolanyl, aziridinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, and the like. When "heterocyclyl" contains a nitrogen atom, the point of attachment of the heterocyclyl group may be the nitrogen atom.

The terms "arylene," "heteroarylene," and "heterocyclylene" are the divalent forms of the "aryl," "heteroaryl," and "heterocyclyl" groups defined above. The terms, "arylenyl", "heteroarylenyl", and "heterocyclylenyl" are used when "arylene," "heteroarylene," and "heterocyclylene", respectively, are substituted. For example, an alkylarylenyl group comprises an arylene moiety to which an alkyl group is attached.

When a group (or substituent or variable) is present more than once in any Formula described herein, each group (or substituent or variable) is independently selected, whether explicitly stated or not. For example, for the formula —C(O)—N(R$_9$)$_2$ each R$_8$ group is independently selected. In another example, when an R$_1$ and an R$_3$ group both contain an R$_4$ group, each R$_4$ group is independently selected. In a further example, when more than one Y group is present (i.e., R$_1$ and R$_3$ both contain a Y group) and each Y group contains one or more R$_7$ groups, then each Y group is independently selected, and each R$_7$ group is independently selected.

The invention is inclusive of the compounds described herein in any of their pharmaceutically acceptable forms, including isomers (e.g., diastereomers and enantiomers), salts, solvates, polymorphs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

For any of the compounds presented herein, each one of the following variables (e.g., R, R', R''', $R_A$, $R_B$, $R_{A1}$, $R_{B1}$, $R_1$, $R_2$, $R_{2a}$, $R_3$, n, X, Y, Y', Z and so on) in any of its embodiments can be combined with any one or more of the other variables in any of their embodiments and associated with any one of the formulas described herein, as would be understood by one of skill in the art. Each of the resulting combinations of variables is an embodiment of the present invention.

In some embodiments, R is selected from the group consisting of halogen, hydroxy, alkyl, alkenyl, haloalkyl, alkoxy, alkylthio, and —N(R$_9$)$_2$. In certain embodiments, R is selected from the group consisting of halogen and hydroxy.

In some embodiments, R$_A$ and R$_B$ are each independently selected from the group consisting of hydrogen, halogen, alkyl, alkenyl, alkoxy, alkylthio, and —N(R$_9$)$_2$. Alternatively, when taken together, R$_A$ and R$_B$ form a fused aryl ring or heteroaryl ring containing one heteroatom selected from the group consisting of N and S, wherein the aryl or heteroaryl ring is unsubstituted or substituted by one or more R''' groups. Alternatively, when taken together, R$_A$ and R$_B$ form a fused 5 to 7 membered saturated ring, optionally containing one heteroatom selected from the group consisting of N and S, and unsubstituted or substituted by one or more R groups.

In some embodiments, particularly embodiments of Formula I, R$_A$ and R$_B$ are each independently selected from the group consisting of hydrogen, halogen, alkyl, alkenyl, alkoxy, alkylthio, and —N(R$_9$)$_2$.

In some embodiments, particularly embodiments of Formula I, R$_A$ and R$_B$ form a fused aryl or heteroaryl ring.

In some embodiments, particularly embodiments of Formula I, R$_A$ and R$_B$ form a fused 5 to 7 membered saturated ring.

In some embodiments, R$_{A1}$ and R$_{B1}$ are each independently selected from the group consisting of hydrogen, halogen, alkyl, alkenyl, alkoxy, alkylthio, and —N(R$_9$)$_2$. Alternatively, R$_{A1}$ and R$_{B1}$ form a fused aryl ring or heteroaryl ring containing one heteroatom selected from the group consisting of N and S, wherein the aryl or heteroaryl ring is unsubstituted or substituted by one or more R groups, or substituted by one R$_3$ group, or substituted by one R$_3$ group and one R group. Alternatively, when taken together, R$_{A1}$ and R$_{B1}$ form a fused 5 to 7 membered saturated ring, optionally containing one heteroatom selected from the group consisting of N and S, and unsubstituted or substituted by one or more R groups.

In some embodiments, particularly embodiments of Formula II, R$_{A1}$ and R$_{B1}$ form a fused benzene ring which is unsubstituted.

In some embodiments, particularly embodiments of Formula II, R$_{A1}$ and R$_{B1}$ form a fused pyridine ring which is unsubstituted.

In some embodiments, particularly embodiments of Formula II, R$_{A1}$ and R$_{B1}$ form a fused 5 to 7 membered saturated ring, optionally containing one heteroatom selected from the group consisting of N and S, wherein the ring is unsubstituted.

In some embodiments, R$_{A2}$ and R$_{B2}$ are each independently selected from the group consisting of hydrogen, halogen, alkyl, alkenyl, alkoxy, alkylthio, and —N(R$_9$)$_2$. In certain of these embodiments, R$_{A2}$ and R$_{B2}$ are each independently alkyl. In some embodiments, R$_{A2}$ and R$_{B2}$ are each methyl.

In some embodiments, R$_c$ and R$_d$ are independently selected from the group consisting of hydrogen, halogen, hydroxy, alkyl, alkenyl, aryl, haloalkyl, alkoxy, alkylthio, and —N(R$_9$)$_2$; or R$_c$ and R$_d$ can join to form a fused aryl ring or fused 5-10 membered heteroaryl ring containing one to four heteroatoms. In certain embodiments, at least one of R$_c$, or R$_d$ is aryl.

In some embodiments, R$_1$ is selected from the group consisting of —R$_4$, —X'—R$_4$, —X'—Y—R$_4$, —X'—Y—X'—Y—R$_4$, —X'—R$_5$, —X''—O—NR$_{1a}$—Y'—R$_{1b}$, and —X''—O—N=C(R$_1$')(R$_1$''). In some embodiments, R$_1$ is selected from the group consisting of —R$_4$, —X'—R$_4$, —X'—Y—R$_4$, —X'—Y—X'—Y—R$_4$, —X'—R$_5$, —X''—O—NH—Y'—R$_1$', and —X''—O—N=C(R$_1$')(R$_1$'').

In some embodiments, R$_1$' is selected from the group consisting of alkyl, arylalkylenyl, aryloxyalkylenyl, hydroxyalkyl, alkylsulfonylalkylenyl, —X'—Y—R$_4$, and —X'—R$_5$. In some embodiments, R$_1$ is 2-methylpropyl, 2-hydroxy-2-methylpropyl, or —X'—Y—R$_4$. In some embodiments, R$_1$ is 2-methylpropyl or —X'—Y—R$_4$. In some embodiments, R$_1$ is 2-methylpropyl or 2-hydroxy-2-methylpropyl. In some embodiments, R$_1$ is 2-methyl-2-[(methylsulfonyl)amino]propyl or 4-[(methylsulfonyl)amino]butyl.

In some embodiments, R' is hydrogen or a non-interfering substituent. In some embodiments, R' is selected from the group consisting of —R$_4$, —X'—R$_4$, —X'—Y—R$_4$, —X'—Y—X'—Y—R$_4$, —X'—R$_5$, —X''—O—NH—Y'—R$_1$', and —X''—O—N=C(R$_1$')(R$_1$''). In some embodiments, R' is selected from the group consisting of —R$_4$, —X'—R$_4$, —X'—Y—R$_4$, —X'—Y—X'—Y—R$_4$, —X'—R$_5$, —X'—O—NR$_{1a}$—Y'—R$_{1b}$, and —X''—O—N=C(R$_1$')(R$_1$'').

In some embodiments, R$_1$' and R$_1$'' are independently the same as R$_2$.

In some embodiments, R$_1$' and R$_1$'' are independently selected from the group consisting of hydrogen, alkyl, alkenyl, aryl, arylalkylenyl, heteroaryl, heteroarylalkylenyl, heterocyclyl, heterocyclylalkylenyl, as well as alkyl, alkenyl, aryl, arylalkylenyl, heteroaryl, heteroarylalkylenyl, heterocyclyl, or heterocyclylalkylenyl, substituted by one or more substituents selected from the group consisting of hydroxy, alkyl, haloalkyl, hydroxyalkyl, alkoxy, dialkylamino, —S(O)$_{0-2}$-alkyl, —S(O)$_{0-2}$-aryl, —NH—S(O)$_2$-alkyl, —NH—S(O)$_2$-aryl, haloalkoxy, halogen, cyano, nitro, aryl, heteroaryl, heterocyclyl, aryloxy, arylalkyleneoxy, —C(O)—O-alkyl, —C(O)—N(R$_8$)$_2$, —N(R$_8$)—C(O)-alkyl, —O—(CO)-alkyl, and —C(O)-alkyl.

In some embodiments, R$_1$' and R$_1$'' can join together to form a ring system selected from the group consisting of:

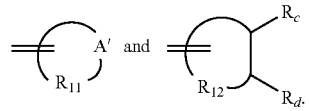

Alternatively, R$_1$' and R$_1$'' can join together to form a ring system selected from the group consisting of:

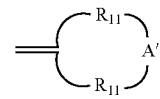

wherein the total number of atoms in the ring is 4 to 9, and

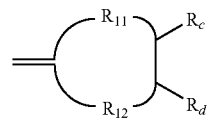

wherein the total number of atoms in the ring is 4 to 9.

In some embodiments, R$_{1a}$ and R$_{1b}$ are independently selected from the group consisting of hydrogen, alkyl, alkenyl, aryl, arylalkylenyl, heteroaryl, heteroarylalkylenyl, heterocyclyl, heterocyclylalkylenyl, as well as alkyl, alkenyl, aryl, arylalkylenyl, heteroaryl, heteroarylalkylenyl, heterocyclyl, or heterocyclylalkylenyl, substituted by one or more substituents selected from the group consisting of hydroxy, alkyl, haloalkyl, hydroxyalkyl, alkoxy, dialkylamino, —S(O)$_{0-2}$-alkyl, —S(O)$_{0-2}$-aryl, —NH—S(O)$_2$-alkyl, —NH—S(O)$_2$-aryl, haloalkoxy, halogen, cyano, nitro, aryl, heteroaryl, heterocyclyl, aryloxy, arylalkyleneoxy, —C(O)—O-alkyl, —C(O)—N(R$_8$)$_2$, —N(R$_8$)—C(O)-alkyl, —O—(CO)-alkyl, and —C(O)-alkyl. Alternatively, R$_{1a}$ and R$_{1b}$ together with the nitrogen atom and Y' to which they are bonded can join to form a ring selected from the group consisting of

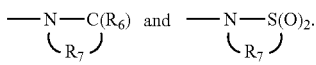

In some embodiments, R$_{1a}$ is hydrogen.

In some embodiments, R$_2$ and R$_{2a}$ are independently selected from the group consisting of hydrogen, alkyl, alkenyl, aryl, arylalkylenyl, heteroaryl, heteroarylalkylenyl, heterocyclyl, heterocyclylalkylenyl, as well as alkyl, alkenyl, aryl, arylalkylenyl, heteroaryl, heteroarylalkylenyl, heterocyclyl, or heterocyclylalkylenyl, substituted by one or more substituents selected from the group consisting of hydroxy (i.e., hydroxyl), alkyl, haloalkyl, hydroxyalkyl, alkoxy, dialkylamino, —S(O)$_{0-2}$-alkyl, —S(O)$_{0-2}$-aryl, —NH—S(O)$_2$-alkyl, —NH—S(O)$_2$-aryl, haloalkoxy, halogen, cyano (i.e., nitrile), nitro, aryl, heteroaryl, heterocyclyl, aryloxy, arylalkyleneoxy, —C(O)—O-alkyl, —C(O)—N(R$_8$)$_2$, —N(R$_8$)—C(O)-alkyl, —O—(CO)-alkyl, and —C(O)-alkyl. Herein, this list of substituents is being referenced when an R$_2$ or R$_{2a}$ group is referred to as substituted or optionally substituted.

Alternatively, R$_2$ and R$_{2a}$ together with the nitrogen atom and Y' to which they are bonded can join to form a ring selected from the group consisting of

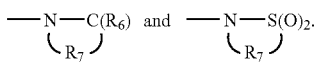

In some embodiments, particularly embodiments of Formulas IIIa and IVa, R$_2$ and R$_{2a}$ are independently selected from the group consisting of hydrogen, alkyl, alkenyl, aryl, heteroaryl, wherein the alkyl, alkenyl, aryl, and heteroaryl are each optionally substituted with one or more substitutents selected from the group consisting of C$_{1-10}$ alkyl, aryl, heteroaryl, C$_{1-10}$ alkoxy, —O—C(O)—C$_{1-10}$ alkyl, —C(O)—O—C$_{1-10}$ alkyl, halogen, and cyano (i.e., nitrile).

In some embodiments, R$_2$ is alkyl or substituted alkyl. In some embodiments, R$_2$ is methyl or cyclopropyl.

In some embodiments, R$_2$ is alkenyl or substituted alkenyl. In some embodiments, R$_2$ is aryl, arylalkylenyl, substituted aryl, or substituted arylalkylenyl. In some embodiments, R$_2$ is heteroaryl, heteroarylalkylenyl, substituted heteroaryl, or substituted heteroarylalkylenyl. In some embodiments, R$_2$ is heterocyclyl, heterocyclylalkylenyl, substituted heterocyclyl, or substituted heterocyclylalkylenyl.

In some embodiments, R$_2$ is selected from the group consisting of methyl, (ethoxycarbonyl)methyl, ethyl, cyclopropyl, cyclopropylmethyl, 2-(ethoxycarbonyl)cyclopropylmethyl, propyl, butyl, 2-methylpropyl, tert-butyl, 3-methylbutyl, 2,2-dimethylpropyl, cyclopentyl, 2-cyclopentylethyl, furyl, fur-3-ylmethyl, furfuryl, furfurylmethyl, cyclohexyl, tetrahydrofuranyl, tetrahydrofuran-3-ylmethyl, 2-(methylthio)ethyl, 3-(methylthio)propyl, phenyl, 2-methylphenyl, 3-methylphenyl, 4-methylphenyl, 2-methoxyphenyl, 3-methoxyphenyl, 4-methoxyphenyl, 2,6-dimethoxyphenyl, 2-chlorophenyl, 3-chlorophenyl, 4-chlorophenyl, 2-fluorophenyl, 3-fluorophenyl, 4-fluorophenyl, 2-cyanophenyl, 3-cyanophenyl, 4-cyanophenyl, 4-(dimethylamino)phenyl, 3-hydroxy-4-methoxyphenyl, 4-acetamidophenyl, 4-(methoxycarbonyl)phenyl, 4-(trifluoromethyl)phenyl, biphenyl, benzyl, 2-methylbenzyl, 3-methylbenzyl, 4-methylbenzyl, 2-fluorobenzyl, 3-fluorobenzyl, 4-fluorobenzyl, 2-chlorobenzyl, 3-chlorobenzyl, 4-chlorobenzyl, 2-cyanobenzyl, 3-cyanobenzyl, 4-cyanobenzyl, 2-methoxybenzyl, 3-methoxybenzyl, 4-methoxybenzyl, 4-dimethylaminobenzyl, 3-hydroxy-4-methoxybenzyl, 4-acetamidobenzyl, 4-(methoxycarbonyl)benzyl, 4-(trifluoromethyl)benzyl, 1-phenylethyl, 2-phenylethyl, 2-phenylpropyl, 3-phenylpropyl, 2-phenylethenyl, phenoxymethyl, 2-pyridyl, 3-pyridyl, 4-pyridyl, 2-pyridylmethyl, 3-pyridylmethyl, 4-pyridylmethy, 1-methylpyrrol-2-yl, 1-methylpyrrol-2-ylmethyl, 1-methylimidazol-2-yl, 1-methylimidazol-2-ylmethyl, 1-methylimidazol-4-yl, 1-methylimidazol-4-ylmethyl, 3-cyclohexen-1-yl, 3-cyclohexen-1-ylmethyl, 3,4-dihydro-2H-pyran-2-yl, 3,4-dihydro-2H-pyran-2-ylmethyl, 1-methylpiperidin-4-yl, 1-acetylpiperidin-4-yl, 1-benzylpiperidin-4-yl, 2-thienyl, 3-thienyl, thien-2-ylmethyl, thiazol-2-yl, thiazol-2-ylmethyl, 5-isoxazolyl, 5-isoxazolylmethyl, quinolin-2-yl, quinolin-2-ylmethyl, pyrrolidinyl, 3,4-dichlorophenyl, α-methylbenzyl, methoxymethyl, trifluoromethyl, and 2,2,2-trifluoroethyl.

In some embodiments, R$_2$ is selected from the group consisting of methyl, (ethoxycarbonyl)methyl, ethyl, cyclopropyl, cyclopropyliethyl, 2-(ethoxycarbonyl)cyclopropylmethyl, propyl, butyl, 2-methylpropyl, tert-butyl, 3-methylbutyl, 2,2-dimethylpropyl, cyclopentyl, 2-cyclopentylethyl, furyl, fur-3-ylmethyl, furfuryl, furfurylmethyl, cyclohexyl, tetrahydrofuranyl, tetrahydrofuran-3-ylmethyl, 2-(methylthio)ethyl, 3-(methylthio)propyl, phenyl, 2-methylphenyl, 3-methylphenyl, 4-methylphenyl, 2-methoxyphenyl, 3-methoxyphenyl, 4-methoxyphenyl, 2,6-dimethoxyphenyl, 2-chlorophenyl, 3-chlorophenyl, 4-chlorophenyl, 2-fluorophenyl, 3-fluorophenyl, 4-fluorophenyl, 2-cyanophenyl, 3-cyanophenyl, 4-cyanophenyl, 4-(dimethylamino)phenyl, 3-hydroxy-4-methoxyphenyl, 4-acetamidophenyl, 4-(methoxycarbonyl)phenyl, 4-(trifluoromethyl)phenyl, biphenyl, benzyl, 2-methylbenzyl, 3-methylbenzyl, 4-methylbenzyl, 2-fluorobenzyl, 3-fluorobenzyl, 4-fluorobenzyl, 2-chlorobenzyl, 3-chlorobenzyl, 4-chlorobenzyl, 2-cyanobenzyl, 3-cyanobenzyl, 4-cyanobenzyl, 2-methoxybenzyl, 3-methoxybenzyl, 4-methoxybenzyl, 4-dimethylaminobenzyl, 3-hydroxy-4-methoxybenzyl, 4-acetamidobenzyl, 4-(methoxycarbonyl)benzyl, 4-(trifluoromethyl)benzyl, 1-phenylethyl, 2-phenylethyl, 2-phenylpropyl, 3-phenylpropyl, 2-phenylethenyl, phenoxymethyl, 2-pyridyl, 3-pyridyl, 4-pyridyl, 2-pyridylmethyl, 3-pyridylmethyl, 4-pyridylmethy, 1-methylpyrrol-2-yl, 1-methylpyrrol-2-ylmethyl, 1-methylimidazol-2-yl, 1-methylimidazol-2-ylmethyl, 1-methylimidazol-4-yl, 1-methylimidazol-4-ylmethyl, 3-cyclohexen-1-yl, 3-cyclohexen-1-ylmethyl, 3,4-dihydro-2H-pyran-2-yl, 3,4-dihydro-2H-pyran-2-ylmethyl, 1-methylpiperidin-4-yl, 1-acetylpiperidin-4-yl, 1-benzylpiperidin-4-yl, 2-thienyl, 3-thienyl, thien-2-ylmethyl, thiazol-2-yl, thiazol-2-ylmethyl, 5-isoxazolyl, 5-isoxazolylmethyl, quinolin-2-yl, quinolin-2-ylmethyl, and pyrrolidinyl.

In some embodiments, particularly embodiments of Formulas IIIa and IVa, R$_{2a}$ is hydrogen.

In some embodiments, R''' is a non-interfering substituent. In some embodiments, R''' is R$_3$. In some embodiments, particularly embodiments of Formula III, R''' is R or R$_3$ when n is 1, R or one R and one R$_3$ when n is 2, or R when n is 3 to 4.

In some embodiments, $R_3$ is selected from the group consisting of —Z—$R_4$, —Z—X'—$R_4$, —Z—X'—Y—$R_4$, —Z—X'—Y—X'—Y—$R_4$, and —Z—X'—$R_5$. In some embodiments, $R_3$ is selected from the group consisting of —Z—$R_4$ and —Z—X'—Y—$R_4$.

In some embodiments, $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo.

In some embodiments, $R_4$ is hydrogen, alkyl, alkenyl, aryl, or heteroaryl. In some embodiments, $R_4$ is hydrogen, alkyl, alkenyl, aryl, or heteroaryl, wherein alkyl and alkenyl are optionally substituted by aryl or aryloxy and wherein aryl is optionally substituted by one or more substituents selected from the group consisting of alkyl, alkoxy, cyano, haloalkyl, and halogen. In some embodiments, $R_4$ is selected from the group consisting of aryl or heteroaryl, each of which may be unsubstituted or substituted by one or more substituents selected from the group consisting of alkyl, hydroxy, cyano, hydroxyalkyl, dialkylamino, and alkoxy.

In some embodiments, $R_5$ is selected from the group consisting of

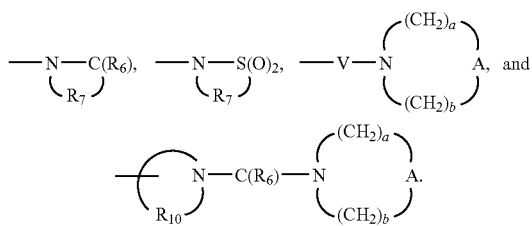

In some embodiments, $R_5$ is

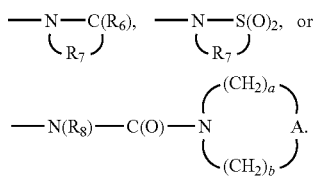

In some embodiments, $R_6$ is selected from the group consisting of =O and =S. In some embodiments, $R_6$ is =O.

In some embodiments, $R_7$ is $C_{2-7}$ alkylene. In some embodiments, $R_7$ is ethylene.

In some embodiments, $R_7$ is propylene.

In some embodiments, $R_8$ is selected from the group consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl. In some embodiments, $R_8$ is hydrogen or methyl. In some embodiments, $R_8$ is hydrogen.

In some embodiments, $R_9$ is selected from the group consisting of hydrogen and alkyl.

In some embodiments, $R_{10}$ is $C_{3-8}$ alkylene. In some embodiments, $R_{10}$ is pentylene.

In some embodiments, $R_{11}$ is $C_{3-9}$ alkylene or $C_{3-9}$ alkenylene, optionally interrupted by one hetero atom. In some embodiments, $R_{11}$ is $C_{1-6}$ alkylene or $C_{2-6}$ alkenylene, wherein the alkylene or alkenylene is optionally interrupted by one heteroatom. In some embodiments, $R_{11}$ is methylene; in some embodiments, $R_{11}$ is ethylene.

In some embodiments, $R_{12}$ is $C_{2-7}$ alkylene or $C_{2-7}$ alkenylene, optionally interrupted by one hetero atom. In some embodiments, $R_{12}$ is selected from the group consisting of a bond, $C_{1-5}$ alkylene, and $C_{2-5}$ alkenylene, wherein the alkylene or alkenylene is optionally interrupted by one heteroatom. In some embodiments, $R_{12}$ is ethylene.

In some embodiments, $R_{13}$ is selected from the group consisting of hydrogen and alkyl which may be optionally interrupted by one or more —O—groups. In some embodiments, $R_{13}$ is hydrogen.

In some embodiments, A is selected from the group consisting of —$CH_2$—, —O—, —C(O)—, —$S(O)_{0-2}$—, and —N($R_4$)—. In some embodiments, A is selected from the group consisting of —$CH_2$— and —O—.

In some embodiments, A' is selected from the group consisting of —O—, —$S(O)_{0-2}$—, —N(-Q-$R_4$)—, and —$CH_2$—. In some embodiments, A' is —$CH_2$—, —O—, or —N(-Q-$R_4$)—.

In some embodiments, Q is selected from the group consisting of a bond, —C($R_6$)—, —C($R_6$)—C($R_6$)—, —$S(O)_2$—, —C($R_6$)—N($R_8$)—W—, —$S(O)_2$—N($R_8$)—, —C($R_6$)—O—, and —C($R_6$)—N($OR_9$)—.

In some embodiments, Q is selected from the group consisting of —C(O)—, —$S(O)_2$—, and —C(O)—N($R_8$)—W—.

In some embodiments, V is selected from the group consisting of —C($R_6$)—, —O—C($R_6$)—, —N($R_8$)—C($R_6$)—, and —$S(O)_2$—. In some embodiments, V is —N($R_8$)—C(O)—.

In some embodiments, W is selected from the group consisting of a bond, —C(O)—, and —$S(O)_2$—. In some embodiments, W is selected from the group consisting of a bond and —C(O)—.

In some embodiments, X is $C_{1-10}$ alkylene or $C_{2-10}$ alkenylene. Preferably, X is $C_{1-10}$ alkylene or $C_{3-10}$ alkenylene. In some embodiments, particularly embodiments of Formulas IIIa and IVa, X is $C_{1-4}$ alkylene. In some embodiments, X is methylene.

In some embodiments, X' is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups. In some embodiments, X' is alkylene. In some embodiments, X' is ethylene, propylene, or butylene (including isobutylene).

In some embodiments, X" is —CH($R_{13}$)-alkylene- or —CH($R_{13}$)-alkenylene-, wherein the alkylene and alkenylene are optionally interrupted by one or more —O— groups. In some embodiments, particularly in embodiments of Formula IIIa and IVa, X" is —CH($R_{13}$)-alkylene- or —CH($R_{13}$)-alkenylene-.

In some embodiments, Y is selected from the group consisting of —$S(O)_{0-2}$—, —$S(O)_2$—N($R_9$)—, —C($R_6$)—, —C($R_6$)—O—, —O—C($R_6$)—, —O—C(O)—O—, —N($R_8$)-Q-, —C($R_6$)—N($R_8$)—, —O—C($R_6$)—N($R_8$)—, —C($R_6$)—N($OR_9$)—,

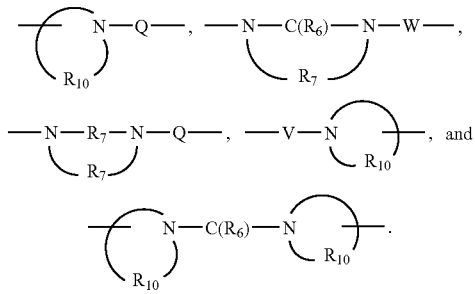

In some embodiments, Y is selected from the group consisting of —S(O)$_{0-2}$—, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, —C(R$_6$)—N(OR$_9$)—,

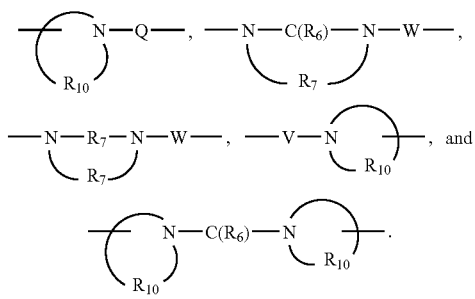

In some embodiments, Y is —N(R$_8$)—C(O)—, —N(R$_8$)—S(O)$_2$—, —N(R$_8$)—S(O)$_2$—N(R$_8$)—, —N(R$_8$)—C(O)—N(R$_8$)—, —N(R$_8$)—C(O)—N(R$_8$)—C(O)—,

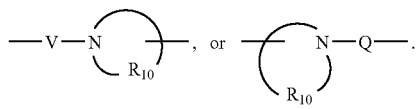

In some embodiments, Y is —NH—C(O)—, —NH—S(O)$_2$—, —NH—S(O)$_2$—N(R$_8$)—, —NH—C(O)—N(R$_8$)—, —NH—C(O)—NH—C(O)—, or

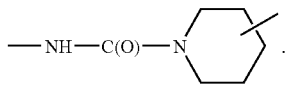

In some embodiments, Y' is selected from the group consisting of a bond, —C(O)—, —C(S)—, —S(O)$_2$—, —S(O)$_2$—N(R$_9$)—,

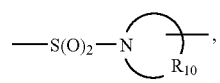

—C(O)—O—, —C(O)—N(R$_9$)—, —C(S)—N(R$_9$)—, —C(O)—N(R$_9$)—S(O)$_2$—, —C(O)—N(R$_8$)—C(O)—, —C(S)—N(R$_8$)—C(O)—,

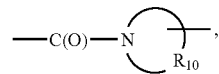

—C(O)—C(O)—, —C(O)—C(O)—O—, and —C(=NH)—N(R$_8$)—.

In some embodiments, Y' is selected from the group consisting of a bond, —C(O)—, —C(O)—O—, —S(O)$_2$—, —S(O)$_2$—N(R$_9$)—, —C(O)—N(R$_8$)—, —C(S)—N(R$_8$)—, —C(O)—N(R$_8$)—C(O)—, and

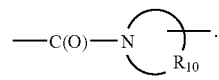

In some embodiments, particularly embodiments of Formulas IIIa and IVa, Y' is selected from the group consisting of a bond, —C(O)—, —C(O)—O—, —S(O)$_2$—, —S(O)$_2$—N(R$_8$)—, —C(O)—N(R$_8$)—, —C(O)—N(R$_8$)—C(O)—, and

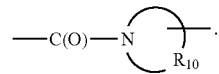

In some embodiments, Y' is selected from the group consisting of —C(O)—, —S(O)$_2$—, and —C(O)—N(R$_8$)—.

In some embodiments, Z is a bond or —O—. In some embodiments, Z is a bond. In some embodiments, Z is —O—.

In some embodiments, a and b are independently integers from 1 to 6 with the proviso that a+b is ≤7. In some embodiments, a and b are each 2.

In some embodiments, n is an integer from 0 to 4. In some embodiments, n is 0 or 1. In some embodiments, particularly embodiments of Formula IVa, n is 0.

In some embodiments, m is 0 or 1. In some embodiments m is 1. In some embodiments, m is 0.

In some embodiments, m is 0 or 1; with the proviso that when m is 1, then n is 0 or 1.

In some embodiments, particularly embodiments of Formula IIIa, m and n are 0. In some embodiments, n is 0 or m is 0.

In some embodiments, p is an integer from 0 to 3. In some embodiments, p is 0 or 1. In some embodiments, p is 0.

In some embodiments, m is 0 or 1, with the proviso that when m is 1, p is 0 or 1.

In some embodiments, p and m are 0.

In some embodiments, particularly embodiments of Formula III, R' is selected from the group consisting of:
—R$_4$,
—X'—R$_4$,
—X'—Y—R$_4$,
—X'—Y—X'—Y—R$_4$,
—X'—R$_5$,
—X"—O—NH—Y'—R$_1$', and
—X"—O—N=C(R$_1$')(R$_1$");
wherein X', X", Y, Y', R$_1$', R$_1$", R$_4$, and R$_5$, are as defined above.

In some embodiments, particularly embodiments of Formula III, R is R or R$_3$ when n is 1, R or one R and one R$_3$ when n is 2, or R when n is 3 to 4;

wherein:
R is selected from the group consisting of:
halogen,
hydroxy,
alkyl,
alkenyl,
haloalkyl,
alkoxy,
alkylthio, and
$N(R_9)_2$;
$R_3$ is selected from the group consisting of:
—Z—$R_4$,
—Z—X'—$R_4$,
—Z—X'—Y—$R_4$,
—Z—X'—Y—X'—Y—$R_4$, and
—Z—X'—$R_5$;
n is an integer from 0 to 4;
Z is a bond or —O—; and
X', Y, $R_4$, $R_5$, and $R_9$ are as defined above.

In some embodiments, particularly embodiments of Formulas IIIa and IVa, $R_2$ is alkyl or substituted alkyl, and $R_{2a}$ is hydrogen.

In some embodiments, $R_2$ is methyl or cyclopropyl, and $R_{2a}$ is hydrogen.

In some embodiments, particularly embodiments of Formulas IIIa and IVa, $R_2$ is alkenyl or substituted alkenyl, and $R_{2a}$ is hydrogen.

In some embodiments, particularly embodiments of Formulas IIIa and IVa, $R_2$ is aryl, arylalkylenyl, substituted aryl, or substituted arylalkylenyl, and $R_{2a}$ is hydrogen.

In some embodiments, particularly embodiments of Formulas IIIa and IVa, $R_2$ is heteroaryl, heteroarylalkylenyl, substituted heteroaryl, or substituted heteroarylalkylenyl, and $R_{2a}$ is hydrogen.

In some embodiments, particularly embodiments of Formulas IIIa and IVa, $R_2$ is heterocyclyl, heterocyclylalkylenyl, substituted heterocyclyl, or substituted heterocyclylalkylenyl, and $R_{2a}$ is hydrogen.

In some embodiments, $R_2$ is selected from the group consisting of methyl, (ethoxycarbonyl)methyl, ethyl, cyclopropyl, cyclopropylmethyl, 2-(ethoxycarbonyl)cyclopropylmethyl, propyl, butyl, 2-methylpropyl, tert-butyl, 3-methylbutyl, 2,2-dimethylpropyl, cyclopentyl, 2-cyclopentylethyl, furyl, fur-3-ylmethyl, furfuryl, furfurylmethyl, cyclohexyl, tetrahydrofuranyl, tetrahydrofuran-3-ylmethyl, 2-(methylthio)ethyl, 3-(methylthio)propyl, phenyl, 2-methylphenyl, 3-methylphenyl, 4-methylphenyl, 2-methoxyphenyl, 3-methoxyphenyl, 4-methoxyphenyl, 2,6-dimethoxyphenyl, 2-chlorophenyl, 3-chlorophenyl, 4-chlorophenyl, 2-fluorophenyl, 3-fluorophenyl, 4-fluorophenyl, 2-cyanophenyl, 3-cyanophenyl, 4-cyanophenyl, 4-(dimethylamino)phenyl, 3-hydroxy-4-methoxyphenyl, 4-acetamidophenyl, 4-(methoxycarbonyl)phenyl, 4-(trifluoromethyl)phenyl, biphenyl, benzyl, 2-methylbenzyl, 3-methylbenzyl, 4-methylbenzyl, 2-fluorobenzyl, 3-fluorobenzyl, 4-fluorobenzyl, 2-chlorobenzyl, 3-chlorobenzyl, 4-chlorobenzyl, 2-cyanobenzyl, 3-cyanobenzyl, 4-cyanobenzyl, 2-methoxybenzyl, 3-methoxybenzyl, 4-methoxybenzyl, 4-dimethylaminobenzyl, 3-hydroxy-4-methoxybenzyl, 4-acetamidobenzyl, 4-(methoxycarbonyl)benzyl, 4-(trifluoromethyl)benzyl, 1-phenylethyl, 2-phenylethyl, 2-phenylpropyl, 3-phenylpropyl, 2-phenylethenyl, phenoxymethyl, 2-pyridyl, 3-pyridyl, 4-pyridyl, 2-pyridylmethyl, 3-pyridylmethyl, 4-pyridylmethy, 1-methylpyrrol-2-yl, 1-methylpyrrol-2-ylmethyl, 1-methylimidazol-2-yl, 1-methylimidazol-2-ylmethyl, 1-methylimidazol-4-yl, 1-methylimidazol-4-ylmethyl, 3-cyclohexen-1-yl, 3-cyclohexen-1-ylmethyl, 3,4-dihydro-2H-pyran-2-yl, 3,4-dihydro-2H-pyran-2-ylmethyl, 1-methylpiperidin-4-yl, 1-acetylpiperidin-4-yl, 1-benzylpiperidin-4-yl, 2-thienyl, 3-thienyl, thien-2-ylmethyl, thiazol-2-yl, thiazol-2-ylmethyl, 5-isoxazolyl, 5-isoxazolylmethyl, quinolin-2-yl, quinolin-2-ylmethyl, pyrrolidinyl, 3,4-dichlorophenyl, α-methylbenzyl, methoxymethyl, trifluoromethyl, and 2,2,2-trifluoroethyl; and $R_{2a}$ is hydrogen.

In some embodiments, particularly embodiments of Formulas IIIa and IVa, $R_2$ is selected from the group consisting of methyl, (ethoxycarbonyl)methyl, ethyl, cyclopropyl, cyclopropylmethyl, 2-(ethoxycarbonyl)cyclopropylmethyl, propyl, butyl, 2-methylpropyl, tert-butyl, 3-methylbutyl, 2,2-dimethylpropyl, cyclopentyl, 2-cyclopentylethyl, furyl, fur-3-ylmethyl, furfuryl, furfurylmethyl, cyclohexyl, tetrahydrofuranyl, tetrahydrofuran-3-ylmethyl, 2-(methylthio)ethyl, 2-(methylthio)propyl, phenyl, 2-methylphenyl, 3-methylphenyl, 4-methylphenyl, 2-methoxyphenyl, 3-methoxyphenyl, 4-methoxyphenyl, 2,6-dimethoxyphenyl, 2-chlorophenyl, 3-chlorophenyl, 4-chlorophenyl, 2-fluorophenyl, 3-fluorophenyl, 4-fluorophenyl, 2-cyanophenyl, 3-cyanophenyl, 4-cyanophenyl, 4-(dimethylamino)phenyl, 3-hydroxy-4-methoxyphenyl, 4-acetamidophenyl, 4-(methoxycarbonyl)phenyl, 4-(trifluoromethyl)phenyl, biphenyl, benzyl, 2-methylbenzyl, 3-methylbenzyl, 4-methylbenzyl, 2-fluorobenzyl, 3-fluorobenzyl, 4-fluorobenzyl, 2-chlorobenzyl, 3-chlorobenzyl, 4-chlorobenzyl, 2-cyanobenzyl, 3-cyanobenzyl, 4-cyanobenzyl, 2-methoxybenzyl, 3-methoxybenzyl, 4-methoxybenzyl, 4-dimethylaminobenzyl, 3-hydroxy-4-methoxybenzyl, 4-acetamidobenzyl, 4-(methoxycarbonyl)benzyl, 4-(trifluoromethyl)benzyl, 1-phenylethyl, 2-phenylethyl, 2-phenylpropyl, 3-phenylpropyl, 2-phenylethenyl, phenoxymethyl, 2-pyridyl, 3-pyridyl, 4-pyridyl, 2-pyridylmethyl, 3-pyridylmethyl, 4-pyridylmethy, 1-methylpyrrol-2-yl, 1-methylpyrrol-2-ylmethyl, 1-methylimidazol-2-yl, 1-methylimidazol-2-ylmethyl, 1-methylimidazol-4-yl, 1-methylimidazol-4-ylmethyl, 3-cyclohexen-1-yl, 3-cyclohexen-1-ylmethyl, 3,4-dihydro-2H-pyran-2-yl, 3,4-dihydro-2H-pyran-2-ylmethyl, 1-methylpiperidin-4-yl, 1-acetylpiperidin-4-yl, 1-benzylpiperidin-4-yl, 2-thienyl, 3-thienyl, thien-2-ylmethyl, thiazol-2-yl, thiazol-2-ylmethyl, 5-isoxazolyl, 5-isoxazolylmethyl, quinolin-2-yl, quinolin-2-ylmethyl, and pyrrolidinyl; and $R_{2a}$ is hydrogen.

In some embodiments of Formulas IIIa and IVa, $R_1$ is selected from the group consisting of alkyl, arylalkylenyl, aryloxyalkylenyl, hydroxyalkyl, alkylsulfonylalkylenyl, —X'—Y—$R_4$, and —X'—$R_5$; wherein X' is alkylene; Y is —$N(R_8)$—C(O)—, —$N(R_8)$—S(O)$_2$—, —$N(R_8)$—S(O)$_2$—$N(R_8)$—, —$N(R_8)$—C(O)—$N(R_8)$—, —$N(R_8)$—C(O)—$N(R_9)$—C(O)—,

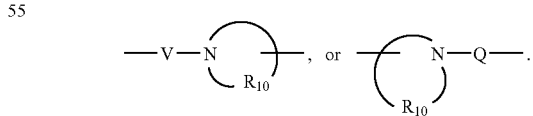

$R_4$ is hydrogen, alkyl, alkenyl, aryl, or heteroaryl; and $R_5$ is

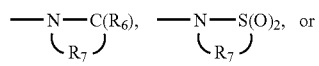

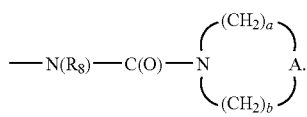

In some embodiments, $R_1$ is 2-methylpropyl or —X'—Y—$R_4$; X' is ethylene, propylene, or butylene; Y is —NH—C(O)—, —NH—S(O)$_2$—, —NH—S(O)$_2$—N($R_8$)—, —NH—C(O)—N($R_8$)—, —NH—C(O)—NH—C(O)—, or

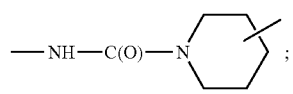

and $R_5$ is hydrogen or methyl.

In some embodiments, $R_1$ is 2-methylpropyl, 2-hydroxy-2-methylpropyl, or —X'—Y—$R_4$; X' is ethylene, propylene, or butylene (including isobutylene); Y is —NH—C(O)—, —NH—S(O)$_2$—, —NH—S(O)$_2$—N($R_8$)—, —NH—C(O)—N($R_8$)—, —NH—C(O)—NH—C(O)—, or

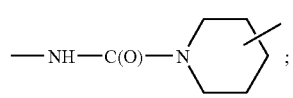

and $R_8$ is hydrogen or methyl.

In some embodiments, $R_1$ is selected from the group consisting of alkyl, arylalkylenyl, aryloxyalkylenyl, hydroxyalkyl, alkylsulfonylalkylenyl, —X'—Y—$R_4$, and —X'—$R_5$; wherein X' is alkylene; Y is —N($R_8$)—C(O)—, —N($R_8$)—S(O)$_2$—, —N($R_8$)—S(O)$_2$—N($R_8$)—, —N($R_8$)—C(O)—N($R_8$)—, —N($R_8$)—C(O)—N($R_8$)—C(O)—,

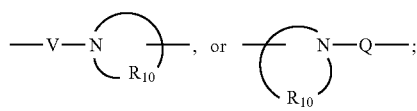

$R_4$ is hydrogen, alkyl, alkenyl, aryl, or heteroaryl, wherein alkyl and alkenyl are optionally substituted by aryl or aryloxy and wherein aryl is optionally substituted by one or more substituents selected from the group consisting of alkyl, alkoxy, cyano, haloalkyl, and halogen; and $R_5$ is

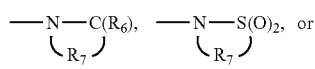

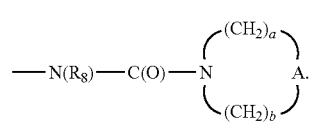

In some embodiments, $R_1$' and $R_1$" can join together to form a ring system selected from the group consisting of:

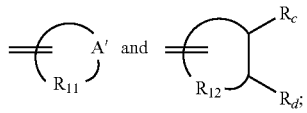

wherein A' is selected from the group consisting of —O—, —S(O)$_{0-2}$—, —N(-Q-$R_4$)—, and —CH$_2$—; $R_{11}$ is $C_{3-9}$ alkylene or $C_{3-9}$ alkenylene, optionally interrupted by one heteroatom; $R_{12}$ is $C_{2-7}$ alkylene or $C_{2-7}$ alkenylene, optionally interrupted by one heteroatom; and $R_c$ and $R_d$ are independently selected from the group consisting of hydrogen, halogen, hydroxy, alkyl, alkenyl, aryl, haloalkyl, alkoxy, alkylthio, and —N($R_9$)$_2$; or $R_c$ and $R_d$ can join to form a fused aryl ring or fused 5-10 membered heteroaryl ring containing one to four heteroatoms.

Alternatively, $R_1$' and $R_1$" can join together to form a ring system selected from the group consisting of:

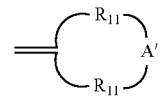

wherein the total number of atoms in the ring is 4 to 9, and

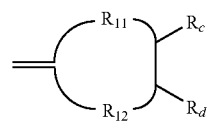

wherein the total number of atoms in the ring is 4 to 9; and further wherein A' is selected from the group consisting of —O—, —S(O)$_{0-2}$—, —N(-Q-$R_4$)—, and —CH$_2$—; $R_{11}$ is $C_{1-6}$ alkylene or $C_{2-6}$ alkenylene, wherein the alkylene or alkenylene is optionally interrupted by one heteroatom; $R_{12}$ is selected from the group consisting of a bond, $C_{1-5}$ alkylene, and $C_{2-5}$ alkenylene, wherein the alkylene or alkenylene is optionally interrupted by one heteroatom; and $R_c$ and $R_d$ are independently selected from the group consisting of hydrogen, halogen, hydroxy, alkyl, alkenyl, aryl, haloalkyl, alkoxy, alkylthio, and —N($R_9$)$_2$; or $R_c$ and $R_d$ can join to form a fused aryl ring or fused 5-10 membered heteroaryl ring containing one to four heteroatoms.

Preparation of the Compounds

Compounds of the invention can be prepared according to Reaction Scheme I where R, $R_1$, X, and n are as defined above, Hal is chloro, bromo, or iodo, and $R_2$' and $R_2$" are the same as $R_1$' and $R_1$" as defined above. In step (1) of Reaction Scheme I, a quinoline-3,4-diamine of Formula X is reacted with a carboxylic acid or an equivalent thereof to provide a 1H-imidazo[4,5-c]quinoline of Formula XI. Suitable equivalents to a carboxylic acid include orthoesters, and 1,1-dialkoxyalkyl alkanoates. The carboxylic acid or equivalent is selected such that it will provide the desired —X-Hal substituent in a compound of Formula XI. For example, Hal-X—CO$_2$H or Hal-X—C(O-alkyl)$_3$ will provide a compound with the desired —X-Hal substituent at the 2-position. The reaction can be run in the absence of solvent or in an inert solvent such as toluene. The reaction is run with sufficient heating to drive off any alcohol or water formed as a byproduct of the reaction. Optionally a catalyst such as pyridine hydrochloride can be included.

Alternatively, step (1) can be carried out by (i) reacting a compound of Formula X with an acyl halide of formula Hal-X—C(O)Cl or Hal-X—C(O)Br and then (ii) cyclizing. In part (i) the acyl halide is added to a solution of a compound of Formula X in an inert solvent such as acetonitrile, pyridine or dichloromethane. The reaction can be carried out at ambient temperature. A catalyst such as pyridine hydrochloride can be included. Alternatively, the reaction can be carried out in the presence of triethylamine. In part (ii) the product of part (i) is heated in pyridine. The two steps can be combined into a single step when the reaction is run in pyridine or solvents such as dichloromethane or dichloroethane in the presence of triethylamine.

Many compounds of Formula X are known and can be readily prepared using known synthetic routes; see for example, U.S. Pat. No. 4,689,338 (Gerster), U.S. Pat. No. 4,929,624 (Gerster et al.), U.S. Pat. No. 5,268,376 (Gerster), U.S. Pat. No. 5,389,640 (Gerster et al.), U.S. Pat. No. 6,331,539 (Crooks et al.), U.S. Pat. No. 6,451,810 (Coleman et al.), U.S. Pat. No. 6,541,485 (Crooks et al.), U.S. Pat. No. 6,660,747 (Crooks et al.), U.S. Pat. No. 6,670,372 (Charles et al.), U.S. Pat. No. 6,683,088 (Crooks et al.), U.S. Pat. No. 6,656,938 (Crooks et al.), and U.S. Pat. No. 6,664,264 (Dellaria et al.).

In step (2) of Reaction Scheme I a 1H-imidazo[4,5-c]quinoline of Formula XI is oxidized to provide an N-oxide of Formula XII using a conventional oxidizing agent that is capable of forming N-oxides. The reaction can be carried out by treating a solution of a compound of Formula XI in a suitable solvent such as chloroform or dichloromethane with 3-chloroperoxybenzoic acid at ambient temperature.

In step (3) of Reaction Scheme I an N-oxide of Formula XII is animated to provide a 1H-imidazo[4,5-c]quinoline-4-amine of Formula XIII. The reaction is carried out in two parts. In part (i) a compound of Formula XII is reacted with an acylating agent. Suitable acylating agents include alkyl- or arylsulfonyl chlorides (e.g., benzenesulfonyl chloride, methanesulfonyl chloride, or p-toluenesulfonyl chloride). In part (ii) the product of part (i) is reacted with an excess of an aminating agent. Suitable aminating agents include ammonia (e.g. in the form of ammonium hydroxide) and ammonium salts (e.g., ammonium carbonate, ammonium bicarbonate, ammonium phosphate). The reaction can be carried out by dissolving a compound of Formula XII in a suitable solvent such as dichloromethane or chloroform, adding ammonium hydroxide to the solution, and then adding p-toluenesulfonyl chloride. The product or a pharmaceutically acceptable salt thereof can be isolated using conventional methods.

In step (4) of Reaction Scheme I a 1H-imidazo[4,5-c]quinoline-4-amine of Formula XIII is treated with N-hydroxyphthalimide to provide an N-phthalimide-protected 1H-imidazo[4,5-c]quinolin-2-yl hydroxylamine of Formula XIV. The reaction is conveniently carried out by adding a base, such as triethylamine, to a solution of N-hydroxyphtlialimide in a suitable solvent such as N,N-dimethylformamide (DMF); and then adding the 1H-imidazo[4,5-c]quinoline-4-amine of Formula XIII in a suitable solvent (for example, DMF) to the resulting mixture. The reaction can be carried out at ambient temperature. The product or a pharmaceutically acceptable salt thereof can be isolated using conventional methods.

In step (5) of Reaction Scheme I an N-phthalimide-protected 1H-imidazo[4,5-c]quinolin-2-yl hydroxylamine of Formula XIV is converted to a 1H-imidazo[4,5-c]quinolin-2-yl hydroxylamine of Formula XV. Removal of the N-phthalimide protecting group is conveniently carried out by adding hydrazine to a suspension of an N-phthalimide-protected 1H-imidazo[4,5-c]quinolin-2-yl hydroxylamine of Formula XIV in a suitable solvent such as ethanol. The reaction can be carried out at ambient temperature. The product or a pharmaceutically acceptable salt thereof can be isolated using conventional methods.

In step (6) of Reaction Scheme I a 1H-imidazo[4,5-c]quinolin-2-yl hydroxylamine of Formula XV is reacted with an aldehyde or ketone of formula $R_2OC(O)R_2"$ to provide a 1H-imidazo[4,5-c]quinolin-2-yl oxime of Formula XVI. Numerous aldehydes and ketones of formula $R_2OC(O)R_2"$ are commercially available; others can be readily prepared using known synthetic methods. The reaction can be conveniently carried out by adding the aldehyde or ketone of formula $R_2OC(O)R_2"$ to a 1H-imidazo[4,5-c]quinolin-4-amine of Formula XV in a suitable solvent such as methanol. The reaction can be carried out at ambient temperature. The product or a pharmaceutically acceptable salt thereof can be isolated using conventional methods.

In step (7) of Reaction Scheme I a 1H-imidazo[4,5-c]quinolin-2-yl oxime of Formula XVI is reduced to provide a 1H-imidazo[4,5-c]quinolin-2-yl hydroxylamine of Formula XVI, which is a subgenus of Formulas I, II, III, and IIIa. The reduction is conveniently carried out by treating a 1H-imidazo[4,5-c]quinolin-2-yl oxime of Formula XVI with excess sodium cyanoborohydride in a suitable solvent or solvent mixture such as methanol/acetic acid. The reaction can be carried out at ambient temperature. The product or a pharmaceutically acceptable salt thereof can be isolated using conventional methods.

Reaction Scheme I

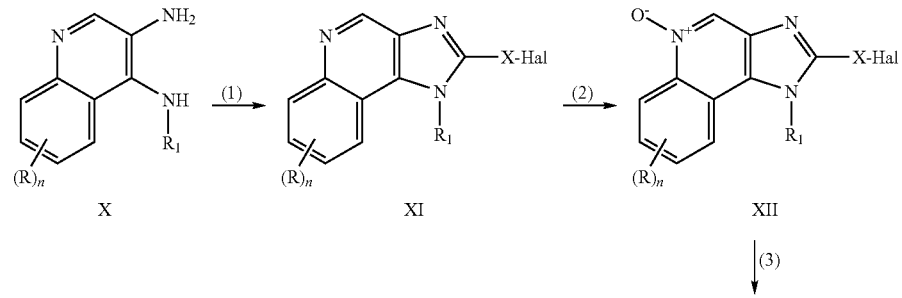

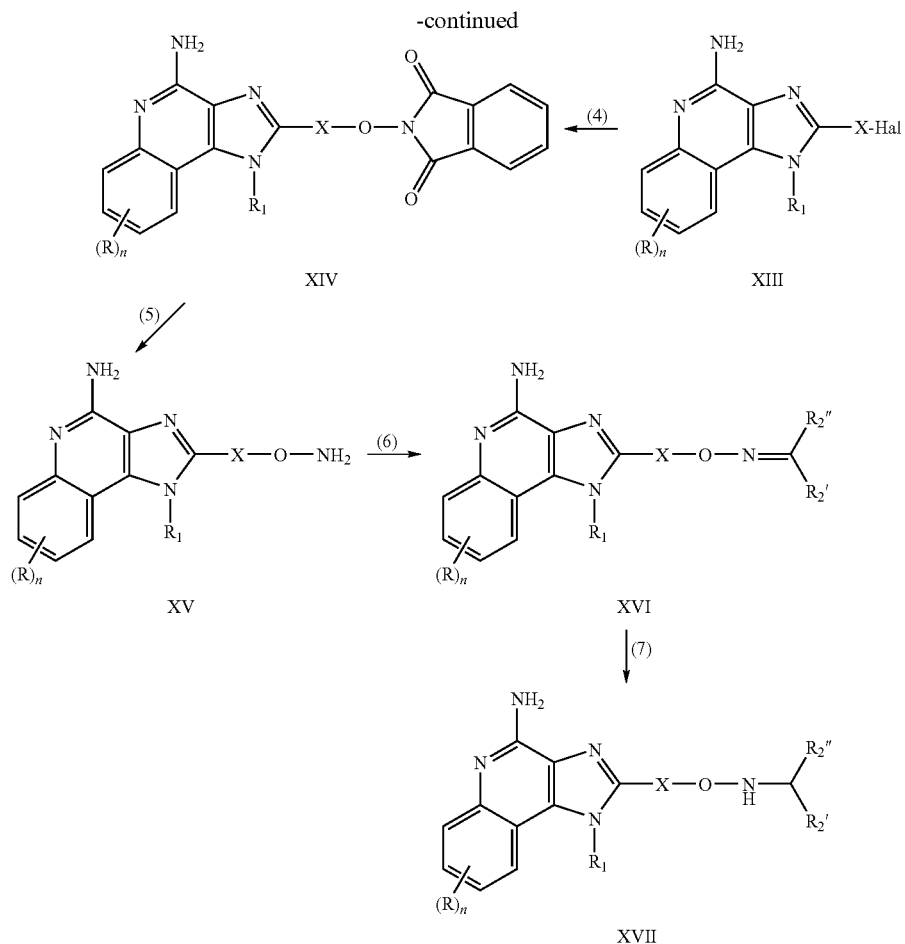

Compounds of the invention can be prepared according to Reaction Scheme II where R, $R_4$, $R_8$, Q, X, X', Hal, and n are as defined above, Boc is tert-butoxycarbonyl, $R_{5a}$ is

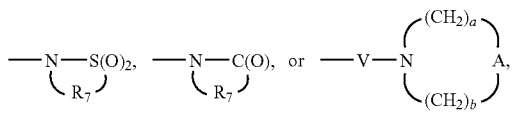

is wherein V is $-N(R_8)-C(R_6)-$, and $R_2'$ and $R_2''$ are the same as $R_1'$ and $R_1'$ as defined above. In step (1) of Reaction Scheme II a 1H-imidazo[4,5-c]quinolin-1-yl tert-butylcarbamate of Formula XVIII is treated with N-hydroxyphthalimide to provide an N-phthalimide-protected 1H-imidazo[4,5-c]quinolin-2-yl hydroxylamine of Formula XIX. The reaction is conveniently carried out by adding a base, such as triethylamine, to N-hydroxyphthalimide dissolved in a suitable solvent such as DMF; and then adding the 1H-imidazo[4,5-c]quinolin-1-yl tert-butylcarbamate of Formula XVIII in a suitable solvent (for example, DMF) to the resulting mixture. The reaction can be carried out at ambient temperature. The product or a pharmaceutically acceptable salt thereof can be isolated using conventional methods.

Compounds of Formula XVIII can be readily prepared using known synthetic routes; see for example, U.S. Pat. No. 6,451,485 (Crooks et al.), and U.S. Pat. No. 6,660,747 (Crooks et al to prepare a quinoline-3,4-diamine that can be treated according to steps (1) to (3) of Reaction Scheme I.

In step (2) of Reaction Scheme II an N-phthalimide-protected 1H-imidazo[4,5-c]quinolin-2-yl hydroxylamine of Formula XIX is converted to a 1H-imidazo[4,5-c]quinolin-2-yl hydroxylamine of Formula XX. Removal of the N-phthalimide protecting group is conveniently carried out by adding hydrazine to a suspension of an N-phthalimide-protected 1H-imidazo[4,5-c]quinolin-2-yl hydroxylamine of Formula XIX in a suitable solvent such as ethanol. The reaction can be carried out at ambient temperature. The product or a pharmaceutically acceptable salt thereof can be isolated using conventional methods.

In step (3) of Reaction Scheme II a 1H-imidazo[4,5-c]quinolin-2-yl hydroxylamine of Formula XX is reacted with an aldehyde or ketone of formula $R_2OC(O)R_2''$ to provide a 1H-imidazo[4,5-c]quinolin-2-yl oxime of Formula XXI. Numerous aldehydes and ketones of formula $R_2OC(O)R_2''$ are commercially available; others can be readily prepared using known synthetic methods. The reaction can be conveniently carried out by adding the aldehyde or ketone of formula $R_2OC(O)R_2''$ to a solution of the 1H-imidazo[4,5-c]quinolin-4-amine of Formula XX in a suitable solvent such as methanol. The reaction can be carried out at ambient temperature. The product or a pharmaceutically acceptable salt thereof can be isolated using conventional methods.

In step (4) of Reaction Scheme II a 1H-imidazo[4,5-c]quinolin-2-yl oxime of Formula XXI is deprotected to provide an amino group at the 1-position of a 1H-imidazo[4,5-c]quinolin-2-yl oxime of Formula XXII. The reaction can be conveniently carried out by dissolving a compound of Formula XXI in a mixture of trifluoroacetic acid and a suitable solvent such as dichloromethane. The reaction can be carried out at ambient temperature. The product or a pharmaceutically acceptable salt thereof, including the trifluoroacetate salt, can be isolated using conventional methods.

In steps (5) and (5a) of Reaction Scheme II a 1H-imidazo[4,5-c]quinolin-2-yl oxime of Formula XXII is converted to a 1H-imidazo[4,5-c]quinolin-2-yl oxime of Formula XXI or XXIV, using conventional methods. For example, sulfonamides of Formula XXIII (Q is —S(O)$_2$—) can be prepared by reacting a compound of Formula XXII with a sulfonyl chloride of formula R$_4$S(O)$_2$Cl. The reaction can be carried out at ambient temperature in an inert solvent such as chloroform or dichloromethane by adding the sulfonyl chloride to a compound of Formula XXII in the presence of a base such as N,N-diisopropylethylamine, triethylamine, or pyridine. Sulfamides of Formula XXIII (Q is, for example, —S(O)$_2$—N(R$_8$)—) can be prepared by reacting a compound of Formula XXII with a sulfamoyl chloride of formula R$_4$(R$_8$)NS(O)$_2$Cl or by reacting a compound of Formula XXII with sulfuryl chloride to generate a sulfamoyl chloride in situ, and then reacting the resulting sulfamoyl chloride with an amine of formula HN(R$_8$)R$_4$. The product or a pharmaceutically acceptable salt thereof can be isolated using conventional methods. Some sulfamoyl chlorides of formula R$_4$(R$_8$)NS(O)$_2$Cl and many sulfonyl chlorides of formula R$_4$S(O)$_2$Cl and amines of formula HN(R$_8$)R$_4$ are commercially available; others can be prepared using known synthetic methods.

In another example, using step (5a) of Reaction Scheme II, a 1H-imidazo[4,5-c]quinolin-2-yl oxime of Formula XXII is reacted with a chloroalkanesulfonyl chloride of formula C$_1$—R$_7$—S(O)$_2$Cl to provide a compound of Formula XXIV, wherein R$_{5a}$ is a ring having the structure

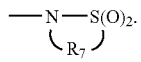

The reaction is preferably carried out by adding the chloroalkanesulfonyl chloride to a solution of a compound of Formula XXII in a suitable solvent such as dichloromethane in the presence of a base such as triethylamine. The intermediate chloroalkanesulfonamide may optionally be isolated before treatment with a stronger base such as 1,8-diazabicyclo[5.4.0]undec-7-ene (DBU) at ambient temperature. If the intermediate chloroalkanesulfonamide is isolated, the reaction with DBU can be carried out in a suitable solvent such as DMF. The product or a pharmaceutically acceptable salt thereof can be isolated using conventional methods.

Amides of Formulas XXIII (Q is, for example, —C(O)—) and XXIV can be prepared from 1H-imidazo[4,5-c]quinolin-2-yl oxime of Formula XXII using conventional methods. For example, a compound of Formula XXII can be reacted with an acid chloride of formula R$_4$C(O)Cl to provide a compound of Formula XXIII. The reaction can be carried out by adding the acid chloride to a solution of a compound of Formula XXII in a suitable solvent such as chloroform, optionally in the presence of a base such as N,N-diisopropylethylamine, triethylamine, or pyridine, at ambient temperature. The product or a pharmaceutically acceptable salt thereof can be isolated using conventional methods.

In another example shown in step (5a), a 1H-imidazo[4,5-c]quinolin-2-yl oxime of Formula XXII is reacted with a chloroalkanoyl chloride compound of formula C$_1$—R$_7$—C(O)Cl to provide a compound of Formula XXIV, wherein R$_{5a}$ is a ring having the structure

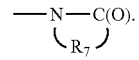

The reaction is preferably carried out by adding the chloroalkanoyl chloride compound to a compound of Formula XXII in a suitable solvent such as dichloromethane in the presence of a base such as N,N-diisopropylethylamine. The intermediate chloroalkanamide may optionally be isolated before treatment with a stronger base such as DBU at ambient temperature. If the intermediate chloroalkanamide is isolated, the reaction with DBU can be carried out in a suitable solvent such as DMF. The product or a pharmaceutically acceptable salt thereof can be isolated using conventional methods.

Ureas and thioureas of Formula XXIII (Q is, for example, —C(O)—N(R$_8$)— or —C(S)—N(R$_8$)—) and XXIV can be prepared from 1H-imidazo[4,5-c]quinolin-2-yl oximes of Formula XXII using conventional methods. For example, a compound of Formula XXII can be reacted with an isocyanate of formula R$_4$N═C═O. The reaction can be carried out by adding the isocyanate to a solution of a compound of Formula XXII in a suitable solvent such as chloroform, optionally in the presence of a base such as N,N-diisopropylethylamine, or triethylamine, at ambient temperature. Alternatively, a compound of Formula XXII can be reacted with, for example, a thioisocyanate of formula R$_4$N═C═S, a sulfonyl isocyanate of formula R$_4$S(O)$_2$N═C═O or a carbamoyl chloride of formula R$_4$N(R$_8$)C(O)Cl. The product or a pharmaceutically acceptable salt thereof can be isolated using conventional methods.

In steps (6) and (6a) of Reaction Scheme II a 1H-imidazo[4,5-c]quinolin-2-yl oxime of Formula XXIII or Formula XXIV is reduced to provide a 1H-imidazo[4,5-c]quinolin-2-yl hydroxylamine of Formula XXV or Formula XXVI, each of which is a subgenus of Formulas I, II, III, and IIIa. The reduction is conveniently carried out by treating a 1H-imidazo[4,5-c]quinolin-2-yl oxime of Formula XXIII or Formula XXIV with excess sodium cyanoborohydride in a suitable solvent or solvent mixture such as methanol/acetic acid. The reaction can be carried out at ambient temperature. The product or a pharmaceutically acceptable salt thereof can be isolated using conventional methods.

Reaction Scheme II

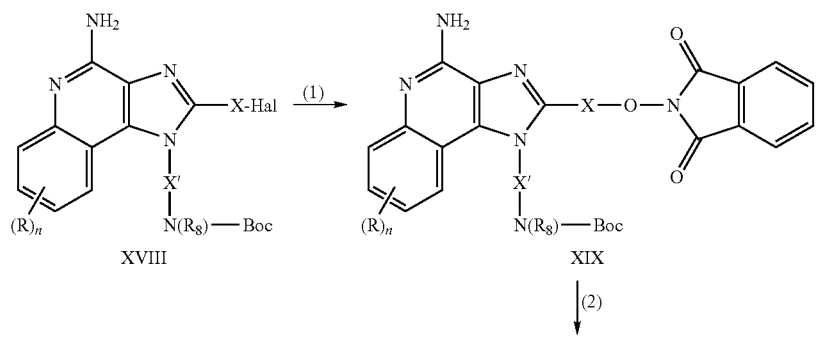

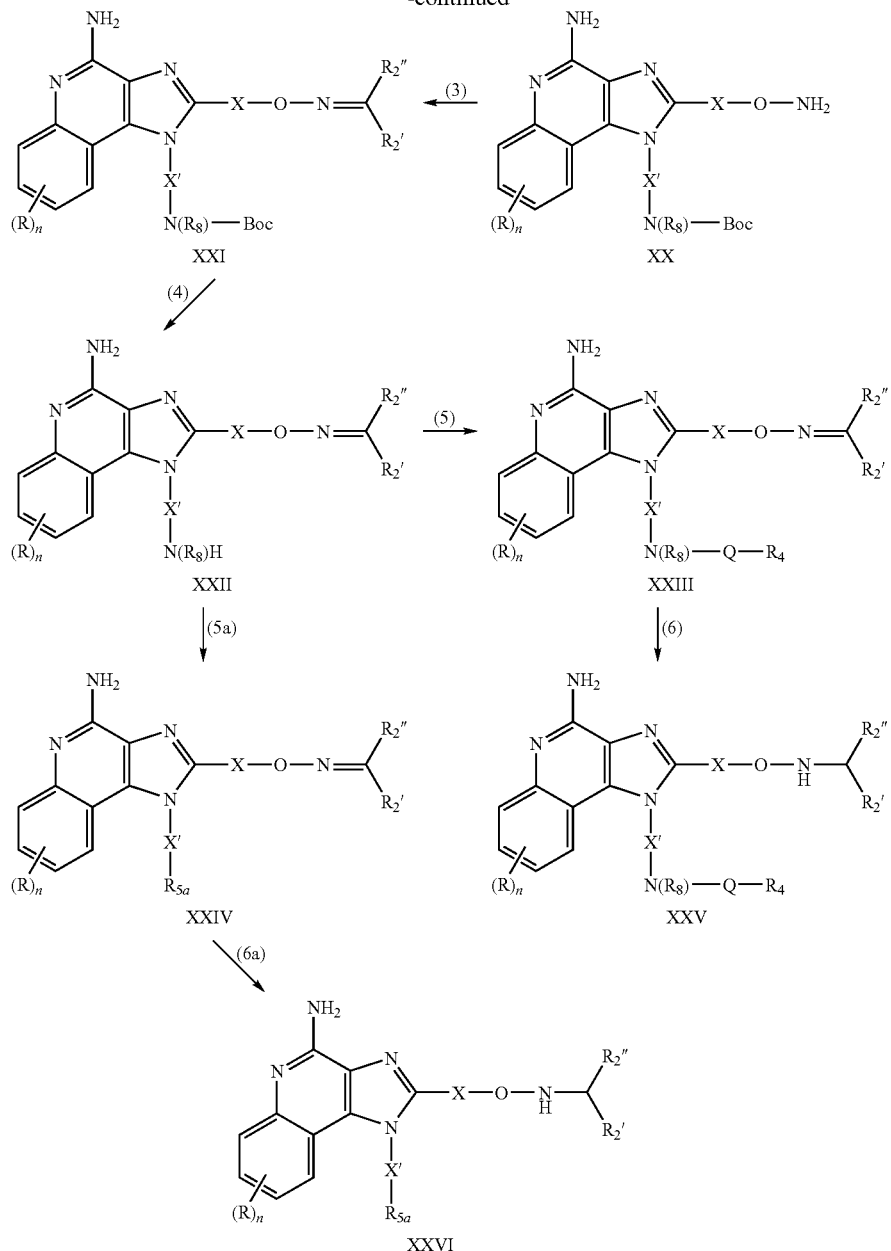

Compounds of the invention can be prepared according to Reaction Scheme III where n is as defined above; each $R_B$ is independently selected from the group consisting of hydroxy, alkyl, alkoxy, —$N(R_9)_2$; $X_c$ is $C_{1\text{-}10}$ alkylene; P is a removable protecting group, such as an alkanoyloxy group (e.g., acetoxy) or an aryloxy group (e.g., benzoyloxy); $R_2'$ and $R_2''$ are the same as $R_1'$ and $R_1''$ as defined above; and $R_{1c}$ is a subset of $R_1$ as defined above, which does not include those groups that one skilled in the art would recognize as being susceptible to reduction in step (5). These groups include, for example, alkenyl, alkynyl, and aryl groups, and groups bearing nitro and —S— substitutents. In step (1) of Reaction Scheme III a quinoline-3,4-diamine of Formula Xa is reacted with a carboxylic acid of the formula, HO—X—$CO_2H$, with a trialkyl orthoester of the formula HO—X—C(O—$C_{1\text{-}4}$ alkyl)$_3$, or with a combination thereof (wherein "alkyl" is a straight or branched chain) to provide a 1H-imidazo[4,5-c]quinolin-2-yl alcohol of Formula XXVII. The reaction is run with sufficient heating to drive off any alcohol or water formed as a byproduct of the reaction. Optionally a catalyst such as pyridine hydrochloride can be included. Compounds of Formula Xa are a subset of compounds of Formula X, which are shown in Reaction Scheme I.

In step (2) of Reaction Scheme III the hydroxyl group of a 1H-imidazo[4,5-c]quinoline of Formula XXVII is protected with a removable protecting group such as an alkanoyloxy group (e.g., acetoxy) or aroyloxy group (e.g., benzoyloxy) to provide a 1H-imidazo[4,5-c]quinoline of Formula XXVII. Suitable protecting groups and reactions for their placement and removal are well known to those skilled in the art. See, for example, U.S. Pat. No. 4,689,338 (Gerster), Examples 115 and 120 and 5,389,640 (Gerster et al.), Examples 2 and 3.

For some embodiments, it is possible to combine steps (1) and (2) when an acid chloride of the Formula PO—X—$CO_2Cl$ is used under the conditions of step (1). Some acid chlorides of this type, for example, acetoxyacetyl chloride, are commercially available.

In step (3) of Reaction Scheme III a 1H-imidazo[4,5-c]quinoline of Formula XXVIII is oxidized to provide an N-oxide of Formula XXIX using a conventional oxidizing agent that is capable of forming N-oxides. The reaction can be carried out by treating a solution of a compound of Formula XXVIII in a suitable solvent such as chloroform or dichloromethane with 3-chloroperoxybenzoic acid at ambient temperature.

In step (4) of Reaction Scheme III an N-oxide of Formula XXIX is aminated and the protecting group removed to provide a 1H-imidazo[4,5-c]quinoline-4-amine of Formula XXX. The amination reaction is carried out in two parts. In part (i) a compound of Formula XXIX is reacted with an acylating agent. Suitable acylating agents include alkyl- or arylsulfonyl chlorides (e.g., benzenesulfonyl chloride, methanesulfonyl chloride, or p-toluenesulfonyl chloride). In part (ii) the product of part (i) is reacted with an excess of an aminating agent. Suitable aminating agents include ammonia (e.g. in the form of ammonium hydroxide) and ammonium salts (e.g., ammonium carbonate, ammonium bicarbonate, ammonium phosphate). The reaction can be carried out by dissolving a compound of Formula XIX in a suitable solvent such as dichloromethane or chloroform, adding ammonium hydroxide to the solution, and then adding p-toluenesulfonyl chloride. The protecting group is removed using well-known methods. The product or a pharmaceutically acceptable salt thereof can be isolated using conventional methods.

In step (5) of Reaction Scheme III a 1H-imidazo[4,5-c]quinoline-4-amine of Formula XXX is reduced to provide a 6,7,8,9-tetrahydro-1H-imidazo[4,5-c]quinoline-4-amine of Formula XXXI. The reaction can be conveniently carried out by suspending or dissolving a compound of Formula XXX in ethanol, adding a catalytic amount of rhodium on carbon, and hydrogenating. Alternatively, the reaction can be carried out by suspending or dissolving a compound of Formula XXX in trifluoroacetic acid, and adding platinum (IV) oxide, and hydrogenating. The reaction can be carried out in a Parr apparatus. The product or a pharmaceutically acceptable salt thereof can be isolated using conventional methods.

In step (6) of Reaction Scheme III a 6,7,8,9-tetrahydro-1H-imidazo[4,5-c]quinoline-4-amine of Formula XXXI is treated with N-hydroxyphthalimide under Mitsunobu reaction conditions to provide an N-phthalimide-protected 6,7,8,9-tetrahydro-1H-imidazo[4,5-c]quinolin-2-yl hydroxylamine of Formula XXXI. The reaction is conveniently carried out by adding triphenylphosphine and N-hydroxyphthalimide to a solution of a compound of Formula XXXI in a suitable solvent such as tetrahydrofuran, and then slowly adding diethyl azodicarboxylate or diisopropyl azodicarboxylate. The reaction can be carried out at ambient temperature or at an elevated temperature, such as 60° C. The product or a pharmaceutically acceptable salt thereof can be isolated using conventional methods.

Alternatively, step (6) may be carried out in two parts by (i) converting the hydroxy group in a compound of Formula XXXI to a leaving group and (ii) displacing the leaving group with N-hydroxyphthalimide in the presence of a base. Part (i) of step (6) is conveniently carried out by treating the hydroxy-substituted 6,7,8,9-tetrahydro-1H-imidazo[4,5-c]quinoline-4-amine of Formula XXXI with thionyl chloride in a suitable solvent such as 1,2-dichloroethane. The reaction may be carried out at ambient temperature, and the product can be isolated by conventional methods. Part (ii) of step (6) may be carried out under the conditions described in step (4) of Reaction Scheme I, and the product of Formula XXXII or pharmaceutically acceptable salt thereof can be isolated using conventional methods.

In step (7) of Reaction Scheme III an N-phthalimide-protected 6,7,8,9-tetrahydro-1H-imidazo[4,5-c]quinolin-2-yl hydroxylamine of Formula XXXII is converted to a 6,7,8,9-tetrahydro-1H-imidazo[4,5-c]quinolin-2-yl hydroxylamine of Formula XXXIII. Removal of the N-phthalimide protecting group is conveniently carried out by adding hydrazine to a suspension of an N-phthalimide-protected 6,7,8,9-tetrahydro-1H-imidazo[4,5-c]quinolin-2-yl hydroxylamine of Formula XXXII in a suitable solvent such as ethanol. The reaction can be carried out at ambient temperature. The product or a pharmaceutically acceptable salt thereof can be isolated using conventional methods.

In step (8) of Reaction Scheme III a 6,7,8,9-tetrahydro-1H-imidazo[4,5-c]quinolin-2-yl hydroxylamine of Formula XXXIII is reacted with an aldehyde or ketone of formula $R_2OC(O)R_2"$ to provide a 6,7,8,9-tetrahydro-1H-imidazo[4,5-c]quinolin-2-yl oxime of Formula XXXIV as in step (3) of Reaction Scheme II. The product or pharmaceutically acceptable salt thereof can be isolated using conventional methods.

In step (9) of Reaction Scheme III a 1H-imidazo[4,5-c]quinolin-2-yl oxime of Formula XXXIV is reduced to provide a 1H-imidazo[4,5-c]quinolin-2-yl hydroxylamine of Formula XXXV, which is a subgenus of Formulas I, II, IV and IVa. The reduction is carried out as described in step (7) of Reaction Scheme I. The product or pharmaceutically acceptable salt thereof can be isolated using conventional methods.

Reaction Scheme III

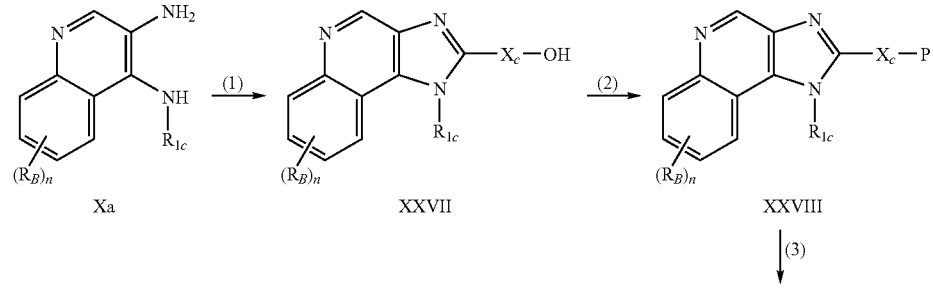

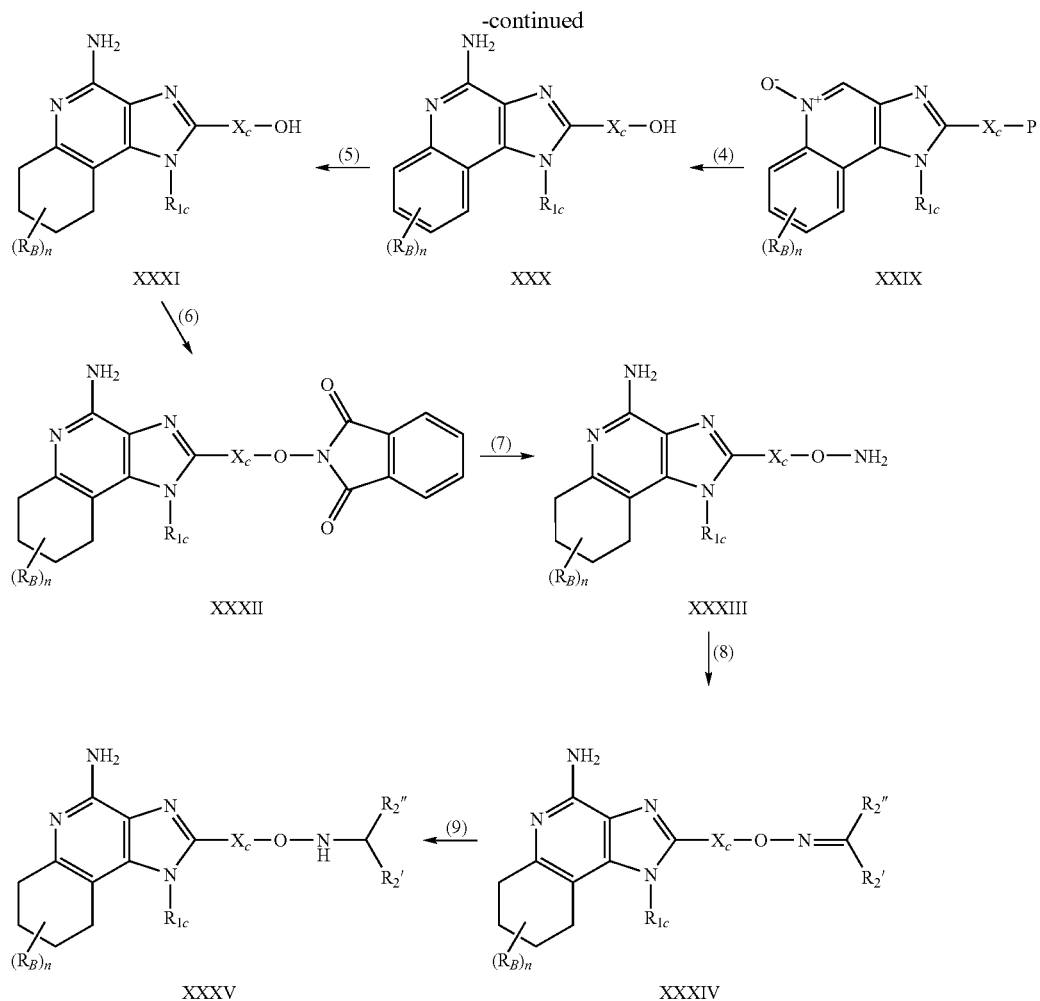

Compounds of the invention can be prepared according to Reaction Scheme IV where $R_1$, R, X, and Hal are as defined above, p is 0 to 3, $R_2'$ and $R_2''$ are the same as $R_1'$ and $R_1''$ as defined above, and $R_{3a}$ is —$R_{4b}$, —$X'_a$—$R_4$, —$X'_b$—Y—$R_4$, or —$X'_b$—$R_5$; where $X'_a$ is alkenylene; $X'_b$ is arylene, heteroarylene, and alkenylene interrupted or terminated by arylene or heteroarylene; $R_{4b}$ is aryl or heteroaryl where the aryl or heteroaryl groups can be unsubstituted or substituted as defined in $R_4$ above; and $R_4$, $R_5$, and Y are as defined above. In step (1) of Reaction Scheme IV a halogen substituted 1H-imidazo[4,5-c]quinolin-2-yl oxime of Formula XXXVI is coupled with a boronic acid of the formula $R_{3a}$—B(OH)$_2$ (or the corresponding anhydride or esters, $R_{3a}$—B(O-alkyl)$_2$, thereof) using Suzuki coupling conditions to provide a 1H-imidazo[4,5-c]quinolin-2-yl oxime of Formula XXXVII. A compound of Formula XXXVI is combined with a boronic acid of the formula $R_{3a}$—B(OH)$_2$ in the presence of palladium (II) acetate, triphenylphosphine and a base such as aqueous sodium carbonate in a suitable solvent such as n-propanol or n-propanol and water. The reaction can be carried out at an elevated temperature (e.g., 80° C.-100° C.). The product or a pharmaceutically acceptable salt thereof can be isolated using conventional methods. Halogen substituted 1H-imidazo[4,5-c]quinolin-2-yl oximes of Formula XXXVI can be prepared as described above in steps (1)-(6) of Reaction Scheme I or steps (1)-(5) or (5a) or Reaction Scheme II, wherein one of the R groups is Hal. Numerous boronic acids of Formula $R_{3a}$—B(OH)$_2$, anhydrides thereof, and boronic acid esters of Formula $R_{3a}$—B(O-alkyl)$_2$ are commercially available; others can be readily prepared using known synthetic methods.

In step (2) of Reaction Scheme IV a 1H-imidazo[4,5-c]quinolin-2-yl oxime of Formula XXXVII is reduced to provide a 1H-imidazo[4,5-c]quinolin-2-yl hydroxylamine of Formula XXXVIII, which is a subgenus of Formulas I, II, III, and IIIa. The reduction is carried out as described in step (7) of Reaction Scheme I. The product or a pharmaceutically acceptable salt thereof can be isolated using conventional methods.

Reaction Scheme IV

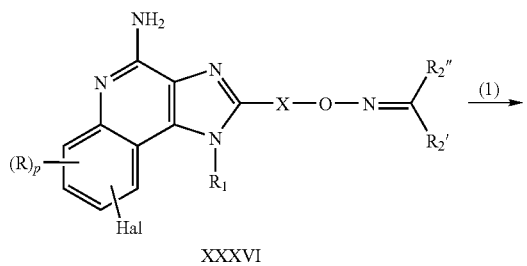

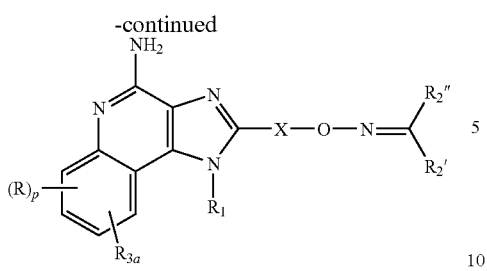

XXXVII

↓(2)

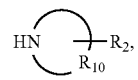... (structure)

XXXVIII

Compounds of the invention can be prepared according to Reaction Scheme V where R, $R_1$, $R_2$, X, and n are as defined above, and $Y_a'$ is Y' defined above, excluding a bond. In step (1) of Reaction Scheme V, a 1H-imidazo[4,5-c]quinolin-2-yl hydroxylamine of Formula XV is converted to a 1H-imidazo[4,5-c]quinolin-2-yl hydroxylamine of Formula XXXIX, a subgenus of Formulas I, II, III, and IIIa, using conventional methods. For example, sulfonamides of Formula XXXIX ($Y_a'$ is —S(O)$_2$—) can be prepared by reacting a compound of Formula XV with a sulfonyl chloride of formula $R_2S(O)_2Cl$. The reaction can be carried out at ambient temperature in an inert solvent such as chloroform or dichloromethane by adding the sulfonyl chloride to a compound of Formula XV in the presence of a base such as N,N-diisopropylethylamine, triethylamine, or pyridine.

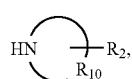

Sulfamides of Formula XXXIX ($Y_a'$ is —S(O)$_2$—N($R_8$)— or can be prepared by reacting a compound of Formula XV with sulfuryl chloride to generate a sulfamoyl chloride in situ, and then reacting the sulfamoyl chloride with an amine of formula HN($R_8$)$R_2$, or

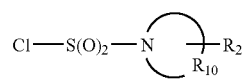

or by reacting a compound of Formula XV with a sulfamoyl chloride of formula $R_2(R_8)NS(O)_2Cl$ or

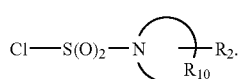

The product or a pharmaceutically acceptable salt thereof can be isolated using conventional methods. Many sulfonyl chlorides of formula $R_2S(O)_2Cl$, amines of formulas HN($R_8$)$R_2$, and

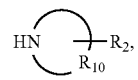

and some sulfamoyl chlorides of formulas $R_2(R_8)NS(O)_2Cl$ and

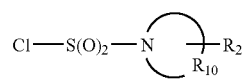

are commercially available; others can be prepared using known synthetic methods.

Amides of Formula XXXIX ($Y_a'$ is —C(O)—) can be prepared from 1H-imidazo[4,5-c]quinolin-2-yl hydroxylamines of Formula XV using conventional methods. For example, a compound of Formula XV can be reacted with an acid chloride of formula $R_2C(O)Cl$ to provide a compound of Formula XXXIX. The reaction can be carried out by adding the acid chloride to a solution of a compound of Formula XV in a suitable solvent such as chloroform, optionally in the presence of a base such as N,N-diisopropylethylamine, triethylamine, or pyridine, at ambient temperature. The product or a pharmaceutically acceptable salt thereof can be isolated using conventional methods.

Ureas and thioureas of Formula XXXIX ($Y_a'$ is —C(O)—N($R_8$)—, —C(S)—N($R_8$)—, —C(O)—N($R_8$)—S(O)$_2$—, —C(O)—N($R_8$)—C(O)—, —C(S)—N($R_8$)—C(O)—, or

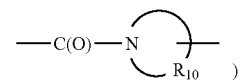

can be prepared from 1H-imidazo[4,5-c]quinolin-2-yl hydroxylamines of Formula XV using conventional methods. For example, a compound of Formula XV can be reacted with an isocyanate of formula $R_2N=C=O$. The reaction can be carried out by adding the isocyanate to a solution of a compound of Formula XV in a suitable solvent such as chloroform, optionally in the presence of a base such as N,N-diisopropylethylamine, or triethylamine, at ambient temperature. Alternatively, a compound of Formula XV can be reacted with a thioisocyanate of formula $R_2N=C=S$, a sulfonyl isocyanate of formula $R_2S(O)_2N=C=O$ or a carbamoyl chloride of formula $R_2N(R_8)C(O)Cl$ or

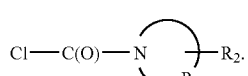

The product or a pharmaceutically acceptable salt thereof can be isolated using conventional methods.

Reaction Scheme V

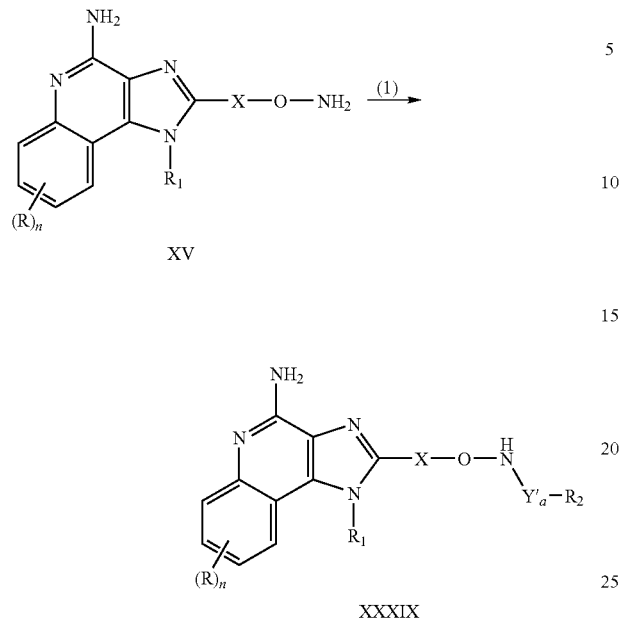

Compounds of the invention wherein $R_{2a}$ is other than hydrogen can be prepared according to Reaction Scheme VI where R, $R_1$, $R_2$, X, Y', and n are as defined above.

In step (1) of Reaction Scheme VI, a 1H-imidazo[4,5-c]quinolin-2-yl hydroxylamine of Formula XL, a subgenus of Formulas I, II, I, and IIIa, is prepared by reductive alkylation of a 1H-imidazo[4,5-c]quinolin-2-yl hydroxylamine of Formula XV. The reaction is carried out in two steps, (i) reacting a compound of Formula XV with the appropriate aldehyde to provide an oxime and (ii) reducing the oxime, using the methods of steps (6) and (7), respectively, of Reaction Scheme I.

In step (2) of Reaction Scheme VI, a 1H-imidazo[4,5-c]quinolin-2-yl hydroxylamine of Formula XL is converted to a 1H-imidazo[4,5-c]quinolin-2-yl hydroxylamine of Formula XLI, a subgenus of Formulas I, II, and III. Compounds of Formula XLI wherein Y' is a bond are prepared by subjecting the compound of Formula XL to a second alkylation. Compounds of Formula XLI wherein Y' is other than a bond are prepared using the methods of Reaction Scheme V. The product or a pharmaceutically acceptable salt thereof can be isolated using conventional methods.

Reaction Scheme VI

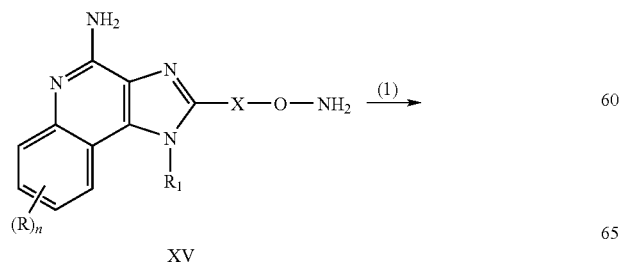

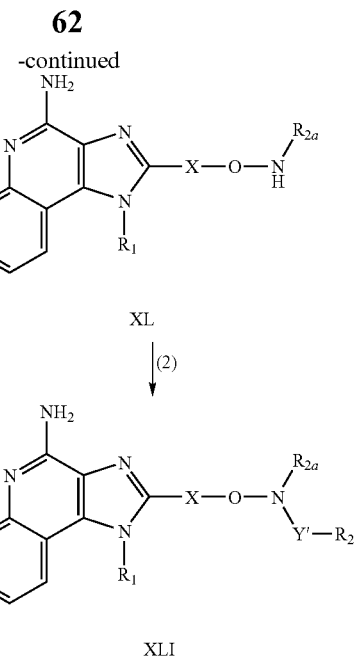

For some embodiments, tetrahydroquinolines of the invention can be prepared according to Reaction Scheme VII, wherein $R_B$, $R_{1c}$, $X_c$, $Y_a'$, $R_2$, and n are as defined above. The reaction in Reaction Scheme VII can be carried out according to one of the methods described in Reaction Scheme V to provide a tetrahydroquinoline of Formula XLII, a subgenus of Formulas I, II, IV, and IVa. The product or pharmaceutically acceptable salt thereof can be isolated by conventional methods. Tetrahydroquinolines of Formula XXXI can also be treated according to the methods described in Reaction Scheme V to provide compounds of the invention.

Reaction Scheme VII

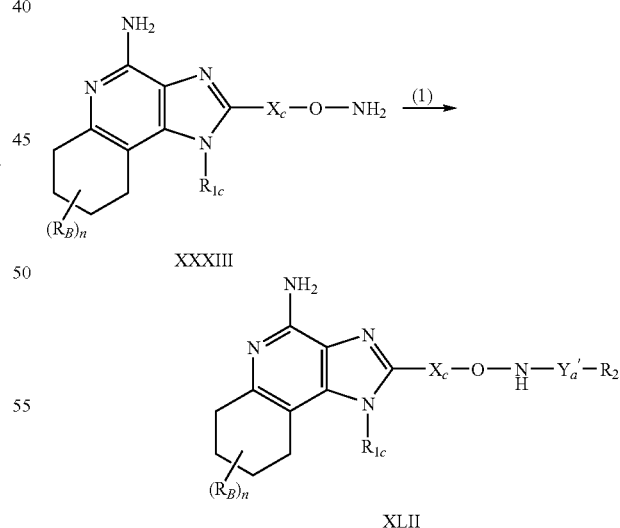

Compounds of the invention can be prepared according to Reaction Scheme VIII where R, $R_1$, $R_2$, $R_2'$, $R_2''$, $R_{2a}$, X, Y', and Hal are as defined above; E is carbon (imidazoquinoline ring) or nitrogen (imidazonaphthyridine ring); n is an integer from 0 to 4 (imidazoquinoline ring) or 0 to 3 (imidazonaphthyridine ring) with the proviso that when m is 1, then n is 0 or 1; and D is —Br, —I, or —OCH₂Ph; wherein Ph is phenyl.

In step (1) of Reaction Scheme VIII, an aniline or aminopyridine of Formula XLIII is treated with the condensation product generated from 2,2-dimethyl-1,3-dioxane-4,6-dione (Meldrum's acid) and triethyl orthoformate to provide an imine of Formula XLIV. The reaction is conveniently carried out by adding a solution of an aniline or aminopyridine of Formula XLIII to a heated mixture of Meldrum's acid and triethyl orthoformate and heating the reaction at an elevated temperature. The product can be isolated using conventional methods. Many anilines and aminopyridines of Formula XLIII are commercially available; others can be prepared by known synthetic methods. For example, benzyloxypyridines of Formula XLIII can be prepared using the method of Holladay et al., *Biorg. Med. Chem. Lett.*, 8, pp. 2797-2802, (1998).

In step (2) of Reaction Scheme VIII, an imine of Formula XLIV undergoes thermolysis and cyclization to provide a compound of Formula XLV. The reaction is conveniently carried out in a medium such as DOWTHERM A heat transfer fluid at a temperature of 200° C. to 250° C. The product can be isolated using conventional methods. Isomers of the compound of Formula XLIII or Formula XLV, wherein E is nitrogen, can also be synthesized and can be used to prepare compounds of the invention.

In step (3) of Reaction Scheme VII, a compound of Formula XLV is nitrated under conventional nitration conditions to provide a compound of Formula XLVI. The reaction is conveniently carried out by adding nitric acid to the compound of Formula XLV in a suitable solvent such as propionic acid and heating the mixture at an elevated temperature. The product can be isolated using conventional methods.

In step (4) of Reaction Scheme VIII, a 3-nitro[1,5]naphthyridin-4-ol or 3-nitroquinolin-4-ol of Formula XLVI is chlorinated using conventional chlorination chemistry to provide a 4-chloro-3-nitro[1,5]naphthyridine or 4-chloro-3-nitroquinoline of Formula XLVII. The reaction is conveniently carried out by treating the compound of Formula XLVI with phosphorous oxychloride in a suitable solvent such as DMF. The reaction can be carried out at ambient temperature or at an elevated temperature such as 100° C., and the product can be isolated using conventional methods.

The 4-chloro-3-nitro[1,5]naphthyridine of Formula XLVII wherein m and n are both 0 is known and can be readily prepared using a known synthetic route; see for example, U.S. Pat. No. 6,194,425 (Gerster et al.).

In step (5) of Reaction Scheme VIII, a 4-chloro-3-nitro[1,5]naphthyridine or 4-chloro-3-nitroquinoline of Formula XLVII is treated with an amine of Formula R₁—NH₂ to provide a compound of Formula XLVIII. Several amines of Formula R₁, —NH₂ are commercially available; others can be prepared by known synthetic methods. The reaction is conveniently carried out by adding the amine of Formula R₁, —NH₂ to a solution of the 4-chloro-3-nitro[1,5]naphthyridine or 4-chloro-3-nitroquinoline of Formula XLVII in a suitable solvent such as dichloromethane in the presence of a tertiary amine such as triethylamine. The reaction can be carried out at ambient temperature or at a sub-ambient temperature such as, for example, 0° C. The reaction product can be isolated using conventional methods.

In step (6) of Reaction Scheme VIII, a compound of Formula XLVIII is reduced to provide a diamine of Formula XLIX. The reaction can be carried out by hydrogenation using a heterogeneous hydrogenation catalyst such as palladium on carbon or platinum on carbon. The hydrogenation is conveniently carried out in a Parr apparatus in a suitable solvent such as toluene, methanol, acetonitrile, or ethyl acetate. For compounds of the Formula XLVIII wherein m is 1 and D is —OCH₂Ph, the preferred catalyst is platinum on carbon. The reaction can be carried out at ambient temperature, and the product can be isolated using conventional methods.

Alternatively, the reduction in step (6) can be carried out using nickel boride, prepared in situ from sodium borohydride and nickel(II) chloride. The reduction is conveniently carried out by adding a solution of a compound of Formula XLVIII in a suitable solvent or solvent mixture such as dichloromethane/methanol to a mixture of excess sodium borohydride and catalytic nickel(II) chloride in methanol. The reaction can be carried out at ambient temperature. The product can be isolated using conventional methods.

In step (7) of Reaction Scheme VIII, a diamine of Formula XLIX, is reacted with a carboxylic acid equivalent to provide a 1H-imidazo[4,5-c][1,5]naphthyridine or 1H-imidazo[4,5-c]quinoline of Formula L. The carboxylic acid or equivalent is selected such that it will provide the desired —X-Hal substituent in a compound of Formula L and the reaction can be carried out as described in step (1) of Reaction Scheme I. When an acid chloride, for example chloroacetyl chloride, is used as the carboxylic acid equivalent, the reaction can be carried out in two steps. Part (i) of step (7) is conveniently carried out by adding the acid chloride to a solution of a diamine of Formula XLIX in a suitable solvent such as dichloromethane, chloroform, or acetonitrile. Optionally, a tertiary amine such as triethylamine, pyridine, or 4-dimethylaminopyridine can be added. The reaction can be carried out at ambient temperature. The amide product or the salt thereof can be isolated and optionally purified using conventional techniques. Part (ii) of step (7) involves heating the amide prepared in part (i) in the presence of base to provide a 1H-imidazo[4,5-c][1,5]naphthyridine or 1H-imidazo[4,5-c]quinoline of Formula L. The reaction is conveniently carried out in a suitable solvent such as ethanol in the presence of a base such aqueous sodium hydroxide, aqueous potassium carbonate, or triethylamine at elevated temperature. In some instances, the product of Formula L may be obtained directly from Part (i). Alternatively, a diamine of Formula XLIX can be treated with ethyl chloroacetimidate hydrochloride as the carboxylic acid equivalent to provide a compound wherein X is methylene. The reaction is carried out in a suitable solvent such as chloroform at ambient temperature and the product of Formula L can be isolated using conventional methods. Ethyl chloroacetimidate hydrochloride is a known compound that can be prepared according to the literature procedure: Stillings, M. R. et al., *J. Med. Chem.*, 29, pp. 2280-2284 (1986).

In steps (8)-(10) of Reaction Scheme VIII, a halogen-substituted 1H-imidazo[4,5-c][1,5]naphthyridine or 1H-imidazo[4,5-c]quinoline of Formula L can be converted into phthalimide-substituted 1H-imidazo[4,5-c][1,5]naphthyridin-4-amine or 1H-imidazo[4,5-c]quinolin-4-amine of Formula LIII using the chemistry described in steps (2)-(4) of Reaction Scheme I. Steps (8) and (9) can alternatively be combined and carried out as a one-pot procedure by adding 3-chloroperoxybenzoic acid to a solution of a compound of Formula L in a solvent such as dichloromethane or chloroform and then adding ammonium hydroxide and p-toluenesulfonyl chloride without isolating the N-oxide of Formula LI. Compounds of Formula LI, LII, and LIII or their pharmaceutically acceptable salts can be isolated using conventional methods.

In steps (11) and (12) of Reaction Scheme V, a phthalimide-substituted 1H-imidazo[4,5-c][1,5]naphthyridin-4-amine or 1H-imidazo[4,5-c]quinolin-4-amine of Formula LIII is converted to a hydroxylamine-substituted 1H-imidazo[4,5-c][1,5]naphthyridin-4-amine or 1H-imidazo[4,5-c]quinolin-4-amine of Formula LIV which is condensed with an aldehyde or ketone to form an oxime of Formula LV, sequentially using the chemistry described in steps (5) and (6)

of Reaction Scheme I. Compounds of Formula LIV and LV or their pharmaceutically acceptable salts can be isolated using conventional methods.

In step (13) of Reaction Scheme VIII, an oxime of Formula LV is reduced to provide a hydroxylamine of Formula LVI, a subgenus of Formulas I and II. The reduction is conveniently carried out by treating the oxime of Formula LV with excess sodium cyanoborohydride in a suitable solvent or solvent mixture such as methanol/acetic acid. Optionally, hydrochloric acid may be added. The reaction can be carried out at ambient temperature or at elevated temperature. The product or pharmaceutically acceptable salt thereof can be isolated using conventional methods.

In step (14) of Reaction Scheme VIII, a hydroxylamine of Formula LVI is converted to a compound of Formula LVI, a subgenus of Formulas I and II. The reaction is carried out using one of the methods described in Reaction Scheme V or step (2) of Reaction Scheme VI. The product or pharmaceutically acceptable salt thereof can be isolated using conventional methods.

Alternatively, a compound of Formula LIV can be converted to a compound of Formula LVIII, a subgenus of Formulas I and II, as shown in step (12a) of Reaction Scheme VIII. The transformation is conveniently carried out by using the conditions described in Reaction Scheme V and step (2) of Reaction Scheme VI. The product or pharmaceutically acceptable salt thereof can be isolated using conventional methods.

In step (13a) of Reaction Scheme VIII, a compound of Formula LVIII is alkylated to provide a compound of Formula LVII. The reaction can be carried out with an alkylating agent that is generated in situ from an alcohol of Formula $R_{2a}$—OH under Mitsunobu reaction conditions (described in step (6) of Reaction Scheme III) or an alkylating agent of Formula $R_{2a}$—Br or $R_{2a}$—I in the presence of a base such as cesium carbonate in a suitable solvent such as DMF. The latter reaction may be carried out at ambient temperature for reactive alkylating agents such as, for example, methyl iodide, benzyl bromide, and substituted benzyl bromides, or at an elevated temperature. Optionally, catalytic tetrabutylammonium hydrogensulfate can be added. The product or pharmaceutically acceptable salt thereof can be isolated by conventional methods. One skilled in the art would recognize that the reactions described for the alkylation step would probably not be successful for $R_{2a}$ groups that are difficult to introduce via bimolecular nucleophilic substitution reactions. These groups include, for example, sterically hindered alkyl groups.

A compound of Formula LVIII in which $R_{2a}$ and $R_2$ together with the nitrogen atom and Y' group to which they are bonded join together to form a ring of Formula

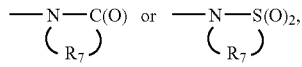

can be prepared in a two-step procedure from a compound of Formula LIV using the methods described in step 5a of Reaction Scheme II. Alternatively, a reagent of the Formula P—O—$R_7$C(O)Cl, wherein P is a protecting group, may react with a compound of Formula LIV to generate an isolable intermediate that can then be deprotected to yield a hydroxyalkanamide. The isolable hydroxyalkanamide is cyclized under Mitsunobu conditions, described in step (6) of Reaction Scheme III. The product or pharmaceutically acceptable salt thereof can be isolated using conventional methods.

For some embodiments, compounds shown in Reaction Scheme VIII can be further elaborated using conventional synthetic methods. For example, an amine of Formula $R_1$—$NH_2$, used in step (5) of Reaction Scheme VIII, may contain a protected functional group, such as a tert-butoxycarbonyl-protected amino group. The protecting group may be removed after step (14) of Reaction Scheme V to reveal an amine on the $R_1$ group. An amino group introduced in this manner may be further functionalized using the chemistry described in steps (5) and (5a) of Reaction Scheme II to provide compounds of the Formula LVII in which $R_1$ is —X'—N($R_8$)-Q-$R_4$ or —X'—$R_{5a}$. Alternatively, the protecting group may be removed after step (7) in Reaction Scheme VIII and the resulting amino group may be functionalized as described above before step (8). The resulting compound of Formula L can be subjected to steps (8)-(14) of Reaction Scheme VIII to provide a compound of Formula LVII wherein $R_1$ is —X'—N($R_8$)-Q-$R_4$ or —X'—$R_{5a}$.

Alternatively, the amine of Formula $R_1$, —$NH_2$ used in step (5) of Reaction Scheme VIII may contain an appropriately-protected hydroxyl group, for example, a tert-butyldimethylsilyl-protected hydroxyl group. The protecting group may be removed after step (14) in Reaction Scheme VIII to provide an alcohol on the $R_1$ group. An alcohol introduced in this manner into a compound of Formula LVII may be converted into a hydroxylamine upon treatment with N-hydroxyphthalimide using the Mitsunobu reaction conditions described in step (6) of Reaction Scheme III, followed by deprotection of the resulting phthalimide-protected hydroxylamine with hydrazine in ethanol. A hydroxylamine on the $R_1$ group can undergo reaction with a ketone or aldehyde of Formula $R_1$'C(O)$R_1$" to form an oxime using the reaction conditions described in step (6) of Reaction Scheme I to yield a compound of Formula LVII in which $R_1$ is —X"—O—N=C($R_1$')($R_1$") where X", $R_1$', and $R_1$" are as defined above.

A hydroxylamine on the $R_1$ group of a compound of Formula LVII, prepared as described above, can also be further functionalized to a compound of the Formula LVII in which $R_1$ is —X"—O—$NR_{1a}$—Y'—$R_{1b}$ wherein Y' is —C(O)—, —S(O)$_2$—, —C(O)—N($R_9$)—, —C(S)—N($R_8$)—, —C(O)—N($R_8$)—S(O)$_2$—, —C(O)—N($R_8$)—C(O)—, —S(O)$_2$—N($R_8$)—; $R_{1a}$ is hydrogen, and $R_{1b}$ is as defined above using, respectively, an acid chloride, a sulfonyl chloride or a sulfonic anhydride; an isocyanate; an acyl isocyanate, an isothiocyanate, a sulfonyl isocyanate, a carbamoyl chloride, or a sulfamoyl chloride. The reaction can be carried out using the conditions described in step (5) of Reaction Scheme II. A large number of the reagents listed above are commercially available; others can be readily prepared using known synthetic methods.

A compound of Formula LVII in which $R_1$ is —X"—O—$NR_{1a}$—Y'—$R_{1b}$ wherein Y' is a bond, —C(O)—, —C(S)—, —S(O)$_2$—, or —C(O)—C(O)—; $R_{1b}$ is defined above, and $R_{1a}$ is hydrogen, can be derivatized further upon treatment with an alkylating agent that is generated in situ from an alcohol of Formula $R_{1a}$—OH under Mitsunobu reaction conditions or an alkylating agent of Formula $R_{1a}$—Br or $R_{1a}$—I as described in step (13a) above.

A compound of Formula LVII in which $R_1$ is —X"—O—$NR_{1a}$—Y'—$R_{1b}$, where $R_{1a}$ and $R_{1b}$ together with the nitrogen atom and Y' group to which they are bonded join together to form a ring of Formula

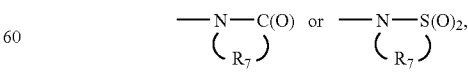

can be prepared in a two-step procedure from a compound of Formula LVII in which $R_1$ is —X"—O—$NH_2$, using one of the methods described in step 5a of Reaction Scheme II or step 13a above.

Reaction Scheme VIII
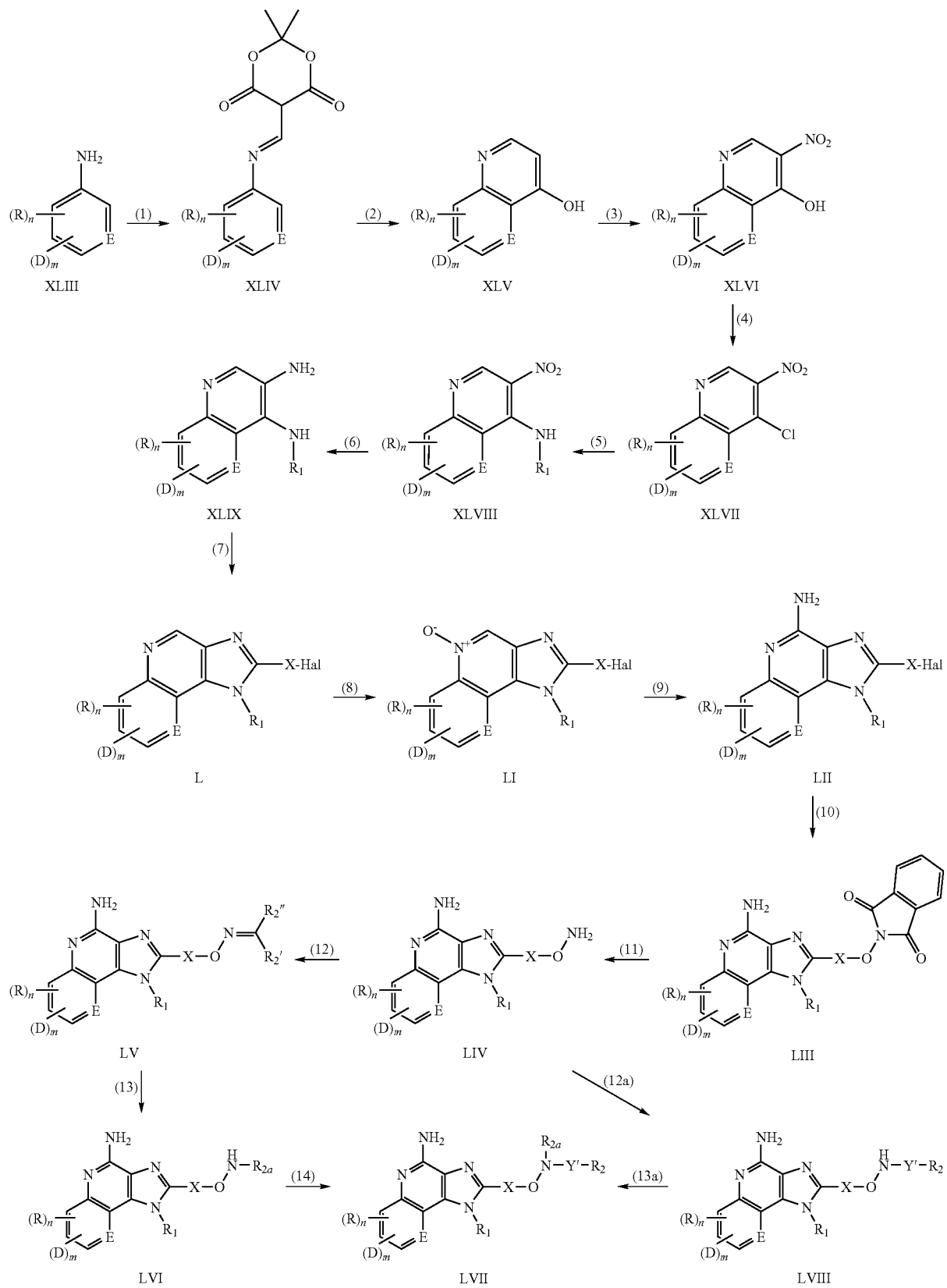

Compounds of the invention can be prepared according to Reaction Scheme IX, wherein D, E, R, $R_1$, $R_2$, $R_{2a}$, X, and Y' are as defined above, m is 1, n is 0 or 1, and $R_{3b}$ and $R_{3c}$ are as defined below. In Reaction Scheme IX, when D is —Br or —I, step (1) is used to react a 1H-imidazo[4,5-c]quinoline-4-amine or 1H-imidazo[4,5-c][1,5]naphthyridine-4-amine of Formula LVII using known palladium-catalyzed coupling reactions such as the Suzuki coupling and the Heck reaction. For example, a bromo or iodo-substituted compound of Formula LVII undergoes Suzuki coupling with a boronic acid of Formula $R_{3a}$—$B(OH)_2$, an anhydride thereof, or a boronic acid ester of Formula $R_{3a}$—$B(O-alkyl)_2$, wherein $R_{3a}$ is as defined above, according to the method described in Reaction Scheme IV. The product of Formula LIX, a subgenus of Formulas I and II wherein $R_{3b}$ is the same as $R_{3a}$, or a pharmaceutically acceptable salt thereof, can be isolated by conventional methods.

The Heck reaction can also be used in step (1) of Reaction Scheme IX to provide compounds of Formula LIX, wherein $R_{3b}$ is —$X'_a$—$R_{4b}$ and —$X'_a$—Y—$R_4$, wherein $X'_a$, Y, $R_{4b}$, and $R_4$ are as defined above. The Heck reaction is carried out by coupling a compound of Formula LVII with a compound of the Formula $H_2C$=$C(H)$—$R_{4b}$ or $H_2C$=$C(H)$—Y—$R_4$. Several of these vinyl-substituted compounds are commercially available; others can be prepared by known methods. The reaction is conveniently carried out by combining the compound of Formula LVII and the vinyl-substituted compound in the presence of palladium (II) acetate, triphenylphosphine or tri-ortho-tolylphosphine, and a base such as triethylamine in a suitable solvent such as acetonitrile or toluene. The reaction can be carried out at an elevated temperature such as 100° C.-120° C. under an inert atmosphere. The product of Formula LIX or pharmaceutically acceptable salt thereof can be isolated using conventional methods.

Compounds of Formula LIX, wherein $R_{3b}$ is —$X'_c$—$R_4$, $X'_c$ is alkynylene, and $R_4$ is as defined above, can also be prepared by palladium catalyzed coupling reactions such as the Stille coupling or Sonogashira coupling. These reactions are carried out by coupling a compound of Formula LVII with a compound of the Formula $(alkyl)_3Sn$—C≡C—$R_4$, $(alkyl)_3Si$—C≡C—$R_4$, or H—C≡C—$R_4$.

Compounds of Formula LIX prepared as described above by palladium-mediated coupling reactions, wherein $R_{3b}$ is —$X'_a$—$R_4$, —$X'_a$, —Y—$R_4$, —$X'_{b2}$—Y—$R_4$, —$X'_{b2}$—$R_5$, or —$X'_c$—$R_4$, where $X'_{b2}$ is alkenylene interrupted or terminated by arylene or heteroarylene, and $X'_a$, $X'_c$, Y, $R_4$, and $R_5$ are as defined above, can undergo reduction of the alkenylene or alkynylene group present to provide compounds of Formula LIX wherein $R_{3b}$ is —$X'_d$—$R_4$, —$X'_d$—Y—$R_4$, —$X'_e$—Y—$R_4$, or —$X'_e$, —$R_5$, where $X'_d$ is alkylene; $X'_e$ is alkylene interrupted or terminated by arylene or heteroarylene; and $R_4$, $R_5$, and Y are as defined above. The reduction can be carried out by hydrogenation using a conventional heterogeneous hydrogenation catalyst such as palladium on carbon. The reaction can conveniently be carried out on a Parr apparatus in a suitable solvent such as ethanol, methanol, or mixtures thereof. The product or pharmaceutically acceptable salt thereof can be isolated using conventional methods.

Compounds of Formula LVII wherein D is —$OCH_2Ph$ can be converted in Reaction Scheme IX to compounds of Formula LXI wherein $R_{3c}$ is —O—$R_{4b}$, —O—X'—$R_4$, —O—X'—Y—$R_4$, or —O—X'—$R_5$; wherein $R_4$, $R_{4b}$, $R_5$, X', and Y are as defined above. In step (1a) of Reaction Scheme IX, the benzyl group in a 1H-imidazo[4,5-c]quinoline-4-amine or 1H-imidazo[4,5-c][1,5]naphthyridine-4-amine of Formula LVII, wherein D is —$OCH_2Ph$, is cleaved to provide a hydroxy group. The cleavage is conveniently carried out on a Parr apparatus under hydrogenolysis conditions using a suitable heterogeneous catalyst such as palladium or platinum on carbon in a solvent such as ethanol. Alternatively, the reaction can be carried out by transfer hydrogenation in the presence of a suitable hydrogenation catalyst. The transfer hydrogenation is conveniently carried out by adding ammonium formate to a solution of a compound of Formula LVII in a suitable solvent such as ethanol in the presence of a catalyst such as palladium on carbon. The reaction is carried out at an elevated temperature, for example, the refluxing temperature of the solvent. The product of Formula LX, a subgenus of Formulas I and II, or pharmaceutically acceptable salt thereof can be isolated using conventional methods.

In step (2) of Reaction Scheme IX, a hydroxy-substituted 1H-imidazo[4,5-c]quinoline-4-amine or 1H-imidazo[4,5-c][1,5]naphthyridine-4-amine of Formula LX is converted to a compound of Formula LXI, a subgenus of Formula I and II wherein $R_{3c}$ is -O—$R_{4b}$, —O—X'—$R_4$, —O—X'—Y—$R_4$, or —O—X'—$R_5$, using a Williamson-type ether synthesis. The reaction is effected by treating a hydroxy-substituted 1H-imidazo[4,5-c]quinoline-4-amine or 1H-imidazo[4,5-c][1,5]naphthyridine-4-amine of Formula LX with an aryl, alkyl, or arylalkylenyl halide of Formula Halide-$R_{4b}$, Halide-alkylene-$R_4$, Halide-alkylene-Y—$R_4$, or Halide-alkylene-$R_5$ in the presence of a base. Numerous alkyl, arylalkylenyl, and aryl halides of these formulas are commercially available, including substituted benzyl bromides and chlorides, substituted or unsubstituted alkyl or arylallylenyl bromides and chlorides, and substituted fluorobenzenes. Other halides of these formulas can be prepared using conventional synthetic methods. The reaction is conveniently carried out by combining an alkyl, arylalkylenyl, or aryl halide with the hydroxy-substituted compound of Formula LX in a solvent such as DMF in the presence of a suitable base such as cesium carbonate. Optionally, catalytic tetrabutylammonium bromide can be added. The reaction can be carried out at ambient temperature or at an elevated temperature, for example 65° C. or 85° C., depending on the reactivity of the halide reagent. Alternatively, step (2) may be carried out using the Ullmann ether synthesis, in which an alkali metal aryloxide prepared from the hydroxy-substituted compound of Formula LX reacts with an aryl halide in the presence of copper salts, to provide a compound of Formula LXI, where $R_{3c}$ is —O—$R_{4b}$, —O—$X'_f$—$R_4$, or —O—$X'_f$—Y—$R_4$, wherein $X'_f$ is an arylene or heteroarylene. Numerous substituted and unsubstituted aryl halides are commercially available; others can be prepared using conventional methods. The product of Formula LXI, prepared by either of these methods, or pharmaceutically acceptable salt thereof can be isolated using conventional methods.

Reaction Scheme IX

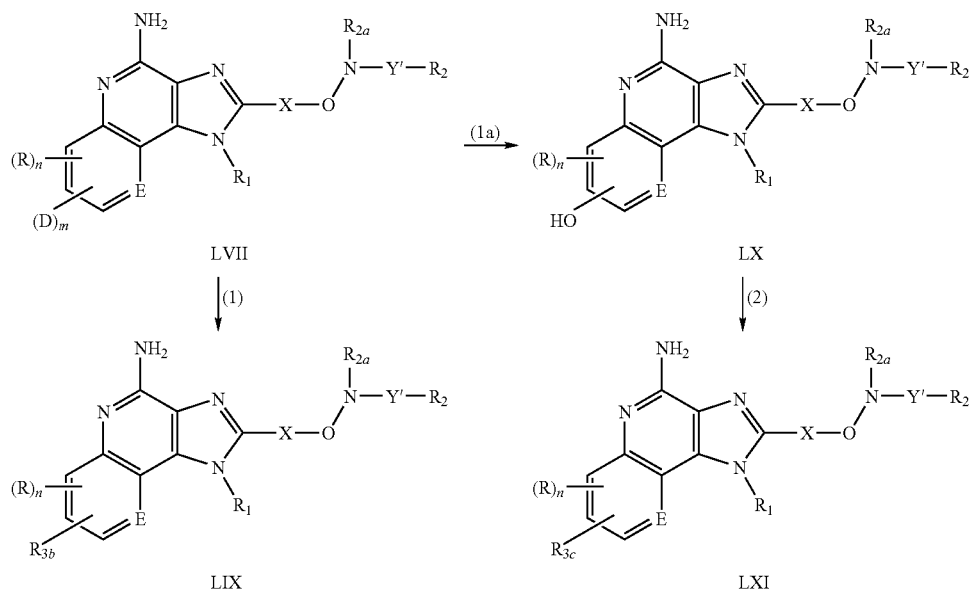

LVII → LX → LIX, LXI

For some embodiments, compounds of the invention are prepared according to Reaction Scheme X, where $R_1$, $R_2$, $R_2'$, $R_2''$, $R_{2a}$, X, Y', $R_{A2}$, $R_{B2}$, and Hal are as defined above, and Ph is phenyl. In step (1) of Reaction Scheme X, a 2,4-dichloro-3-nitropyridine of Formula LXII is reacted with an amine of the Formula $H_2N-R_1$, to form a 2-chloro-3-nitropyridine of Formula LXIII. The reaction is conveniently carried out by combining an amine of Formula $H_2N-R_1$, and a 2,4-dichloro-3-nitropyridine of Formula LXII in the presence of a base such as triethylamine in an inert solvent such as DMF. The reaction can be carried out at ambient temperature, and the product can be isolated from the reaction mixture using conventional methods. Many amines of Formula $H_2N-R_1$, are commercially available; others can be prepared by known synthetic methods. Many 2,4-dichloro-3-nitropyridines of the Formula LXII are known and can be readily prepared using known synthetic methods (see, for example, Dellaria et al, U.S. Pat. No. 6,525,064 and the references cited therein).

In step (2) of Reaction Scheme X, a 2-chloro-3-nitropyridine of Formula LXII is reacted with an alkali metal azide to provide an 8-nitrotetrazolo[1,5-a]pyridin-7-amine of Formula LXIV. The reaction can be carried out by combining the compound of Formula LXIII with an alkali metal azide, for example, sodium azide, in a suitable solvent such as acetonitrile/water, preferably 90/10 acetonitrile/water, in the presence of cerium(III) chloride, preferably cerium(III) chloride heptahydrate. Optionally, the reaction can be carried out with heating, for example, at the reflux temperature. Alternatively, the reaction can be carried out by combining the compound of Formula LXIII with an alkali metal azide, for example, sodium azide, in a suitable solvent such as DMF and heating, for example to about 50° C.-60° C., optionally in the presence of ammonium chloride. The product can be isolated from the reaction mixture using conventional methods.

In step (3) of Reaction Scheme X, an 8-nitrotetrazolo[1,5-a]pyridin-7-amine of Formula LXIV is reduced to provide a compound of Formula LXV. The reaction can be carried out by hydrogenation using a heterogeneous hydrogenation catalyst such as palladium on carbon or platinum on carbon. The hydrogenation is conveniently carried out in a Parr apparatus in a suitable solvent such as toluene, methanol, acetonitrile, or ethyl acetate. The reaction can be carried out at ambient temperature, and the product can be isolated using conventional methods.

In step (4) of Reaction Scheme X, a tetrazolo[1,5-a]pyridine-7,8-diamine of Formula LXV, is reacted with a carboxylic acid or an equivalent thereof to provide a 7H-imidazo[4,5-c]tetrazolo[1,5-a]pyridine of Formula LXVI. The carboxylic acid or equivalent is selected such that it will provide the desired —X-Hal substituent in a compound of Formula LXVI. The reaction can be carried out as described in step (7) of Reaction Scheme VIII. The product can be isolated using conventional methods.

In step (5) of Reaction Scheme X, a 7H-imidazo[4,5-c]tetrazolo[1,5-a]pyridine of Formula LXVI is treated with N-hydroxyphthalimide to provide a compound of Formula LXVII, which contains a N-phthalimide-protected hydroxylamine. The reaction is conveniently carried out as described in step (4) of Reaction Scheme I. The product or a pharmaceutically acceptable salt thereof can be isolated using conventional methods.

In step (6) of Reaction Scheme X, the N-phthalimide-protected hydroxylamine of Formula LXVII is treated with hydrazine in a suitable solvent such as ethanol to provide a hydroxylamine of Formula LXVII. The reaction can be carried out at ambient temperature and the product can be isolated from the reaction mixture using conventional methods.

In step (7) Reaction Scheme X, the hydroxylamine group in a 7H-imidazo[4,5-c]tetrazolo[1,5-a]pyridine of Formula LXVII reacts with an aldehyde or ketone of Formula $R_2OC(O)R_2''$ to provide an oxime of Formula LXIX. The reaction can be carried out using the conditions described above in step (6) of Reaction Scheme I and the product can be isolated from the reaction mixture using conventional methods.

In step (8) of Reaction Scheme X, the tetrazolo ring is removed from a 7H-imidazo[4,5-c]tetrazolo[1,5-a]pyridine of Formula LXIX by reaction with triphenylphosphine to form an N-triphenylphosphinyl intermediate of Formula LXX. The reaction with triphenylphosphine can be run in a suitable solvent such as toluene or 1,2-dichlorobenzene under an atmosphere of nitrogen with heating, for example at the reflux temperature.

In step (9) of Reaction Scheme X, an N-triphenylphosphinyl intermediate of Formula LXX is hydrolyzed to provide an oxime-substituted 1H-imidazo[4,5-c]pyridin-4-amine of Formula LXXI. The hydrolysis can be carried out by general methods well known to those skilled in the art, for example, by heating in a lower alkanol or an alkanol/water solution in the presence of an acid such as trifluoroacetic acid, acetic acid, or hydrochloric acid. The product can be isolated from the reaction mixture using conventional methods as the compound of Formula LXXI or as a pharmaceutically acceptable salt thereof.

A compound of the Formula LXXI may also be obtained through an alternative two-step route from a compound of Formula LXVII. In step (6a) of Reaction Scheme X, a compound of Formula LXVII is treated sequentially according to the reaction conditions described in steps (8) and (9) of Reaction Scheme X using hydrochloric acid as the acid in step (9). Under these reaction conditions, the N-phthalimide is removed to provide the hydroxylamine-substituted 1H-imidazo[4,5-c]pyridin-4-amine of Formula LXXII. The product can be isolated and purified using conventional methods.

In step (7a) of Reaction Scheme X, a hydroxylamine-substituted 1H-imidazo[4,5-c]pyridin-4-amine of Formula LXXII reacts with an aldehyde or ketone of Formula $R_2OC(O)R_2''$ to provide an oxime of Formula LXXI. The reaction can be carried out using the conditions described above in step (6) of Reaction Scheme I, and the product or the pharmaceutically acceptable salt thereof can be isolated from the reaction mixture using conventional methods.

In step (10) of Reaction Scheme X, the oxime of Formula LXXI is reduced using the conditions described in step (7) of Reaction Scheme I to afford a compound of Formula LXXIII, a subgenus of Formulas I, II, and VI. The product or pharmaceutically acceptable salt thereof can be isolated by conventional methods.

In step (11) of Reaction Scheme X, a hydroxylamine of Formula LXXIII is converted into a compound of Formula LXXIV, a subgenus of Formulas I, II, and VI, using the reagents and conditions described in Reaction Scheme V or step (2) of Reaction Scheme VI. The product or pharmaceutically acceptable salt thereof can be isolated by conventional methods.

Alternatively, in steps (10a) and (11a) of Reaction Scheme X, a hydroxylamine of Formula LXXII is converted into a compound of Formula LXXIV using the reagents and methods described in steps (12a) and (13a), respectively, of Reaction Scheme VIII. The product or pharmaceutically acceptable salt thereof can be isolated by conventional methods.

For some embodiments, compounds shown in Reaction Scheme X can be further elaborated using conventional synthetic methods. For Example, amines of Formula $R_1$—$NH_2$, used in step (1) of Reaction Scheme X, may contain a protected functional group, such as a tert-butoxycarbonyl-protected amino group. The protecting group may be removed later in Reaction Scheme X after step (4) to reveal, for example, an amine on the $R_1$ group of a compound of Formula LXVI. An amino group introduced in this manner may be further functionalized by applying the chemistry described in steps (5) and (5a) of Reaction Scheme II to provide compounds of the Formula LXVI in which $R_1$ is —X'—N(R_8)-Q-R_4 or X'—$R_{5a}$, which can be converted into compounds of the Formula LXXIII or LXXIV using the chemistry described in steps (5)-(10) or (11), respectively, of Reaction Scheme X. Alternatively, the protecting group may be removed after step (7) of Reaction Scheme X to reveal an amine on the $R_1$ group of a compound of Formula LXIX. The amino group may be further functionalized as described above to provide compounds of the Formula LXIX in which $R_1$ is —X'—N(R_8)-Q-R_4 or —X'—$R_{5a}$, which can be converted into compounds of the Formula LXXIII or LXXIV using the chemistry described in steps (8)-(10) or (11) of Reaction Scheme X.

Compounds of the Formula LXXIII, LXXIV, or LXXV in which $R_1$ is —X"—O—N=C($R_1'$)($R_1''$) or —X"—O—$NR_{1a}$—Y'—$R_{1b}$ can be synthesized from compounds shown in Reaction Scheme X using the chemistry described above in association with Reaction Scheme VIII.

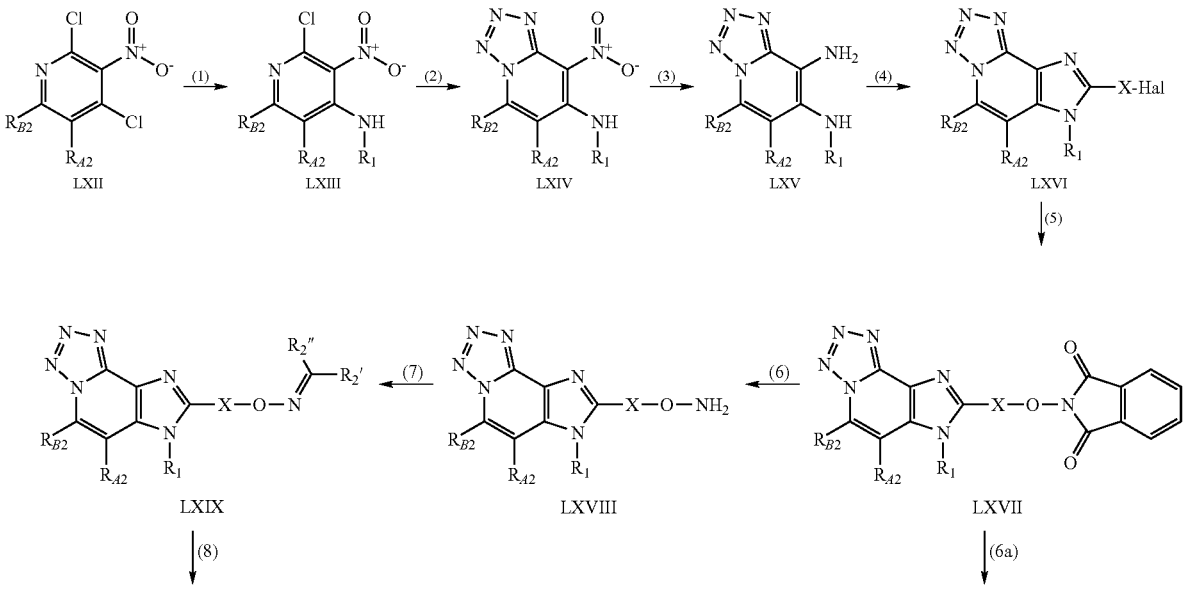

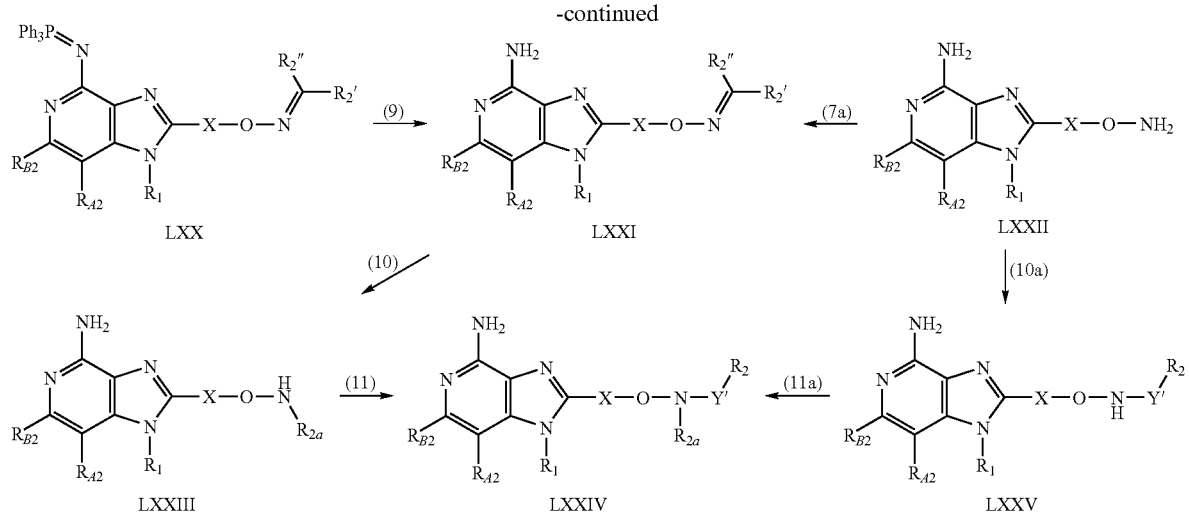

Pharmaceutical Compositions and Biological Activity

Pharmaceutical compositions of the invention contain a therapeutically effective amount of a compound or salt of the invention as described above in combination with a pharmaceutically acceptable carrier.

The terms "a therapeutically effective amount" and "effective amount" mean an amount of the compound or salt sufficient to induce a therapeutic or prophylactic effect, such as cytokine induction, immunomodulation, antitumor activity, and/or antiviral activity. Although the exact amount of active compound or salt used in a pharmaceutical composition of the invention will vary according to factors known to those of skill in the art, such as the physical and chemical nature of the compound or salt, the nature of the carrier, and the intended dosing regimen, it is anticipated that the compositions of the invention will contain sufficient active ingredient to provide a dose of about 100 nanograms per kilogram (ng/kg) to about 50 milligrams per kilogram (mg/kg), preferably about 10 micrograms per kilogram (μg/kg) to about 5 mg/kg, of the compound or salt to the subject. A variety of dosage forms may be used, such as tablets, lozenges, capsules, parenteral formulations, syrups, creams, ointments, aerosol formulations, transdermal patches, transmucosal patches and the like.

The compounds or salts of the invention can be administered as the single therapeutic agent in the treatment regimen, or the compounds or salts of the invention may be administered in combination with one another or with other active agents, including additional immune response modifiers, antivirals, antibiotics, antibodies, proteins, peptides, oligonucleotides, etc.

Compounds or salts of the invention have been shown to induce the production of certain cytokines and certain compounds or salts of the invention may inhibit the production of certain cytokines in experiments performed according to the tests set forth below. These results indicate that the compounds or salts are useful as immune response modifiers that can modulate the immune response in a number of different ways, rendering them useful in the treatment of a variety of disorders.

Cytokines whose production may be induced by the administration of compounds or salts of the invention generally include interferon-α (IFN-α) and/or tumor necrosis factor-α (TNF-α) as well as certain interleukins (IL). Cytokines whose biosynthesis may be induced by compounds or salts of the invention include IFN-α, TNF-α, IL-1, IL-6, IL-10 and IL-12, and a variety of other cytokines. Among other effects, these and other cytokines can inhibit virus production and tumor cell growth, making the compounds or salts useful in the treatment of viral diseases and neoplastic diseases. Accordingly, the invention provides a method of inducing cytokine biosynthesis in an animal comprising administering an effective amount of a compound or salt or composition of the invention to the animal. The animal to which the compound or salt or composition is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts of the invention can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. Further, the compounds or salts may cause proliferation and differentiation of B-lymphocytes.

Compounds or salts of the invention can also have an effect on the acquired immune response. For example, the production of the T helper type 1 ($T_H1$) cytokine IFN-γ may be induced indirectly and the production of the T helper type 2 ($T_H2$) cytokines IL-4, IL-5 and IL-13 may be inhibited upon administration of the compounds or salts.

Other cytokines whose production may be inhibited by the administration of compounds or salts of the invention include tumor necrosis factor-α (TNF-α). Among other effects, inhibition of TNF-α production can provide prophylaxis or therapeutic treatment of TNF-α mediated diseases in animals, making the compounds or salt useful in the treatment of, for example, autoimmune diseases. Accordingly, the invention provides a method of inhibiting TNF-α biosynthesis in an animal comprising administering an effective amount of a compound or salt or composition of the invention to the animal. The animal to which the compound or salt or composition is administered for inhibition of TNF-α biosynthesis may have a disease as described infra, for example an autoimmune disease, and administration of the compound or salt may provide therapeutic treatment. Alternatively, the compound or salt may be administered to the animal prior to the animal acquiring the disease so that administration of the compound or salt may provide a prophylactic treatment.

Whether for prophylaxis or therapeutic treatment of a disease, and whether for effecting innate or acquired immunity, the compound or salt or composition may be administered alone or in combination with one or more active components as in, for example, a vaccine adjuvant. When administered with other components, the compound or salt and other component or components may be administered separately; together but independently such as in a solution; or together and associated with one another such as (a) covalently linked or (b) non-covalently associated, e.g., in a colloidal suspension.

Conditions for which IRMs identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus,* or *Bordetella;*

(c) other infectious diseases, such chlamydia, fungal diseases including but not limited to candidiasis, aspergillosis, histoplasmosis, cryptococcal meningitis, or parasitic diseases including but not limited to malaria, *pneumocystis carnii* pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to myelogeous leukemia, chronic lymphocytic leukemia, multiple myeloma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia areata; and (g) diseases associated with wound repair such as, for example, inhibition of keloid formation and other types of scarring (e.g., enhancing wound healing, including chronic wounds).

Additionally, an IRM compound or salt of the present invention may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens, toxoids, toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, *hemophilus influenza* b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Certain IRM compounds or salts of the present invention may be particularly helpful in individuals having compromised immune function. For example, certain compounds or salts may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An amount of a compound or salt effective to induce or inhibit cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased (induced) or decreased (inhibited) over a background level of such cytokines. The precise amount will vary according to factors known in the art but is expected to be a dose of about 100 ng/kg to about 50 mg/kg, preferably about 10 µg/kg to about 5 mg/kg. The invention also provides a method of treating a viral infection in an animal and a method of treating a neoplastic disease in an animal comprising administering an effective amount of a compound or salt or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 µg/kg to about 5 mg/kg. An amount of a compound or salt effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 µg/kg to about 5 mg/kg.

Objects and advantages of this invention are further illustrated by the following examples, but the particular materials and amounts thereof recited in these examples, as well as other conditions and details, should not be construed to unduly limit this invention.

EXAMPLES

Example 1

O-{[4-Amino-1-(2-methylpropyl)-1H-imidazo[4,5-c]quinolin-2-yl]methyl}hydroxylamine

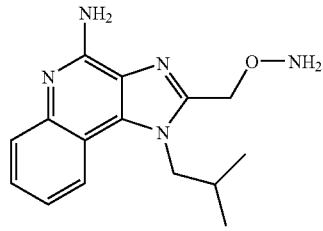 [SMILES: CC(C)Cn1c(CON)nc2c(N)nc3ccccc3c21]

Part A $N^4$-(2-Methylpropyl)quinoline-3,4-diamine (41 g), dichloromethane (550 mL), triethylamine (40 mL, 1.5 eq), and chloroacetyl chloride (16.7 mL, 1.1 eq.) were combined and then stirred at ambient temperature over the weekend. The reaction mixture was diluted with 1,2-dichloroethane (75 mL) and then washed with saturated aqueous sodium bicarbonate (3×400 mL). The organic layer was dried over magnesium sulfate, filtered through a layer of CELITE filter aid, and then concentrated under reduced pressure to provide 52.81 g of 2-chloromethyl-1-(2-methylpropyl)-1H-imidazo[4,5-c]quinoline as a brown solid.

Part B

3-Chlioroperoxybenzoic acid (mCPBA) (16.4 g of 77% max, 73.1 mmol) was added to a solution of 2-chloromethyl-1-(2-methylpropyl)-1H-imidazo[4,5-c]quinoline (10 g, 36.5 mmol) in chloroform (250 mL). The reaction mixture was stirred at ambient temperature overnight. Ammonium hydroxide (100 mL) was added and the reaction was stirred vigorously for 15 minutes. Para-toluenesulfonyl chloride (8.4 g, 43.8 mmol) was added in portions over a period of 10 minutes. The reaction mixture was stirred at ambient temperature for 1 hour and then filtered to remove a precipitate. The filtrate was transferred to a separatory funnel and the layers were separated. The aqueous layer was extracted with dichloromethane (2×100 mL). The combined organics were dried over magnesium sulfate, filtered through a layer of CELITE filter aid, and then concentrated under reduced pressure to provide 16 g of crude product as a yellow foam. The foam was dissolved in 10% methanol in dichloromethane (20 mL). The solution was divided and loaded onto two FLASH 40+M silica cartridges (90 g), (available from Biotage, Inc, Charlottesville, Va., USA). The cartridges were eluted sequentially with 1 L 1:1 ethyl acetate:hexanes, 2% methanol in 1:1 ethyl acetate:hexanes, and 5% methanol in 1:1 ethyl acetate:hexanes. The fractions containing product were combined and then concentrated under reduced pressure to provide 6.4 g of 2-chloromethyl-1-(2-methylpropyl)-1H-imidazo[4,5-c]quinolin-4-amine as an orange foam.

Part C

Triethylamine (536 mg, 5.19 mmol) was added to a solution of N-hydroxyphthalimide (678 mg, 4.16 mmol) in N,N-dimethylformamide (DMF); after 5 minutes a solution of 2-chloromethyl-1-(2-methylpropyl)-1H-imidazo[4,5-c]quinolin-4-amine (1 g) in DMF (10 mL) was added. The reaction mixture was stirred at ambient temperature for 2 hours. The reaction mixture was diluted with dichloromethane (50 mL) and then washed with water (1×100 mL). The aqueous layer was extracted with dichloromethane (2×50 mL) and ethyl acetate (1×50 mL). The combined organics were dried over magnesium sulfate, filtered through a layer of CELITE filter aid, and then concentrated under reduced pressure to provide 1.8 g of crude product as a yellow solid. The solid was dissolved in 5% methanol in chloroform (10 mL) and loaded onto a FLASH 40+M silica cartridge (90 g). The cartridge was eluted sequentially with 1 L 1% methanol in chloroform and 3% methanol in chloroform. The fractions containing the desired product were combined and then concentrated under reduced pressure to provide 950 mg of a yellow solid. This material was recrystallized from acetonitrile, isolated by filtration, washed sequentially with acetonitrile and diethyl ether, and then dried in a vacuum oven at 65° C. overnight to provide 640 mg of 2-{[4-amino-1-(2-methylpropyl)-1H-imidazo[4,5-c]quinolin-2-yl]methoxy}isoindole-1,3-dione as a yellow crystalline solid, mp 221-222° C.

$^1$H NMR (300 MHz, DMSO-$d_6$) δ 8.10 (d, J=7.6 Hz, 1H), 7.88 (s, 4H), 7.63 (dd, J=8.3 Hz, 1.2 Hz, 1H), 7.48 (m, 1H), 7.32 (m, 1H), 6.69 (br s, 2H), 5.51 (s, 2H), 4.73 (d, J=7.6 Hz, 2H), 2.35 (m, 1H), 1.01 (d, J=6.6 Hz, 6H);

MS (APCI) m/z 448.0 (M+H)$^+$;

Anal. Calc'd for $C_{23}H_{21}N_5O_3 \cdot 0.5CH_3CN \cdot 0.5H_2O$: C, 64.78; H, 5.32; N, 17.31. Found: C, 64.87; H, 5.28; N, 17.63.

Part D

Hydrazine (15 mL) was added to a solution of 2-{[4-amino-1-(2-methylpropyl)-1H-imidazo[4,5-c]quinolin-2-yl]methoxy}isoindole-1,3-dione (51 g of crude material from a large scale reaction) in ethanol (200 mL) and a precipitate formed almost immediately. The reaction mixture was stirred at ambient temperature for 1.5 hours and then filtered. The filter cake was washed with several portions of dichloromethane. The filtrate was concentrated under reduced pressure to provide 40 g of crude product as a brown semi-solid. The solid was partitioned between 1M aqueous hydrochloric acid (300 mL) and dichloromethane (100 mL). The layers were separated. The aqueous layer was extracted with dichloromethane (2×100 mL). Analysis by liquid chromatography/mass spectroscopy (LCMS) showed that the organics did not contain product. The aqueous layer was made basic (pH ~10) with solid sodium carbonate and then extracted with dichloromethane (3×100 mL). The combined extracts were dried over magnesium sulfate, filtered, and then concentrated under reduced pressure to provide 9.29 g of product as a brown foam. A portion (1.7 g) of this material was purified on a FLASH 40+S silica cartridge (40 g), (available from Biotage, Inc, Charlottesville, Va., USA), eluting sequentially with 500 mL of 2%, 5%, 5%, and 10% methanol in ethyl acetate. The fractions containing product were combined and then concentrated under reduced pressure to provide 950 mg of an oil. The oil was dissolved in dichloromethane and then combined with 4M hydrochloric acid in dioxane. The resulting precipitate was isolated by filtration and then partitioned between dichloromethane (50 mL) and saturated aqueous sodium bicarbonate (50 mL). The aqueous layer was extracted with dichloromethane (3×50 mL). The combined organics were concentrated under reduced pressure to provide 500 mg of a foam. This material was dissolved in dichloromethane (50 mL) and then combined with 4M hydrochloric acid in dioxane (30 mL). A precipitate formed. The mixture was concentrated and then dissolved in hot ethanol. The solution was allowed to cool to ambient temperature, chilled (−10° C.) in a freezer overnight, and then allowed to warm to ambient temperature. A precipitate was isolated by filtration, washed with ethanol and acetonitrile, and then dried under high vacuum overnight to provide 261 mg of O-{[4-amino-1-(2-methylpropyl)-1H-imidazo[4,5-c]quinolin-2-yl]methyl}hydroxylamine dihydrochloride as a white crystalline solid, mp 205-207° C.

$^1$H NMR (300 MHz, DMSO-d$_6$) δ 8.23 (d, J=8.0 Hz, 1H), 7.86 (dd, J=8.3 Hz, 1.0 Hz, 1H), 7.75 (dd, J=7.3, 7.3 Hz, 1H), 7.62 (m, 1H), 5.57 (s, 2H), 4.64 (d, J=7.6 Hz, 2H), 2.20 (m, 1H), 0.98 (d, J=6.6 Hz, 6H);

$^{13}$C NMR (75 MHz, DMSO-d$_6$) δ 149.6, 149.2, 135.8, 134.4, 130.4, 125.5, 125.3, 122.7, 119.0, 112.9, 66.9, 52.5, 29.1, 19.3 (2);

MS (APCI) m/z 286.1 (M+H)$^+$;

Anal. Calc'd for C$_{15}$H$_{19}$N$_5$O.2.0 HCl.0.3H$_2$O: C, 49.54; H, 5.99; N, 19.26.

Found: C, 49.87; H, 6.36; N, 18.94.

Example 2

N-{[4-Amino-1-(2-methylpropyl)-1H-imidazo[4,5-c]quinolin-2-yl]methoxy}methanesulfonamide

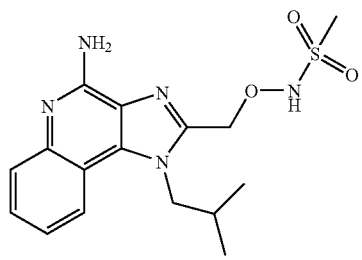 [SMILES: CC(C)Cn1c(CONS(C)(=O)=O)nc2c(N)nc3ccccc3c21]

Triethylamine (1.47 mL, 10.5 mmol) was added to a solution of O-{[4-amino-1-(2-methylpropyl)-1H-imidazo[4,5-c]quinolin-2-yl]methyl}hydroxylamine (1.5 g, 5.3 mmol) in dichloromethane (50 mL). Methanesulfonyl chloride (0.448 mL, 5.78 mmol) was added and the reaction mixture was stirred at ambient temperature for 2 hours. The reaction mixture was washed with saturated aqueous sodium bicarbonate (1×30 mL) and brine (1×30 mL), dried over magnesium sulfate, filtered, and then concentrated under reduced pressure to provide 2.16 g of crude product as a brown foam. This material was dissolved in dichloromethane (10 mL) and then loaded onto a FLASH 40+S silica cartridge (40 g). The cartridge was eluted sequentially with 500 mL ethyl acetate, 2%, 3%, and 5% methanol in ethyl acetate. The fractions containing product were combined and then concentrated under reduced pressure to provide 850 mg of a yellow solid. The material was recrystallized from 3:2 ethanol:acetonitrile and dried under high vacuum to provide 206 mg of N-{[4-amino-1-(2-methylpropyl)-1H-imidazo[4,5-c]quinolin-2-yl]methoxy}methanesulfonamide as a yellow crystalline solid, mp 215-216° C. $^1$H NMR (300 MHz, DMSO-d$_6$) δ 10.3 (br s, 1H), 8.04 (d, J=8.0 Hz, 1H), 7.63 (d, J=7.4 Hz, 1H), 7.46 (m, 1H), 7.29 (m, 1H), 6.69 (br s, 2H), 5.23 (s, 2H), 4.50 (d, J=7.6 Hz, 2H), 3.05 (s, 3H), 2.25 (m, 1H), 0.93 (d, J=6.6 Hz, 6H);

$^{13}$C NMR (75 MHz, DMSO-d$_6$) δ 152.9, 147.8, 146.3, 134.0, 127.9, 127.6, 127.3, 122.1, 121.5, 115.6, 70.9, 52.7, 37.6, 29.6, 20.1 (2);

MS (APCI) m/z 364.1 (M+H)$^+$;

Anal. Calc'd for C$_{16}$H$_{21}$N$_5$O$_3$S: C, 52.88; H, 5.82; N, 19.27. Found: C, 52.96; H, 5.81; N, 19.04.

Example 3

N-{[4-Amino-1-(2-methylpropyl)-1H-imidazo[4,5-c]quinolin-2-yl]methoxy}-N'-isopropylurea

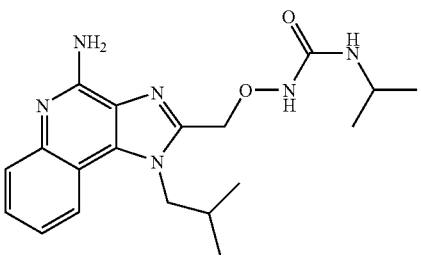 [SMILES: CC(C)Cn1c(CONC(=O)NC(C)C)nc2c(N)nc3ccccc3c21]

Isopropyl isocyanate (0.620 mL, 6.31 mmol) was added to a solution of O-{[4-amino-1-(2-methylpropyl)-1H-imidazo[4,5-c]quinolin-2-yl]methyl}hydroxylamine (1.5 g, 5.3 mmol) in dichloromethane (50 mL). The reaction mixture was stirred at ambient temperature for 1 hour and then concentrated under reduced pressure to provide crude product as a brown foam. This material was dissolved in dichloromethane (10 mL) and then loaded onto a FLASH 40+S silica cartridge (40 g). The cartridge was eluted sequentially with 500 mL 2%, 4%, 6%, and 8% methanol in ethyl acetate. The fractions containing product were combined and then concentrated under reduced pressure to provide 880 mg of a yellow solid. This solid was recrystallized from acetonitrile, isolated by filtration, washed with acetonitrile and diethyl ether, and then dried under high vacuum to provide 365 mg of N-{[4-amino-1-(2-methylpropyl)-1H-imidazo[4,5-c]quinolin-2-yl]methoxy}-N'-isopropylurea as a light yellow crystalline solid, mp 218-219° C.

$^1$H NMR (300 MHz, DMSO-d$_6$) δ 9.21 (s, 1H), 8.02 (d, J=8.1 Hz, 1H), 7.62 (d, J=7.4 Hz, 1H), 7.45 (dd, J=7.3, 7.3 Hz, 1H), 7.28 (dd, J=7.1, 7.1 Hz, 1H), 6.66 (br s, 2H), 6.49 (d, J=8.1 Hz, 1H), 5.07 (s, 2H), 4.49 (d, J=7.5 Hz, 2H), 3.71 (m, 1H), 2.22 (m, 1H), 1.01 (d, J=6.5 Hz, 6H), 0.93 (d, J=6.6 Hz, 6H);

MS (APCI) m/z 371.1 (M+H)$^+$;

Anal. Calc'd for C$_{19}$H$_{26}$N$_6$O$_2$: C, 61.60; H, 7.07; N, 22.69. Found: C, 61.41; H, 7.40; N, 22.37.

Examples 4-42

An acid chloride, sulfonyl chloride, sulfamoyl chloride, carbamoyl chloride or isocyanate from the table below (1.1 equivalents) was added to a test tube containing a solution of O-{[4-amino-1-(2-methylpropyl)-1H-imidazo[4,5-c]quinolin-2-yl]methyl}hydroxylamine (30 mg) and triethylamine (2.0 eq.) in dichloromethane (1 mL). The test tube was capped and placed on a shaker at ambient temperature overnight (approximately 18 hours). The reaction was quenched by adding 2 drops of water and then vortexing the test tube. The solvent was removed by vacuum centrifugation. The compounds were purified by preparative high performance liquid chromatography (prep HPLC) using a Waters Fraction Lynx automated purification system. The prep HPLC fractions were analyzed using a Micromass LC-TOFMS, and the appropriate fractions were centrifuge evaporated to provide the trifluoroacetate salt of the desired compound. Column:

Phenomenex LUNA C18(2), 21.2×50 millimeters (mm), 10 micron particle size, 100 Angstroms (Å) pore; flow rate: 25 mL/min; non-linear gradient elution from 5-95% B in 9 min, then hold at 95% B for 2 min, where A is 0.05% trifluoroacetic acid/water and B is 0.05% trifluoroacetic acid/acetonitrile; fraction collection by mass-selective triggering. The table below shows the acid chloride, sulfonyl chloride, sulfamoyl chloride, carbamoyl chloride or isocyanate used for each example, the structure of the resulting compound, and the observed accurate mass for the isolated trifluoroacetate salt.

| Example | Reagent | R | Measured Mass (M + H) |
|---|---|---|---|
| 4 | Benzyloxy chloroformate | | 420.2029 |
| 5 | 2,6-Dimethoxybenzoyl chloride | | 450.2139 |
| 6 | Acetyl chloride | | 328.1793 |
| 7 | Cyclopropanecarbonyl chloride | | 354.1964 |
| 8 | Pentanoyl chloride | | 370.2253 |
| 9 | Isoxazole-5-carbonyl chloride | | 381.1691 |
| 10 | Cyclopentanecarbonyl chloride | | 382.2254 |

-continued
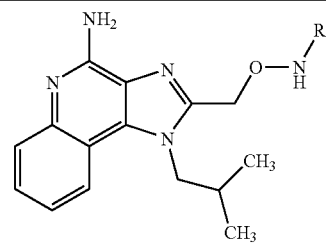
| Example | Reagent | R | Measured Mass (M + H) |
|---|---|---|---|
| 11 | Acetoxyacetyl chloride | | 386.1861 |
| 12 | Thiophene-2-carbonyl chloride | | 396.1524 |
| 13 | Cyclohexanecarbonyl chloride | | 396.2410 |
| 14 | m-Toluoyl chloride | | 404.2123 |
| 15 | 2-Fluorobenzoyl chloride | | 408.1862 |
| 16 | 3-Fluorobenzoyl chloride | | 408.1859 |
| 17 | 4-Fluorobenzoyl chloride | | 408.1833 |
| 18 | 2-Thiopheneacetyl chloride | | 410.1675 |

-continued
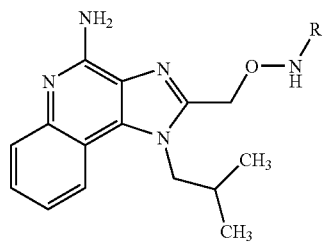
| Example | Reagent | R | Measured Mass (M + H) |
|---|---|---|---|
| 19 | 3-Cyclopentylpropionyl chloride | | 410.2574 |
| 20 | 3-Cyanobenzoyl chloride | | 415.1883 |
| 21 | Cinnamoyl chloride | | 416.2099 |
| 22 | Hydrocinnamoyl chloride | | 418.2263 |
| 23 | 2-Methoxybenzoyl chloride | | 420.2025 |
| 24 | 3-Methoxybenzoyl chloride | | 420.2057 |

-continued
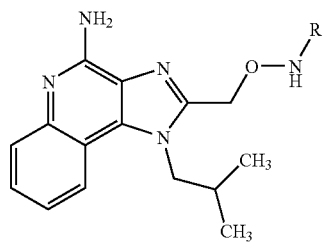
| Example | Reagent | R | Measured Mass (M + H) |
|---|---|---|---|
| 25 | 4-Methoxybenzoyl chloride | H₃C—O—C₆H₄—C(=O)— | 420.2047 |
| 26 | Ethanesulfonyl chloride | H₃C—CH₂—S(=O)₂— | 378.1633 |
| 27 | Isopropylsulfonyl chloride | (H₃C)(CH₃)CH—S(=O)₂— | 392.1779 |
| 28 | Dimethylsulfamoyl chloride | (H₃C)(CH₃)N—S(=O)₂— | 393.1730 |
| 29 | 1-Butanesulfonyl chloride | H₃C—(CH₂)₃—S(=O)₂— | 406.1936 |
| 30 | Benzenesulfonyl chloride | C₆H₅—S(=O)₂— | 426.1626 |
| 31 | 1-Methylimidazole-4-sulfonyl chloride | 1-methylimidazol-4-yl—S(=O)₂— | 430.1666 |

-continued
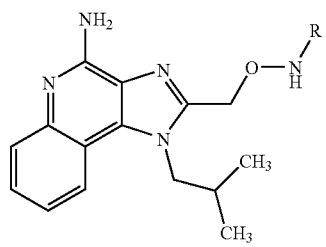
| Example | Reagent | R | Measured Mass (M + H) |
|---|---|---|---|
| 32 | 4-Cyanobenzenesulfonyl chloride | 4-cyanophenyl-SO2- | 451.1553 |
| 33 | Beta-styrenesulfonyl chloride | PhCH=CH-SO2- | 452.1757 |
| 34 | n-Butyl isocyanate | n-BuNH-C(O)- | 385.2363 |
| 35 | Tert-Butyl isocyanate | t-BuNH-C(O)- | 385.2388 |
| 36 | Cyclohexyl isocyanate | CyNH-C(O)- | 411.2525 |
| 37 | Ethyl isocyanatoacetate | EtO2CCH2NH-C(O)- | 415.2110 |

-continued

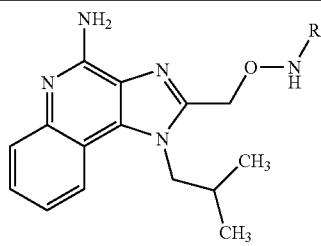

| Example | Reagent | R | Measured Mass (M + H) |
|---|---|---|---|
| 38 | 1-Pyrrolidinecarbonyl chloride | *pyrrolidine-C(=O)–* | 383.2214 |
| 39 | 3-Cyanophenyl isocyanate | *3-cyanophenyl-NH-C(=O)-CH2-* | 430.2019 |
| 40 | Benzoyl isocyanate | *PhC(=O)-NH-C(=O)-CH2-* | 433.1987 |
| 41 | 3-Methoxyphenyl isocyanate | *3-methoxyphenyl-NH-C(=O)-CH2-* | 435.2169 |
| 42 | N-Methyl N-phenylcarbamoyl chloride | *PhN(CH3)-C(=O)-CH2-* | 419.2201 |

Examples 43-68

Part A

Triethylamine (9 mL, 64.7 mmol) was added to a solution of tert-butyl[3-(3-aminoquinolin-4-ylamino)propyl]carbamate (13.65 g, 43.1 mmol) in dichloromethane (150 mL). Chloroacetyl chloride (3.8 mL, 47.5 mmol) was added dropwise over a period of 10 minutes. The reaction mixture was stirred at ambient temperature over the weekend and then concentrated under reduced pressure. The residue was partitioned between ethyl acetate (100 mL) and 1:1 water:saturated aqueous sodium bicarbonate. The organic layer was washed with brine (100 mL). The combined aqueous layers were extracted with ethyl acetate (2×100 mL). The combined organics were dried over magnesium sulfate, filtered, and then concentrated under reduced pressure to provide 14.1 g of crude product as a brown foam. The foam was dissolved in a mixture of dichloromethane (15 mL) and methanol (0.5 mL). The solution was divided and loaded onto two FLASH 40+M silica cartridges (90 g). The cartridges were eluted sequentially with 1 L 1:1 ethyl acetate:hexanes, 5% methanol in 1:1 ethyl acetate:hexanes, and 10% methanol in 1:1 ethyl acetate:hexanes. The fractions containing product were combined and concentrated under reduced pressure to provide 8.96 g of tert-butyl [3-(2-chloromethyl-1H-imidazo[4,5-c]quinolin-1-yl)propyl]carbamate as a light brown foam.

95

Part B

3-Chloroperoxybenzoic acid (13.3 g of 77% max, 59.4 eq.) was added in portions over a period of 5 minutes to a solution of tert-butyl[3-(2-chloromethyl-1H-imidazo[4,5-c]quinolin-1-yl)propyl]carbamate (8.9 g, 23.7 mmol) in chloroform (200 mL). The reaction mixture was allowed to stir at ambient temperature overnight. Ammonium hydroxide (50 mL) was added and the reaction mixture was stirred vigorously. Para-toluensulfonyl chloride (5.43 g, 28.5 mmol) was added over a period of 5 minutes. The reaction mixture was stirred at ambient temperature for 2 hours; an additional 1 g of para-toluensulfonyl chloride was added and the reaction mixture was stirred for another hour. The reaction mixture was filtered to remove solids. The filtrate was transferred to a separatory funnel and the layers were separated. The organic layer was washed with 1:1 water:saturated aqueous sodium bicarbonate (2×150 mL). The combined aqueous was extracted with dichloromethane (2×150 mL) and ethyl acetate (1×100 mL). The combined organic extracts were concentrated under reduced pressure to provide 13.6 g of crude product as a brown foam. The foam was dissolved in dichloromethane (20 mL). The solution was divided and loaded onto two FLASH 40+M silica cartridges (90 g). The first cartridge was eluted sequentially with 1 L 1:1 ethyl acetate:hexanes, 5% methanol in 1:1 ethyl acetate:hexanes, and 10% methanol in 1:1 ethyl acetate:hexanes. The second cartridge was eluted sequentially with 1 L 1:1 ethyl acetate:hexanes, 7% methanol in 1:1 ethyl acetate:hexanes, and 7% methanol in 1:1 ethyl acetate:hexanes. The fractions containing product were combined and then concentrated under reduced pressure to provide 4.3 g of tert-butyl[3-(4-amino-2-chloromethyl-1H-imidazo[4,5-c]quinolin-1-yl)propyl]carbamate as a light yellow foam.

Part C

Triethylamine (4.6 mL, 33.1 mmol) was added to a solution of N-hydroxyphthalimide (2.16 g, 13.2 mmol) in DMF (10 mL). A solution of tert-butyl[3-(4-amino-2-chloromethyl-1H-imidazo[4,5-c]quinolin-1-yl)propyl]carbamate (4.3 g, 11.0 mmol) in DMF (20 ml) was added. The reaction was stirred at ambient temperature for 3.5 hours and then diluted with water (100 mL). The resulting precipitate was isolated by filtration, washed with water, and then dried in a vacuum oven at 60° C. over the weekend to provide 4.25 g of tert-butyl (3-{4-amino-2-[(1,3-dioxo-1,3-dihydroisoindol-2-yl)oxymethyl]-1H-imidazo[4,5-c]quinolin-1-yl}propyl)carbamate as a light yellow solid.

$^1$H NMR (300 MHz, DMSO-d$_6$) δ 8.2 (d, J=8.0 Hz, 1H), 7.9 (s, 4H), 7.7 (m, 1H), 7.5 (m, 1H), 7.3 (m, 1H), 7.2 (m, 1H), 6.7 (br s, 2H), 5.5 (s, 2H), 4.8 (m, 2H), 3.2 (m, 2H), 2.2 (m, 2H), 1.4 (s, 9H);

MS (APCI) m/z 517.3 (M+H)$^+$.

Part D

Hydrazine hydrate (8 mL of 55%) was added to a suspension of tert-butyl (3-{4-amino-2-[(1,3-dioxo-1,3-dihydroisoindol-2-yl)oxymethyl]-1H-imidazo[4,5-c]quinolin-1-yl}propyl)carbamate (4.25 g, 8.23 mmol) in ethanol (70 mL). The reaction became homogeneous after about 2 minutes. A precipitate started forming after about 1 hour. After stirring at ambient temperature for a total of 2 hours the reaction mixture was filtered and the filter cake was washed with dichloromethane. The filtrate was concentrated under reduced pressure. The residue was azeotroped twice with toluene to provide 3.63 g of tert-butyl[3-(4-amino-2-aminooxymethyl-1H-imidazo[4,5-c]quinolin-1-yl)propyl]carbamate as a white solid.

Part E

Acetone (20 mL) was added to a solution of tert-butyl[3-(4-amino-2-aminooxymethyl-1H-imidazo[4,5-c]quinolin-1-yl)propyl]carbamate (3.6 g) in methanol (70 mL). The reaction mixture was stirred at ambient temperature overnight and then concentrated under reduced pressure to provide 4.12 g of tert-butyl[3-(4-amino-2-isopropylideneaminoxymethyl-1H-imidazo[4,5-c]quinolin-1-yl)propyl]carbamate as a light yellow foam.

Part F

Trifluoroacetic acid (7 mL) was added to a suspension of tert-butyl[3-(4-amino-2-isopropylideneaminoxymethyl-1H-imidazo[4,5-c]quinolin-1-yl)propyl]carbamate (4.12 g) in dichloromethane (70 mL). The reaction became homogeneous and was stirred at ambient temperature for 2.5 hours. More trifluoroacetic acid (10 mL) was added and the reaction was stirred for another hour. The reaction mixture was concentrated under reduced pressure and placed under high vacuum overnight to provide 7.68 g of propan-2-one 0-{[4-amino-1-(3-aminopropyl)-1H-imidazo[4,5-c]quinolin-2-yl]methyl}oxime a white solid. Based on the weight this material was assumed to contain 5 equivalents of trifluoroacetic acid.

Part G

An acid chloride, sulfonyl chloride, sulfamoyl chloride, carbamoyl chloride or isocyanate from the table below (1.1 equivalents) was added to a test tube containing propan-2-one 0-{[4-amino-1-(3-aminopropyl)-1H-imidazo[4,5-c]quinolin-2-yl]methyl}oxime trifluoroacetate (~90 mg) prepared in Part F, N,N-diisopropylethylamine (350 μL, 10 equivalents), and chloroform (2 mL). The test tube was capped and placed on a shaker at ambient temperature overnight (approximately 18 hours). Water (1 drop) was added to the test tube and then the solvent was removed by vacuum centrifugation. The residue was dissolved in methanol (5 mL).

Part H

A portion (2.5 mL) of the solution from Part G was transferred to a fresh test tube and then the solvent was removed by vacuum centrifugation. Methanol (1 mL), glacial acetic acid (1 mL), and 400 μL of a 1.0 M solution of sodium cyanoborohydride in tetrahydrofuran were added to the test tube. The test tube was capped and placed on a shaker at ambient temperature overnight (approximately 18 hours). The solvent was removed by vacuum centrifugation. The compounds were purified by preparative high performance liquid chromatography (prep HPLC) using a Waters Fraction Lynx automated purification system using the method described above for Examples 4-42. The table below shows the acid chloride, sulfonyl chloride, sulfamoyl chloride, carbamoyl chloride or isocyanate used for each example, the structure of the resulting compound, and the observed accurate mass for the isolated trifluoroacetate salt.

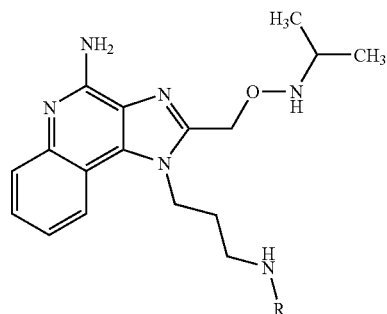
| Example | Reagent | R | Measured Mass (M + H) |
|---|---|---|---|
| 43 | Pentanoyl chloride | | 413.2688 |
| 44 | Thiophene-2-carbonyl chloride | | 439.1887 |
| 45 | Cyclohexanecarbonyl chloride | | 439.2802 |
| 46 | m-Toluoyl chloride | | 447.2496 |
| 47 | Phenylacetyl chloride | | 447.2506 |
| 48 | 3-Fluorobenzoyl chloride | | 451.2300 |
| 49 | 3-Cyclopentanepropionyl chloride | | 453.2965 |
| 50 | Cinnamoyl chloride | | 459.2536 |

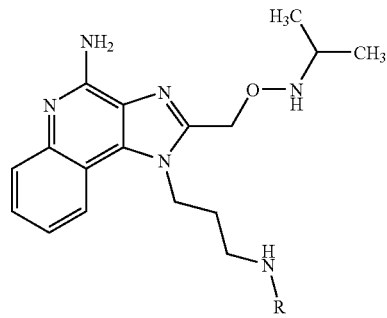
| Example | Reagent | R | Measured Mass (M + H) |
|---|---|---|---|
| 51 | m-Anisoyl chloride | *3-methoxybenzoyl* | 463.2481 |
| 52 | Ethanesulfonyl chloride | *ethylsulfonyl* | 421.2022 |
| 53 | Dimethylsulfamoyl chloride | *dimethylsulfamoyl* | 436.2159 |
| 54 | Benzenesulfonyl chloride | *phenylsulfonyl* | 469.2024 |
| 55 | 2-Thiophenesulfonyl chloride | *2-thienylsulfonyl* | 475.1577 |
| 56 | 3-Methylbenzenesulfonyl chloride | *3-methylphenylsulfonyl* | 483.2185 |

-continued

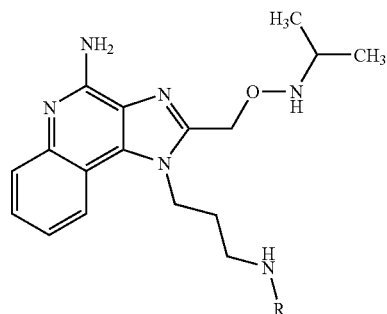

| Example | Reagent | R | Measured Mass (M + H) |
|---|---|---|---|
| 57 | 4-Methoxybenzenesulfonyl chloride | 4-methoxyphenylsulfonyl | 499.2121 |
| 58 | 4-Chlorobenzensulfonyl chloride | 4-chlorophenylsulfonyl | 503.1618 |
| 59 | n-Propyl isocyanate | n-propylaminocarbonyl | 414.2620 |
| 60 | Phenyl isocyanate | phenylaminocarbonyl | 448.2486 |
| 61 | Cyclohexyl isocyanate | cyclohexylaminocarbonyl | 454.2916 |
| 62 | o-Tolyl isocyanate | o-tolylaminocarbonyl | 462.2619 |
| 63 | Benzoyl isocyanate | benzoylaminocarbonyl | 476.2406 |

-continued

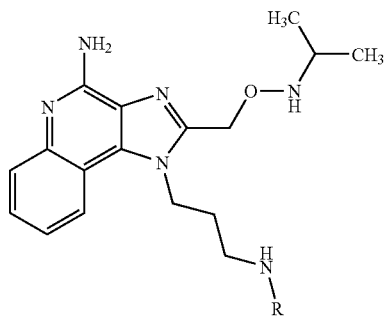

| Example | Reagent | R | Measured Mass (M + H) |
|---|---|---|---|
| 64 | 2-Phenylethyl isocyanate | | 476.2772 |
| 65 | 1-Piperidinecarbonyl chloride | | 440.2767 |
| 66 | 2-Methoxyphenyl isocyanate | | 478.2539 |
| 67 | 4-Dimethylaminophenyl isocyanate | | 491.2894 |
| 68 | N-Methyl N-phenylcarbamoyl chloride | | 462.2595 |

Examples 69-97

Part A

Using the general method of Examples 43-68 Part A, tert-butyl[2-(3-aminoquinolin-4-ylamino)ethyl]carbamate (43.5 g, 144 mmol) was reacted with chloroacetyl chloride (17.72 g, 158 mmol) to provide 37.39 g of tert-butyl[2-(2-chloromethyl-1H-imidazo[4,5-c]quinolin-1-yl)ethyl]carbamate.

Part B

Using the general method of Examples 43-68 Part B, a solution of tert-butyl[2-(2-chloromethyl-1H-imidazo[4,5-c]quinolin-1-yl)ethyl]carbamate (27.45 g, 76.1 mmol) in chloroform (500 mL) was treated with 3-chloroperoxybenzoic acid (25.6 g of 77% max, 114 mmol) and the resulting 5-oxide was aminated using ammonium hydroxide (150 mL) and para-toluenesulfonyl chloride (17.4 g, 91.3 mmol) to provide 41.83 g of crude tert-butyl[2-(4-amino-2-chloromethyl-1H-imidazo[4,5-c]quinolin-1-yl)ethyl]carbamate as a brown solid. A portion (~32 g) of the crude material was dissolved in dichloromethane and then washed with 1 N hydrochloric acid (×3). The organic layer was allowed to stand for several days and a precipitate formed. This material was isolated by filtration to provide 7.0 g of tert-butyl[2-(4-amino-2-chloromethyl-1H-imidazo[4,5-c]quinolin-1-yl)ethyl]carbamate as an off white solid.

Part C

Using the general method of Examples 43-68 Part C, tert-butyl[2-(4-amino-2-chloromethyl-1H-imidazo[4,5-c]quinolin-1-yl)ethyl]carbamate (7 g, 19 mmol)) was reacted with N-hydroxyphthalimide (3.65 g, 22.3 mmol) to provide 6.37 g of tert-butyl (2-{4-amino-2-[(1,3-dioxo-1,3-dihydroisoindol-2-yl)oxymethyl]-1H-imidazo[4,5-c]quinolin-1-yl}ethyl)carbamate as a yellow solid.

$^1$H NMR (300 MHz, DMSO-$d_6$) δ 8.3 (d, J=8.5 Hz, 1H), 7.9 (s, 4H), 7.6 (m, 1H), 7.5 (m, 1H), 7.3 (m, 1H), 7.1 (m, 1H), 6.6 (br s, 2H), 5.5 (s, 2H), 4.9 (m, 2H), 3.6 (m, 2H), 1.3 (s, 9H);

MS (APCI) m/z 503.2 (M+H)$^+$.

Part D

Using the general method of Examples 43-68 Part D, the N-phthalimide protecting group was removed from tert-butyl (2-{4-amino-2-[(1,3-dioxo-1,3-dihydroisoindol-2-yl)oxymethyl]-1H-imidazo[4,5-c]quinolin-1-yl}ethyl)carbamate (6.35 g) to provide crude tert-butyl[2-(4-amino-2-aminooxymethyl-1H-imidazo[4,5-c]quinolin-1-yl)ethyl]carbamate.

Part E

Acetone (25 mL) was added to a suspension of the crude material from Part D in methanol (100 mL). The resulting solution was stirred at ambient temperature for 3 hours and then concentrated under reduced pressure. The residue was azeotroped once with toluene, slurried with ethanol (100 mL) and then filtered. The filter cake was washed with additional ethanol. The filtrate was concentrated under reduced pressure to provide 3.9 g of product as a yellow solid. Additional product (0.9 g) was obtained by extracting the filter cake with dichloromethane. The two lots were combined to provide 4.8 g of tert-butyl[2-(4-amino-2-isopropylideneaminooxymethyl-1H-imidazo[4,5-c]quinolin-1-yl)ethyl]carbamate.

Part F

Trifluoroacetic acid (10 mL) was added to a suspension of tert-butyl[2-(4-amino-2-isopropylideneaminooxymethyl-1H-imidazo[4,5-c]quinolin-1-yl)ethyl]carbamate (4.8 g) in dichloromethane (100 mL). The reaction became homogeneous and was stirred at ambient temperature. At 2.5 hours and 3.5 hours more trifluoroacetic acid (10 mL and 5 mL respectively) was added. After a total reaction time of 4 hours the reaction mixture was concentrated under reduced pressure. The residue was azeotroped with toluene (×3) and then placed under high vacuum overnight to provide 9.97 g of propan-2-one O-{[4-amino-1-(2-aminoethyl)-1H-imidazo[4,5-c]quinolin-2-yl]methyl}oxime as a yellow solid. Based on the weight this material was assumed to contain 5 equivalents of trifluoroacetic acid.

Part G

An acid chloride, sulfonyl chloride, sulfamoyl chloride, carbamoyl chloride or isocyanate from the table below (1.1 equivalents) was added to a test tube containing propan-2-one O-{[4-amino-1-(2-aminoethyl)-1H-imidazo[4,5-c]quinolin-2-yl]methyl}oxime trifluoroacetate (~90 mg) prepared in Part F, N,N-diisopropylethylamine (350 µL, 10 equivalents), and chloroform (2 mL). The test tube was capped and placed on a shaker at ambient temperature overnight (approximately 18 hours).

Part H

A portion (1 mL) of the solution from Part G was transferred to a fresh test tube and then the solvent was removed by vacuum centrifugation. Methanol (1 mL), glacial acetic acid (1 mL), and 300 µL of a 1.0 M solution of sodium cyanoborohydride in tetrahydrofuran were added to the test tube. The test tube was capped and placed on a shaker at ambient temperature overnight (approximately 18 hours). The solvent was removed by vacuum centrifugation. The compounds were purified by preparative high performance liquid chromatography (prep HPLC) using a Waters Fraction Lynx automated purification system using the method described above for Examples 4-42. The table below shows the acid chloride, sulfonyl chloride, sulfamoyl chloride, carbamoyl chloride or isocyanate used for each example, the structure of the resulting compound, and the observed accurate mass for the isolated trifluoroacetate salt.

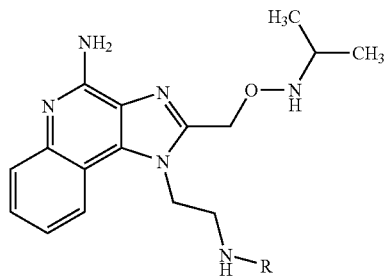

| Example | Reagent | R | Measured Mass (M + H) |
|---|---|---|---|
| 69 | Pentanoyl chloride | 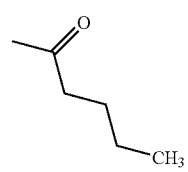 | 399.2517 |
| 70 | Benzoyl chloride | 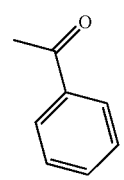 | 419.2220 |

-continued
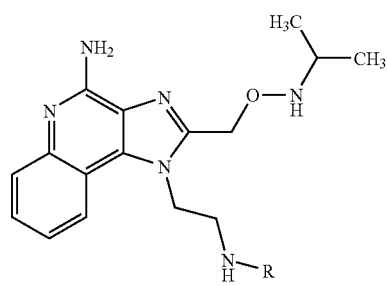
| Example | Reagent | R | Measured Mass (M + H) |
|---|---|---|---|
| 71 | Thiophene-2-carbonyl chloride | (2-thienyl)C(=O)– | 425.1739 |
| 72 | Cyclohexanecarbonyl chloride | cyclohexyl-C(=O)– | 425.2692 |
| 73 | m-Toluoyl chloride | (3-methylphenyl)C(=O)– | 433.2369 |
| 74 | Phenylacetyl chloride | PhCH$_2$C(=O)– | 433.2391 |
| 75 | 3-Fluorobenzoyl chloride | (3-fluorophenyl)C(=O)– | 437.2117 |
| 76 | 3-Cyanobenzoyl chloride | (3-cyanophenyl)C(=O)– | 444.2170 |

-continued
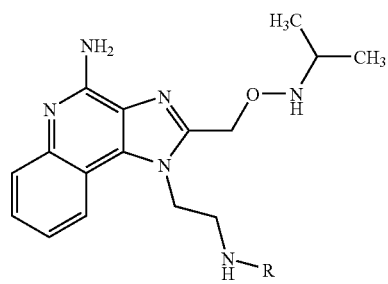
| Example | Reagent | R | Measured Mass (M + H) |
|---|---|---|---|
| 77 | m-Anisoyl chloride | 3-methoxybenzoyl | 449.2313 |
| 78 | Phenoxyacetyl chloride | phenoxyacetyl | 449.2321 |
| 79 | 3-Chlorobenzoyl chloride | 3-chlorobenzoyl | 453.1832 |
| 80 | Trans-2-Phenyl-1-cyclopropanecarbonyl chloride | trans-2-phenyl-1-cyclopropanecarbonyl | 459.2547 |
| 81 | Methyl 4-chlorocarbonyl benzoate | 4-(methoxycarbonyl)benzoyl | 477.2285 |
| 82 | Dimethylsulfamoyl choride | dimethylsulfamoyl | 422.1976 |

-continued

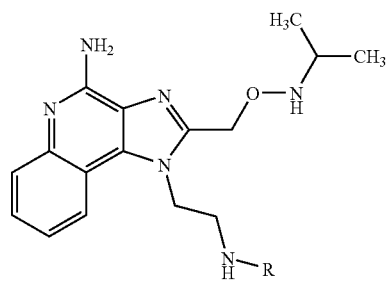

| Example | Reagent | R | Measured Mass (M + H) |
|---|---|---|---|
| 83 | Benzenesulfonyl chloride | methylsulfonyl-phenyl | 455.1888 |
| 84 | 2-Thiophenesulfonyl chloride | methylsulfonyl-thiophene | 461.1451 |
| 85 | 3-Methylbenzenesulfonyl chloride | methylsulfonyl-(3-methylphenyl) | 469.2006 |
| 86 | 4-Cyanobenzenesulfonyl chloride | methylsulfonyl-(4-cyanophenyl) | 480.1805 |
| 87 | Beta-Styrenesulfonyl chloride | methylsulfonyl-styryl | 481.2017 |
| 88 | 4-Methoxybenzenesulfonyl chloride | methylsulfonyl-(4-methoxyphenyl) | 485.1993 |
| 89 | 4-Trifluoromethyl benzenesulfonyl chloride | methylsulfonyl-(4-trifluoromethylphenyl) | 523.1732 |
| 90 | 4-Biphenylsulfonyl chloride | methylsulfonyl-(4-biphenyl) | 531.2167 |

-continued
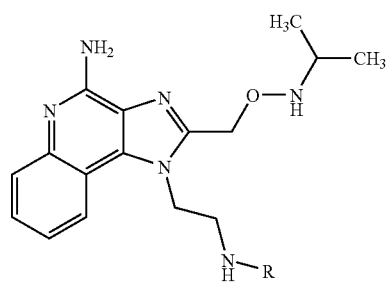
| Example | Reagent | R | Measured Mass (M + H) |
|---|---|---|---|
| 91 | n-Propyl isocyanate | -C(O)NH-CH2CH2CH3 | 400.2466 |
| 92 | N,N-Dimethylcarbamoyl chloride | -C(O)N(CH3)2 | 386.2315 |
| 93 | Phenyl isocyanate | -C(O)NH-Ph | 434.2301 |
| 94 | 1-Piperidinecarbonyl chloride | -C(O)-piperidinyl | 426.2625 |
| 95 | 2-Chlorophenyl isocyanate | -C(O)NH-(2-Cl-Ph) | 468.1926 |
| 96 | N-Methyl N-phenylcarbamoyl chloride | -C(O)N(CH3)(Ph) | 448.2464 |
| 97 | Benzenesulfonyl isocyanate | -C(O)NH-SO2-Ph | 498.1898 |

Example 98

N-[4-(4-Amino-2-{[(isopropylamino)oxy]methyl}-6,7-dimethyl-1H-imidazo[4,5-c]pyridin-1-yl)butyl]benzamide

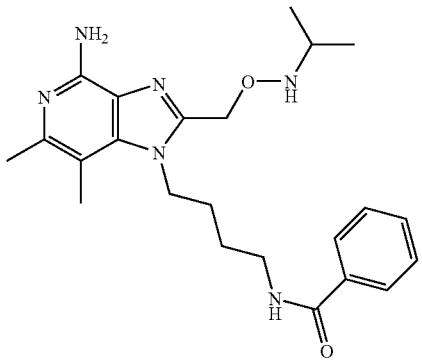 [SMILES: Cc1nc(N)c2nc(CONC(C)C)n(CCCCNC(=O)c3ccccc3)c2c1C]

Part A

A solution of tert-butyl 4-aminobutylcarbamate (8.50 g, 45.2 mmol) in DMF (20 mL) in an addition funnel was added over 1 hour to a stirred solution of 2,4-dichloro-5,6-dimethyl-3-nitropyridine (10.0 g, 45.2 mmol) and triethylamine (9.30 mL, 67.8 mmol) in DMF (100 mL). The addition funnel was rinsed with DMF (17 mL) and the solution was added to the reaction vessel. After the reaction solution was stirred overnight at room temperature, additional tert-butyl 4-aminobutylcarbamate (0.1 equivalent) was added. The solution was allowed to stir an additional 2 hours, then was concentrated under reduced pressure. The resulting oil was partitioned between ethyl acetate (400 mL) and water (100 mL). The organic phase was washed with water (4×50 mL), then was dried over magnesium sulfate, filtered, and concentrated under reduced pressure. The crude product was purified by flash chromatography (silica gel, elution with 33% ethyl acetate in hexanes followed by 66% ethyl acetate in hexanes) to afford 9.2 g of tert-butyl 4-[(2-chloro-5,6-dimethyl-3-nitropyridin-4-yl)amino]butylcarbamate.

Part B

The purified tert-butyl 4-[(2-chloro-5,6-dimethyl-3-nitropyridin-4-yl)amino]butylcarbamate from A was combined with crude tert-butyl 4-[(2-chloro-5,6-dimethyl-3-nitropyridin-4-yl)amino]butylcarbamate from a similar experiment to yield 38 g (approximately 101 mmol) of material, which was combined with sodium azide (13.0 g, 202 mmol), cerium(III) chloride heptahydrate (19.0 g, 51.0 mmol), and 9:1 acetonitrile/water (300 mL). The reaction mixture was heated at reflux for 3 days, then was allowed to cool to room temperature and was filtered. The filter cake was rinsed with DMF. The filtrate was concentrated under reduced pressure to yield an oil that was purified by flash chromatography (silica gel, elution with 2:1:1 ethyl acetate/hexanes/chloroform, followed by 4:1 ethyl acetate/chloroform) to afford 23 g of tert-butyl 4-[(5,6-dimethyl-8-nitrotetraazolo[1,5-a]pyridin-7-yl)amino]butylcarbamate.

Part C

A mixture of tert-butyl 4-[(5,6-dimethyl-8-nitrotetraazolo[1,5-a]pyridin-7-yl)amino]butylcarbamate (9.00 g, 23.7 mmol), 10% palladium on carbon (900 mg), and acetonitrile (100 mL) was hydrogenated on a Parr apparatus for 5 hours. The mixture was filtered through CELITE filter agent, which was rinsed afterwards with methanol. The filtrate was concentrated under reduced pressure to yield 6.70 g of tert-butyl 4-[(8-amino-5,6-dimethyltetraazolo[1,5-a]pyridin-7-yl)amino]butylcarbamate.

Part D

Ethyl 2-chloroethanimidoate hydrochloride (ethyl chloroacetimidate hydrochloride) (2.58 g, 16.4 mmol) was added to a solution of tert-butyl 4-[(8-amino-5,6-dimethyltetraazolo[1,5-a]pyridin-7-yl)amino]butylcarbamate (3.80 g, 10.9 mmol) in chloroform (75 mL). The solution was stirred for 3 days, then saturated aqueous sodium bicarbonate (40 mL) was added. The aqueous phase was extracted with chloroform (3×40 mL). The organic phases were combined, washed with water (2×20 mL) and saturated aqueous sodium bicarbonate (20 mL), dried over magnesium sulfate, filtered, and concentrated under reduced pressure to afford 4.3 g of tert-butyl 4-[8-(chloromethyl)-5,6-dimethyl-7H-imidazo[4,5-c]tetraazolo[1,5-a]pyridin-7-yl]butylcarbamate, which was used in the next step without purification.

Part E

Concentrated hydrochloric acid (10 mL) was added to a suspension of tert-butyl 4-[8-(chloromethyl)-5,6-dimethyl-7H-imidazo[4,5-c]tetraazolo[1,5-a]pyridin-7-yl]butylcarbamate (1.00 g, 2.30 mmol) in methanol (23 mL). The reaction mixture was stirred at room temperature for 2 hours, then was concentrated under reduced pressure to yield a residue. The residue was concentrated twice from toluene to remove residual water, then was triturated with methanol. A solid was isolated by filtration and was dried under vacuum to provide 0.68 g of 4-[8-(chloromethyl)-5,6-dimethyl-7H-imidazo[4,5-c]tetraazolo[1,5-a]pyridin-7-yl]butan-1-amine hydrochloride.

Part F

Benzoic anhydride (3.1 g, 13.8 mmol) was added to a flask containing 4-[8-(chloromethyl)-5,6-dimethyl-7H-imidazo[4,5-c]tetraazolo[1,5-a]pyridin-7-yl]butan-1-amine hydrochloride (4.30 g, 12.5 mmol), triethylamine (3.70 mL, 26.3 mmol), and dichloromethane (100 mL) at 0° C. The reaction mixture was stirred at room temperature for 1 day and additional triethylamine (0.5 mL) and benzoic anhydride (0.8 g) were added. The reaction mixture was stirred for 6 hours at room temperature. The volatiles were removed under reduced pressure and water (50 mL) followed by ethyl acetate (50 mL) were added to the solid residue. The mixture was sonicated for 1 minute, then the solid was isolated by filtration, washed with water and ethyl acetate, and dried under vacuum to afford 4.7 g of N-{4-[8-(chloromethyl)-5,6-dimethyl-7H-imidazo[4,5-c]tetraazolo[1,5-a]pyridin-7-yl]butyl}benzamide.

Part G

N-Hydroxyphthalimide (2.60 g, 16.0 mmol) and triethylamine (2.20 mL, 16.0 mmol) were added to a suspension of N-{4-[8-(chloromethyl)-5,6-dimethyl-7H-imidazo[4,5-c]tetraazolo[1,5-a]pyridin-7-yl]butyl}benzamide (4.70 g, 11.4 mmol) in DMF (285 mL). The reaction mixture was allowed to stir for 3 days, then was concentrated under reduced pressure to a white slurry. Methanol was added and a white solid was isolated by filtration, washed with methanol, and dried under vacuum to afford 5.70 g of N-[4-(8-{[(1,3-dioxo-1,3-dihydro-2H-isoindol-2-yl)oxy]methyl}-5,6-dimethyl-7H-imidazo[4,5-c]tetraazolo[1,5-a]pyridin-7-yl)butyl]benzamide.

Part H

Anhydrous hydrazine (0.47 mL, 15 mmol) was added to a stirred suspension of N-[4-(8-{[(1,3-dioxo-1,3-dihydro-2H-isoindol-2-yl)oxy]methyl}-5,6-dimethyl-7H-imidazo[4,5-c]tetraazolo[1,5-a]pyridin-7-yl)butyl]benzamide (2.8 g, 5.0 mmol) in ethanol (50 mL). After two hours, a solid was isolated by filtration and the filter cake was washed with ethanol. Acetone (25 mL) and methanol (25 mL) were added to the solid and the mixture was stirred overnight. The volatiles were removed under reduced pressure to afford a solid that was triturated with 1 M aqueous sodium hydroxide (10 mL) and 1:1 methanol/acetone (4 mL). The solid was isolated by filtration, washed with water, and dissolved in chloroform (100 mL). The solution was dried over magnesium sulfate, filtered, concentrated under reduced pressure, and dried under vacuum to afford 1.9 g of a N-{4-[5,6-dimethyl-8-({[(1-methylethylidene)amino]oxy}methyl)-7H-imidazo[4,5-c]tetraazolo[1,5-a]pyridin-7-yl]butyl}benzamide as a white solid.

Part I

A mixture of N-{4-[5,6-dimethyl-8-({[(1-methylethylidene)amino]oxy}methyl)-7H-imidazo[4,5-c]tetraazolo[1,5-a]pyridin-7-yl]butyl}benzamide (1.9 g, 4.2 mmol), triphenylphosphine (2.2 g, 8.4 mmol), and 1,2-dichlorobenzene (40 mL) was heated at 125° C. for 2 days. The reaction was allowed to cool to room temperature and was concentrated under reduced pressure. The residue was dissolved in methanol (20 mL) and 1 M aqueous hydrochloric acid (20 mL) and heated at 40° C. for 6 hours. The reaction was allowed to stand at room temperature overnight and a white precipitate formed that was removed by filtration. The filtrate was concentrated under reduced pressure and the residue was partitioned between 1 M aqueous hydrochloric acid (20 mL) and chloroform (10 mL). The aqueous layer was extracted with chloroform (3×10 mL). The organic layers were combined, washed with saturated aqueous sodium carbonate, dried over sodium sulfate, filtered, and concentrated under reduced pressure. The solid was purified by chromatography using a HORIZON HPFC system (an automated, modular high-performance flash purification product available from Biotage, Inc, Charlottesville, Va., USA) (silica gel, gradient elution with 10-35% CMA in chloroform, where CMA is 80:18:2 chloroform/methanol/concentrated ammonium hydroxide). The appropriate fractions were combined and concentrated under reduced pressure. The solid was triturated with ethyl acetate and was isolated by filtration, washed with ethyl acetate, and dried under vacuum at 50° C. overnight to provide 0.85 g of N-{4-[4-amino-6,7-dimethyl-2-({[(1-methylethylidene)amino]oxy}methyl)-1H-imidazo[4,5-c]pyridin-1-yl]butyl}benzamide as a white powder, mp 206.0-208.0° C. Anal. Calcd for $C_{23}H_{30}N_6O_2 \cdot 0.06$ CHCl$_3$: C, 64.46; H, 7.05; N, 19.56. Found: C, 64.31; H, 7.06; N, 19.55.

Part J

A solution of sodium cyanoborohydride in tetrahydrofuran (1 M, 6 mL) was added to a solution of N-{4-[4-amino-6,7-dimethyl-2-({[(1-methylethylidene)amino]oxy}methyl)-1H-imidazo[4,5-c]pyridin-1-yl]butyl}benzamide (260 mg, 0.62 mmol) in 1:2 acetic acid/methanol (9 mL). The reaction mixture was stirred overnight, concentrated under reduced pressure, and partitioned between 1 M aqueous hydrochloric acid (20 mL) and chloroform (5 mL). After the bubbling subsided, the layers were separated and the aqueous phase was washed with chloroform (2×5 mL). The organic layers were combined and back-extracted with 1 M aqueous hydrochloric acid (2×5 mL). The aqueous layers were combined and adjusted to pH 10 with 1 M aqueous sodium hydroxide, then were extracted with chloroform (4×). The organic layers were combined, washed with saturated aqueous sodium bicarbonate (5 mL), dried over sodium sulfate, filtered, and concentrated under reduced pressure to yield a foam. The foam was purified by chromatography on a HORIZON HPFC system (silica gel, gradient elution with 3-35% CMA in chloroform) followed by crystallization from acetonitrile. The crystals were isolated by filtration and dried under vacuum at 70° C. to yield 80 mg of N-[4-(4-amino-2-{[(isopropylamino)oxy]methyl}-6,7-dimethyl-1H-imidazo[4,5-c]pyridin-1-yl)butyl]benzamide as a white powder, mp 161.0-162.0° C.

Anal. Calcd for $C_{23}H_{32}N_6O_2$: C, 65.07; H, 7.60; N, 19.80. Found: C, 64.85; H, 7.92; N, 20.00.

Example 99

N-[4-(4-Amino-2-{[(isopropylamino)oxy]methyl}-6,7-dimethyl-1H-imidazo[4,5-c]pyridin-1-yl)butyl]-2-methylpropanamide

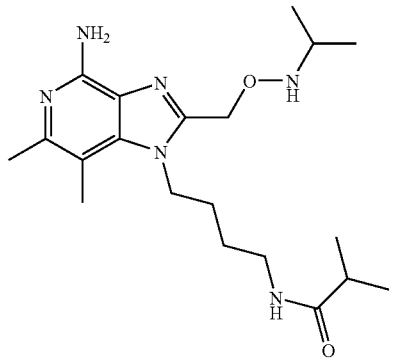 [SMILES: Cc1nc(N)c2nc(CONC(C)C)n(CCCCNC(=O)C(C)C)c2c1C]

Part A

Isobutyric anhydride (2.28 mL, 13.8 mmol) was added to a flask containing 4-[8-(chloromethyl)-5,6-dimethyl-7H-imidazo[4,5-c]tetraazolo[1,5-a]pyridin-7-yl]butan-1-amine hydrochloride (prepared as described in Parts A-E of Example 98, 4.30 g, 12.5 mmol), triethylamine (3.66 mL, 26.3 mmol), and dichloromethane (100 mL) at 0° C. The reaction mixture was stirred at room temperature for 3 hours. The solution was concentrated under reduced pressure and water (50 mL) followed by ethyl acetate (50 mL) were added to the solid residue. The mixture was sonicated for 1 minute, then the solid was isolated by filtration, washed with water and ethyl acetate. Toluene was added to the solid and the mixture was concentrated under reduced pressure. The solid was dried under vacuum to afford 4.12 g of N-{4-[8-(chloromethyl)-5,6-dimethyl-7H-imidazo[4,5-c]tetraazolo[1,5-a]pyridin-7-yl]butyl}-2-methylpropanamide.

Part B

The general method described in Part G of Example 98 was used to convert 4.10 g N-{4-[8-(chloromethyl)-5,6-dimethyl-7H-imidazo[4,5-c]tetraazolo[1,5-a]pyridin-7-yl]butyl}-2-methylpropanamide into 4.92 g of N-[4-(8-{[(1,3-dioxo-1,3-dihydro-2H-isoindol-2-yl)oxy]methyl}-5,6-dimethyl-7H-imidazo[4,5-c]tetraazolo[1,5-a]pyridin-7-yl)butyl]-2-methylpropanamide.

Part C

Anhydrous hydrazine (0.91 mL, 29 mmol) was added to a stirred suspension of N-[4-(8-{[(1,3-dioxo-1,3-dihydro-2H-isoindol-2-yl)oxy]methyl}-5,6-dimethyl-7H-imidazo[4,5-c]tetraazolo[1,5-a]pyridin-7-yl)butyl]-2-methylpropanamide (4.90 g, 9.71 mmol) in ethanol (100 mL). Dichloromethane (50 mL) was added. After four hours, acetone (50 mL) was added and the reaction mixture was stirred overnight. A solid was removed by filtration and washed with methanol. The filtrate was concentrated to provide a solid that was triturated with 1:1 saturated aqueous sodium bicarbonate/water. The solid was isolated by filtration, washed with water, and dissolved in chloroform (300 mL). The solution was washed with water (2×50 mL), dried over sodium sulfate, filtered, concentrated under reduced pressure, and dried under vacuum to afford N-{4-[5,6-dimethyl-8-({[(1-methylethylidene)amino]oxy}methyl)-7H-imidazo[4,5-c]tetraazolo[1,5-a]pyridin-7-yl]butyl}-2-methylpropanamide that was used in the next experiment.

Part D

A mixture of N-{4-[5,6-dimethyl-8-({[(1-methylethylidene)amino]oxy}methyl)-7H-imidazo[4,5-c]tetraazolo[1,5-a]pyridin-7-yl]butyl}-2-methylpropanamide (from Part C, approximately 9.71 mmol), triphenylphosphine (5.1 g, 19 mmol), and 1,2-dichlorobenzene (97 mL) was heated at 125° C. for 2 days, then stirred at room temperature for 3 days, then heated at 130° C. for 5 hours. The reaction was allowed to cool to room temperature and was concentrated under reduced pressure. The residue was dissolved in methanol (80 mL) and 1 M aqueous hydrochloric acid (40 mL) and heated at 40° C. for 6 hours. The reaction was allowed to stir at room temperature overnight and a white precipitate formed that was removed by filtration. The filtrate was concentrated under reduced pressure and the residue was partitioned between 1 M aqueous hydrochloric acid (20 mL) and chloroform (10 mL). The aqueous layer was extracted with chloroform (3×10 mL). The organic layers were combined, washed with saturated aqueous sodium bicarbonate, dried over sodium sulfate, filtered, and concentrated under reduced pressure. The solid was purified by chromatography using a HORIZON HPFC system (silica gel, gradient elution with 5-55% CMA in chloroform). The appropriate fractions were combined and concentrated under reduced pressure. The resulting solid was triturated with acetonitrile and then was recrystallized from acetonitrile to provide N-{4-[4-amino-6,7-dimethyl-2-({[(1-methylethylidene)amino]oxy}methyl)-1H-imidazo[4,5-c]pyridin-1-yl]butyl}-2-methylpropanamide as a white powder, mp 180.0-181.0° C. Anal. Calcd for $C_{20}H_{32}N_6O_2$: C, 61.83; H, 8.30; N, 21.63. Found: C, 61.65; H, 8.65; N, 21.70.

Part E

A modification on the method described in Part J of Example 98 was used to convert 1.10 g of N-{4-[4-amino-6,7-dimethyl-2-({[(1-methylethylidene)amino]oxy}methyl)-1H-imidazo[4,5-c]pyridin-1-yl]butyl}-2-methylpropanamide into 0.052 g of N-[4-(4-amino-2-{[(isopropylamino)oxy]methyl}-6,7-dimethyl-1H-imidazo[4,5-c]pyridin-1-yl)butyl]-2-methylpropanamide. After the work-up, the crude material was not purified by chromatography, rather by trituration with acetonitrile. The purified product was isolated by filtration and was dried under vacuum to afford N-[4-(4-amino-2-{[(isopropylamino)oxy]methyl}-6,7-dimethyl-1H-imidazo[4,5-c]pyridin-1-yl)butyl]-2-methylpropanamide as a white powder, mp 156.0-157.0° C.

Anal. Calcd for $C_{20}H_{34}N_6O_2 \cdot 0.2H_2O \cdot 0.03\,CH_3CN$: C, 60.91; H, 8.80; N, 21.38. Found: C, 60.94; H, 9.20; N, 21.77.

Example 100

1-{4-Amino-2-[(aminooxy)methyl]-1H-imidazo[4,5-c]quinolin-1-yl}-2-methylpropan-2-ol

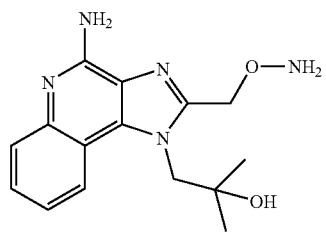

Part A

Triethylamine (50.0 mL, 360 mmol) was added to a suspension of 4-chloro-3-nitroquinoline (50.0 g, 240 mmol) in DMF (200 mL), followed by dropwise addition of a solution of 1-amino-2-methyl-propan-2-ol (23.5 g, 264 mmol) in DMF (50 mL). The reaction mixture was stirred overnight at room temperature, then water (500 mL) was added and stirring was continued for 30 minutes. A solid was isolated by filtration, washed with water, and dried to yield 60.9 g of 2-methyl-1-[(3-nitroquinolin-4-yl)amino]propan-2-ol, which was used without further purification.

Part B

A mixture of 2-methyl-1-[(3-nitroquinolin-4-yl)amino]propan-2-ol (60.9 g, 233 mmol), 5% platinum on carbon (6.1 g), and ethanol (500 mL) was hydrogenated on a Parr apparatus at 30 psi (2.1×10$^5$ Pa) for 3 hours. The mixture was filtered through CELITE filter agent, which was subsequently rinsed with methanol and dichloromethane. The filtrate was concentrated under reduced pressure to yield an oil that was concentrated twice from toluene to afford 56.6 g of a brown oil that was used directly in the next step.

Part C

Triethylamine (49.0 mL, 350 mmol) was added to a stirred suspension of the material from Part B in dichloromethane (450 mL). A solution of chloroacetyl chloride (21.0 mL, 257 mmol) in dichloromethane (50 mL) was added dropwise over 45 minutes. The reaction mixture was stirred for approximately 3 days at room temperature. The solution was concentrated under reduced pressure. The residue was partitioned between ethyl acetate (500 mL) and 1:1 saturated aqueous sodium bicarbonate/water (500 mL). The aqueous layer was extracted with ethyl acetate (3×250 mL) and chloroform (250 mL). The organic layers were combined, dried over magnesium sulfate, filtered, and concentrated under reduced pressure. The resulting pale brown solid was crystallized from dichloromethane (80 mL) to afford 25.7 g of 1-[2-(chloromethyl)-1H-imidazo[4,5-c]quinolin-1-yl]-2-methylpropan-2-ol as pale yellow crystals. The mother liquor was concentrated and crystallized from dichloromethane (40 mL) to yield an additional 3.56 g of product. The mother liquor was concentrated under reduced pressure and the resulting residue was purified by chromatography using a HORIZON HPFC system (silica gel, gradient elution with 3-13% methanol in ethyl acetate) to afford 15.5 g of 1-[2-(chloromethyl)-1H-imidazo[4,5-c]quinolin-1-yl]-2-methylpropan-2-ol.

Part D mCPBA (77% pure, 36.5 g, 163 mmol) was added over 10 minutes to a stirred suspension of 1-[2-(chloromethyl)-1H-imidazo[4,5-c]quinolin-1-yl]-2-methylpropan-2-ol (23.6 g, 81.4 mmol) in chloroform (500 mL). The resulting solution was stirred at room temperature for 1.5 hours. Concentrated ammonium hydroxide (200 mL) was added. After 5 minutes, p-toluenesulfonyl chloride (18.6 g, 97.7 mmol) was added in portions. The mixture was stirred at room temperature for 2.3 hours, then was transferred to a separatory funnel. The layers were separated and the aqueous layer was extracted with dichloromethane (2×100 mL, then 3×200 mL). The organic layers were combined, dried over magnesium sulfate, filtered, and concentrated under reduced pressure to yield a foam. The crude product was purified in portions by chromatography on a HORIZON HPFC system (silica gel, elution with 5% methanol in chloroform followed by gradient elution with 5-15% methanol in chloroform) to yield 9.42 g of 1-[4-amino-2-(chloromethyl)-1H-imidazo[4,5-c]quinolin-1-yl]-2-methylpropan-2-ol as a pale yellow solid.

Part E

A solution of 1-[4-amino-2-(chloromethyl)-1H-imidazo[4,5-c]quinolin-1-yl]-2-methylpropan-2-ol (1.00 g, 3.28 mmol) in DMF (3.0 mL) was added to a solution of N-hydroxyphthalimide (642 mg, 3.94 mmol) and triethylamine (0.915 mL, 6.56 mmol) in DMF (3.0 mL). The flask containing the solution of 1-[4-amino-2-(chloromethyl)-1H-imidazo

[4,5-c]quinolin-1-yl]-2-methylpropan-2-ol was rinsed with DMF (3.0 mL), which was added to the reaction solution. The solution was stirred at room temperature for 3 hours and a solid formed. The solid was isolated by filtration, washed with dichloromethane, and dried. The off-white solid was dissolved in hot DMF (20 mL). Acetonitrile (50 mL) was added to the solution, which was then placed in a freezer. Crystals formed and were isolated by filtration, washed with acetonitrile, and dried to provide 288 mg of 2-{[4-amino-1-(2-hydroxy-2-methylpropyl)-1H-imidazo[4,5-c]quinolin-2-yl]methoxy}-1H-isoindole-1,3(2H)-dione as orange crystals, mp 270-272° C.

$^1$H NMR (300 MHz, DMSO-$d_6$) δ 8.36 (d, J=8.1 Hz, 1H), 7.85 (s, 4H), 7.60 (dd, J=8.3, 1.3 Hz, 1H), 7.44 (ddd, J=8.1, 7.0, 1.1 Hz, 1H), 7.24 (ddd, J=8.1, 7.2, 1.3 Hz, 1H), 6.57 (br s, 2H), 5.67 (br s, 2H), 4.97 (s, 1H), 4.96 (br s, 2H), 1.24 (br s, 6H);

MS (APCI) m/z 432.0 (M+H)$^+$;

Anal. calcd for $C_{23}H_{21}N_5O_4$: C, 64.03; H, 4.91; N, 16.23. Found: C, 63.65; H, 4.65; N, 16.50.

Part F

Hydrazine (20 mL) was added to a stirred suspension of 2-{[4-amino-1-(2-hydroxy-2-methylpropyl)-1H-imidazo[4,5-c]quinolin-2-yl]methoxy}-1H-isoindole-1,3(2H)-dione (14.0 g, 32.4 mmol) in ethanol (100 mL). The mixture was stirred at room temperature and after 5 minutes a solution formed. After 1 hour, a solid began to form and additional ethanol (100 mL) was added. After 4.5 hours, the solid was isolated by filtration, washed with dichloromethane, and dried to yield 9.30 g of 1-{4-amino-2-[(aminooxy)methyl]-1H-imidazo[4,5-c]quinolin-1-yl}-2-methylpropan-2-ol as a yellow solid, some of which was used without further purification in the next step. Two batches of the product (6.63 g and 1.00 g) were purified by chromatography using a HORIZON HPFC system (silica gel, gradient elution with 5-15% of 2 M $NH_3$ in methanol/chloroform) to provide 4.45 g and 650 mg of 1-{4-amino-2-[(aminooxy)methyl]-1H-imidazo[4,5-c]quinolin-1-yl}-2-methylpropan-2-ol as a yellow solid, respectively. Some of the chromatographed product (650 mg) was crystallized from acetonitrile to yield 377 mg of 1-{4-amino-2-[(aminooxy)methyl]-1H-imidazo[4,5-c]quinolin-1-yl}-2-methylpropan-2-ol as pale yellow crystals, mp 178-179° C.

$^1$H NMR (300 MHz, DMSO-$d_6$) δ 8.28 (d, J=8.1 Hz, 1H), 7.60 (dd, J=8.3, 0.9 Hz, 1H), 7.40 (m, 1H), 7.21 (m, 1H), 6.58 (br s, 2H), 6.24 (br s, 2H), 5.02 (br s, 2H), 4.85, (s, 1H) 4.71 (br s, 2H), 1.17 (br s, 6H);

MS (APCI) m/z 302.2 (M+H)$^+$;

Anal. calcd for $C_{15}H_{19}N_5O_2$: C, 59.79; H, 6.36; N, 23.24. Found: C, 59.93; H, 6.38; N, 23.40.

Example 101

N-{[4-Amino-1-(2-hydroxy-2-methylpropyl)-1H-imidazo[4,5-c]quinolin-2-yl]methoxy}-N-isopropylurea

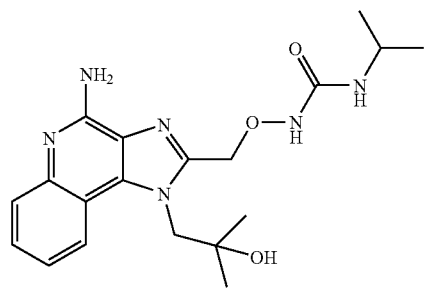 [SMILES: CC(C)NC(=O)NOCc1nc2c(N)nc3ccccc3c2n1CC(C)(C)O]

Isopropyl isocyanate (0.234 mL, 2.39 mmol) was added to a stirred solution of 1-{4-amino-2-[(aminooxy)methyl]-1H-imidazo[4,5-c]quinolin-1-yl}-2-methylpropan-2-ol (prepared as described in Example 100, 600 mg, 1.99 mmol) in DMF (5 mL). After 5 minutes, a solid formed. The mixture was stirred for 1 hour and 45 minutes, then additional isopropyl isocyanate (0.234 mL) and DMF (2 mL) was added. The mixture was stirred at room temperature for 45 minutes. Water (40 mL) was added and a solid was isolated by filtration. The solid was washed with water and dried under vacuum to provide 272 mg of N-{[4-amino-1-(2-hydroxy-2-methylpropyl)-1H-imidazo[4,5-c]quinolin-2-yl]methoxy}-N'-isopropylurea as a white solid. The filtrate was allowed to stand overnight at room temperature and crystals formed. The crystals were isolated by filtration, washed with acetonitrile, and dried in a vacuum oven at 60° C. to afford additional 38 mg of N-{[4-amino-1-(2-hydroxy-2-methylpropyl)-1H-imidazo[4,5-c]quinolin-2-yl]methoxy}-N'-isopropylurea, as yellow crystals, mp 231-233° C.

$^1$H NMR (300 MHz, DMSO-$d_6$) δ 9.16 (s, 1H), 8.27 (d, J=7.7 Hz, 1H), 7.60 (dd, J=8.4, 1.3 Hz, 1H), 7.41 (m, 1H), 7.22 (ddd, J=8.3, 7.3, 1.4 Hz, 1H), 6.62 (br s, 2H), 6.46 (d, J=8.1 Hz, 1H), 5.17 (br s, 2H), 4.93 (s, 1H), 4.70 (br s, 2H), 3.67 (m, 1H), 1.17 (br s, 6H), 0.97 (d, J=6.7 Hz, 6H);

MS (APCI) m/z 387.1 (M+H)$^+$;

Anal. calcd for $C_{19}H_{26}N_6O_3$: C, 59.05; H, 6.78; N, 21.75. Found: C, 58.78; H, 6.86; N, 21.64.

Example 102

N-{[4-Amino-1-(2-hydroxy-2-methylpropyl)-1H-imidazo[4,5-c]quinolin-2-yl]methoxy}-N'-methylurea

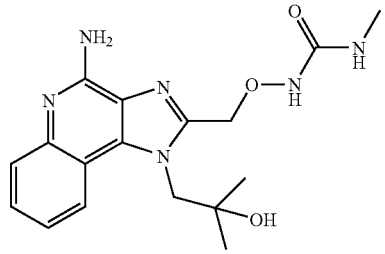 [SMILES: CNC(=O)NOCc1nc2c(N)nc3ccccc3c2n1CC(C)(C)O]

Methyl isocyanate (0.148 mL, 2.39 mmol) was added to a stirred solution of 1-{4-amino-2-[(aminooxy)methyl]-1H-imidazo[4,5-c]quinolin-1-yl}-2-methylpropan-2-ol (prepared as described in Example 100, 600 mg, 1.99 mmol) in DMF (5 mL). A solid formed immediately. The mixture was stirred for 2 hours at room temperature, then was heated to form a solution to which acetonitrile (10 mL) was added. Crystals formed that were isolated by filtration and purified by chromatography using a HORIZON HPFC (silica gel, gradient elution with 5-20% 2 M $NH_3$ in methanol/chloroform). The appropriate fractions were combined and concentrated to a solid that was dried in a vacuum oven overnight to afford N-{[4-amino-1-(2-hydroxy-2-methylpropyl)-1H-imidazo[4,5-c]quinolin-2-yl]methoxy}-N-methylurea as white crystals, mp 206-207° C.

$^1$H NMR (300 MHz, DMSO-$d_6$) δ 9.17 (s, 1H), 8.26 (d, J=8.1 Hz, 1H), 7.60 (dd, J=8.3, 1.3 Hz, 1H), 7.41 (ddd, J=8.1, 7.0, 1.1 Hz, 1H), 7.21 (ddd, J=8.3, 6.9, 1.3 Hz, 1H), 7.04 (q, J=4.7 Hz, 1H), 6.60 (br s, 2H), 5.17 (br s, 2H), 4.92 (s, 1H), 4.67 (br s, 2H), 2.60 (d, J=4.7 Hz, 3H), 1.17 (br s, 6H);

MS (APCI) m/z 359.0 (M+H)$^+$;

Anal. calcd for $C_{17}H_{22}N_6O_3$: C, 56.97; H, 6.19; N, 23.45. Found: C, 56.80; H, 6.27; N, 23.45.

Example 103

N-{[4-Amino-1-(2-hydroxy-2-methylpropyl)-1H-imidazo[4,5-c]quinolin-2-yl]methoxy}methanesulfonamide

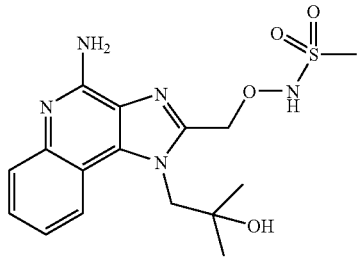 [SMILES: CC(C)(O)Cn1c(CONS(C)(=O)=O)nc2c(N)nc3ccccc3c21]

Triethylamine (0.634 mL, 4.55 mmol) and methanesulfonyl chloride (0.211 mL, 2.73 mmol) were added to a solution of 1-{4-amino-2-[(aminooxy)methyl]-1H-imidazo[4,5-c]quinolin-1-yl}-2-methylpropan-2-ol (prepared as described in Example 100, 685 mg, 2.27 mmol) in DMF (5 mL). A solid formed immediately. The mixture was stirred for 3.5 hours at room temperature, then additional triethylamine (0.634 mL) and methanesulfonyl chloride (0.211 mL) were added. The reaction mixture was stirred for an additional 1.5 hours, then was partitioned between water (20 mL) and dichloromethane (30 mL). The aqueous layer was extracted with dichloromethane (2×30 mL). The organic layers were combined and allowed to stand overnight at room temperature. Crystals formed and were isolated by filtration to provide 40 mg of N-{[4-amino-1-(2-hydroxy-2-methylpropyl)-1H-imidazo[4,5-c]quinolin-2-yl]methoxy}methanesulfonamide. Additional crystals were isolated from the mother liquor after a seed crystal was added. The two crops were combined and dried in a vacuum oven to provide 160 mg of N-{[4-amino-1-(2-hydroxy-2-methylpropyl)-1H-imidazo[4,5-c]quinolin-2-yl]methoxy}methanesulfonamide as pale yellow crystals, mp 232-234° C.

$^1$H NMR (300 MHz, DMSO-$d_6$) δ 10.1 (br s, 1H), 8.30 (d, J=8.4 Hz, 1H), 7.60 (dd, J=8.3, 1.3 Hz, 1H), 7.41 (ddd, J=8.1, 7.0, 1.1 Hz, 1H), 7.21 (ddd, J=8.1, 7.2, 1.3 Hz, 1H), 6.62 (br s, 2H), 5.35 (br s, 2H), 4.91 (s, 1H), 4.72 (br s, 2H), 3.01 (s, 3H), 1.17 (br s, 6H);

MS (APCI) m/z 380.1 (M+H)$^+$;

Anal. calcd for $C_{16}H_{21}N_5O_4S$: C, 50.65; H, 5.58; N, 18.46. Found: C, 50.69; H, 5.89; N, 18.76.

Example 104

N-{[4-Amino-1-(2-hydroxy-2-methylpropyl)-1H-imidazo[4,5-c]quinolin-2-yl]methoxy}cyclopropanecarboxamide

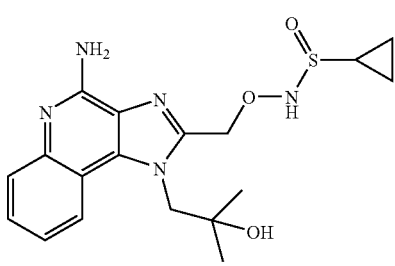 [SMILES: CC(C)(O)Cn1c(CONS(=O)C2CC2)nc2c(N)nc3ccccc3c21]

Triethylamine (0.634 mL, 4.55 mmol) and cyclopropanecarbonyl chloride (0.248 mL, 2.73 mmol) were added to a solution of 1-{4-amino-2-[(aminooxy)methyl]-1H-imidazo[4,5-c]quinolin-1-yl}-2-methylpropan-2-ol (prepared as described in Example 100, 685 mg, 2.27 mmol) in DMF (5 mL). The cloudy mixture was stirred for 2 hours at room temperature, then was partitioned between water (20 mL) and dichloromethane (30 mL). The aqueous layer was extracted with dichloromethane (2×30 mL). The organic layers were combined and allowed to stand overnight at room temperature. Crystals formed and were isolated by filtration, washed with dichloromethane and acetonitrile, and dried in a vacuum oven to provide 442 mg of N-{[4-Amino-1-(2-hydroxy-2-methylpropyl)-1H-imidazo[4,5-c]quinolin-2-yl]methoxy}cyclopropanecarboxamide as a hydrate, white crystals, mp 209-210° C.

$^1$H NMR (300 MHz, DMSO-$d_6$) δ 11.3 (br s, 1H), 8.30 (d, J=8.1 Hz, 1H), 7.60 (dd, J=8.4, 1.3 Hz, 1H), 7.41 (m, 1H), 7.22 (m, 1H), 6.62 (br s, 2H), 5.27 (br s, 2H), 4.86 (s, 1H), 4.81 (br s, 2H), 1.38 (m, 1H), 1.18 (br s, 6H), 0.70 (d, J=6.4 Hz, 4H);

MS (APCI) m/z 370.0 (M+H)$^+$;

Anal. calcd for $C_{19}H_{23}N_5O_3 \cdot H_2O$: C, 58.90; H, 6.50; N, 18.08. Found: C, 59.08; H, 6.87; N, 18.48.

Examples 105-122

A reagent from the table below (1.1 equivalents, 0.10 mmol) was added to a test tube containing a solution of 1-{4-amino-2-[(aminooxy)methyl]-1H-imidazo[4,5-c]quinolin-1-yl}-2-methylpropan-2-ol (prepared as described in Example 100, 29 mg, 0.09 mmol) and triethylamine (26 μL, 0.20 mmol) in DMF (1 mL). The test tubes were capped and placed on a shaker at ambient temperature overnight (approximately 18 hours). The solvent was removed from the test tubes by vacuum centrifugation. The compounds were purified by preparative high performance liquid chromatography (prep HPLC) using a Waters FractionLynx automated purification system. The prep HPLC fractions were analyzed using a Waters LC/TOF-MS, and the appropriate fractions were centrifuge evaporated to provide the trifluoroacetate salt of the desired compound. Reversed phase preparative liquid chromatography was performed with non-linear gradient elution from 5-95% B where A is 0.05% trifluoroacetic acid/water and B is 0.05% trifluoroacetic acid/acetonitrile. Fractions were collected by mass-selective triggering. The table below shows the reagent used for each example, the structure of the resulting compound, and the observed accurate mass for the isolated trifluoroacetate salt.

Examples 105-122

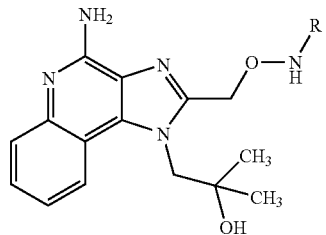

| Example | Reagent | R | Measured Mass (M + H) |
|---|---|---|---|
| 105 | None | H— | 302.1606 |
| 106 | Acetyl chloride | $H_3C-C(=O)-$ | 344.1752 |
| 107 | Propionyl chloride | $-C(=O)CH_2CH_3$ | 358.1905 |
| 108 | Methyl chloroformate | $-C(=O)OCH_3$ | 360.1704 |
| 109 | Ethyl chloroformate | $-C(=O)OCH_2CH_3$ | 374.1866 |
| 110 | Methoxyacetyl chloride | $-C(=O)CH_2OCH_3$ | 374.1858 |
| 111 | Pivaloyl chloride | $-C(=O)C(CH_3)_3$ | 386.2218 |
| 112 | Hydrocinnamoyl chloride | $-C(=O)CH_2CH_2Ph$ | 434.2190 |
| 113 | 3,4-Dichlorobenzoyl chloride | $-C(=O)-C_6H_3Cl_2$ | 474.1079 |
| 114 | Methanesulfonyl chloride | $-S(=O)_2CH_3$ | 380.1404 |
| 115 | Ethanesulfonyl chloride | $-S(=O)_2CH_2CH_3$ | 394.1535 |

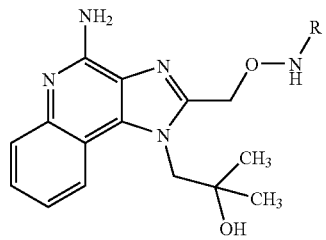
| Example | Reagent | R | Measured Mass (M + H) |
|---|---|---|---|
| 116 | Trifluoromethanesulfonyl chloride | −SO₂CF₃ | 442.1525 |
| 117 | Benzenesulfonyl chloride | −SO₂Ph | 442.1527 |
| 118 | 1-Methylimidazole-4-sulfonyl chloride | −SO₂(1-methylimidazol-4-yl) | 446.1650 |
| 119 | 2,2,2-Trifluoroethanesulfonyl chloride | −SO₂CH₂CF₃ | 448.1269 |
| 120 | alpha-Toluenesulfonyl chloride | −SO₂CH₂Ph | 456.1681 |
| 121 | Methyl isothiocyanate | −C(=S)NHCH₃ | 375.1618 |
| 122 | Benzoyl isocyanate | −C(=O)NHC(=O)Ph | 449.1935 |

Example 123

2-[(Aminooxy)methyl]-1-(2-methylpropyl)-6,7,8,9-tetrahydro-1H-imidazo[4,5-c]quinolin-4-amine

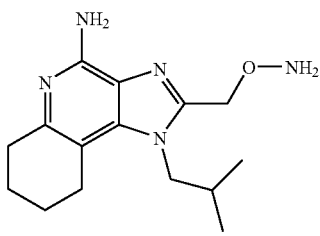 [SMILES: CC(C)Cn1c(CON)nc2c(N)nc3c(c21)CCCC3]

Part A

A mixture of [4-amino-1-(2-methylpropyl)-1H-imidazo[4,5-c]quinolin-2-yl]methanol (15.2 g, 56.2 mmol, U.S. Pat. No. 5,389,640 Example 9), platinum(IV) oxide (7.6 g), and trifluoroacetic acid (75 mL) was hydrogenated at 50 psi (3.5× $10^5$ Pa) of hydrogen on a Parr apparatus for 2 days. The mixture was diluted with dichloromethane and filtered through CELITE filter agent, which was rinsed afterwards with dichloromethane and methanol. The filtrate was concentrated under reduced pressure and the residue was partitioned between dichloromethane (250 mL) and 1:1 saturated aqueous sodium bicarbonate/water (250 mL). Some solid formed that was isolated by filtration. The aqueous layer was extracted with dichloromethane (2×200 mL). The solid was dissolved in methanol and the resulting solution was combined with the organic layers, concentrated under reduced pressure, and purified by chromatography using a HORIZON HPFC system (silica gel, elution with 10% 1 M $NH_3$ in methanol/dichloromethane) to afford 4.98 g of [4-amino-1-(2-methylpropyl)-6,7,8,9-tetrahydro-1H-imidazo[4,5-c]quinolin-2-yl]methanol as a grey solid.

Part B

Thionyl chloride (2.65 mL, 36.2 mmol) was added dropwise to a stirred suspension of [4-amino-1-(2-methylpropyl)-6,7,8,9-tetrahydro-1H-imidazo[4,5-c]quinolin-2-yl]methanol (4.97 g, 18.1 mmol) in 1,2-dichloroethane (200 mL). The suspension dissolved, then a precipitate formed after 5 minutes. The reaction mixture was stirred at room temperature for 6 hours, then was concentrated under reduced pressure to yield crude 2-(chloromethyl)-1-(2-methylpropyl)-6,7,8,9-tetrahydro-1H-imidazo[4,5-c]quinolin-4-amine hydrochloride, all of which was used in the next step.

Part C

A solution of N-hydroxyphthalimide (3.54 g, 21.7 mmol) and triethylamine (7.6 mL, 54.3 mmol) in DMF (25 mL) was added to a suspension of the material from Part B in DMF (25 mL) at room temperature. The reaction mixture was stirred at room temperature overnight, then was concentrated under reduced pressure and used without purification in the next step.

Part D

Hydrazine hydrate (8.8 mL, 181 mmol) was added to a solution of the material from Part C in ethanol (180 mL). The reaction mixture was stirred overnight and a solid formed that was removed by filtration. The filtrate was concentrated under reduced pressure, then was purified by chromatography using a HORIZON HPFC system (silica gel, gradient elution with 5-10% 1 M $NH_3$ in methanol/dichloromethane) to afford 4.52 g of 2-[(aminooxy)methyl]-1-(2-methylpropyl)-6,7,8,9-tetrahydro-1H-imidazo[4,5-c]quinolin-4-amine as a pale yellow foam.

MS (APCI) m/z 290.2 (M+H)$^+$;

$^1$H NMR (300 MHz, DMSO-$d_6$) δ 6.26 (br s, 2H), 5.85 (br s, 2H), 4.77 (s, 2H), 4.14 (d, J=7.6 Hz, 2H), 2.91 (m, 2H), 2.67 (m, 2H), 2.00 (m, 1H), 1.76 (m, 4H), 0.84 (d, J=6.7 Hz, 6H).

Example 124

N-{[4-Amino-1-(2-methylpropyl)-6,7,8,9-tetrahydro-1H-imidazo[4,5-c]quinolin-2-yl]methoxy}methanesulfonamide hydrochloride

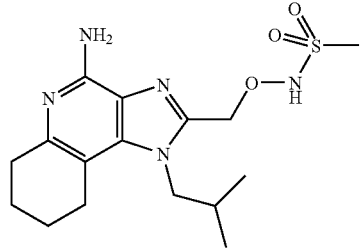 [SMILES: CC(C)Cn1c(CONS(C)(=O)=O)nc2c(N)nc3c(c21)CCCC3]

A solution of methanesulfonyl chloride (0.253 mL, 3.27 mmol) in dichloromethane (10 mL) was added dropwise to a stirred solution of 2-[(aminooxy)methyl]-1-(2-methylpropyl)-6,7,8,9-tetrahydro-1H-imidazo[4,5-c]quinolin-4-amine (prepared as described in Example 123, 860 mg, 2.97 mmol) and triethylamine (1.24 mL, 8.92 mmol) in dichloromethane (20 mL) at 0° C. After 1 hour, additional methanesulfonyl chloride (0.125 mL in dichloromethane (5 mL)) and triethylamine (0.5 mL) were added. The reaction mixture was stirred for an additional 30 minutes, then was concentrated under reduced pressure to afford a yellow foam. The foam was purified by chromatography using a HORIZON HPFC system (silica gel, gradient elution with 5-15% 1 M $NH_3$ in methanol/dichloromethane) followed by crystallization from methanol/acetonitrile. The crystals were isolated by filtration, washed with acetonitrile, and dried in a vacuum oven to yield 160 mg of N-{[4-amino-1-(2-methylpropyl)-6,7,8,9-tetrahydro-1H-imidazo[4,5-c]quinolin-2-yl]methoxy}methanesulfonamide hydrochloride as a white crystals, mp 211-213° C.

$^1$NMR (300 MHz, DMSO-$d_6$) δ 13.6 (br s, 1H), 10.4 (s, 1H), 8.26 (br s, 2H), 5.18 (s, 2H), 4.28 (d, J=7.7 Hz, 2H), 3.04 (s, 3H), 2.94 (br s, 2H), 2.79 (br s, 2H), 2.06 (m, 1H), 1.80 (br s, 4H), 0.88 (d, J=6.6 Hz, 6H);

MS (APCI) m/z 368.2 (M+H)$^+$;

Anal. calcd for $C_{16}H_{25}N_5O_3S$—HCl: C, 47.58; H, 6.49; N, 17.34. Found: C, 47.68; H, 6.51; N, 17.38.

Example 125

N-{[4-Amino-1-(2-methylpropyl)-6,7,8,9-tetrahydro-1H-imidazo[4,5-c]quinolin-2-yl]methoxy}acetamide

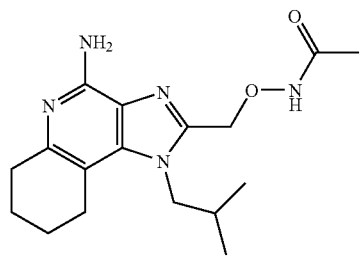 [SMILES: CC(=O)NOCc1nc2c(N)nc3c(c2n1CC(C)C)CCCC3]

A solution of acetyl chloride (0.232 mL, 3.27 mmol) in dichloromethane (10 mL) was added dropwise to a stirred solution of 2-[(aminooxy)methyl]-1-(2-methylpropyl)-6,7,8,9-tetrahydro-1H-imidazo[4,5-c]quinolin-4-amine (prepared as described in Example 123, 860 mg, 2.97 mmol) and triethylamine (1.24 mL, 8.92 mmol) in dichloromethane (20 mL) at 0° C. After 1 hour, additional acetyl chloride (0.232 mL) in dichloromethane (10 mL) and triethylamine (1.0 mL) were added. The reaction mixture was stirred for an additional 30 minutes, then was concentrated under reduced pressure. The crude product was purified by chromatography using a HORIZON HPFC system (silica gel, gradient elution with 5-15% 1 M $NH_3$ in methanol/dichloromethane) followed by crystallization from acetonitrile. The crystals were isolated by filtration, washed with acetonitrile, and dried in a vacuum oven to yield 257 mg of N-{[4-amino-1-(2-methylpropyl)-6,7,8,9-tetrahydro-1H-imidazo[4,5-c]quinolin-2-yl]methoxy}acetamide as pale yellow crystals, mp 187-188° C.

$^1$H NMR (300 MHz, DMSO-$d_6$) δ 11.1 (br s, 1H), 5.91 (br s, 2H), 4.99 (br s, 2H), 4.32 (d, J=7.2 Hz, 2H), 2.93 (br s, 2H), 2.67 (br s, 2H), 2.02 (m, 1H), 1.76 (m, 7H), 0.86 (d, J=6.7 Hz, 6H);

MS (APCI) m/z 332.2 $(M+H)^+$;

Anal. calcd for $C_{17}H_{25}N_5O_2$: C, 61.61; H, 7.60; N, 21.13. Found: C, 61.52; H, 7.73; N, 21.38.

Examples 126-135

A reagent from the table below (1.1 equivalents, 0.11 mmol) was added to a test tube containing a solution of 2-[(aminooxy)methyl]-1-(2-methylpropyl)-6,7,8,9-tetrahydro-1H-imidazo[4,5-c]quinolin-4-amine (prepared as described in Example 123, 29 mg, 0.10 mmol) and N,N-diisopropylethylamine (36 μL, 0.20 mmol) in chloroform (1 mL). The test tubes were capped and placed on a shaker at ambient temperature for 4 hours. Water (two drops) was added to each test tube and the volatiles were removed from the test tubes by vacuum centrifugation. The compounds were purified as described in Examples 105-122. The table below shows the reagent used for each example, the structure of the resulting compound, and the observed accurate mass for the isolated trifluoroacetate salt.

Examples 126-135

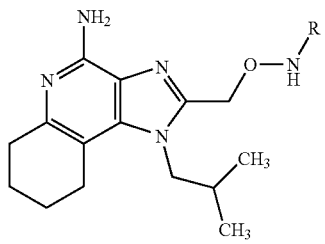

| Example | Reagent | R | Measured Mass (M + H) |
|---|---|---|---|
| 126 | None | H– | 290.1982 |
| 127 | 3-Chlorobenzoyl chloride | 3-chlorobenzoyl | 428.1879 |
| 128 | 4-Chlorobenzoyl chloride | 4-chlorobenzoyl | 428.1862 |
| 129 | 3,4-Dichlorobenzoyl chloride | 3,4-dichlorobenzoyl | 462.1498 |
| 130 | Ethanesulfonyl chloride | ethanesulfonyl | 382.1924 |
| 131 | 1-Propanesulfonyl chloride | 1-propanesulfonyl | 396.2091 |

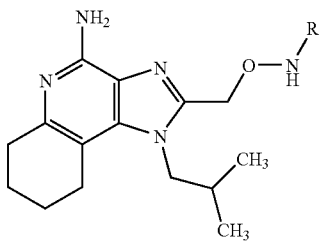

| Example | Reagent | R | Measured Mass (M + H) |
|---|---|---|---|
| 132 | alpha-Toluenesulfonyl chloride | [benzylsulfonyl group] | 444.2097 |
| 133 | Phenyl isocyanate | [phenylcarbamoyl group] | 409.2379 |
| 134 | (R)-(+)-alpha-Methylbenzyl isocyanate | [(R)-1-phenylethylcarbamoyl group] Chiral | 437.2697 |
| 135 | (S)-(−)-alpha-Methylbenzyl isocyanate | [(S)-1-phenylethylcarbamoyl group] Chiral | 437.2682 |

Example 136

2-[(Aminooxy)methyl]-1-(2-methylpropyl)-1H-imidazo[4,5-c][1,5]naphthyridin-4-amine

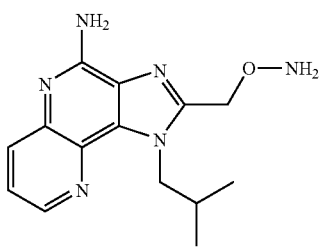 [SMILES: CC(C)Cn1c(CON)nc2c(N)nc3cccnc3c21]

Part A

Isobutylamine (15.6 mL, 157 mmol) was added dropwise to a 5° C. solution of 4-chloro-3-nitro[1,5]naphthyridine (15.0 g, 71.6 mmol) in dichloromethane (300 mL). The reaction was allowed to stir at room temperature for 4 hours, then was concentrated under reduced pressure to afford a residue that was treated with water (300 mL). The mixture was stirred for 30 minutes, then a solid was isolated by filtration, rinsed with water (100 mL), and dried in a vacuum oven at 50° C. overnight to afford 17.25 g of N-(2-methylpropyl)-3-nitro[1,5]naphthyridin-4-amine as a yellow solid.

Part B

The general method described in Part B of Example 92 was used to convert N-(2-methylpropyl)-3-nitro[1,5]naphthyridin-4-amine (17.25 g, 70.0 mmol) into $N^4$-(2-methylpropyl)[1,5]naphthyridine-3,4-diamine, which was isolated as a thick, yellow oil and used directly in the next step without purification.

Part C

The general method described in Part C of Example 92 was used to convert $N^4$-(2-methylpropyl)[1,5]naphthyridine-3,4-diamine (from Part B) into 2-chloro-N-{4-[(2-methylpropyl)amino][1,5]naphthyridin-3-yl}acetamide hydrochloride, which was isolated as a pale yellow solid that was used directly in the next step without purification.

Part D

To a solution of 2-chloro-N-{4-[(2-methylpropyl)amino][1,5]naphthyridin-3-yl}acetamide hydrochloride (from Part C, approximately 70 mmol) in 3:1 ethanol/water (280 mL) was added 6 M aqueous potassium carbonate (17.5 mL). The reaction mixture was stirred at room temperature over the weekend. The volatiles were removed under reduced pressure and the residue was partitioned between dichloromethane (200 mL) and brine (100 mL). The aqueous layer was extracted with dichloromethane (2×50 mL). The organic layers were combined, dried over magnesium sulfate, filtered, and concentrated under reduced pressure to afford 19.5 g of 2-(chloromethyl)-1-(2-methylpropyl)-1H-imidazo[4,5-c][1,5]naphthyridine, which contained a small amount of dichloromethane and was used without further purification in the next step.

Part E mCPBA (70% pure, 9.85 g, 40.0 mmol) was added to a solution of 2-(chloromethyl)-1-(2-methylpropyl)-1H-imidazo[4,5-c][1,5]naphthyridine (5.49 g, 20.0 mmol) in chloroform (80 mL). The reaction mixture was allowed to stir for 1.5 hours, then was diluted with dichloromethane (150 mL) and washed with saturated aqueous sodium bicarbonate (2×75 mL). The aqueous layers were combined and back-extracted with dichloromethane (2×30 mL). The organic layers were combined, dried over magnesium sulfate, filtered, and concentrated to afford a yellow semi-solid that was used immediately without purification in the next step.

Part F

The material from Part E was dissolved in methanol (70 mL) and the solution was cooled to 0° C. Concentrated ammonium hydroxide (6.7 mL) was added, followed by dropwise addition of benzenesulfonyl chloride (5.25 mL, 42.0 mmol). The reaction mixture was stirred at 0° C. for 1 hour. The volatiles were removed under reduced pressure and the residue was partitioned between dichloromethane (150 mL) and saturated aqueous sodium bicarbonate (75 mL). The aqueous layer was extracted with dichloromethane (50 mL). The organic layers were combined, dried over magnesium sulfate, filtered, and concentrated. The crude product was purified by chromatography using a HORIZON HPFC system (silica gel, gradient elution with 0-25% CMA in chloroform) to afford 4.14 g of approximately 85% pure 2-(chloromethyl)-1-(2-methylpropyl)-1H-imidazo[4,5-c][1,5]naphthyridin-4-amine, which was used in the next step without further purification.

Part G

The general method described in Part H of Example 92 was used to convert the material from Part F (85% pure, 4.14 g, 14.3 mmol) into 2.81 g of 2-{[4-amino-1-(2-methylpropyl)-1H-imidazo[4,5-c][1,5]naphthyridin-2-yl]methoxy}-1H-isoindole-1,3(2H)-dione.

Part H

Anhydrous hydrazine (0.640 mL, 20.2 mmol) was added to a suspension of 2-{[4-amino-1-(2-methylpropyl)-1H-imidazo[4,5-c][1,5]naphthyridin-2-yl]methoxy}-1H-isoindole-1,3(2H)-dione (2.81 g, 6.75 mmol) in ethanol (40 mL). Gradually, a solution formed from which a solid began to precipitate. The reaction mixture was stirred overnight at room temperature, then was concentrated under reduced pressure. The residue was triturated with 1 M aqueous hydrochloric acid (50 mL). The mixture was sonicated and the solid was isolated by filtration. The filtrate was adjusted to pH 8 with solid sodium carbonate and extracted with dichloromethane (3×25 mL). The organic layers were combined, dried over magnesium sulfate, filtered, and concentrated to afford a yellow solid. The solid was triturated with methanol to afford 0.863 g of 2-[(aminooxy)methyl]-1-(2-methylpropyl)-1H-imidazo[4,5-c][1,5]naphthyridin-4-amine as a white powder.

$^1$H NMR (500 MHz, DMSO-d6) δ 8.52 (dd, J=4.3, 1.6 Hz, 1H), 7.91 (dd, J=8.4, 1.6 Hz, 1H), 7.44 (dd, J=8.4, 4.3 Hz, 1H), 6.88 (br s, 2H), 6.35 (br s, 2H), 4.90 (s, 2H), 4.73 (d, J=7.5 Hz, 2H), 2.37 (septet, J=7.0 Hz, 1H), 0.89 (d, J=6.7 Hz, 6H);

MS (APCI) m/z 287 (M+1)$^+$.

Examples 136-148

A reagent from the table below (1.1 equivalents, 0.11 mmol) was added to a test tube containing a solution of 2-[(aminooxy)methyl]-1-(2-methylpropyl)-1H-imidazo[4,5-c][1,5]naphthyridin-4-amine (prepared as described in Example 136, 29 mg, 0.10 mmol) and N,N-diisopropylethylamine (35 µL, 0.20 mmol) in chloroform (1 mL). The test tubes were capped and placed on a shaker at ambient temperature for 4 hours. The solvent was removed from the test tubes by vacuum centrifugation. The compounds were purified as described in Examples 105-122. The table below shows the reagent used for each example, the structure of the resulting compound, and the observed accurate mass for the isolated trifluoroacetate salt.

Examples 136-148

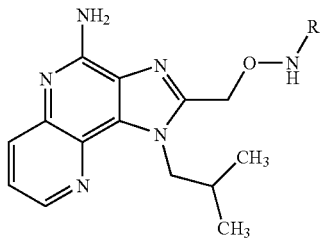

| Example | Reagent | R | Measured Mass (M + H) |
|---|---|---|---|
| 136 | None | H | 287.1622 |
| 137 | Acetyl chloride | H₃C—C(=O)— | 329.1753 |
| 138 | Methyl chloroformate | CH₃O—C(=O)— | 345.1709 |
| 139 | Cyclopropanecarbonyl chloride | cyclopropyl—C(=O)— | 355.1909 |
| 140 | Benzoyl chloride | Ph—C(=O)— | 391.1922 |
| 141 | Nicotinoyl chloride hydrochloride | pyridyl—C(=O)— | 392.1858 |
| 142 | Methanesulfonyl chloride | CH₃—S(=O)₂— | 365.1428 |

-continued

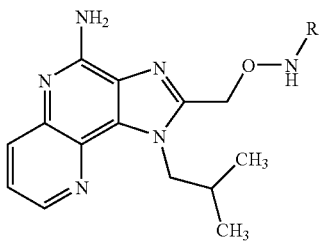

| Example | Reagent | R | Measured Mass (M + H) |
|---|---|---|---|
| 143 | Dimethylsulfamoyl chloride | O=S(=O)-N(CH3)CH3 | 394.1627 |
| 144 | Benzenesulfonyl chloride | O=S(=O)-phenyl | 427.1565 |
| 145 | Methyl isocyanate | C(=O)-NH-CH3 | 344.1871 |
| 146 | Cyclopropyl isocyanate | C(=O)-NH-cyclopentyl | 398.2327 |
| 147 | Phenyl isocyanate | C(=O)-NH-phenyl | 406.1998 |
| 148 | N,N-Dimethylcarbamoyl chloride | C(=O)-N(CH3)CH3 | 358.2017 |

Examples 149-167

Part A

A mixture of triethyl orthoformate (154 g, 1.04 mol) and Meldrum's acid (142 g, 0.983 mol) was heated to 55° C. for 4 hours. After cooling to 50° C., a solution of 3-bromoaniline (162.6 g, 0.945 mol) in ethanol (300 mL) was added such that the temperature of the reaction was maintained between 50-55° C. After half of the 3-bromoaniline had been added, stirring became difficult due to the formation of solids, so more ethanol (1 L) was added to facilitate stirring. Upon complete addition, the reaction was cooled to room temperature, and the solids were collected by filtration. The filter cake was washed with ice cold ethanol until the washings were nearly colorless, and the product was dried at 65° C. under vacuum to afford 287 g of 5-[(3-bromophenylimino)methyl]-2,2-dimethyl-1,3-dioxane-4,6-dione as an off-white solid.

¹H NMR (300 MHz, CDCl₃) δ 11.19 (brd, J=12.8 Hz, 1H), 8.60 (d, J=14.0 Hz, 1H), 7.44-7.38 (m, 2H), 7.30 (t, J=8.0 Hz, 1H), 7.18 (ddd, J=8.0, 2.2, 0.9 Hz, 1H), 1.75 (s, 6H).

Part B

7-Bromoquinolin-4-ol was prepared in accordance with the literature procedure (D. Dibyendu et al., J. Med. Chem., 41, 4918-4926 (1998)) or by thermolysis of 5-[(3-bromophenylimino)methyl]-2,2-dimethyl-1,3-dioxane-4,6-dione in DOWTHERM A heat transfer fluid and had the following spectral properties:

¹H NMR (300 MHz, d₆-DMSO) δ 11.70 (brs, 1H), 8.00 (d, J=8.7 Hz, 1H), 7.92 (d, J=7.5 Hz, 1H), 7.74 (d, J=1.9 Hz, 1H), 7.44 (dd, J=8.7, 1.9 Hz, 1H), 6.05 (d, J=7.5 Hz, 1H).

Part C

A stirred suspension of 7-bromoquinolin-4-ol (162 g, 0.723 mol) in propionic acid (1500 mL) was brought to 110° C. Nitric acid (85 g of 70%) was added dropwise over 1 hour such that the temperature was maintained between 110-115° C. After half of the nitric acid had been added, stirring became difficult due to the formation of solids and an additional 200 mL of propionic acid was added. Upon complete addition, the reaction was stirred for 1 hour at 110° C., cooled to room temperature, and the solid was collected by filtration. The filter cake was washed with ice cold ethanol until the washings were nearly colorless (800 mL), and the product was dried at 60° C. under vacuum to afford 152 g of 7-bromo-3-nitro-quinolin-4-ol as a pale yellow solid.

¹H NMR (300 MHz, d₆-DMSO) δ 13.0 (brs, 1H), 9.22 (s, 1H), 8.15 (d, J=8.4 Hz, 1H), 7.90 (d, J=1.6 Hz, 1H), 7.66 (dd, J=8.7, 1.9 Hz, 1H).

Part D

7-Bromo-3-nitroquinolin-4-ol (42 g, 156 mmol) was suspended in POCl₃ (130 mL) and brought to 102° C. under an atmosphere of N₂. After 45 min, all of the solids had dissolved, so the reaction was cooled to room temperature. The resulting solids were collected by filtration, washed with H₂O, and then partitioned with CH₂Cl₂ (3 L) and 2M Na₂CO₃ (500 mL). The organic layer was separated, washed with H₂O (1×), dried over Na₂SO₄, filtered, and concentrated under reduced pressure to afford 33.7 g of 7-bromo-4-chloro-3-nitroquinoline as a beige solid.

¹H NMR (300 MHz, CDCl₃) δ 9.26 (s, 1H), 8.41 (d, J=1.8 Hz, 1H), 8.30 (d, J=9.0 Hz, 1H), 7.90 (dd, J=8.9, 2.1 Hz, 1H).

Part E

To a suspension of 7-bromo-4-chloro-3-nitroquinoline (25.0 g, 87.0 mmol) in DMF (70 mL) was added triethylamine (18.2 mL, 130 mmol). A solution of iso-butylamine (9.50 mL, 95.7 mmol) in DMF (20 mL) was added dropwise. The viscous reaction mixture was stirred overnight at ambient temperature. Water (200 mL) was added and the mixture was stirred for 1 hour. A solid was isolated by filtration, washed with water, and dried in a vacuum oven overnight to yield 26.1 g of 7-bromo-N-(2-methylpropyl)-3-nitroquinolin-4-amine as a yellow powder.

Part F

A mixture of 7-bromo-N-(2-methylpropyl)-3-nitroquinolin-4-amine (25.1 g, 77.4 mmol) and 5% platinum on carbon (2.5 g), dichloroethane (160 mL), and ethanol (80 mL) was hydrogenated on a Parr apparatus at 30 psi (2.1×10⁵ Pa) for 2 hours. The mixture was filtered through CELITE filter agent and the filtrate was concentrated under reduced pressure to yield 23.1 g of a brown oil.

Part G

To a stirred solution of the material from Part F (23.1 g) and triethylamine (16.4 mL, 118 mmol) in dichloromethane (300 mL) was added dropwise chloroacetyl chloride (6.9 mL, 86.3 mmol). The reaction mixture was allowed to stir at room temperature for 7 days, then was concentrated under reduced pressure. The resulting brown foam was partitioned between ethyl acetate (400 mL) and 1:1 saturated aqueous sodium bicarbonate/water (400 mL). The water layer was extracted with dichloromethane (2×200 mL). The organic layers were combined and concentrated under reduced pressure. The crude product was divided into three portions, which were purified by chromatography on a HORIZON HPFC system (silica gel, gradient elution with ethyl acetate in hexanes). The purified material was combined to yield 18.32 g of 7-bromo-2-(chloromethyl)-1-(2-methylpropyl)-1H-imidazo[4,5-c]quinoline as a yellow solid.

Part H

To a solution of 7-bromo-2-(chloromethyl)-1-(2-methylpropyl)-1H-imidazo[4,5-c]quinoline (13.9 g, 39.4 mmol) in chloroform (300 mL) at room temperature was added mCPBA (77% pure, 17.7 g, 78.8 mmol) over ten minutes. The reaction mixture was stirred at room temperature for 3 hours, then concentrated ammonium hydroxide (150 mL) was added, followed by p-toluenesulfonyl chloride (9.00 g, 47.3 mmol, added in portions over 10 minutes). The mixture was stirred at room temperature for 1 hour, then was transferred to a separatory funnel. The layers were separated and the aqueous layer was extracted with dichloromethane (2×100 mL). The organic layers were combined, dried over magnesium sulfate, filtered through CELITE filter agent, and concentrated under reduced pressure. The crude product was purified by chromatography using a HORIZON HPFC system (silica gel, gradient elution with ethyl acetate in hexanes) to yield 7.69 g of 7-bromo-2-(chloromethyl)-1-(2-methylpropyl)-1H-imidazo[4,5-c]quinolin-4-amine as a yellow foam.

Part I

A solution of 7-bromo-2-(chloromethyl)-1-(2-methylpropyl)-1H-imidazo[4,5-c]quinolin-4-amine (7.65 g, 20.8 mmol) in DMF (20 mL) was added dropwise via addition funnel to a solution of N-hydroxyphthalimide (4.07 g, 25.0 mmol) and triethylamine (4.3 mL, 31.2 mmol) in DMF (20 mL). The addition funnel was rinsed with DMF (20 mL) and the rinse was added to the reaction solution, which was stirred at room temperature. After 30 minutes, a precipitate formed. The viscous mixture was stirred at room temperature overnight, then diethyl ether (150 mL) was added. The solid was isolated by filtration, washed with diethyl ether, and dried under vacuum to provide 7.44 g of 2-{[4-amino-7-bromo-1-(2-methylpropyl)-1H-imidazo[4,5-c]quinolin-2-yl]methoxy}-1H-isoindole-1,3(2H)-dione, which contained some triethylamine hydrochloride. The filtrate was concentrated to yield 8.5 g of a brown oil, which was found to contain product and was combined with the material from above and used in the next step.

Part J

Anhydrous hydrazine (20 mL) was added to a stirred suspension of the material from Part I (approximately 20.8 mmol) in ethanol (150 mL) at room temperature. The mixture became homogeneous after 2 minutes. After 30 minutes, a precipitate had formed. The mixture was stirred for another 1.5 hours, then was filtered through CELITE filter agent. The filtrate was concentrated under reduced pressure to afford crude 2-[(aminooxy)methyl]-7-bromo-1-(2-methylpropyl)-1H-imidazo[4,5-c]quinolin-4-amine as a brown solid, which was used in the next step without purification.

Part K

The material from Part J was dissolved in methanol (150 mL) and acetone (50 mL). The solution was stirred at room temperature for 3 hours, then was concentrated under reduced pressure to yield a brown solid. Dichloromethane (100 mL) was added and the mixture was stirred for 30 minutes, then filtered. The filtrate was concentrated under reduced pressure and purified by chromatography three times on a HORIZON HPFC system (silica gel) to yield 4.11 g of acetone 0-{[4-amino-7-bromo-1-(2-methylpropyl)-1H-imidazo[4,5-c]quinolin-2-yl]methyl}oxime as a pale orange solid.

Part L

3-Bromo-5-(tert-butyldimethylsilanyloxymethyl)pyridine was prepared according to the published procedure (Zhang, N. et al, *J. Med. Chem.*, 45, 2832-2840 (2002)). Under a nitrogen atmosphere, a solution of 3-bromo-5-(tert-butyldimethylsilanyloxymethyl)pyridine (28.70 g, 94.94 mmol) and triisopropyl borate (26.3 mL, 114 mmol) in dry THF was cooled to −70° C. n-Butyllithium (45.6 mL, 114 mmol) was added dropwise over a period of 1.5 hours. The reaction was stirred for an additional 30 minutes and then allowed to warm to −20° C. Dilute aqueous ammonium chloride was added, and the mixture was allowed to warm to ambient temperature. The aqueous layer was separated and extracted with diethyl ether. The combined organic fractions were concentrated under reduced pressure, and methanol was added to the resulting oil. A solid formed, which was stirred with water for two days, isolated by filtration, and dried under reduced pressure to provide 18.19 g of 5-(tert-butyldimethylsilanyloxymethyl)pyridine-3-boronic acid as a white solid.

Part M

The compounds in the table below can be prepared according to the following method. A solution of acetone 0-{[4-amino-7-bromo-1-(2-methylpropyl)-1H-imidazo[4,5-c]quinolin-2-yl]methyl}oxime (prepared as described in Parts A-K above, 0.20 mmol) in 7:3 volume:volume (v:v) chloroform:methanol (2 mL) can be added to a test tube, and the solvent can be removed by vacuum centrifugation. The boronic acid (0.22 mmol) indicated in the table below and n-propanol (3.2 mL) can be sequentially added, and the test tube can be purged with nitrogen. The reaction mixture can be sonicated until a solution forms. Palladium (II) acetate (0.292 mL of a 0.018 M solution in toluene, 0.0053 mmol), 2M aqueous sodium carbonate solution (1.2 mL), deionized water (225 µL), and a solution of 0.15 M triphenylphosphine in n-propanol (106 µL, 0.0159 mmol) can be added sequentially. The test tube can be purged with nitrogen, capped, and then heated to 80° C. overnight in a sand bath. For Example 158, the solvent can be removed by vacuum centrifugation, and glacial acetic acid (1 mL), tetrahydrofuran (1 mL), and deionized water (1 mL) can be added to the test tube. The reaction can be heated overnight at 60° C. The solvent can be removed from the test tubes by vacuum centrifugation.

The contents of each test tube can be passed through a Waters Oasis Sample Extractions Cartridge MCX (6 cc) according to the following procedure. Hydrochloric acid (3 mL of 1 N) can be added to adjust each example to pH 5-7, and the resulting solution can be passed through the cartridge optionally using light nitrogen pressure. The cartridge can be washed with methanol (5 mL) optionally using light nitrogen pressure and transferred to a clean test tube. A solution of 1% ammonia in methanol (2×5 mL) can be then passed through the cartridge optionally using light nitrogen pressure, and the basic solution can be collected and concentrated.

The residue in each test tube can be dissolved in methanol (1 mL) and glacial acetic acid (1 mL). To each solution can be added a solution of sodium cyanoborohydride in tetrahydrofuran (1 M, 300-500 μL, 0.3-0.5 mmol). The test tubes can be capped and placed on a shaker at ambient temperature overnight. The solvent can be removed from the test tubes by vacuum centrifugation. The compounds can be purified as described in Examples 105-122. The table below shows the boronic acid that can be used for each example and the structure of the resulting compound.

Examples 149-167

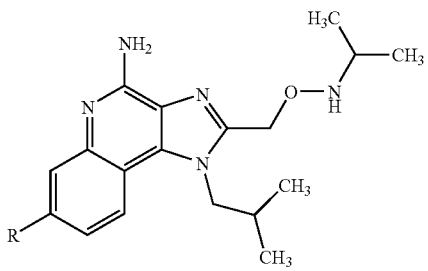

| Example | Reagent | R |
|---|---|---|
| 149 | Phenylboronic acid |  |
| 150 | Pyridine-3-boronic acid | 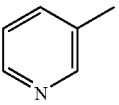 |
| 151 | Thiophene-3-boronic acid |  |
| 152 | 3-Methylphenylboronic acid | 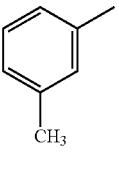 |
| 153 | 4-Methylphenylboronic acid |  |
| 154 | o-Tolylboronic acid |  |
| 155 | (2-Hydroxyphenyl)boronic acid | 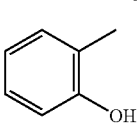 |
| 156 | 4-Cyanophenylboronic acid | 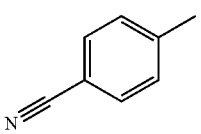 |
| 157 | (2-Hydroxymethylphenyl)boronic acid dehydrate | 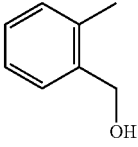 |
| 158 | 5-(tert-Butyldimethylsilanyloxymethyl)pyridine-3-boronic acid | 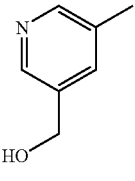 |
| 159 | 4-Chlorophenylboronic acid | 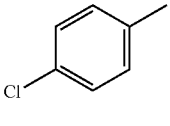 |
| 160 | 2-Chlorophenylboronic acid | 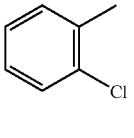 |
| 161 | 3-Chlorophenylboronic acid | 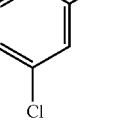 |
| 162 | Benzo[B]furan-2-boronic acid | 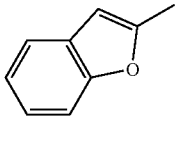 |
| 163 | 3-Acetylphenylboronic acid | 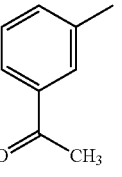 |

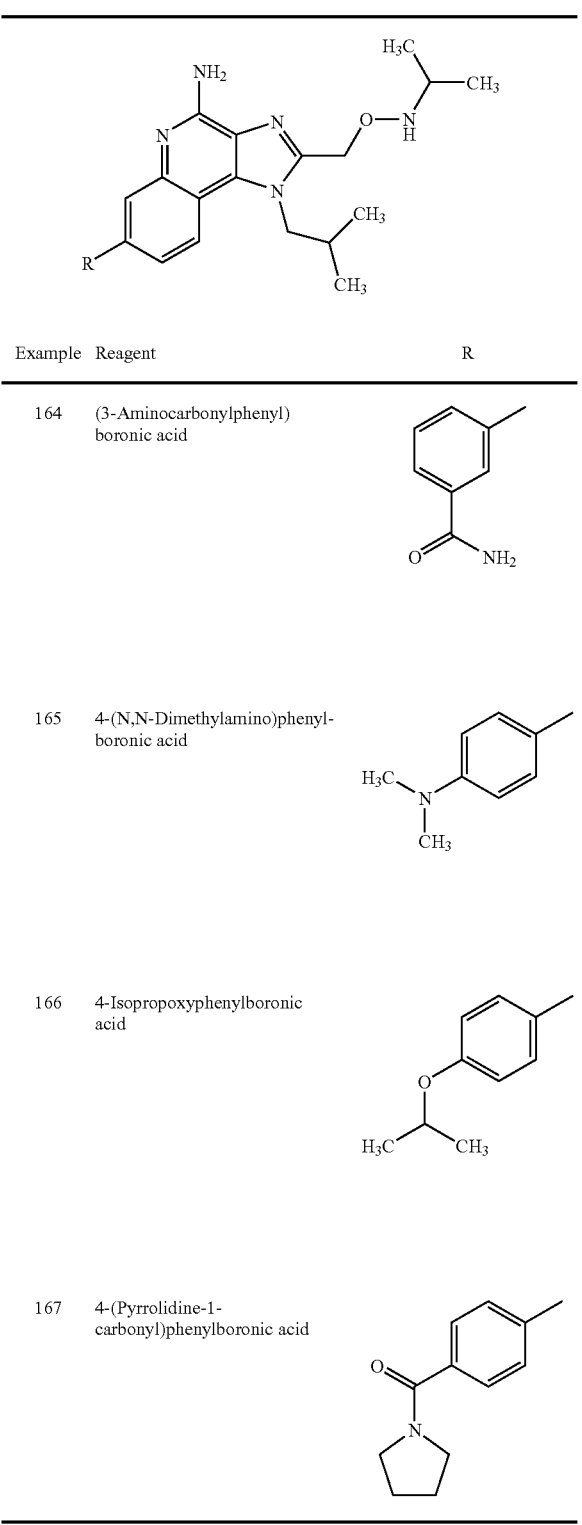

| Example | Reagent | R |
|---|---|---|
| 164 | (3-Aminocarbonylphenyl)boronic acid | |
| 165 | 4-(N,N-Dimethylamino)phenylboronic acid | |
| 166 | 4-Isopropoxyphenylboronic acid | |
| 167 | 4-(Pyrrolidine-1-carbonyl)phenylboronic acid | |

Exemplary Compounds

Certain exemplary compounds, including some of those described above in the Examples, have the following Formulas (IIIc, IVc, Va, and VIa) and the following Y' and $R_1$ substituents, wherein each line of the table is matched with Formula IIIc, IVc, Va, or VIa to represent a specific embodiment of the invention.

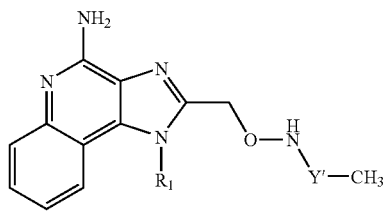

IIIc

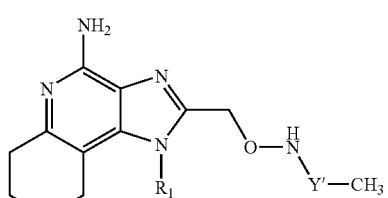

IVc

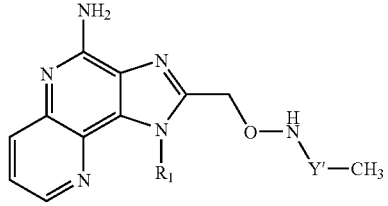

Va

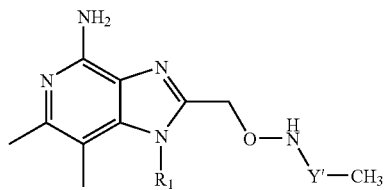

VIa

| Y' | $R_1$ |
|---|---|
| —C(O)— | 2-methylpropyl |
| —C(O)— | 2-hydroxy-2-methylpropyl |
| —C(O)— | 2-methyl-2-[(methylsulfonyl)amino]propyl |
| —C(O)— | 4-[(methylsulfonyl)amino]butyl |
| —S(O)$_2$— | 2-methylpropyl |
| —S(O)$_2$— | 2-hydroxy-2-methylpropyl |
| —S(O)$_2$— | 2-methyl-2-[(methylsulfonyl)amino]propyl |
| —S(O)$_2$— | 4-[(methylsulfonyl)amino]butyl |
| —C(O)—N(H)— | 2-methylpropyl |
| —C(O)—N(H)— | 2-hydroxy-2-methylpropyl |
| —C(O)—N(H)— | 2-methyl-2-[(methylsulfonyl)amino]propyl |
| —C(O)—N(H)— | 4-[(methylsulfonyl)amino]butyl |

Cytokine Induction in Human Cells

Compounds of the invention have been found to induce cytokine biosynthesis when tested using the method described below.

An in vitro human blood cell system is used to assess cytokine induction. Activity is based on the measurement of interferon (α) and tumor necrosis factor (α) (IFN-α and TNF-α, respectively) secreted into culture media as described by Testerman et. al. in "Cytokine Induction by the Immunomodulators Imiquimod and S-27609", *Journal of Leukocyte Biology*, 58, 365-372 (September, 1995).

Blood Cell Preparation for Culture

Whole blood from healthy human donors is collected by venipuncture into EDTA vacutainer tubes. Peripheral blood mononuclear cells (PBMC) are separated from whole blood by density gradient centrifugation using HISTOPAQUE-1077. Blood is diluted 1:1 with Dulbecco's Phosphate Buffered Saline (DPBS) or Hank's Balanced Salts Solution (HBSS). The PBMC layer is collected and washed twice with DPBS or HBSS and resuspended at $4\times10^6$ cells/mL in RPMI complete. The PBMC suspension is added to 48 well flat bottom sterile tissue culture plates (Costar, Cambridge, Mass. or Becton Dickinson Labware, Lincoln Park, N.J.) containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 µM.

Incubation

The solution of test compound is added at 60 µM to the first well containing RPMI complete and serial 3 fold dilutions are made in the wells. The PBMC suspension is then added to the wells in an equal volume, bringing the test compound concentrations to the desired range (30-0.014 µM). The final concentration of PBMC suspension is $2\times10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed with a sterile polypropylene pipet and transferred to sterile polypropylene tubes. Samples are maintained at −30 to −70° C. until analysis. The samples are analyzed for interferon (α) by ELISA and for tumor necrosis factor (α) by ELISA or IGEN Assay.

Interferon (α) and Tumor Necrosis Factor (α) Analysis by ELISA

Interferon (α) concentration is determined by ELISA using a Human Multi-Species kit from PBL Biomedical Laboratories, New Brunswick, N.J. Results are expressed in pg/mL.

Tumor necrosis factor (α) (TNF) concentration is determined using ELISA kits available from Biosource International, Camarillo, Calif. Alternately, the TNF concentration can be determined by ORIGEN M-Series Immunoassay and read on an IGEN M-8 analyzer from IGEN International, Gaithersburg, Md. The immunoassay uses a human TNF capture and detection antibody pair from Biosource International, Camarillo, Calif. Results are expressed in pg/mL.

Certain compounds of the invention may modulate cytokine biosynthesis by inhibiting production of tumor necrosis factor α (TNF-α) when tested using the method described below.

TNF-α Inhibition in Mouse Cells

The mouse macrophage cell line Raw 264.7 is used to assess the ability of compounds to inhibit tumor necrosis factor-α (TNF-α) production upon stimulation by lipopolysaccharide (LPS).

Single Concentration Assay:

Blood Cell Preparation for Culture

Raw cells (ATCC) are harvested by gentle scraping and then counted. The cell suspension is brought to $3\times10^5$ cells/mL in RPMI with 10% fetal bovine serum (FBS). Cell suspension (100 µL) is added to 96-well flat bottom sterile tissues culture plates (Becton Dickinson Labware, Lincoln Park, N.J.). The final concentration of cells is $3\times10^4$ cells/well. The plates are incubated for 3 hours. Prior to the addition of test compound the medium is replaced with colorless RPMI medium with 3% FBS.

Compound Preparation

The compounds are solubilized in dimethyl sulfoxide (DMSO). The DMSO concentration should not exceed a final concentration of 1% for addition to the culture wells. Compounds are tested at 5 µM. LPS (Lipopolysaccharide from *Salmonella typhimurium*, Sigma-Aldrich) is diluted with colorless RPMI to the $EC_{70}$ concentration as measured by a dose response assay.

Incubation

A solution of test compound (1 µl) is added to each well. The plates are mixed on a microtiter plate shaker for 1 minute and then placed in an incubator. Twenty minutes later the solution of LPS (1 µL, $EC_{70}$ concentration ~10 ng/ml) is added and the plates are mixed for 1 minute on a shaker. The plates are incubated for 18 to 24 hours at 37° C. in a 5% carbon dioxide atmosphere.

TNF-α Analysis

Following the incubation the supernatant is removed with a pipet. TNF-α concentration is determined by ELISA using a mouse TNF-α kit (from Biosource International, Camarillo, Calif.). Results are expressed in pg/mL. TNF-α expression upon LPS stimulation alone is considered a 100% response.

Dose Response Assay:

Blood Cell Preparation for Culture

Raw cells (ATCC) are harvested by gentle scraping and then counted. The cell suspension is brought to $4\times10^5$ cells/mL in RPMI with 10% FBS. Cell suspension (250 µL) is added to 48-well flat bottom sterile tissues culture plates (Costar, Cambridge, Mass.). The final concentration of cells is $1\times10^5$ cells/well. The plates are incubated for 3 hours. Prior to the addition of test compound the medium is replaced with colorless RPMI medium with 3% FBS.

Compound Preparation

The compounds are solubilized in dimethyl sulfoxide (DMSO). The DMSO concentration should not exceed a final concentration of 1% for addition to the culture wells. Compounds are tested at 0.03, 0.1, 0.3, 1, 3, 5 and 10 µM. LPS (Lipopolysaccharide from *Salmonella typhimurium*, Sigma-Aldrich) is diluted with colorless RPMI to the $EC_{70}$ concentration as measured by dose response assay.

Incubation

A solution of test compound (200 µl) is added to each well. The plates are mixed on a microtiter plate shaker for 1 minute and then placed in an incubator. Twenty minutes later the solution of LPS (200 µL, $EC_{70}$ concentration ~10 ng/ml) is added and the plates are mixed for 1 minute on a shaker. The plates are incubated for 18 to 24 hours at 37° C. in a 5% carbon dioxide atmosphere.

TNF-α Analysis

Following the incubation the supernatant is removed with a pipet. TNF-α concentration is determined by ELISA using a mouse TNF-α kit (from Biosource International, Camarillo, Calif.). Results are expressed in pg/mL. TNF-α expression upon LPS stimulation alone is considered a 100% response.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A compound of the Formula II:

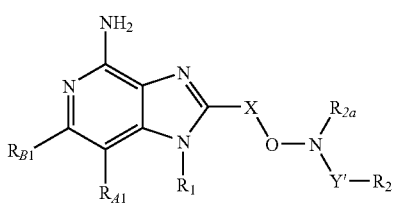

wherein:
X is $C_{1-10}$ alkylene;
$R_{A1}$ and $R_{B1}$ are taken together to form a fused aryl ring, wherein the aryl ring is unsubstituted or substituted by one $R_3$ group;
$R_3$ is selected from the group consisting of:
—Z—$R_4$,
—Z—X'—$R_4$, and
—Z—X'—Y—$R_4$;
Y' is selected from the group consisting of:
a bond,
—C(O)—,
—S(O)$_2$—,
—S(O)$_2$—N($R_8$)—,
—C(O)—O—,
—C(O)—N($R_8$)—,
—C(S)—N($R_8$)—,
—C(O)—N($R_8$)—C(O)—, and

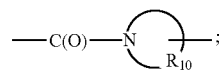

$R_1$ is selected from the group consisting of:
—$R_4$,
—X'—$R_4$, and
—X'—Y—$R_4$;
$R_2$ and $R_{2a}$ are independently selected from the group consisting of:
hydrogen,
alkyl,
aryl,
arylalkylenyl,
heteroaryl,
heteroarylalkylenyl,
heterocyclyl,
heterocyclylalkylenyl, and
alkyl, aryl, arylalkylenyl, heteroaryl, heteroarylalkylenyl, heterocyclyl, or heterocyclylalkylenyl, substituted by one or more substituents selected from the group consisting of:
alkyl,
haloalkyl,
alkoxy,
halogen, and
aryl;
X' is selected from the group consisting of alkylene and arylene;
Y is selected from the group consisting of:
—C($R_6$)—,
—N($R_8$)-Q-, and
—C($R_6$)—N($R_8$)—;
Z is a bond;
$R_4$ is selected from the group consisting of hydrogen, alkyl, alkenyl, alkynyl, and aryl, wherein the alkyl, alkenyl, alkynyl, and aryl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, amino, alkylamino, and dialkylamino;
$R_6$ is =O;
$R_7$ is $C_{2-7}$ alkylene;
$R_8$ is selected from the group consisting of hydrogen and $C_{1-10}$ alkyl;
$R_{10}$ is $C_{3-8}$ alkylene;
Q is selected from the group consisting of a bond, —C($R_6$)—, —S(O)$_2$—, and —C($R_6$)—N($R_8$)—W—; and
W is selected from the group consisting of a bond, —C(O)—, and —S(O)$_2$—;

or a pharmaceutically acceptable salt thereof.

2. The compound of claim 1 of the Formula IIIa:

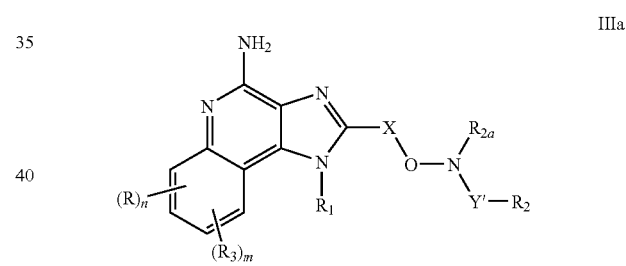

wherein:
X is $C_{1-10}$ alkylene;
Y' is selected from the group consisting of:
a bond,
—C(O)—,
—S(O)$_2$—,
—S(O)$_2$—N($R_8$)—,
—C(O)—O—,
—C(O)—N($R_8$)—,
—C(S)—N($R_8$)—,
—C(O)—N($R_8$)—C(O)—, and

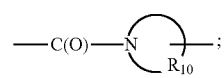

$R_1$ is selected from the group consisting of:
—$R_4$,
—X'—$R_4$, and
—X'—Y—$R_4$;

$R_2$ and $R_{2a}$ are independently selected from the group consisting of:
hydrogen,
alkyl,
aryl,
arylalkylenyl,
heteroaryl,
heteroarylalkylenyl,
heterocyclyl,
heterocyclylalkylenyl, and
alkyl, aryl, arylalkylenyl, heteroaryl, heteroarylalkylenyl, heterocyclyl, or
heterocyclylalkylenyl, substituted by one or more substituents selected from the group consisting of:
alkyl,
haloalkyl,
alkoxy,
halogen, and
aryl;

$R_3$ is selected from the group consisting of:
—Z—$R_4$,
—Z—X'—$R_4$, and
—Z—X'—Y—$R_4$;

n is 0;
m is 0 or 1;
X' is selected from the group consisting of alkylene and arylene;
Y is selected from the group consisting of:
—C($R_6$)—, and
—N($R_8$)-Q-;
Z is a bond;
$R_4$ is selected from the group consisting of hydrogen, alkyl, alkenyl, alkynyl, and aryl wherein the alkyl, alkenyl, alkynyl, and aryl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, amino, alkylamino, and dialkylamino;
$R_6$ is =O;
$R_7$ is $C_{2-7}$ alkylene;
$R_8$ is selected from the group consisting of hydrogen and $C_{1-10}$ alkyl;
$R_{10}$ is $C_{3-8}$ alkylene;
Q is selected from the group consisting of a bond, —C($R_6$)—, —S(O)$_2$—, and —C($R_6$)—N($R_8$)—W—; and
W is selected from the group consisting of a bond, —C(O)—, and —S(O)$_2$—;
or a pharmaceutically acceptable salt thereof.

3. The compound of claim 1 of the Formula IIIaa:

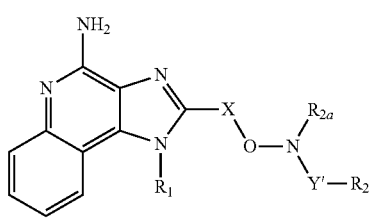

IIIaa wherein:
X is $C_{1-10}$ alkylene;
Y' is selected from the group consisting of:
a bond,
—C(O)—,
—S(O)$_2$—,
—S(O)$_2$—N($R_8$)—,
—C(O)—O—,
—C(O)—N($R_8$)—,
—C(S)—N($R_8$)—,
—C(O)—N($R_8$)—C(O)—, and

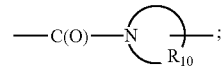

$R_2$ and $R_{2a}$ are independently selected from the group consisting of:
hydrogen,
alkyl,
aryl,
arylalkylenyl,
heteroaryl,
heteroarylalkylenyl,
heterocyclyl,
heterocyclylalkylenyl, and
alkyl, aryl, arylalkylenyl, heteroaryl, heteroarylalkylenyl, heterocyclyl, or heterocyclylalkylenyl, substituted by one or more substituents selected from the group consisting of:
alkyl,
haloalkyl,
alkoxy,
halogen, and
aryl;

$R_1$ is selected from the group consisting of:
—$R_4$,
—X'—$R_4$, and
—X'—Y—$R_4$;

X' is selected from the group consisting of alkylene and arylene
Y is selected from the group consisting of:
—C($R_6$)—,
—N($R_8$)-Q-, and
—C($R_6$)—N($R_8$)—;
$R_4$ is selected from the group consisting of hydrogen, alkyl, alkenyl, alkynyl, and aryl wherein the alkyl, alkenyl, alkynyl, and aryl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, amino, alkylamino, and dialkylamino;
$R_6$ is =O;
$R_8$ is selected from the group consisting of hydrogen and $C_{1-10}$ alkyl;
$R_{10}$ is $C_{3-8}$ alkylene;
Q is selected from the group consisting of a bond, —C($R_6$)—, —S(O)$_2$—, and —C($R_6$)—N($R_8$)—W—; and
W is selected from the group consisting of a bond, —C(O)—, and —S(O)$_2$—;
or a pharmaceutically acceptable salt thereof.

4. The compound or salt of claim 2 wherein m and n are 0.
5. The compound or salt of claim 1 wherein $R_1$ is selected from the group consisting of alkyl, arylalkylenyl, hydroxyalkyl, and —X'—Y—$R_4$; wherein X' is alkylene; Y is —N($R_8$)—C(O)—, —N($R_8$)—S(O)$_2$—, —N($R_8$)—C(O)—N($R_8$)—, or —N($R_8$)—C(O)—N($R_8$)—C(O)—, and $R_4$ is hydrogen, alkyl, alkenyl, or aryl, wherein alkyl and alkenyl are optionally substituted by aryl and wherein aryl is optionally substituted by one or more substituents selected from the group consisting of alkyl, alkoxy, cyano, haloalkyl, and halogen.

6. The compound or salt of claim 5 wherein $R_1$ is 2-methylpropyl, 2-hydroxy-2-methylpropyl, or —X'—Y—$R_4$; X' is ethylene, propylene, or butylene; Y is —NH—C(O)—, —NH—S(O)$_2$—, —NH—C(O)—N($R_8$)—, or —NH—C(O)—NH—C(O)—; and $R_8$ is hydrogen or methyl.

7. The compound or salt of claim 1 wherein X is $C_{1-4}$ alkylene.

8. The compound or salt of claim 7 wherein X is methylene.

9. The compound or salt of claim 1 wherein Y' is selected from the group consisting of a bond, —C(O)—, —C(O)—O—, —S(O)$_2$—, —S(O)$_2$—N($R_8$)—, —C(O)—N($R_8$)—, —C(S)—N($R_8$)—, —C(O)—N($R_8$)—C(O)—, and

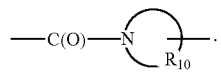

10. The compound or salt of claim 9 wherein Y' is selected from the group consisting of —C(O)—, —S(O)$_2$—, and —C(O)—N($R_8$)—.

11. The compound or salt of claim 1 wherein $R_2$ and $R_{2a}$ are independently selected from the group consisting of: hydrogen, alkyl, aryl, arylalkylenyl, heteroaryl, heteroarylalkylenyl, heterocyclyl, heterocyclylalkylenyl, and alkyl, aryl, arylalkylenyl, heteroaryl, heteroarylalkylenyl, heterocyclyl, or heterocyclylalkylenyl, substituted by one or more substituents selected from the group consisting of: alkyl, haloalkyl, alkoxy, halogen, and aryl.

12. The compound or salt of claim 1 wherein $R_{2a}$ is hydrogen.

13. The compound or salt of claim 1 wherein $R_2$ and $R_{2a}$ are independently selected from the group consisting of hydrogen, alkyl, aryl, heteroaryl, wherein the alkyl, aryl, and heteroaryl are each optionally substituted with one or more substituents selected from the group consisting of $C_{1-10}$ alkyl, aryl, $C_{1-10}$ alkoxy, and halogen.

14. The compound or salt of claim 1 wherein $R_2$ is alkyl or substituted alkyl, and $R_{2a}$ is hydrogen.

15. The compound or salt of claim 14 wherein $R_2$ is methyl or cyclopropyl, and $R_{2a}$ is hydrogen.

16. A pharmaceutical composition comprising a therapeutically effective amount of a compound or salt of claim 1 in combination with a pharmaceutically acceptable carrier.

17. The compound or salt of claim 2 wherein $R_1$ is selected from the group consisting of alkyl, arylalkylenyl, hydroxyalkyl, and —X'—Y—$R_4$; wherein X' is alkylene; Y is —N($R_8$)—C(O)—, —N($R_8$)—S(O)$_2$—, N($R_8$)—C(O)—N($R_8$)—, or —N($R_8$)—C(O)—N($R_8$)—C(O)—; and $R_4$ is hydrogen, alkyl, alkenyl, or aryl, wherein alkyl and alkenyl are optionally substituted by aryl and wherein aryl is optionally substituted by one or more substituents selected from the group consisting of alkyl, alkoxy, cyano, haloalkyl, and halogen.

18. The compound or salt of claim 17 wherein $R_1$ is 2-methylpropyl, 2-hydroxy-2-methylpropyl, or —X'—Y—$R_4$; X' is ethylene, propylene, or butylene; Y is —NH—C(O)—, —NH—S(O)$_2$—, —NH—C(O)—N($R_8$)—, or —NH—C(O)—NH—C(O)—; and $R_8$ is hydrogen or methyl.

19. The compound or salt of claim 2 wherein X is $C_{1-4}$ alkylene.

20. The compound or salt of claim 19 wherein X is methylene.

21. The compound or salt of claim 2 wherein Y' is selected from the group consisting of a bond, —C(O)—, —C(O)—O—, —S(O)$_2$—, —S(O)$_2$—N($R_8$)—, —C(O)—N($R_8$)—, —C(S)—N($R_8$)—, —C(O)—N($R_8$)—C(O)—, and

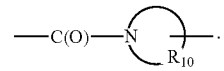

22. The compound or salt of claim 21 wherein Y' is selected from the group consisting of —C(O)—, —S(O)$_2$—, and —C(O)—N($R_8$)—.

23. The compound or salt of claim 2 wherein $R_2$ and $R_{2a}$ are independently selected from the group consisting of: hydrogen, alkyl, alkenyl, aryl, arylalkylenyl, heteroaryl, heteroarylalkylenyl, heterocyclyl, heterocyclylalkylenyl, and alkyl, alkenyl, aryl, arylalkylenyl, heteroaryl, heteroarylalkylenyl, heterocyclyl, or heterocyclylalkylenyl, substituted by one or more substituents selected from the group consisting of: alkyl, haloalkyl, alkoxy, dialkylamino, halogen, and aryl.

24. The compound or salt of claim 2 wherein $R_{2a}$ is hydrogen.

25. The compound or salt of claim 2 wherein $R_2$ and $R_{2a}$ are independently selected from the group consisting of hydrogen, alkyl, alkenyl, aryl, heteroaryl, wherein the alkyl, alkenyl, aryl, and heteroaryl are each optionally substituted with one or more substituents selected from the group consisting of $C_{1-10}$ alkyl, aryl, $C_{1-10}$ alkoxy, and halogen.

26. The compound or salt of claim 2 wherein $R_2$ is alkyl or substituted alkyl, and $R_{2a}$ is hydrogen.

27. The compound or salt of claim 26 wherein $R_2$ is methyl or cyclopropyl, and $R_{2a}$ is hydrogen.

28. A pharmaceutical composition comprising a therapeutically effective amount of a compound or salt of claim 2 in combination with a pharmaceutically acceptable carrier.

29. The compound or salt of claim 3 wherein $R_1$ is selected from the group consisting of alkyl, arylalkylenyl, and —X'—Y—$R_4$; wherein X' is alkylene; Y is —N($R_8$)—C(O)—, —N($R_8$)—S(O)$_2$—, —N($R_8$)—C(O)—N($R_8$)—, or —N($R_8$)—C(O)—N($R_8$)—C(O)—, and $R_4$ is hydrogen, alkyl, alkenyl, or aryl, wherein alkyl and alkenyl are optionally substituted by aryl and wherein aryl is optionally substituted by one or more substituents selected from the group consisting of alkyl, alkoxy, cyano, haloalkyl, and halogen.

30. The compound or salt of claim 29 wherein $R_1$ is 2-methylpropyl, 2-hydroxy-2-methylpropyl, or —X'—Y—$R_4$; X' is ethylene, propylene, or butylene; Y is —NH—C(O)—, —NH—S(O)$_2$—, —NH—C(O)—N($R_8$)—, or —NH—C(O)—NH—C(O)—; and $R_8$ is hydrogen or methyl.

31. The compound or salt of claim 3 wherein X is $C_{1-4}$ alkylene.

32. The compound or salt of claim 31 wherein X is methylene.

33. The compound or salt of claim 3 wherein Y' is selected from the group consisting of a bond, —C(O)—, —C(O)—O—, —S(O)$_2$—, —S(O)$_2$—N($R_8$)—, —C(O)—N($R_8$)—, —C(S)—N($R_8$)—, —C(O)—N($R_8$)—C(O)—, and

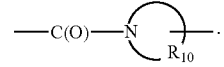

34. The compound or salt of claim 33 wherein Y' is selected from the group consisting of —C(O)—, —S(O)$_2$—, and —C(O)—N(R$_8$)—.

35. The compound or salt of claim 3 wherein R$_2$ and R$_{2a}$ are independently selected from the group consisting of: hydrogen, alkyl, alkenyl, aryl, arylalkylenyl, heteroaryl, heteroarylalkylenyl, heterocyclyl, heterocyclylalkylenyl, and alkyl, alkenyl, aryl, arylalkylenyl, heteroaryl, heteroarylalkylenyl, heterocyclyl, or heterocyclylalkylenyl, substituted by one or more substituents selected from the group consisting of: alkyl, haloalkyl, alkoxy, dialkylamino, halogen, and aryl.

36. The compound or salt of claim 3 wherein R$_{2a}$ is hydrogen.

37. The compound or salt of claim 3 wherein R$_2$ and R$_{2a}$ are independently selected from the group consisting of hydrogen, alkyl, alkenyl, aryl, heteroaryl, wherein the alkyl, alkenyl, aryl, and heteroaryl are each optionally substituted with one or more substituents selected from the group consisting of C$_{1-10}$ alkyl, aryl, C$_{1-10}$ alkoxy and halogen.

38. The compound or salt of claim 3 wherein R$_2$ is alkyl or substituted alkyl, and R$_{2a}$ is hydrogen.

39. The compound or salt of claim 38 wherein R$_2$ is methyl or cyclopropyl, and R$_{2a}$ is hydrogen.

40. A pharmaceutical composition comprising a therapeutically effective amount of a compound or salt of claim 3 in combination with a pharmaceutically acceptable carrier.

* * * * *